US009018258B2

(12) United States Patent
Lampe et al.

(10) Patent No.: US 9,018,258 B2
(45) Date of Patent: Apr. 28, 2015

(54) SUBSTITUTED 1-BENZYLCYCLOALKYLCARBOXYLIC ACIDS AND THE USE THEREOF

(75) Inventors: Thomas Lampe, Düsseldorf (DE); Michael G. Hahn, Langenfeld (DE); Johannes-Peter Stasch, Solingen (DE); Karl-Heinz Schlemmer, Wuppertal (DE); Frank Wunder, Wuppertal (DE); Sherif El Sheikh, Essen (DE); Volkhart Min-Jian Li, Velbert (DE); Eva-Maria Becker, Wuppertal (DE); Friederike Stoll, Düsseldorf (DE); Andreas Knorr, Erkrath (DE); Peter Kolkhof, Wuppertal (DE); Elisabeth Woltering, Hilden (DE)

(73) Assignee: Bayer Intellectual Property GmbH, Monheim (DE)

( * ) Notice: Subject to any disclaimer, the term of this patent is extended or adjusted under 35 U.S.C. 154(b) by 812 days.

(21) Appl. No.: 13/312,320

(22) Filed: Dec. 6, 2011

(65) Prior Publication Data
US 2012/0172448 A1 Jul. 5, 2012

(30) Foreign Application Priority Data

Dec. 7, 2010 (DE) .......................... 10 2010 062 544
Apr. 7, 2011 (DE) .......................... 10 2011 006 974

(51) Int. Cl.
*A61K 31/196* (2006.01)
*C07C 233/55* (2006.01)
*C07C 231/02* (2006.01)
*C07C 233/24* (2006.01)

(52) U.S. Cl.
CPC ............. *C07C 231/02* (2013.01); *A61K 31/196* (2013.01); *C07C 233/55* (2013.01); *C07C 233/24* (2013.01)

(58) Field of Classification Search
CPC ............................ C07C 233/55; A61K 31/196
USPC ........................................ 514/563; 562/441
See application file for complete search history.

(56) References Cited

U.S. PATENT DOCUMENTS

| 5,041,453 A | 8/1991 | Huang et al. |
| 5,693,650 A | 12/1997 | Müller et al. |
| 5,811,429 A | 9/1998 | Connell et al. |
| 5,935,984 A | 8/1999 | Goldmann et al. |
| 6,667,334 B1 | 12/2003 | Neises et al. |
| 6,693,102 B2 | 2/2004 | Stasch et al. |
| 6,743,798 B1 | 6/2004 | Straub et al. |
| 6,833,364 B1 | 12/2004 | Straub et al. |
| 6,835,752 B2 | 12/2004 | Tani et al. |
| 6,884,821 B1 | 4/2005 | Shinoda et al. |
| 7,005,440 B1 | 2/2006 | Jayyosi et al. |
| 7,173,037 B2 | 2/2007 | Alonso-Alija et al. |
| 7,176,204 B2 | 2/2007 | Miyachi et al. |
| 7,238,716 B2 | 7/2007 | Momose et al. |
| 7,241,785 B2 | 7/2007 | Momose et al. |
| 7,244,861 B2 | 7/2007 | Matsuura et al. |
| 7,368,578 B2 | 5/2008 | Momose et al. |
| 7,371,777 B2 | 5/2008 | Clark et al. |
| 7,465,825 B2 | 12/2008 | Van Zandt et al. |
| 7,491,748 B2 | 2/2009 | Tani et al. |
| 7,816,367 B2 | 10/2010 | Akerman et al. |
| 2005/0187266 A1 | 8/2005 | Su |
| 2005/0234066 A1 | 10/2005 | Bailey et al. |
| 2011/0034450 A1* | 2/2011 | Hahn et al. ................. 514/229.2 |
| 2011/0092554 A1 | 4/2011 | Chesworth et al. |
| 2011/0130445 A1 | 6/2011 | Lampe et al. |
| 2012/0028971 A1 | 2/2012 | Lampe et al. |
| 2013/0079412 A1 | 3/2013 | Hahn et al. |

FOREIGN PATENT DOCUMENTS

| EP | 0 608 709 A1 | 8/1994 |
| EP | 1 229 010 A1 | 8/2002 |
| EP | 1 285 908 A1 | 2/2003 |
| WO | 96/12473 A1 | 5/1996 |
| WO | 96/30036 A1 | 10/1996 |
| WO | 00/64888 A1 | 11/2000 |
| WO | 2004/099170 A2 | 11/2004 |
| WO | 2006/050097 A1 | 5/2006 |

OTHER PUBLICATIONS

U.S. Appl. No. 14/045,630, filed Oct. 3, 2013.
Evgenov, et al.:"NO-Independent Stimulators and Activators of Soluble Guanylate Cyclase: Discovery and Theraputic Potential," Nature Reviews, Sep. 2006, 5(9): 755-768.
Hayashi :"Rhodium-Catalyzed Asymmetric 1,4-Addition of Organoboronic Acids and Their Derivatives to Electron Deficient Olefins," Synlett, 2001, Special Issue: 879-887.
Mase, et al.:"Synthesis of a Muscarinic Receptor Antagonist via a Diastereoselective Michael Reaction, Selective Deoxyfluorination and Aromatic Metal-Halogne Exchange Reaction," J. Org. Chem., 2001, 66: 6775-6786.
Moradi, et al.:"Palladium-Catalyzed α-Arylation of Esters," J. Am. Chem. Soc.,2001, 123: 7996-8002.
Sakai, et al.:"Rhodium-Catalyzed Conjugate Addition of Aryl- or 1-Alkenylboronic Acids to Enones," Organometallics, Sep. 30, 1997, 16(20): 4229-4231.
Stasch, et al.:"NO-and Haem-independent Activation of Soluble Guanylyl Cyclase: Molecular Basis and Cardiovascular Implications of a New Pharmacological Principle," British Journal of Pharmacology, 2002, 136:773-783.
Stasch, et al.: Targeting the Heme-Oxidized Nitric Oxide Receptor for Selective Vasodilation of Diseased Blood Vessels, Sep. 2006, 116(9): 2552-2561.

(Continued)

*Primary Examiner* — Joseph Kosack
*Assistant Examiner* — Matthew Coughlin
(74) *Attorney, Agent, or Firm* — Buchanan Ingersoll & Rooney PC

(57) ABSTRACT

The present application relates to novel substituted 1-benzyl-cycloalkylcarboxylic acid derivatives, to processes for their preparation, to their use for the treatment and/or prevention of diseases, and to their use for producing medicaments for the treatment and/or prevention of diseases, especially for the treatment and/or prevention of cardiovascular disorders.

10 Claims, No Drawings

(56) References Cited

OTHER PUBLICATIONS

Varchi, et al.:"Copper Catalyzed Conjugate Addition of Highly Functionalized Arylmagnesium Compounds to Enones," Tetrahedron, 2000, 56: 2727-2731.

Weintraub, et al.:" Synthesis of Steroidal Vinyl Ethers Using Palladium Acetate-Phenanthroline as Catalyst," J.Org. Chem., 1997, 62:1560-1562.

Wolfe, et al.:"Palladium-Catalyzed Amination of Aryl Halides and Aryl Triflates: N-Hexyl-2-Methyl-4-Methoxyaniline and N-Methyl-N-(4-Chlorophenyl) Aniline," Organic Synthesis, Coll. vol. 10: 423 (2004); 78:23 (2002).

U.S. Appl. No. 13/312,230, filed Dec. 7, 2010.

* cited by examiner ations and proliferation of smooth muscle cells, in platelet
SUBSTITUTED 1-BENZYLCYCLOALKYLCARBOXYLIC ACIDS AND THE USE THEREOF The present application relates to novel substituted 1-benzylcycloalkylcarboxylic acid derivatives, to processes for their preparation, to their use for the treatment and/or prevention of diseases, and to their use for producing medicaments for the treatment and/or prevention of diseases, especially for the treatment and/or prevention of cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment [O. V. Evgenov et al., *Nature Rev. Drug Disc.* 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543 and BAY 63-2521. Together with the recently published structurally different substances CMF-1571 and A-350619, these compounds form the new class of the sGC stimulators [Evgenov et al., ibid.]. A common characteristic of this substance class is an NO-independent and selective activation of the haem-containing sGC. In addition, the sGC stimulators in combination with NO have a synergistic effect on sGC activation based on a stabilization of the nitrosyl-haem complex. The exact binding site of the sGC stimulators at the sGC is still being debated. If the haem group is removed from the soluble guanylate cyclase, the enzyme still has a detectable catalytic basal activity, i.e. cGMP is still being formed. The remaining catalytic basal activity of the haem-free enzyme cannot be stimulated by any of the stimulators mentioned above [Evgenov et al., ibid.].

In addition, NO- and haem-independent sGC activators, with BAY 58-2667 as prototype of this class, have been identified. Common characteristics of these substances are that in combination with NO they only have an additive effect on enzyme activation, and that the activation of the oxidized or haem-free enzyme is markedly higher than that of the haem-containing enzyme [Evgenov et al., ibid.; J. P. Stasch et al., *Br. J. Pharmacol.* 136 (2002), 773; J. P. Stasch et al., *J. Clin. Invest.* 116 (2006), 2552]. Spectroscopic studies show that BAY 58-2667 displaces the oxidized haem group which, as a result of the weakening of the iron-histidine bond, is attached only weakly to the sGC. It has also been shown that the characteristic sGC haem binding motif Tyr-x-Ser-x-Arg is absolutely essential both for the interaction of the negatively charged propionic acids of the haem group and for the action of BAY 58-2667. Against this background, it is assumed that the binding site of BAY 58-2667 at the sGC is identical to the binding site of the haem group [J. P. Stasch et al., *J. Clin. Invest.* 116 (2006), 2552].

The compounds described in the present invention are now likewise capable of activating the haem-free form of soluble guanylate cyclase. This is also confirmed by the fact that these novel activators firstly have no synergistic action with NO at the haem-containing enzyme and that secondly their action cannot be blocked by the haem-dependent inhibitor of soluble guanylate cyclase, 1H-1,2,4-oxadiazolo[4,3-a]quinoxalin-1-one (ODQ), but is even potentiated by this inhibitor [cf. O. V. Evgenov et al., *Nature Rev. Drug Disc.* 5 (2006), 755; J. P. Stasch et al., *J. Clin. Invest.* 116 (2006), 2552].

It was thus an object of the present invention to provide novel compounds which act as activators of soluble guanylate cyclase in the manner described above and can be used as such in particular for the treatment and prevention of cardiovascular disorders.

WO 00/64888-A1, EP 1 216 980-A1, EP 1 285 908-A1, EP 1 348 698-A1, EP 1 375 472-A1, EP 1 452 521-A1 and US 2005/0234066-A1 describe various arylalkanecarboxylic acid derivatives as PPAR agonists for treating diabetes, dyslipidaemia, arteriosclerosis, obesity and other disorders. Furthermore, substituted arylalkanecarboxylic acids are disclosed in EP 1 312 601-A1 and EP 1 431 267-A1 as $PGE_2$ receptor antagonists for the treatment of, for example, urological disorders, states of pain, Alzheimer's disease and cancer. WO 2009/067493-A2 claims 3,5-disubstituted phenylacetic acid derivatives as active compounds for the treatment of Alzheimer's disease. WO 2009/127338-A1 and WO 2010/102717-A1 disclose oxoheterocyclically substituted carboxylic acid derivatives which act as activators of soluble guanylate cyclase.

The present invention provides compounds of the general formula (I)

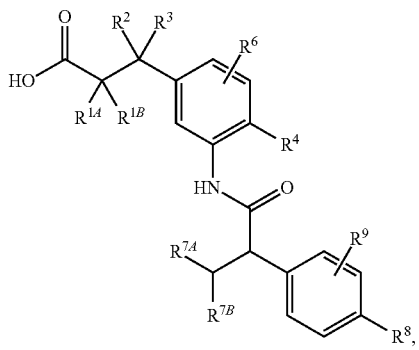

(I)

in which

R$^{1A}$ and R$^{1B}$ are attached to one another and together with the carbon atom to which they are attached form a cycloalkyl group of the formula

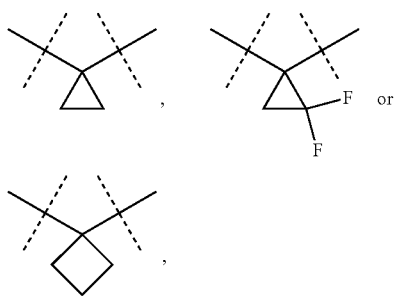

R$^2$ represents hydrogen, methyl, ethyl, vinyl, hydroxyl, methoxy, trideuteromethoxy, trifluoromethoxy, ethoxy or cyclopropyloxy, R$^3$ represents hydrogen, methyl, ethyl, isopropyl or cyclopropyl, R$^4$ represents hydrogen, fluorine, chlorine, bromine, cyano, methyl, trifluoromethyl, ethyl, isopropyl, cyclopropyl, cyclobutyl, methoxy or trifluoromethoxy, R$^5$ represents hydrogen, fluorine, chlorine, methyl, trifluoromethyl or trifluoromethoxy, R$^6$ represents hydrogen, fluorine, chlorine, methyl, trifluoromethyl or trifluoromethoxy, R$^{7A}$ represents methyl or ethyl, R$^{7B}$ represents trifluoromethyl, or R$^{7A}$ and R$^{7B}$ are attached to one another and together with the carbon atom to which they are attached form an optionally difluoro-substituted cyclopentyl ring of the formula

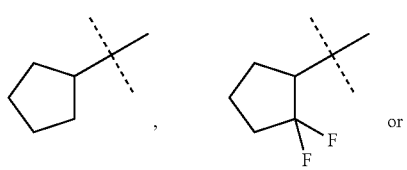

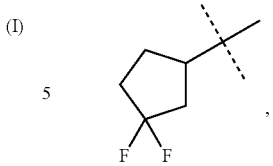

R$^8$ represents fluorine, chlorine, bromine, nitro, cyano, trifluoromethoxy, acetyl, 2-cyanovinyl, (C$_1$-C$_4$)-alkyl, (C$_2$-C$_4$)-alkenyl, cyclopropyl or cyclobutyl, where
(C$_1$-C$_4$)-alkyl and (C$_2$-C$_4$)-alkenyl may be substituted up to three times by fluorine,
and
cyclopropyl and cyclobutyl may be substituted up to two times by fluorine,
and
R$^9$ represents hydrogen, fluorine, chlorine, methyl, trifluoromethyl, ethyl, methoxy or tri-fluoromethoxy,
and salts, solvates and solvates of the salts thereof.

Compounds according to the invention are the compounds of the formula (I) and their salts, solvates and solvates of the salts, the compounds included in the formula (I) of the formulae mentioned in the following and their salts, solvates and solvates of the salts, and the compounds included in the formula (I) and mentioned in the following as embodiment examples and their salts, solvates and solvates of the salts, where the compounds included in the formula (I) and mentioned in the following are not already salts, solvates and solvates of the salts.

Preferred salts in the context of the present invention are physiologically acceptable salts of the compounds according to the invention. Salts which are not themselves suitable for pharmaceutical uses but can be used, for example, for isolation, purification or storage of the compounds according to the invention are also included.

Physiologically acceptable salts of the compounds according to the invention include in particular salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylpiperidine, N-methylmorpholine, arginine, lysine and 1,2-ethylenediamine.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers or diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action of or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by processes known to those skilled in the art, for example by the methods described below and the methods described in the working examples, by using corresponding isotopic modifications of the particular reagents and/or starting compounds therein.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The present invention comprises in particular hydrolysable ester derivatives of the carboxylic acids of the formula (I) according to the invention. These are to be understood as meaning esters which can be hydrolysed to the free carboxylic acids, as the compounds that are mainly active biologically, in physiological media, under the conditions of the biological tests described later and in particular in vivo by enzymatic or chemical routes. ($C_1$-$C_4$)-alkyl esters, in which the alkyl group can be straight-chain or branched, are preferred as such esters. Particular preference is given to methyl, ethyl or tert-butyl esters.

In the context of the present invention, the substituents have the following meaning, unless specified otherwise:

($C_1$-$C_4$)-Alkyl in the context of the invention represents a straight-chain or branched alkyl radical having 1 to 4 carbon atoms. The following may be mentioned by way of example and by way of preference: methyl, ethyl, n-propyl, isopropyl, n-butyl, isobutyl, sec-butyl and tert-butyl.

($C_2$-$C_4$)-Alkenyl and ($C_2$-$C_3$)-alkenyl in the context of the invention represent a straight-chain or branched alkenyl radical having a double bond and 2 to 4 and 2 or 3 carbon atoms, respectively. A straight-chain or branched alkenyl radical having 2 or 3 carbon atoms is preferred. The following may be mentioned by way of example and by way of preference: vinyl, allyl, n-prop-1-en-1-yl, iso-propenyl, n-but-1-en-1-yl, n-but-2-en-1-yl, n-but-3-en-1-yl, 2-methylprop-1-en-1-yl and 2-methylprop-2-en-1-yl.

In the context of the present invention, all radicals which occur more than once are defined independently of one another. If radicals in the compounds according to the invention are substituted, the radicals may be mono- or polysubstituted, unless specified otherwise. Substitution by one, two or three identical or different substituents is preferred. Particular preference is given to substitution by one or two identical or different substituents.

In the context of the present invention, preference is given to compounds of the formula (I) in which $R^{1A}$ and $R^{1B}$ are attached to one another and together with the carbon atom to which they are attached form a cycloalkyl group of the formula

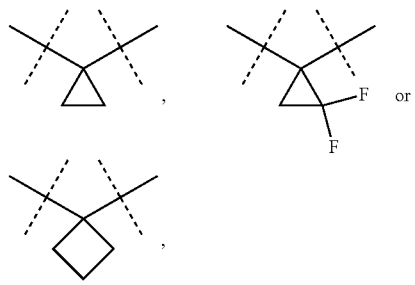

$R^2$ represents hydrogen, methyl, ethyl, hydroxyl, methoxy, trideuteromethoxy, ethoxy or cyclopropyloxy, $R^3$ represents hydrogen, methyl or ethyl, $R^4$ represents hydrogen, fluorine, chlorine, methyl or cyclopropyl, $R^5$ represents hydrogen, fluorine, chlorine or methyl, $R^6$ represents hydrogen, fluorine, chlorine or methyl, $R^{7A}$ represents methyl, $R^{7B}$ represents trifluoromethyl, or $R^{7A}$ and $R^{7B}$ are attached to one another and together with the carbon atom to which they are attached form an optionally difluoro-substituted cyclopentyl ring of the formula

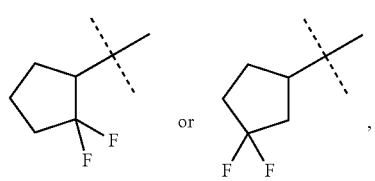

$R^8$ represents fluorine, chlorine, acetyl, 2-cyanovinyl, ($C_1$-$C_4$)-alkyl, ($C_2$-$C_3$)-alkenyl, cyclopropyl or cyclobutyl, where ($C_1$-$C_4$)-alkyl and ($C_2$-$C_3$)-alkenyl may be substituted up to three times by fluorine, and $R^9$ represents hydrogen, fluorine, chlorine, methyl, trifluoromethyl or methoxy, and salts, solvates and solvates of the salts thereof.

A particular embodiment of the present invention comprises compounds of the formula (I) in which $R^{1A}$ and $R^{1B}$ are attached to one another and together with the carbon atom to which they are attached form an optionally difluoro-substituted cyclopropyl ring of the formula

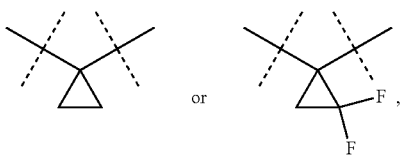

$R^2$ represents hydrogen, methyl or ethyl,
and
$R^3$ represents hydrogen,
and salts, solvates and solvates of the salts thereof A further particular embodiment of the present invention comprises compounds of the formula (I) in which
$R^{1A}$ and $R^{1B}$ are attached to one another and together with the carbon atom to which they are attached form a cyclopropyl or cyclobutyl ring of the formula

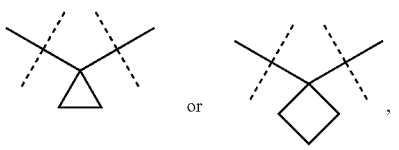

$R^2$ represents hydroxyl, methoxy, trideuteromethoxy or ethoxy,
and
$R^3$ represents hydrogen,
and salts, solvates and solvates of the salts thereof.

A further particular embodiment of the present invention comprises compounds of the formula (I) in which
$R^4$ represents hydrogen, fluorine or chlorine,
and salts, solvates and solvates of the salts thereof.

A further particular embodiment of the present invention comprises compounds of the formula (I) in which
$R^5$ represents hydrogen or fluorine
and
$R^6$ represents hydrogen,
and salts, solvates and solvates of the salts thereof.

A further particular embodiment of the present invention comprises compounds of the formula (I) in which
$R^{7A}$ represents methyl
and
$R^{7B}$ represents trifluoromethyl,
and salts, solvates and solvates of the salts thereof.

A further particular embodiment of the present invention comprises compounds of the formula (I) in which
$R^{7A}$ and $R^{7B}$ are attached to one another and together with the carbon atom to which they are attached form a difluoro-substituted cyclopentyl ring of the formula

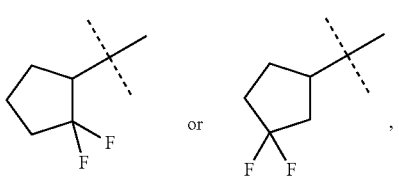

and salts, solvates and solvates of the salts thereof.

A further particular embodiment of the present invention comprises compounds of the formula (I) in which
$R^8$ represents chlorine, $(C_1-C_4)$-alkyl, $(C_2-C_3)$-alkenyl or cyclopropyl, where $(C_1-C_4)$-alkyl and $(C_2-C_3)$-alkenyl may be substituted up to three times by fluorine,
and salts, solvates and solvates of the salts thereof.

A further particular embodiment of the present invention comprises compounds of the formula (I) in which
$R^9$ represents hydrogen, fluorine, chlorine or methoxy,
and salts, solvates and solvates of the salts thereof.

Particular preference in the context of the present invention is given to compounds of the formula (I) in which
$R^{1A}$ and $R^{1B}$ are attached to one another and together with the carbon atom to which they are attached form a cyclopropyl ring of the formula

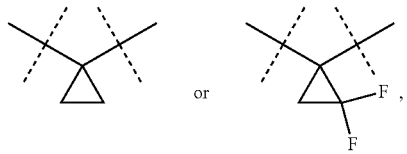

$R^2$ represents hydrogen or ethyl,
$R^3$ represents hydrogen,
$R^4$ represents hydrogen, fluorine or chlorine,
$R^5$ represents hydrogen or fluorine,
$R^6$ represents hydrogen,
$R^{7A}$ represents methyl,
$R^{7B}$ represents trifluoromethyl,
or
$R^{7A}$ and $R^{7B}$ are attached to one another and together with the carbon atom to which they are attached form a difluoro-substituted cyclopentyl ring of the formula

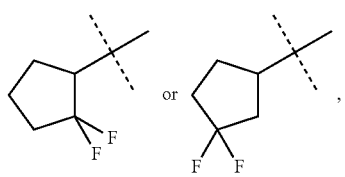

$R^8$ represents chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl, 2,2-difluorovinyl or cyclopropyl,
and
$R^9$ represents hydrogen, fluorine, chlorine or methoxy,
and salts, solvates and solvates of the salts thereof.

Particular preference in the context of the present invention is also given to compounds of the formula (I) in which
$R^{1A}$ and $R^{1B}$ are attached to one another and together with the carbon atom to which they are attached form a cyclopropyl or cyclobutyl ring of the formula

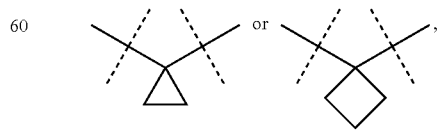

$R^2$ represents hydroxyl, methoxy, trideuteromethoxy, ethoxy or cyclopropyloxy, $R^3$ represents hydrogen,
$R^4$ represents hydrogen, fluorine or chlorine,
$R^5$ represents hydrogen or fluorine,
$R^6$ represents hydrogen,
$R^{7A}$ represents methyl,
$R^{7B}$ represents trifluoromethyl,
or
$R^{7A}$ and $R^{7B}$ are attached to one another and together with the carbon atom to which they are attached form a difluoro-substituted cyclopentyl ring of the formula

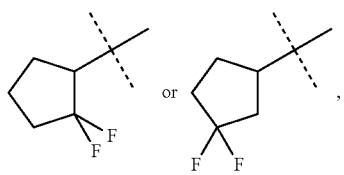

$R^8$ represents chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl, 2,2-difluorovinyl or cyclopropyl,
and
$R^9$ represents hydrogen, fluorine, chlorine or methoxy,
and salts, solvates and solvates of the salts thereof.

Of particular importance in the context of the present invention are compounds of the formula (I-A)

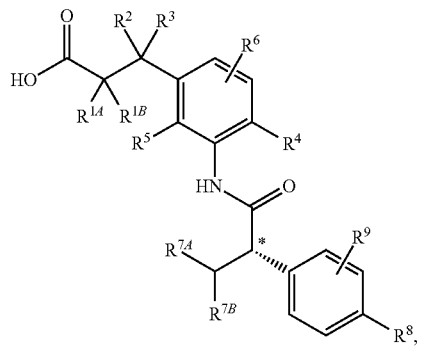

(I-A)

in which the carbon atom marked * of the phenylacetamide grouping has the S-configuration shown
and
the radicals $R^{1A}$, $R^{1B}$, $R^2$, $R^3$, $R^4$, $R^5$, $R^6$, $R^{7A}$, $R^{7B}$, $R^8$ and $R^9$ each have the meanings given above,
and salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations. Combinations of two or more of the abovementioned preferred ranges are very particularly preferred.

The invention furthermore provides a process for preparing the compounds of the formula (I) according to the invention, characterized in that a carboxylic acid of the formula (II)

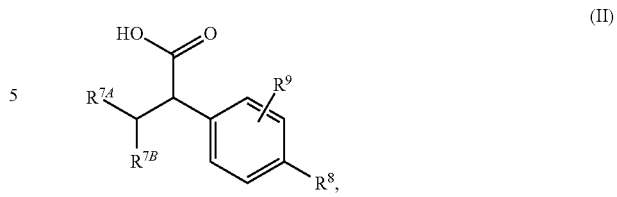

(II)

in which $R^{7A}$, $R^{7B}$, $R^8$ and $R^9$ have the meanings given above, is coupled in an inert solvent with the aid of a condensing agent or via the intermediate of the corresponding carbonyl chloride in the presence of a base with an amine of the formula (III)

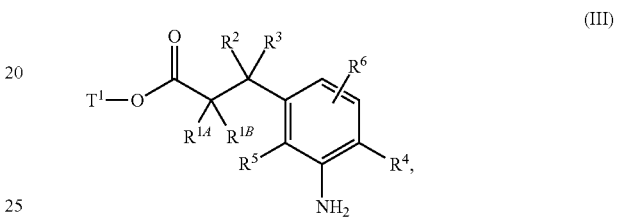

(III)

in which $R^{1A}$, $R^{1B}$, $R^2$, $R^3$, $R^4$, $R^5$ and $R^6$ have the meanings given above
and
$T^1$ represents $(C_1-C_4)$-alkyl or benzyl,
to give a carboxamide of the formula (IV)

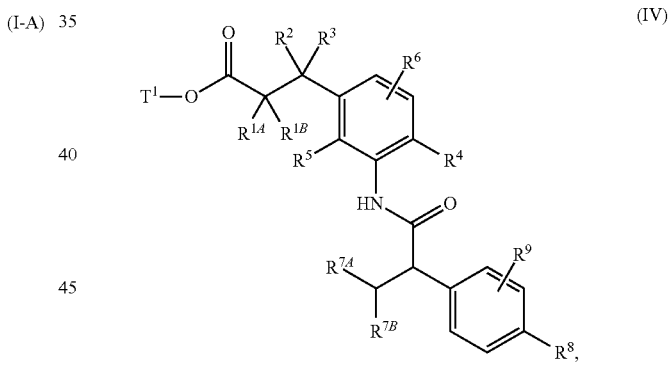

(IV)

in which $R^{1A}$, $R^{1B}$, $R^2$, $R^3$, $R^4$, $R^5$, $R^6$, $R^{7A}$, $R^{7B}$, $R^8$, $R^9$ and $T^1$ have the meanings given above, and the ester radical $T^1$ is then removed by basic or acidic solvolysis or, in the case that $T^1$ represents benzyl, also by hydrogenolysis to give the carboxylic acid of the formula (I)
and the compounds of the formula (I) are optionally separated by methods known to the person skilled in the art into their enantiomers and/or diastereomers and/or reacted with the appropriate (i) solvents and/or (ii) bases to give their solvates, salts and/or solvates of the salts.

Inert solvents for the process step (II)+(III)→(IV) [amide coupling] are, for example, ethers such as diethyl ether, tert-butyl methyl ether, tetrahydrofuran, 1,4-dioxane, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, acetonitrile, ethyl acetate, pyridine, dimethyl sulphoxide (DMSO), N,N-dimethylformamide (DMF), N,N'-dimethylpropyleneurea (DMPU) or N-methylpyrrolidinone (NMP). It is also possible to use mixtures of the solvents mentioned. Preference is given to using dichloromethane, tetrahydrofuran, dimethylformamide or mixtures of these solvents.

Suitable condensing agents for these coupling reactions are, for example, carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acyl-amino compounds such as 2-ethoxy-1-ethoxycarbonyl-1,2-dihydroquinoline, α-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxy-tris(dimethylamino)phosphonium hexafluorophosphate or benzotriazol-1-yl-oxy-tris (pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyl-uronium hexafluorophosphate (HATU) or O-(1H-6-chlorobenzotriazol-1-yl)-1,1,3,3-tetramethyl-uronium tetrafluoroborate (TCTU), if appropriate in combination with further auxiliaries such as 1-hydroxybenzotriazole (HOBt) or N-hydroxysuccinimide (HOSu), and as bases alkali metal carbonates, for example sodium carbonate or potassium carbonate, or organic bases such as triethylamine, N-methylmorpholine, N-methylpiperidine, N,N-diisopropylethylamine, pyridine or 4-N,N-dimethylaminopyridine. Preference is given to using O-(7-azabenzotriazol-1-yl)-N,N,N',N'-tetramethyluronium hexafluorophosphate (HATU) in combination with pyridine or N,N-diisopropylethylamine, or N-(3-dimethylaminoisopropyl)-N'-ethylcarbodiimide hydrochloride (EDC) in combination with 1-hydroxybenzotriazole (HOBt) and triethylamine, or 1-chloro-2-methyl-1-dimethylamino-1-propene together with pyridine.

The reaction (II)+(III)→(IV) is generally carried out in a temperature range of from 0° C. to +60° C., preferably at from +10° C. to +40° C.

When a carbonyl chloride corresponding to the compound (II) is used, the coupling with the amine component (III) is carried out in the presence of a customary organic auxiliary base such as triethylamine, N-methylmorpholine, N-methylpiperidine, N,N-diisopropylethylamine, pyridine, 4-N,N-dimethylaminopyridine, 1,8-diazabicyclo[5.4.0]undec-7-ene (DBU) or 1,5-diazabicyclo-[4.3.0]non-5-ene (DBN). Preference is given to using triethylamine or N,N-diisopropylethylamine.

The reaction of the amine (III) with the carbonyl chloride is generally carried out in a temperature range of from −20° C. to +60° C., preferably in the range from −10° C. to +30° C.

For their part, the preparation of the carbonyl chlorides is carried out in a customary manner by treating the carboxylic acid (II) with thionyl chloride or oxalyl chloride.

The removal of the ester group $T^1$ in process step (IV)→(I) is carried out by customary methods by treating the ester in inert solvents with acids or bases, where in the latter variant the salt initially formed is converted by treatment with acid into the free carboxylic acid. In the case of the tert-butyl esters, the ester cleavage is preferably carried out using acids. Benzyl esters are preferably cleaved by hydrogenolysis (hydrogenation) in the presence of a suitable catalyst such as, for example, palladium on activated carbon.

Suitable inert solvents for these reactions are water or organic solvents customary for ester cleavage. These preferably include alcohols such as methanol, ethanol, n-propanol, isopropanol, n-butanol or tert-butanol, or ethers such as diethyl ether, tetrahydrofuran, dioxane or glycol dimethyl ether, or other solvents such as acetone, dichloromethane, dimethylformamide or dimethyl sulphoxide. It is also possible to use mixtures of the solvents mentioned above. In the case of a basic ester hydrolysis, preference is given to using mixtures of water with dioxane, tetrahydrofuran, methanol and/or ethanol. In the case of the reaction with trifluoroacetic acid, preference is given to using dichloromethane and in the case of the reaction with hydrogen chloride, preference is given to using tetrahydrofuran, diethyl ether, dioxane or water.

Suitable bases are the customary inorganic bases. These include in particular alkali or alkaline earth metal hydroxides such as, for example, lithium hydroxide, sodium hydroxide, potassium hydroxide or barium hydroxide, or alkali or alkaline earth metal carbonates such as sodium carbonate, potassium carbonate or calcium carbonate. Preference is given to lithium hydroxide, sodium hydroxide or potassium hydroxide.

Suitable acids for the ester cleavage are, in general, sulphuric acid, hydrogen chloride/hydrochloric acid, hydrogen bromide/hydrobromic acid, phosphoric acid, aectic acid, trifluoroacetic acid, toluenesulphonic acid, methanesulphonic acid or trifluoromethanesulphonic acid or mixtures thereof, if appropriate with addition of water. Preference is given to hydrogen chloride or trifluoroacetic acid in the case of the tert-butyl esters and hydrochloric acid in the case of the methyl esters.

The ester cleavage is generally carried out in a temperature range of from −20° C. to +100° C., preferably at from 0° C. to +60° C.

The intermediates of the formula (II) can be prepared, for example, by

[A] initially deprotonating a carboxylic ester of the formula (V)

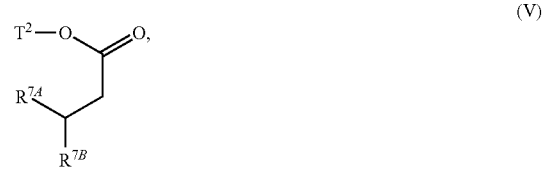

(V)

in which $R^{7A}$ and $R^{7B}$ have the meanings given above and $T^2$ represents $(C_1-C_4)$-alkyl or benzyl, in an inert solvent with the aid of a base and then arylating in the presence of a suitable palladium catalyst with a phenyl bromide of the formula (VI)

(VI)

in which $R^8$ and $R^9$ have the meanings given above,
to give a compound of the formula (VII)

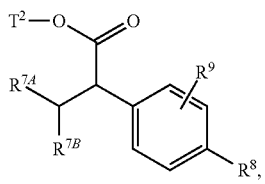
(VII)

in which $R^{7A}$, $R^{7B}$, $R^8$, $R^9$ and $T^2$ have the meanings given above, or

[B] alkylating a phenylacetic ester of the formula (VIII)

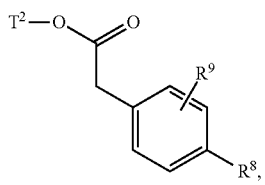
(VIII)

in which $R^8$ and $R^9$ have the meanings given above
and
$T^2$ represents $(C_1$-$C_4)$-alkyl or benzyl,
in an inert solvent in the presence of a base with a compound of the formula (IX)

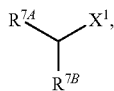
(IX)

in which $R^{7A}$ and $R^{7B}$ have the meanings given above
and
$X^1$ represents a suitable leaving group such as, for example, bromine or iodine, to give the compound of the formula (VII)

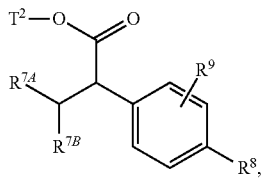
(VII)

in which $R^{7A}$, $R^{7B}$, $R^8$, $R^9$ and $T^2$ have the meanings given above,
and in each case removing the ester radical $T^2$ by basic or acidic solvolysis or, in the case that $T^2$ represents benzyl, also by hydrogenolysis, giving the carboxylic acid (II).

The arylation reaction in process step (V)+(VI)→(VII) is preferably carried out in toluene or toluene/tetrahydrofuran mixtures in a temperature range of from +20° C. to +100° C. Here, the base used for deprotonating the ester (V) is preferably lithium bis(trimethylsilyl)amide. Suitable palladium catalysts are, for example, palladium(II) acetate or tris(dibenzylideneacetone)di-palladium, in each case in combination with an electron-rich, sterically demanding phosphine ligand such as 2-dicyclohexylphosphino-2'-(N,N-dimethylamino)biphenyl or 2-di-tert-butylphosphino-2'-(N,N-dimethylamino)biphenyl [cf., for example, W. A. Moradi, S. L. Buchwald, J. Am. Chem. Soc. 123, 7996-8002 (2001)].

Inert solvents for the alkylation reaction (VIII)+(IX)→(VII) are, for example, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or mineral oil fractions, or dipolar aprotic solvents such as N,N-dimethylformamide (DMF), dimethyl sulphoxide (DMSO), N,N'-dimethylpropyleneurea (DMPU) or N-methylpyrrolidinone (NMP). It is also possible to use mixtures of the solvents mentioned. Preference is given to using tetrahydrofuran, dimethylformamide or mixtures thereof.

Suitable bases for the process step (VIII)+(IX)→(VII) are customary strong inorganic or organic bases. These include in particular alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, or amides such as lithium bis(trimethylsilyl)amide, sodium bis(trimethylsilyl)amide or potassium bis(trimethylsilyl)amide or lithium diisopropylamide. Preference is given to using potassium tert-butoxide, sodium hydride or lithium diisopropylamide.

The reaction (VIII)+(IX)→(VII) is generally carried out in a temperature range of from −80° C. to +40° C., preferably at from −20° C. to +20° C.

The removal of the ester group $T^2$ in process step (VII)→(II) is carried out in an analogous manner as described above for the ester radical $T^1$.

Alternatively, intermediates of the formula (II-A)

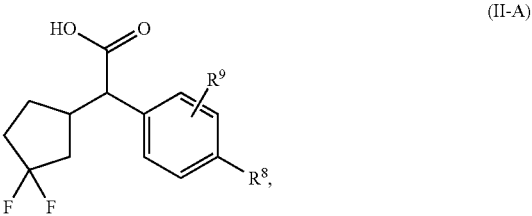
(II-A)

in which $R^8$ and $R^9$ have the meanings given above, can also be prepared by initially converting the phenylacetic ester of the formula (VIII)

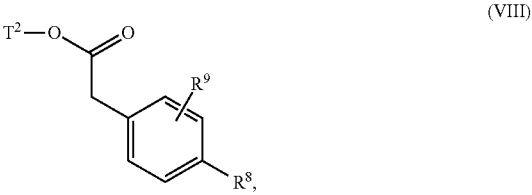
(VIII)

in which $R^8$, $R^9$ and $T^2$ have the meanings given above,
by base-induced addition to 2-cyclopenten-1-one into a compound of the formula (X)

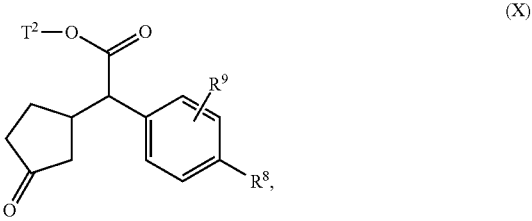
(X)

in which $R^8$, $R^9$ and $T^2$ have the meanings given above,
then fluorinating this compound with 1,1'-[(trifluoro-$\lambda^4$-sulphanyl)imino]bis(2-methoxyethane) under boron trifluoride catalysis to give a compound of the formula (VII-A)

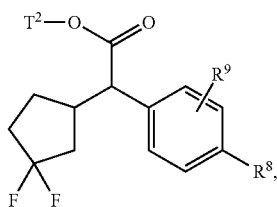

(VII-A)

in which $R^8$, $R^9$ and $T^2$ have the meanings given above,
and subsequently removing the ester group $T^2$ again giving the carboxylic acid (II-A).

In process step (VIII)→(X), for deprotonating the ester (VIII), preference is given to using an amide base such as lithium diisopropylamide or lithium bis(trimethylsilyl)amide. For the deoxyfluorination in the transformation (X)→(VII-A), instead of the 1,1'-[(trifluoro-λ$^4$-sulphanyl)-imino]bis(2-methoxyethane) ("Desoxofluor") mentioned above, it is also possible, if appropriate, to employ other known fluorinating agents, such as diethylaminosulphur trifluoride (DAST) or morpholinosulphur trifluoride (morpho-DAST) [for the reaction sequence (VIII)→(X)→(VII-A), cf., for example, T. Mase et al., *J. Org. Chem.* 66 (20), 6775-6786 (2001)].

Depending on the nature of the radical $R^2$, the intermediates of the formula (III) can be prepared, for example, by alkylating a carboxylic ester of the formula (XI)

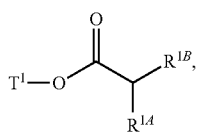

(XI)

in which $R^{1A}$, $R^{1B}$ and $T^1$ have the meanings given above,
in an inert solvent after α-deprotonation either
[C] with a 3-bromobenzyl compound of the formula (XII)

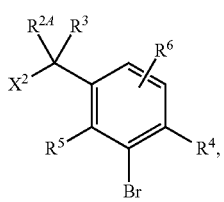

(XII)

in which $R^3$, $R^4$, $R^5$ and $R^6$ have the meanings given above, $R^{2A}$ represents hydrogen, methyl, ethyl or vinyl
and
$X^2$ represents a suitable leaving group such as chlorine, bromine, iodine, mesylate, triflate or tosylate,
to give a compound of the formula (XIII)

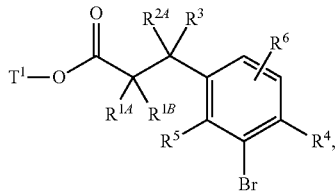

(XIII)

in which $R^{1A}$, $R^{1B}$, $R^{2A}$, $R^3$, $R^4$, $R^5$, $R^6$ and $T^1$ have the meanings given above, then reacting with benzylamine in the presence of a base and a palladium catalyst to give a compound of the formula (XIV)

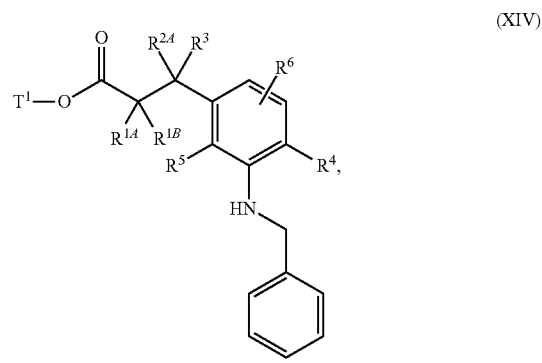

(XIV)

in which $R^{1A}$, $R^{1B}$, $R^{2A}$, $R^3$, $R^4$, $R^5$, $R^6$ and a $T^1$ have the meanings given above,
and then removing the N-benzyl group by hydrogenolysis giving a 3-aminophenyl derivative of the formula (III-A)

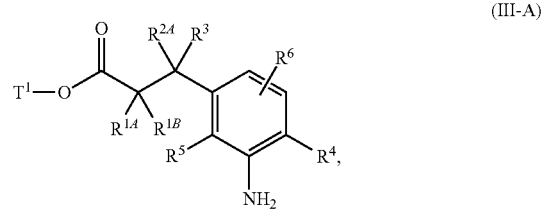

(III-A)

in which $R^{1A}$, $R^{1B}$, $R^{2A}$, $R^3$, $R^4$, $R^5$, $R^6$ and $T^1$ have the meanings given above,
or
[D] reacting with a 3-bromobenzoyl compound of the formula (XV)

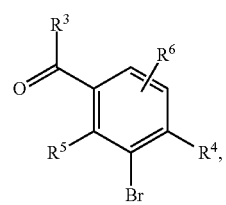

(XV)

in which $R^3$, $R^4$, $R^5$ and $R^6$ have the meanings given above, to give a compound of the formula (XVI)

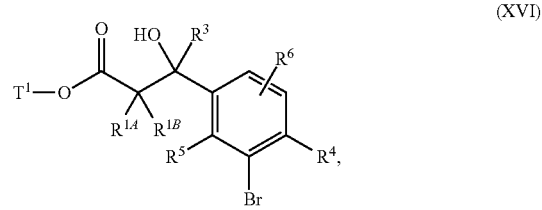

(XVI)

in which $R^{1A}$, $R^{1B}$, $R^3$, $R^4$, $R^5$, $R^6$ and $T^1$ have the meanings given above,
then, if desired, alkylating this with a compound of the formula (XVII)

$$R^{10}-X^3$$ (XVII)

in which
R$^{10}$ represents methyl, trideuteromethyl, trifluoromethyl, ethyl or cyclopropyl
and
X$^3$ represents a suitable leaving group such as chlorine, bromine, iodine, mesylate, triflate or tosylate
in the presence of a base to give a compound of the formula (XVIII)

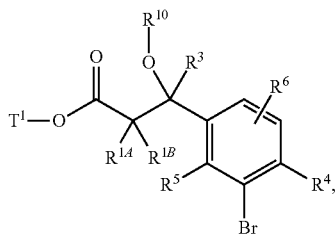

in which R$^{1A}$, R$^{1B}$, R$^3$, R$^4$, R$^5$, R$^6$, R$^{10}$ and T$^1$ have the meanings given above,
then converting the compound of the formula (XVI) or (XVIII) analogously to the reaction sequence described under [C] with benzylamine under palladium catalysis to give a compound of the formula (XIX)

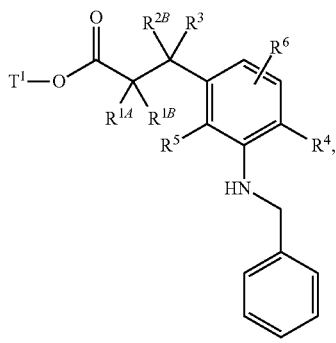

in which R$^{1A}$, R$^{1B}$, R$^3$, R$^4$, R$^5$, R$^6$ and T$^1$ have the meanings given above
and
R$^{2B}$ represents hydroxyl, methoxy, trideuteromethoxy, trifluoromethoxy, ethoxy or cyclopropyloxy,
and finally removing the N-benzyl group by hydrogenolysis, to give a 3-aminophenyl derivative of the formula (III-B)

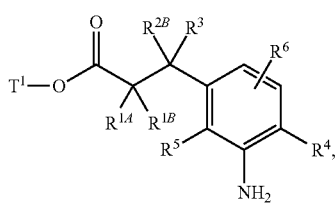

in which R$^{1A}$, R$^{1B}$, R$^{2B}$, R$^3$, R$^4$, R$^5$, R$^6$ and T$^1$ have the meanings given above.
Particularly suitable for the α-deprotonation of the carboxylic ester (XI) in the reactions (XI)+(XII)→(XIII) and (XI)+(XV)→(XVI) are non-nucleophilic strong bases such as, for example, sodium tert-butoxide or potassium tert-butoxide, sodium hydride or potassium hydride, lithium diisopropylamide or lithium bis(trimethylsilyl)amide, sodium bis(trimethylsilyl)amide or potassium bis(trimethylsilyl)amide; preference is given to using lithium diisopropylamide. Preferred inert solvents for these reactions are ethers such as diethyl ether, diisopropyl ether, methyl tert-butyl ether, tetrahydrofuran, glycol dimethyl ether or diethylene glycol dimethyl ether. The reactions are usually carried out in a temperature range of from −80° C. to +25° C.

For the transformations (XIII)→(XIV) and (XVI) or (XVIII)→(XIX) [Buchwald-Hartwig coupling with benzylamine], the preferred catalyst is tris(dibenzylideneacetone) dipalladium(0) in combination with (±)-2,2'-bis(diphenylphosphino)-1,1'-binaphthyl as phosphine ligand, and the preferred base is sodium tert-butoxide or potassium tert-butoxide [cf., for example, J. P. Wolfe and S. L. Buchwald, *Organic Syntheses*, Coll. Vol. 10, 423 (2004), Vol. 78, 23 (2002)].

The hydrogenolytic removal of the N-benzyl group in the process steps (XIV)→(III-A) and (XIX)→(III-B) is generally carried out under a stationary hydrogen atmosphere at atmospheric pressure. Here, the catalyst used is preferably palladium on activated carbon (as support material).

Suitable bases for the alkylation reaction (XVI)+(XVII)→(XVIII) are likewise customary strong non-nucleophilic bases such as sodium tert-butoxide or potassium tert-butoxide, sodium hydride or potassium hydride, lithium bis(trimethylsilyl)amide, sodium bis(trimethylsilyl)amide or potassium bis(trimethylsilyl)amide or lithium diisopropylamide; here, preference is given to using sodium hydride. Inert solvents suitable for this reaction are in particular ethers, such as diethyl ether, diisopropyl ether, methyl tert-butyl ether, tetrahydrofuran, glycol dimethyl ether or diethylene glycol dimethyl ether, or dipolar aprotic solvents, such as N,N-dimethylformamide (DMF), dimethyl sulphoxide (DMSO), N-methylpyrrolidinone (NMP) or N,N'-dimethylpropyleneurea (DMPU); preference is given to using N,N-dimethylformamide. The reaction is generally carried out in a temperature range of from −20° C. to +40° C.

The reactions described above can be carried out at atmospheric pressure, at elevated pressure or at reduced pressure (for example in the range of from 0.5 to 5 bar); in general, they are in each case carried out at atmospheric pressure.

Separation of the compounds according to the invention into the corresponding enantiomers and/or diastereomers can take place where appropriate, depending on expediency, even at the stage of the compounds (II), (III), (IV), (VII), (XIII), (XIV), (XVI), (XVIII) or (XIX), which are then reacted further in separated form in accordance with the above-described process sequences. Such a separation of the stereoisomers can be carried out by conventional methods known to the person skilled in the art. Preference is given to using chromatographic methods on achiral or chiral separation phases; in the case of carboxylic acids as intermediates or end products, separation may alternatively also be via diastereomeric salts.

The compounds of the formulae (V), (VI), (VIII), (IX), (XI), (XII), (XV) and (XVII) are either commercially available or described as such in the literature, or they can be prepared in a manner obvious to the person skilled in the art analogously to the methods published in the literature. Numerous detailed procedures and literature references for preparing the starting materials can also be found in the Experimental Part in the section on the preparation of the starting materials and intermediates.

The preparation of the compounds according to the invention can be illustrated in an exemplary manner by the reaction schemes below:
Scheme 1
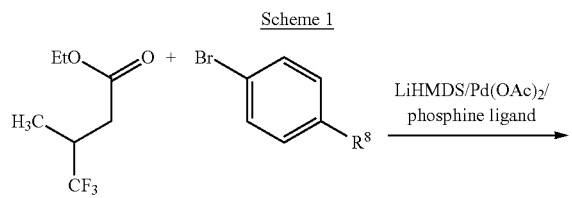
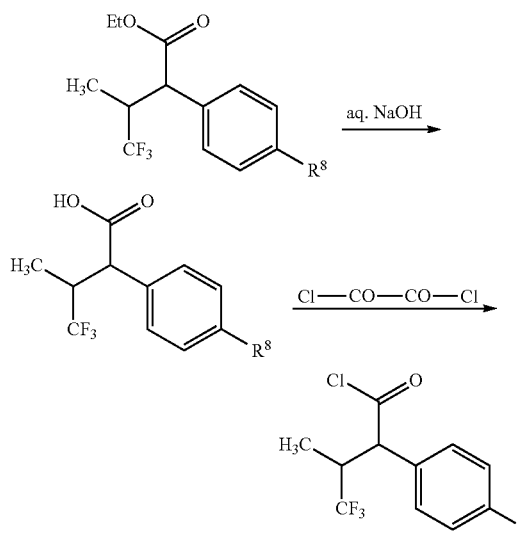
Scheme 2
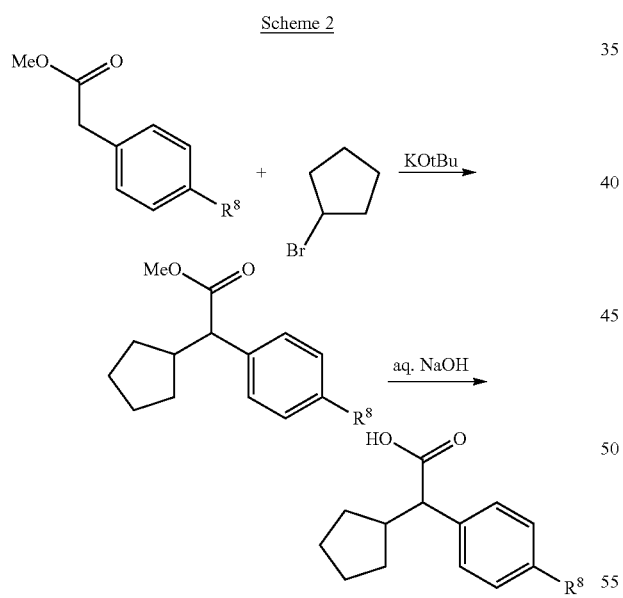
Scheme 3
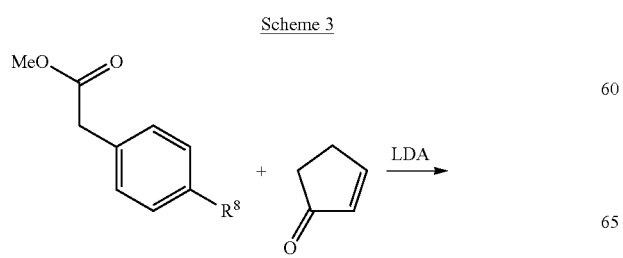
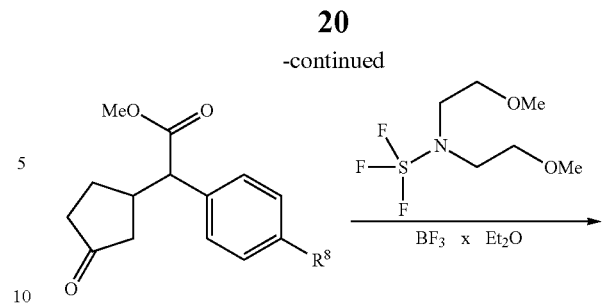
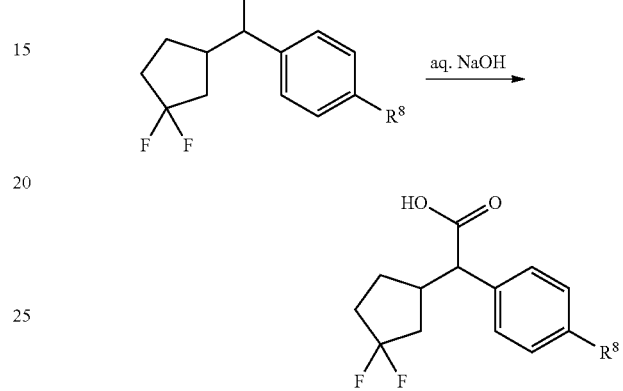
Scheme 4
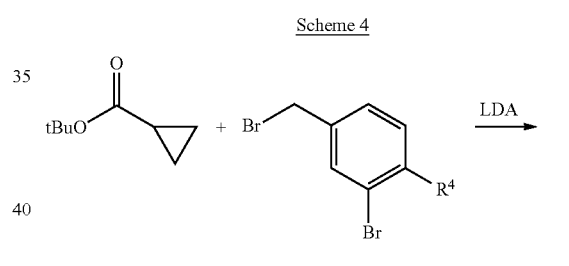
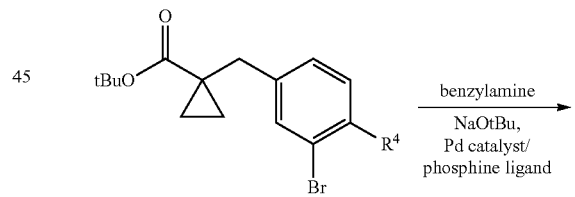
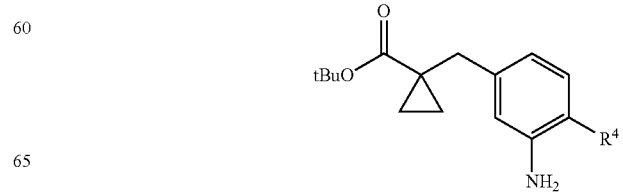

Scheme 5

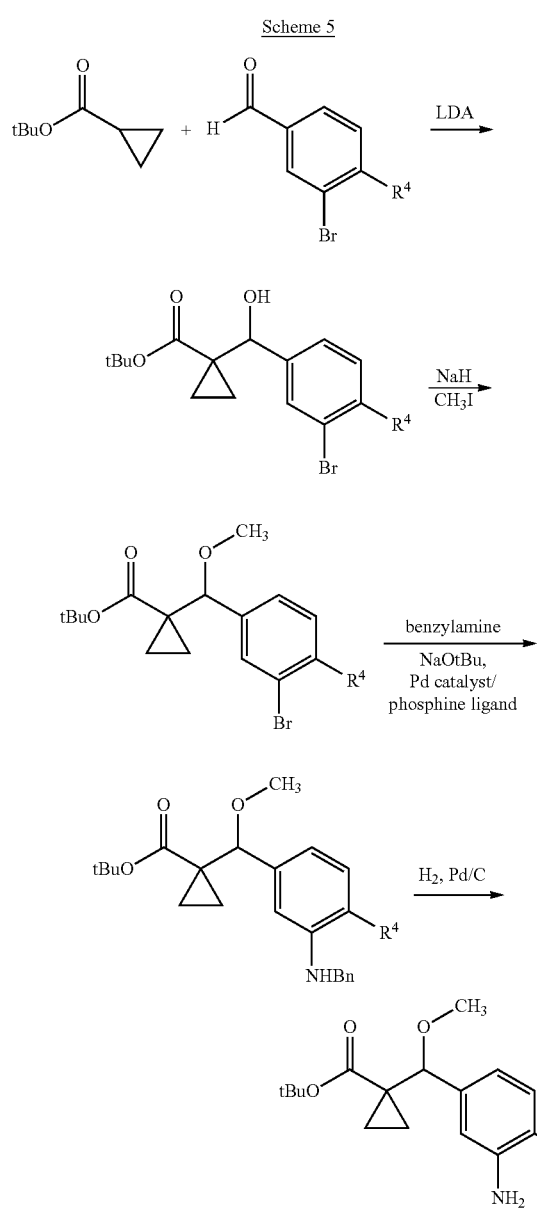

Scheme 6

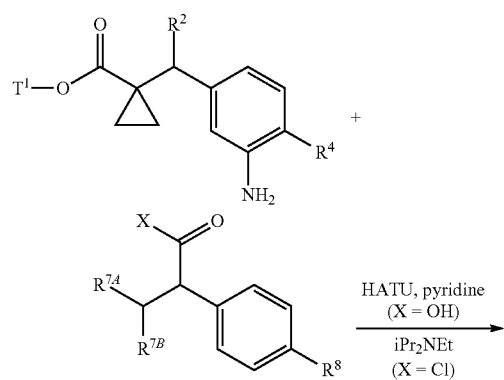

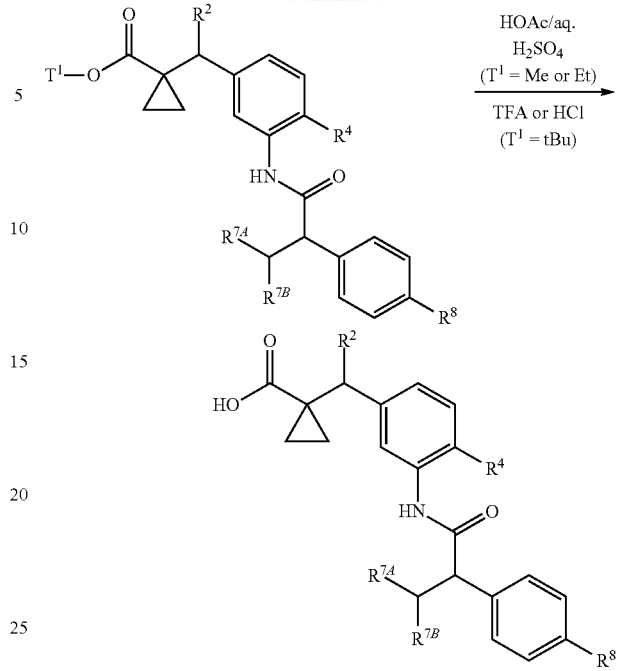

The compounds according to the invention have valuable pharmacological properties and can be used for the prevention and treatment of disorders in humans and animals.

The compounds according to the invention are potent activators of soluble guanylate cyclase. They lead to vasorelaxation, inhibition of platelet aggregation and lowering of blood pressure and increase of coronary blood flow. These effects are mediated via direct haem-independent activation of soluble guanylate cyclase and an increase of intracellular cGMP.

In addition, the compounds according to the invention have good pharmacokinetic properties, in particular with respect to their bioavailability and/or duration of action after intravenous or oral administration.

The compounds according to the invention are particularly suitable for the treatment and/or prevention of cardiovascular, pulmonary, thromboembolic and fibrotic disorders.

Accordingly, the compounds according to the invention can be used in medicaments for the treatment and/or prevention of cardiovascular disorders such as, for example, high blood pressure (hypertension), heart failure, coronary heart disease, stable and unstable angina pectoris, pulmonary arterial hypertension (PAH) and other forms of pulmonary hypertension (PH), renal hypertension, peripheral and cardiovascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prevention of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, microvascular and macrovascular damage (vasculitis), to prevent restenoses, for example after thrombolysis therapies, percutaneous transluminal angioplasties (PTA), transluminal coronary angioplasties (PTCA), heart transplants and bypass operations, and also for the treatment and/or prevention of arteriosclerosis.

In the context of the present invention, the term heart failure also includes more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

Furthermore, the compounds according to the invention can be used for the treatment and/or prevention of primary and secondary Raynaud's phenomenon, of microcirculation impairments, claudication, tinnitus, peripheral and autonomic neuropathies, diabetic microangiopathies, diabetic retinopathy, diabetic ulcers on the extremities, gangrene, CREST syndrome, erythematosis, onychomycosis and rheumatic disorders.

In addition, the compounds according to the invention can be used for preventing ischaemia- and/or reperfusion-related damage to organs or tissues and also as additives for perfusion and preservation solutions of organs, organ parts, tissues or tissue parts of human or animal origin, in particular for surgical interventions or in the field of transplantation medicine.

The compounds according to the invention are furthermore suitable for the treatment and/or prevention of kidney disorders, in particular of renal insufficiency and renal failure. In the context of the present invention, the terms renal insufficiency and renal failure comprise both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminurea, macroalbuminurea, lesions on glomerulae and arterioles, tubular dilatation, hyperphosphataemia and/or need for dialysis. The present invention also comprises the use of the compounds according to the invention for the treatment and/or prevention of sequelae of renal insufficiency, such as, for example hypertension, pulmonary oedema, heart failure, uraemia, anaemia, electrolyte disturbances (for example hypercalaemia, hyponatraemia) and disturbances in bone and carbohydrate metabolism.

In addition, the compounds according to the invention are suitable for the treatment and/or prevention of disorders of the urogenital system such as, for example, hyperactive bladder, disturbance of micturition, lower urinary tract syndrome (LUTS), incontinence, benign prostate hyperplasia (BPH), erectile dysfunction and female sexual dysfunction.

The compounds according to the invention are also suitable for the treatment and/or prevention of asthmatic disorders, chronic-obstructive pulmonary disease (COPD), acute respiratory distress syndrome (ARDS) and acute lung injury (ALI), alpha-1-antitrypsin deficiency (AATD), pulmonary fibrosis, pulmonary emphysema (for example pulmonary emphysema induced by cigarette smoke) and cystic fibrosis (CF), and also of pulmonary arterial hypertension (PAH) and other forms of pulmonary hypertension (PH) including left-heart disease, HIV, sickle cell anaemia, thromboembolisms, sarcoidosis, COPD or pulmonary fibrosis-associated pulmonary hypertension.

The compounds described in the present invention also represent active compounds for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jakob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention are furthermore also suitable for controlling cerebral blood flow and thus represent effective agents for controlling migraine. They are also suitable for the prophylaxis and control of the sequelae of cerebral infarctions (Apoplexia cerebri) such as stroke, cerebral ischaemias and craniocerebral trauma. The compounds according to the invention can likewise be employed for controlling states of pain.

In addition, the compounds according to the invention have antiinflammatory action and can therefore be used as antiinflammatory agents for the treatment and/or prevention of sepsis, multiple organ failure, inflammatory disorders of the kidney, rheumatoid disorders, inflammatory skin diseases and inflammatory eye diseases.

The compounds according to the invention are furthermore suitable for the treatment and/or prevention of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring, naevi, diabetic retinopathy, proliferative vitreoretinopathy and disorders of the connective tissue (for example sarcoidosis). The compounds according to the invention can also be used to promote wound healing, for controlling postoperative scarring, for example as a result of glaucoma operations, and cosmetically for ageing and keratinized skin.

By virtue of their activity profile, the compounds according to the invention are particularly suitable for the treatment and/or prevention of cardiovascular disorders such as heart failure, angina pectoris, hypertension and pulmonary hypertension, and also of thromboembolic disorders and ischaemias, vascular disorders, disturbances of microcirculation, renal insufficiency, fibrotic disorders and arteriosclerosis.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to the use of the compounds according to the invention in a method for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prevention of the aforementioned disorders. Preferred examples of suitable active compound combinations include:
organic nitrates and NO donors, for example sodium nitroprusside, nitroglycerin, isosorbide mononitrate, isosorbide dinitrate, molsidomine or SIN-1, and inhaled NO;
compounds which inhibit the breakdown of cyclic guanosine monophosphate (cGMP), such as, for example, inhibitors of phosphodiesterases (PDE) 1, 2 and/or 5, in particular PDE 5 inhibitors such as sildenafil, vardenafil and tadalafil;
NO-independent, but haem-dependent stimulators of guanylate cyclase, such as, in particular, riociguat and the compounds described in WO 00/06568, WO 00/06569, WO 02/42301 and WO 03/095451;
agents having an antithrombotic effect, for example and with preference from the group of platelet aggregation inhibitors, of anticoagulants or of profibrinolytic substances;
active compounds which lower blood pressure, for example and preferably from the group of calcium antagonists, angiotensin AII antagonists, ACE inhibitors, endothelin antagonists, renin inhibitors, alpha-receptor blockers, beta-receptor blockers, mineralocorticoid receptor antagonists, and of diuretics; and/or
active compounds which alter lipid metabolism, for example and with preference from the group of thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Agents having antithrombotic activity preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as, by way of example and preferably, aspirin, clopidogrel, ticlopidin or dipyridamol.

In a preferred embodiment of the invention, the compounds according to the invention are administered in combination with a thrombin inhibitor such as, by way of example and preferably, ximelagatran, melagatran, dabigatran, bivalirudin or clexane.

In a preferred embodiment of the invention, the compounds according to the invention are administered in combination with a GPIIb/IIIa antagonist such as, by way of example and preferably, tirofiban or abciximab.

In a preferred embodiment of the invention, the compounds according to the invention are administered in combination with a factor Xa inhibitor such as, by way of example and preferably, rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as, by way of example and preferably, coumarin.

Agents which lower blood pressure are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist such as, by way of example and preferably, nifedipine, amlodipine, verapamil or diltiazem.

In a preferred embodiment of the invention, the compounds according to the invention are administered in combination with an alpha-1 receptor blocker such as, by way of example and preferably, prazosin.

In a preferred embodiment of the invention, the compounds according to the invention are administered in combination with a beta receptor blocker such as, by way of example and preferably, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as, by way of example and preferably, losartan, candesartan, valsartan, telmisartan or embusartan.

In a preferred embodiment of the invention, the compounds according to the invention are administered in combination with an ACE inhibitor such as, by way of example and preferably, enalapril, captopril, lisinopril, ramipril, delapril, fosinopril, quinopril, perindopril or trandopril.

In a preferred embodiment of the invention, the compounds according to the invention are administered in combination with an endothelin antagonist such as, by way of example and preferably, bosentan, darusentan, ambrisentan or sitaxsentan.

In a preferred embodiment of the invention, the compounds according to the invention are administered in combination with a renin inhibitor such as, for example and preferably, aliskiren, SPP-600 or SPP-800.

In a preferred embodiment of the invention, the compounds according to the invention are administered in combination with a mineralocorticoid receptor antagonist such as, for example and preferably, spironolactone or eplerenone.

In a preferred embodiment of the invention, the compounds according to the invention are administered in combination with a diuretic, such as, for example and preferably, furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Active compounds which alter lipid metabolism are preferably understood to mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein (a) antagonists.

In a preferred embodiment of the invention, the compounds according to the invention are administered in combination with a CETP inhibitor such as, by way of example and preferably, torcetrapib (CP-529 414), JTT-705 or CETP vaccine (Avant).

In a preferred embodiment of the invention, the compounds according to the invention are administered in combination with a thyroid receptor agonist such as, by way of example and preferably, D-thyroxin, 3,5,3'-triiodothyronin (T3), CGS 23425 or axitirome (CGS 26214).

In a preferred embodiment of the invention, the compounds according to the invention are administered in combination with an HMG-CoA reductase inhibitor from the class of the statins such as, by way of example and preferably, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor such as, by way of example and preferably, BMS-188494 or TAK-475.

In a preferred embodiment of the invention, the compounds according to the invention are administered in combination with an ACAT inhibitor such as, by way of example and preferably, avasimibe, melinamide, pactimibe, eflucimibe or SMP-797.

In a preferred embodiment of the invention, the compounds according to the invention are administered in combination with an MTP inhibitor such as, by way of example and preferably, implitapide, BMS-201038, R-103757 or JTT-130.

In a preferred embodiment of the invention, the compounds according to the invention are administered in combination with a PPAR-gamma agonist such as, by way of example and preferably, pioglitazone or rosiglitazone.

In a preferred embodiment of the invention, the compounds according to the invention are administered in combination with a PPAR-delta agonist such as, for example and preferably, GW 501516 or BAY 68-5042.

In a preferred embodiment of the invention, the compounds according to the invention are administered in combination with a cholesterol absorption inhibitor such as, by way of example and preferably, ezetimibe, tiqueside or pamaqueside.

In a preferred embodiment of the invention, the compounds according to the invention are administered in combination with a lipase inhibitor such as, by way of example and preferably, orlistat.

In a preferred embodiment of the invention, the compounds according to the invention are administered in combination with a polymeric bile acid adsorbent such as, by way of example and preferably, cholestyramine, colestipol, colesolvam, CholestaGel or colestimide.

In a preferred embodiment of the invention, the compounds according to the invention are administered in combination with a bile acid reabsorption inhibitor such as, by way of example and preferably, ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein (a) antagonist such as, by way of example and preferably, gemcabene calcium (CI-1027) or nicotinic acid.

The present invention further provides medicaments which comprise at least one compound according to the invention, typically together with one or more inert, nontoxic, pharmaceutically suitable auxiliaries, and the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral or parenteral administration is preferred, especially oral and intravenous administration.

The compounds according to the invention can be converted to the administration forms mentioned. This can be done in a manner known per se, by mixing with inert, non-toxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration data for liquid/liquid solutions are based in each case on volume.

EXAMPLES

A. Synthesis

Abbreviations and Acronyms:
abs. absolute
Ac acetyl
AIBN 2,2'-azobis-(2-methylpropionitrile)
aq. aqueous, aqueous solution
ATP adenosine 5'-triphosphate
Bn benzyl
Brij® polyethylene glycol dodecyl ether
BSA bovine serum albumin
Ex. example
Bu butyl
c concentration
cat. catalytic
CI chemical ionization (in MS)
d day(s)
DAST diethylaminosulphur trifluoride
DC thin-layer chromatography
DCI direct chemical ionization (in MS)
DDQ 2,3-dichloro-5,6-dicyano-1,4-benzoquinone
de diastereomeric excess
DMF dimethylformamide
DMSO dimethyl sulphoxide
DTT dithiothreitol
EDC N'-(3-dimethylaminopropyl)-N-ethylcarbodiimide hydrochloride
ee enantiomeric excess
EI electron impact ionization (in MS)
ent enantiomerically pure, enantiomer
eq. equivalent(s)
ESI electrospray ionization (in MS)
Et ethyl
GC gas chromatography
sat. saturated
GTP guanosine 5'-triphosphate
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high pressure, high performance liquid chromatography
iPr isopropyl
conc. concentrated
LC-MS liquid chromatography-coupled mass spectroscopy
LDA lithium diisopropylamide
LiHMDS lithium hexamethyldisilazide[lithium bis(trimethylsilyl)amide]
Me methyl
min minute(s)
MS mass spectroscopy
NBS N-bromosuccinimide
NMP N-methylpyrrolidin-2-one
NMR nuclear magnetic resonance spectroscopy
p para
Pd/C palladium on activated carbon
Ph phenyl
PMB p-methoxybenzyl
Pr propyl
rac racemic, racemate
$R_f$ retention index (in TLC)
RP reverse phase (in HPLC)
RT room temperature
$R_t$ retention time (in HPLC or GC)
tBu tert-butyl
TEA triethanolamine
TFA trifluoroacetic acid
THF tetrahydrofuran
UV ultraviolet spectroscopy
v/v ratio by volume (of a solution)
GC-MS and LC-MS Methods:
Method 1 (GC-MS):
Instrument: Micromass GCT, GC 6890; column: Restek RTX-35, 15 m×200 µm×0.33 µm; constant helium flow: 0.88 ml/min; oven: 70° C.; inlet: 250° C.; gradient: 70° C., 30° C./min→310° C. (maintained for 3 min)
Method 2 (LC-MS):
MS instrument type: Waters Micromass Quattro Micro; HPLC instrument type: Agilent 1100 Series; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
Method 3 (LC-MS):
MS instrument type: Micromass ZQ; HPLC instrument type: HP 1100 Series; UV DAD; column: Phenomenex Gemini 3μ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 4 (LC-MS):
Instrument: Micromass Quattro Premier with Waters HPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.
Method 5 (LC-MS):
Instrument: Waters Acquity SQD HPLC System; column: Waters Acquity HPLC HSS T3 1.8μ, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.
Method 6 (GC-MS):
Instrument: Thermo DFS, Trace GC Ultra; column: Restek RTX-35, 15 m×200 μm×0.33 μm; constant helium flow: 1.20 ml/min; oven: 60° C.; inlet: 220° C.; gradient: 60° C., 30° C./min→300° C. (maintained for 3.33 min)
Method 7 (LC-MS):
Instrument: Waters Acquity SQD HPLC System; column: Waters Acquity HPLC HSS T3 1.8μ, 30 mm×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.60 ml/min; oven: 50° C.; UV detection: 208-400 nm.

Starting Materials and Intermediates

Example 1A tert-Butyl 1-(3-bromobenzyl)cyclopropanecarboxylate

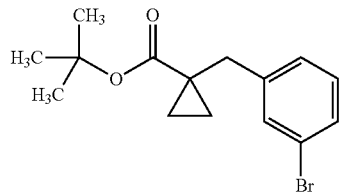 [SMILES: CC(C)(C)OC(=O)C1(Cc2cccc(Br)c2)CC1]

Under argon, 14.8 ml (105.48 mmol) of diisopropylamine were initially charged in 66 ml of dry THF, and the mixture was cooled to –40° C. 42.2 ml (105.48 mmol) of n-butyllithium solution (2.5 M in hexane) were slowly added dropwise and the mixture was stirred for 30 min. The reaction solution was then cooled to –78° C., and a solution of 10.0 g (70.32 mmol) of tert-butyl cyclopropanecarboxylate in 17 ml of THF was added. After 4 h of stirring at –78° C., a solution of 19.34 g (77.36 mmol) of 3-bromobenzyl bromide in 17 ml THF was added. The reaction mixture was slowly warmed to RT overnight, and aqueous ammonium chloride solution was then added carefully and the mixture was extracted three times with ethyl acetate. The combined organic phases were washed with saturated sodium chloride solution, dried over magnesium sulphate and concentrated under reduced pressure. The crude product was purified by chromatography on 750 g of silica gel (mobile phase cyclohexane/dichloromethane 50:1, then 5:1). This gave 13.3 g (60.7% of theory) of the title compound.

GC-MS (Method 1): $R_t$=5.94 min; m/z=256 (M–$C_4H_8$)$^+$.

$^1$H-NMR (400 MHz, DMSO-$d_6$): δ [ppm]=7.46 (s, 1H), 7.38 (m, 1H), 7.25 (m, 2H), 2.82 (s, 2H), 1.28 (s, 9H), 1.08 (q, 2H), 0.87 (q, 2H).

Example 2A tert-Butyl 1-(3-bromo-4-fluorobenzyl)cyclopropanecarboxylate

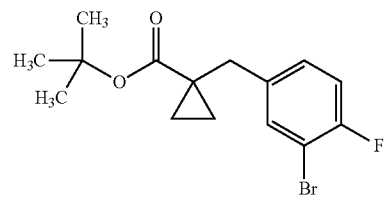 [SMILES: CC(C)(C)OC(=O)C1(Cc2ccc(F)c(Br)c2)CC1]

Under argon, 199.5 ml (1.42 mol) of diisopropylamine were initially charged in 1300 ml of dry THF, and the mixture was cooled to –50° C. 569.1 ml (1.42 mol) of n-butyllithium solution (2.5 M in hexane) were slowly added dropwise. The resulting mixture was warmed to 0° C. and then cooled to –70° C. A solution of 161.9 g (1.14 mol) of tert-butyl cyclopropanecarboxylate in 380 ml of THF was added to the reaction solution, and during the addition the temperature was kept below –60° C. After 4 h of stirring at –78° C., a solution of 262 g (0.95 mol) of 2-bromo-4-(bromomethyl)-1-fluorobenzene in 480 ml of THF was added, and the temperature was once more kept below –60° C. The reaction mixture was slowly warmed to RT overnight, after which 1.5 liters of saturated aqueous ammonium chloride solution and 3.0 liters of ethyl acetate were added. After phase separation the aqueous phase was extracted with ethyl acetate. The combined organic phases were washed with saturated sodium chloride solution, dried over magnesium sulphate and concentrated under reduced pressure. The crude product was purified by chromatography on 3 kg of silica gel (mobile phase cyclohexane/dichloromethane 9:1, then 5:1). This gave 189.9 g (50.4% of theory) of the title compound.

$^1$H-NMR (400 MHz, DMSO-$d_6$): δ [ppm]=0.86-0.92 (m, 2H), 1.06-1.12 (m, 2H), 1.30 (s, 9H), 2.81 (s, 2H), 7.27-7.33 (m, 2H), 7.55-7.60 (m, 1H).

Example 3A tert-Butyl 1-[3-(benzylamino)benzyl]cyclopropanecarboxylate

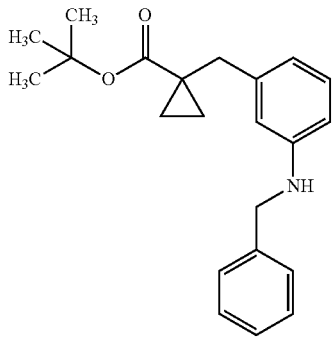 [SMILES: CC(C)(C)OC(=O)C1(Cc2cccc(NCc3ccccc3)c2)CC1]

Under argon and dry conditions, 13.3 g (42.73 mmol) of tert-butyl 1-(3-bromobenzyl)-cyclopropanecarboxylate, 5.6 ml (51.28 mmol) of benzylamine, 1.96 g (2.14 mmol) of tris(dibenzylideneacetone)dipalladium, 4.93 g (51.28 mmol) of sodium tert-butoxide and 1.06 g (1.71 mmol) of (+/−)-2, 2'-bis(diphenylphosphino)-1,1'-binaphthyl were suspended in 50 ml of toluene. The reaction mixture was then stirred at 110° C. for 1.5 h. The mixture was then filtered off with suction through kieselguhr, the residue was washed with toluene and the filtrate was concentrated. The filtrate residue was taken up in ethyl acetate and washed twice with aqueous ammonium chloride solution. The organic phase was dried over magnesium sulphate and concentrated under reduced pressure. The crude product was purified by chromatography on silica gel (mobile phase cyclohexane/ethyl acetate 20:1). This gave 6.98 g (48.4% of theory) of the title compound.

LC-MS (Method 2): $R_t$=2.75 min; m/z=338 (M+H)$^+$.

$^1$H-NMR (400 MHz, DMSO-d$_6$): δ [ppm]=7.35-7.26 (m, 4H), 7.20 (t, 1H), 6.91 (t, 1H), 6.45 (s, 1H), 6.38 (m, 2H), 6.12 (t, 1H), 4.23 (d, 2H), 2.69 (s, 2H), 1.28 (s, 9H), 0.99 (q, 2H), 0.69 (q, 2H).

Example 4A tert-Butyl 1-[3-(benzylamino)-4-fluorobenzyl]cyclopropanecarboxylate

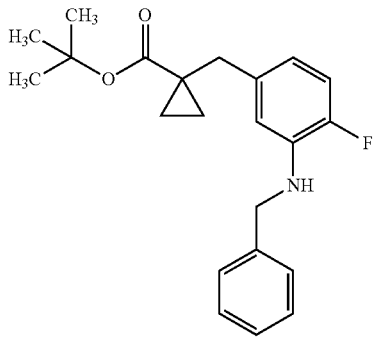 [SMILES: CC(C)(C)OC(=O)C1(Cc2ccc(F)c(NCc3ccccc3)c2)CC1]

Under argon and dry conditions, 174.0 g (528.5 mmol) of tert-butyl 1-(3-bromo-4-fluorobenzyl)cyclopropanecarboxylate, 69.2 ml (634.2 mmol) of benzylamine, 4.84 g (5.29 mmol) of tris(dibenzylideneacetone)dipalladium, 60.95 g (634.2 mmol) of sodium tert-butoxide and 3.29 g (5.29 mmol) of (+/−)-2,2'-bis(diphenylphosphino)-1,1'-binaphthyl were suspended in 1218 ml of toluene. The reaction mixture was then stirred at 110° C. for 2.0 h. After cooling, 2.1 liters of ethyl acetate and 1.7 liters of semisaturated aqueous ammonium chloride solution were added to the reaction mixture. After phase separation, the organic phase was washed with saturated ammonium chloride solution and saturated sodium chloride solution, dried over magnesium sulphate and concentrated under reduced pressure. The crude product was purified by chromatography on 3.7 kg of silica gel (mobile phase petroleum ether/ethyl acetate 20:1). This gave 145.0 g (68.7% of theory) of the title compound.

$^1$H-NMR (400 MHz, DMSO-d$_6$): δ [ppm]=0.51-0.66 (m, 2H), 0.86-0.99 (m, 2H), 1.25 (m, 9H), 2.65 (s, 2H), 4.30 (d, 2H), 6.07 (t, 1H), 6.29-6.54 (m, 2H), 6.88 (dd, 1H), 7.15-7.25 (m, 1H), 7.25-7.42 (m, 4H).

Example 5A tert-Butyl 1-(3-aminobenzyl)cyclopropanecarboxylate

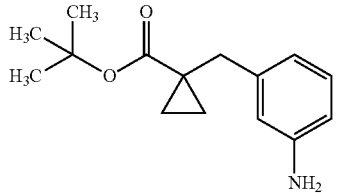

6.98 g (22.43 mmol) of tert-butyl 1-[3-(benzylamino)benzyl]cyclopropanecarboxylate were dissolved in 50 ml of ethanol and 50 ml THF, and 0.48 g (0.45 mmol) of palladium (10% on carbon) were added. At RT, the mixture was stirred under a hydrogen atmosphere at atmospheric pressure for 2 h. The reaction mixture was then filtered off with suction through kieselguhr, the residue was washed with THF and the filtrate was concentrated. The crude product was purified by chromatography on silica gel (mobile phase cyclohexane/ethyl acetate 10:1). This gave 3.66 g (65.9% of theory) of the title compound.

LC-MS (Method 3): $R_t$=1.84 min; m/z=192 (M+H)$^+$.

$^1$H-NMR (400 MHz, DMSO-d$_6$): δ [ppm]=6.88 (t, 1H), 6.42 (s, 1H), 6.37 (dd, 2H), 4.89 (d, 2H), 2.69 (s, 2H), 1.31 (s, 9H), 1.03 (q, 2H), 0.75 (q, 2H).

Example 6A tert-Butyl 1-(3-amino-4-fluorobenzyl)cyclopropanecarboxylate

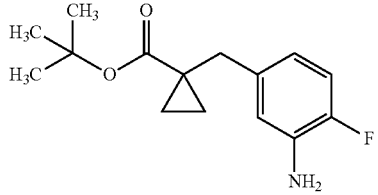

145.0 g (407.9 mmol) of tert-butyl 1-[3-(benzylamino)-4-fluorobenzyl]cyclopropanecarboxylate were dissolved in 1450 ml of ethanol, and 9.67 g of palladium hydroxide (20% on carbon) were added. At RT, the suspension was stirred under a hydrogen atmosphere at atmospheric pressure for 18 h. The reaction mixture was then filtered off with suction through kieselguhr and the filtrate was concentrated. After drying under high vacuum, 500 ml of pentane were added to the residue, whereupon the product precipitated as a solid. The suspension was stirred in an ice bath for 1 h. The solid was then filtered off with suction, washed twice with a little pentane and dried under high vacuum. This gave 88.5 g (73.6% of theory) of the title compound.

$^1$H-NMR (400 MHz, DMSO-$d_6$): δ [ppm]=0.70-0.80 (m, 2H), 1.00-1.10 (m, 2H), 1.30 (s, 9H), 2.68 (s, 2H), 4.98 (s, 2H), 6.28-6.45 (m, 1H), 6.63 (dd, 1H), 6.84 (dd, 1H).

General Procedure 1: Preparation of Benzyl Alcohols from Benzoic Acids

At RT, 1.3 eq. of triethylamine and then 1.2 eq. of methyl chloroformate were added to a 0.5 M solution of the benzoic acid in question in toluene. The mixture was stirred at RT overnight. The suspension formed was then filtered through Celite and the residue was washed with toluene. The filtrate was concentrated, and the filtrate residue was dissolved in THF (1.5 ml/mmol) and then added dropwise to a suspension, cooled to −78° C., of 1.2 eq. of lithium aluminium hydride in THF (1 ml/mmol). After 1.5 h at −78° C., the reaction mixture was warmed to RT, and stirring was continued overnight. The suspension formed was poured into 5% strength aqueous sodium hydroxide solution (5 ml/mmol), the mixture was filtered through Celite and the residue was washed with ethyl acetate. The filtrate was extracted repeatedly with ethyl acetate. The combined organic phases were washed with saturated sodium chloride solution, dried over magnesium sulphate and concentrated under reduced pressure.

According to this procedure, the two compounds below were prepared from the corresponding benzoic acids:

| Example | Name/Structure | Analytical data |
|---|---|---|
| 7A | (3-bromo-5-fluorophenyl)methanol | LC-MS (Method 4): $R_t$ = 0.96 min; m/z = 187 [M − H$_2$O]$^+$. |
| 8A | (3-bromo-2-fluorophenyl)methanol | LC-MS (Method 5): $R_t$ = 0.81 min; m/z = 187 [M − H$_2$O]$^+$. $^1$H-NMR (400 MHz, DMSO-$d_6$): δ [ppm] = 7.54-7.66 (m, 1H), 7.47 (t, 1H), 7.16 (t, 1H), 5.39 (t, 1H), 4.56 (d, 2H). |

General Procedure 2: Preparation of Benzyl Bromides from Benzyl Alcohols

Method 2A: The benzyl alcohol in question was initially charged in DMF (2 ml/mmol), and 2 eq. of carbon tetrabromide were added. Over a period of 30 min, 2 eq. of triphenylphosphine were then added a little at a time, and the mixture was stirred at RT overnight. The reaction mixture was then poured into water and extracted with tert-butyl methyl ether. The organic phases were dried over magnesium sulphate and concentrated. The crude product was then purified by flash chromatography on silica gel (mobile phase cyclohexane).

Method 2B: The benzyl alcohol in question was initially charged in dichloromethane (2 ml/mmol), 1.2 eq. of triphenylphosphine dibromide were added and the mixture was stirred at RT overnight. The reaction mixture was then washed with water, and the organic phase was dried over magnesium sulphate and concentrated. The crude product was purified by flash chromatography on silica gel (mobile phase cyclohexane).

The compounds below were prepared according to these methods:

| Example | Name/Structure | Method | Analytical data |
|---|---|---|---|
| 9A | 1-bromo-3-(bromomethyl)-5-fluorobenzene | 2A | LC-MS (Method 5): $R_t$ = 1.17 min; m/z = 289 [M + NH$_4$]$^+$. |
| 10A | 1-bromo-3-(bromomethyl)-2-fluorobenzene | 2B | GC-MS (Method 1): $R_t$ = 4.32 min; m/z = 268 [M]$^+$. $^1$H-NMR (400 MHz, DMSO-$d_6$): δ [ppm] = 7.66-7.78 (m, 1H), 7.49-7.63 (m, 1H), 7.18 (t, 1H), 4.73 (s, 2H). |
| 11A | 2-bromo-4-(bromomethyl)-1-methylbenzene [from (3-bromo-4-methylphenyl)methanol (CAS Reg.-No. 68120-35-4)] | 2B | GC-MS (Method 1): $R_t$ = 4.93 min; m/z = 263 [M]$^+$. |

General Procedure 3: Alkylation of Ester Enolates with Benzyl Bromides

Under argon, a 0.3 M solution of diisopropylamine in THF was cooled to −40° C., and 1 eq. of n-butyllithium (as a solution in hexane) was added. After 30 min, the solution was cooled to −78° C. and 0.8 eq. of a solution of the carboxylic ester in question in THF (0.7 M) was added. The reaction mixture was stirred at −78° C. for 4 h, and 0.75 eq. of the benzyl bromide in THF (0.6 M) was then added. The reaction mixture was stirred overnight, warming to RT. Saturated aqueous ammonium chloride solution was then added. The mixture was extracted with ethyl acetate, and the organic phase was dried over magnesium sulphate and concentrated. The crude product obtained in this manner was purified by flash chromatography on silica gel (typical mobile phase mixture: cyclohexane/ethyl acetate 15:1→10:1).

The following compounds were prepared according to General Procedure 3:

| Example | Name/Structure | Analytical data |
|---|---|---|
| 12A | tert-butyl 1-(3-bromo-5-fluorobenzyl)-cyclopropanecarboxylate | GC-MS (Method 1): $R_t$ = 5.64 min; m/z = 272/274 $[M - C_4H_9]^+$. <br> $^1$H-NMR (400 MHz, DMSO-$d_6$): δ [ppm] = 7.37 (dd, 1H), 7.33 (s, 1H), 7.13 (d, 1H), 2.84 (s, 2H), 1.25-1.32 (m, 9H), 1.06-1.14 (m, 2H), 0.89-0.93 (m, 2H). |
| 13A | tert-butyl 1-(3-bromo-2-fluorobenzyl)-cyclopropanecarboxylate | $^1$H-NMR (400 MHz, DMSO-$d_6$): δ [ppm] = 7.50-7.59 (m, 1H), 7.39 (t, 1H), 7.11 (t, 1H), 2.91 (s, 2H), 1.22-1.29 (m, 9H), 1.10-1.16 (m, 2H), 0.84-0.91 (m, 2H). |
| 14A | tert-butyl 1-(3-bromo-4-methylbenzyl)-cyclopropanecarboxylate | LC-MS (Method 2): $R_t$ = 3.02 min; m/z = 325/327 $[M + H]^+$. |

General Procedure 4: Buchwald-Hartwig Reaction of Phenyl Bromides to N-benzylphenylamines Under an atmosphere of argon, 1.2 eq. of sodium tert-butoxide were suspended in toluene (1.5 ml/mmol), 1 eq. of the phenyl bromide in question, 1.2 eq. of benzylamine, 0.05 eq. of tris(dibenzylideneacetone)dipalladium and 0.04 eq. of rac-2,2'-bis(diphenylphosphino)-1,1'-binaphthyl were added and the mixture was then heated at 110° C. for 2 h. After cooling to RT, saturated aqueous ammonium chloride solution and ethyl acetate were added and the mixture was filtered through Celite. The organic phase was washed in each case once with saturated ammonium chloride solution and saturated sodium chloride solution, then dried over magnesium sulphate and concentrated. The crude product obtained in this manner was purified by flash chromatography on silica gel (typical mobile phase mixture: cyclohexane/ethyl acetate 50:1).

The following compounds were prepared according to General Procedure 4:

| Example | Name/Structure | Analytical data |
|---|---|---|
| 15A | tert-butyl 1-[3-(benzylamino)-5-fluorobenzyl]-cyclopropanecarboxylate | LC-MS (Method 4): $R_t$ = 1.60 min; m/z = 356 $[M + H]^+$. <br> $^1$H-NMR (400 MHz, DMSO-$d_6$): δ [ppm] = 7.28-7.37 (m, 4H), 7.16-7.28 (m, 1H), 6.50 (t, 1H), 6.31 (s, 1H), 6.04-6.20 (m, 2H), 4.23 (d, 2H), 2.68 (s, 2H), 1.22-1.32 (m, 9H), 0.97-1.06 (m, 2H), 0.67-0.79 (m, 2H). |

-continued

| Example | Name/Structure | Analytical data |
|---|---|---|
| 16A | tert-butyl 1-[3-(benzylamino)-4-fluorobenzyl]-cyclopropanecarboxylate | LC-MS (Method 4): $R_t$ = 1.63 min; m/z = 356 [M + H]$^+$. $^1$H-NMR (400 MHz, DMSO-$d_6$): δ [ppm] = 7.27-7.39 (m, 4H), 7.22 (d, 1H), 6.88 (dd, 1H), 6.43 (dd, 1H), 6.31-6.38 (m, 1H), 6.02-6.13 (m, 1H), 4.30 (d, 2H), 2.64 (s, 2H), 1.25 (s, 9H), 0.89-0.96 (m, 2H), 0.55-0.63 (m, 2H). |
| 17A | tert-butyl 1-[3-(benzylamino)-2-fluorobenzyl]-cyclopropanecarboxylate | LC-MS (Method 4): $R_t$ = 1.66 min; m/z = 356 [M + H]$^+$. $^1$H-NMR (400 MHz, DMSO-$d_6$): δ [ppm] = 7.25-7.41 (m, 4H), 7.13-7.25 (m, 1H), 6.75 (t, 1H), 6.48 (t, 1H), 6.39 (t, 1H), 6.02-6.16 (m, 1H), 4.32 (d, 2H), 2.85 (s, 2H), 1.29 (s, 9H), 1.03-1.12 (m, 2H), 0.70-0.83 (m, 2H). |
| 18A | tert-butyl 1-[3-(benzylamino)-4-methylbenzyl]-cyclopropanecarboxylate | LC-MS (Method 5): $R_t$ = 1.42 min; m/z = 352 [M + H]$^+$. |

General Procedure 5: Hydrogenation of N-benzylphenylamines to Phenylamines

The N-benzylphenylamine in question was dissolved in a 1:1 mixture of ethanol and THF (5 ml/mmol), 10% of palladium on activated carbon (35 mg/mmol) was added and the mixture was stirred at RT and a hydrogen atmosphere of 1 bar overnight. The reaction mixture was then filtered through Celite, the residue was washed with ethanol and the filtrate was concentrated. The crude product obtained in this manner was purified by flash chromatography on silica gel (typical mobile phase mixture: cyclohexane/ethyl acetate 3:1).

The following compounds were prepared according to General Procedure 5:

| Example | Name/Structure | Analytical data |
|---|---|---|
| 19A | tert-butyl 1-(3-amino-5-fluorobenzyl)-cyclopropanecarboxylate | LC-MS (Method 5): $R_t$ = 1.14 min; m/z = 266 [M + H]$^+$. $^1$H-NMR (400 MHz, DMSO-d$_6$): δ [ppm] = 6.25 (s, 1H), 6.11 (d, 1H), 6.14 (d, 1H), 5.28 (s, 2H), 2.68 (s, 2H), 1.30 (s, 9H), 1.01-1.11 (m, 2H), 0.71-0.85 (m, 2H). |
| 20A | tert-butyl 1-(3-amino-5-fluorobenzyl)-cyclopropanecarboxylate | LC-MS (Method 5): $R_t$ = 1.14 min; m/z = 266 [M + H]$^+$. $^1$H-NMR (400 MHz, DMSO-d$_6$): δ [ppm] = 6.68-6.87 (m, 1H), 6.51-6.66 (m, 1H), 6.39-6.51 (m, 1H), 4.98 (s, 2H), 2.83 (s, 2H), 1.25-1.38 (m, 9H), 1.01-1.13 (m, 2H), 0.68-0.84 (m, 2H). |
| 21A | tert-butyl 1-(3-amino-4-methylbenzyl)-cyclopropanecarboxylate | GC-MS (Method 1): $R_t$ = 6.45 min; m/z = 261 [M]$^+$. |

Example 22A and Example 23A tert-Butyl 1-(3-amino-2-chlorobenzyl)cyclopropanecarboxylate and tert-butyl 1-(5-amino-2-chlorobenzyl)cyclopropanecarboxylate 1.0 g (4.40 mmol) of tert-butyl 1-(3-aminobenzyl)cyclopropanecarboxylate was initially charged in 10.0 ml of acetonitrile, and 540 mg (4.40 mmol) of N-chlorosuccinimide were added a little at a time at 0° C. After 30 min, the mixture was warmed to RT and stirred at this temperature overnight. After concentration under reduced pressure, the residue was taken up in dichloromethane and washed with saturated sodium bicarbonate solution and saturated sodium chloride solution. The organic phase was dried over sodium sulphate and concentrated under reduced pressure. By chromatography on silica gel (mobile phase gradient cyclohexane/ethyl acetate 10:1→6:1), 217 mg of a mixed fraction (about 1:1) consisting of tert-butyl 1-(3-amino-2-chlorobenzyl)cyclopropanecarboxylate and tert-butyl 1-(3-amino-4-chlorobenzyl)cyclopropanecarboxylate, and also 995.5 mg of tert-butyl 1-(5-amino-2-chlorobenzyl)cyclopropanecarboxylate, slightly contaminated by the starting material tert-butyl 1-(3-aminobenzyl)cyclopropanecarboxylate, were isolated from the crude product obtained in this manner. The mixed fraction (217 mg) was separated further by preparative RP-HPLC [column: Sunfire C18 5 μm, 250 mm×20 mm; injection volume: 0.50 ml; temperature: 25° C.; mobile phase: 55% acetonitrile/40% water/5% (water+1% TFA); flow rate: 35 ml/min; detection: 210 nm]. In this manner, it was possible to isolate 85 mg (7.5% of theory) of tert-butyl 1-(3-amino-2-chlorobenzyl)cyclopropanecarboxylate (Example 22A). Starting with 995.5 mg of the slightly contaminated material, 677.6 mg (59.5% of theory) of pure tert-butyl 1-(5-amino-2-chlorobenzyl)cyclopropanecarboxylate (Example 23A) were isolated by preparative RP-HPLC (mobile phase: acetonitrile/water gradient).

Example 22A tert-Butyl 1-(3-amino-2-chlorobenzyl)cyclopropanecarboxylate

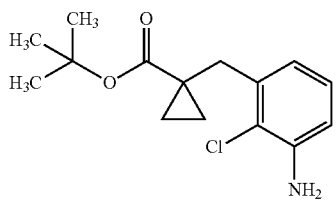 [SMILES: CC(C)(C)OC(=O)C1(Cc2cccc(N)c2Cl)CC1]

LC-MS (Method 4): $R_t$=1.38 min; m/z=282 (M+H)$^+$.

$^1$H-NMR (400 MHz, DMSO-d$_6$): δ [ppm]=0.67-0.77 (m, 2H), 1.06-1.15 (m, 2H), 1.28 (s, 9H), 2.94 (s, 2H), 6.57 (d, 1H), 6.61-6.72 (m, 1H), 6.95 (t, 1H).

Example 23A tert-Butyl 1-(5-amino-2-chlorobenzyl)cyclopropanecarboxylate

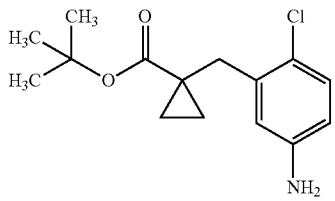 [SMILES: CC(C)(C)OC(=O)C1(Cc2cc(N)ccc2Cl)CC1]

LC-MS (Method 5): $R_t$=1.17 min; m/z=282 (M+H)$^+$.

$^1$H-NMR (400 MHz, DMSO-d$_6$): δ [ppm]=0.63-0.79 (m, 2H), 1.03-1.16 (m, 2H), 1.29 (s, 9H), 2.86 (s, 2H), 5.14 (s, 2H), 6.39 (dd, 1H), 6.58 (d, 1H), 6.98 (d, 1H).

Examples 24A-26A tert-Butyl 1-(3-amino-4-chloro-2-fluorobenzyl)cyclopropanecarboxylate tert-butyl 1-(3-amino-6-chloro-2-fluorobenzyl)cyclopropanecarboxylate and tert-butyl 1-(3-amino-4,6-dichloro-2-fluorobenzyl)cyclopropanecarboxylate 129 mg (0.486 mmol) of tert-butyl 1-(3-amino-2-fluorobenzyl)cyclopropanecarboxylate were dissolved in 1.3 ml of acetonitrile, and 71.4 mg (0.535 mmol) of N-chlorosuccinimide were added a little at a time at RT. The reaction mixture was warmed to 50° C. and stirred for 1.5 h. After cooling, the solvent was removed under reduced pressure. The residue was taken up in dichloromethane and washed with saturated sodium bicarbonate solution and saturated sodium chloride solution. The organic phase was dried over sodium sulphate and concentrated under reduced pressure. The crude product obtained in this manner was partially separated into its components by preparative RP-HPLC (mobile phase: acetonitrile/water). This gave 37 mg (25% of theory) of a mixture (about 1.5:1) of tert-butyl 1-(3-amino-4-chloro-2-fluorobenzyl)cyclopropanecarboxylate and tert-butyl 1-(3-amino-6-chloro-2-fluorobenzyl)cyclopropanecarboxylate (Example 24A and Example 25A, respectively) and 34 mg (21% of theory) of tert-butyl 1-(3-amino-4,6-dichloro-2-fluorobenzyl)cyclopropanecarboxylate (Example 26A).

Example 24A and Example 25A tert-Butyl 1-(3-amino-4-chloro-2-fluorobenzyl)cyclopropanecarboxylate and tert-butyl 1-(3-amino-6-chloro-2-fluorobenzyl)cyclopropanecarboxylate (about 1.5:1 mixture)

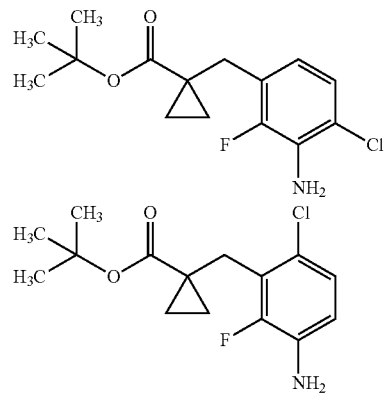

LC-MS (Method 4): $R_t$=1.43 min; m/z=282 (M+H)$^+$ and $R_t$=1.45 min; m/z=282 (M+H)$^+$ (ratio about 1:1.5).

tert-Butyl 1-(3-amino-4-chloro-2-fluorobenzyl)cyclopropanecarboxylate

Example 24A $^1$H-NMR (400 MHz, DMSO-d$_6$): δ [ppm]=0.74-0.82 (m, 2H), 1.05-1.11 (m, 2H), 1.29 (s, 9H), 2.82 (s, 2H), 5.25 (s, 2H), 6.53 (t, 1H), 6.99 (dd, 1H).

tert-Butyl 1-(3-amino-6-chloro-2-fluorobenzyl)cyclopropanecarboxylate

Example 25A $^1$H-NMR (400 MHz, DMSO-d$_6$): δ [ppm]=0.36-0.46 (m, 2H), 0.95-1.01 (m, 2H), 1.38 (s, 9H), 3.19 (d, 2H), 5.25 (s, 2H), 6.65 (t, 1H), 6.89-6.95 (m, 1H).

Example 26A tert-Butyl 1-(3-amino-4,6-dichloro-2-fluorobenzyl)cyclopropanecarboxylate

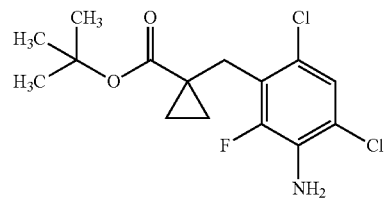 [SMILES: CC(C)(C)OC(=O)C1(Cc2c(Cl)cc(Cl)c(N)c2F)CC1]

LC-MS (Method 4): $R_t$=1.57 min; m/z=278/280.

$^1$H-NMR (400 MHz, DMSO-d$_6$): δ [ppm]=0.41-0.49 (m, 2H), 0.96-1.06 (m, 2H), 1.37 (s, 9H), 3.17 (d, 2H), 5.53 (s, 2H), 7.22 (d, 1H).

Example 27A tert-Butyl 1-(5-amino-2-chloro-4-fluorobenzyl)cyclopropanecarboxylate

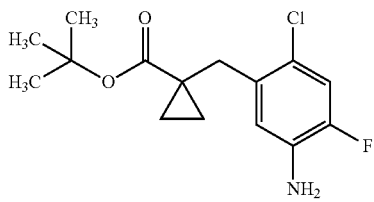 [SMILES: CC(C)(C)OC(=O)C1(Cc2cc(N)c(F)cc2Cl)CC1]

2.0 g (7.54 mmol) of tert-butyl 1-(3-amino-4-fluorobenzyl)cyclopropanecarboxylate were dissolved in 20.0 ml of acetonitrile, and 1.06 g (7.92 mmol) of N-chlorosuccinimide were added in several portions at RT. The reaction mixture was stirred at RT for 80 min and then at 45° C. for 8 h. After cooling, the acetonitrile was removed under reduced pressure. The residue was taken up in dichloromethane and washed with saturated sodium bicarbonate solution and saturated sodium chloride solution. The organic phase was dried over sodium sulphate and concentrated under reduced pressure. By chromatography on silica gel (mobile phase cyclohexane/ethyl acetate 30:1) 1.41 g (62.3% of theory) of the title compound were isolated from the crude product obtained in this manner.

LC-MS (Method 5): $R_t$=1.23 min; m/z=244.

$^1$H-NMR (400 MHz, DMSO-$d_6$): δ [ppm]=0.72-0.79 (m, 2H), 1.09-1.15 (m, 2H), 1.29 (s, 9H), 2.84 (s, 2H), 5.24 (s, 2H), 6.80 (d, 1H), 7.09 (d, 1H).

Example 28A

2-Bromo-4-(bromomethyl)-1-chlorobenzene

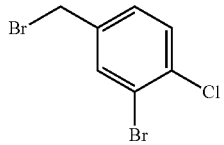

Step 1:
199.0 g (0.845 mol) of 3-bromo-4-chlorobenzoic acid were dissolved in 2.5 liters of THF, the mixture was cooled to −10° C. and 1.69 liters (1.69 mol) of a 1 M solution of borane in THF were added at this temperature. The reaction mixture was warmed to RT overnight, and saturated aqueous ammonium chloride solution was then added. After addition of water, the mixture was extracted twice with ethyl acetate. The combined organic phases were dried over magnesium sulphate and concentrated under reduced pressure. This gave 206 g of (3-bromo-4-chlorophenyl)methanol as a crude product which was reacted without further purification.

Step 2:
260 g (crude product of several batches, about 1.05 mol) of (3-bromo-4-chlorophenyl)methanol were dissolved in 2.86 liters of dichloromethane, the mixture was cooled to −5° C. and 127.1 g (44.6 ml, 459.6 mmol) of phosphorus tribromide were added slowly. After the addition had ended, the mixture was stirred at −5° C. for another 1 h and then diluted with dichloromethane and water. The organic phase was separated off, dried over magnesium sulphate and concentrated under reduced pressure. This gave, as a crude product, 280.5 g (about 84% of theory) of 2-bromo-4-(bromomethyl)-1-chlorobenzene.

GC-MS (Method 1): $R_t$=5.36 min; m/z=281/283/285 (M+H)$^+$.

$^1$H-NMR (400 MHz, DMSO-$d_6$): δ [ppm]=4.71 (s, 2H), 7.49 (dd, 1H), 7.63 (d, 1H), 7.89 (d, 1H).

Example 29A tert-Butyl 1-(3-bromo-4-chlorobenzyl)cyclopropanecarboxylate

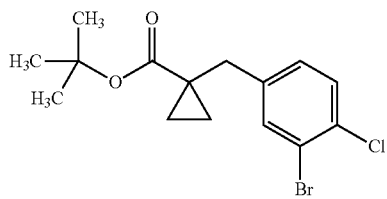 [SMILES: CC(C)(C)OC(=O)C1(Cc2ccc(Cl)c(Br)c2)CC1]

Under argon, 140.2 ml (1.0 mol) of diisopropylamine were dissolved in 1200 ml of dry THF, and the mixture was cooled to −30° C. 400 ml (1.0 mol) of n-butyllithium solution (2.5 M in hexane) were added dropwise. The resulting mixture was warmed to 0° C. and then cooled to −70° C. A solution of 94.8 g (0.667 mol) of tert-butyl cyclopropanecarboxylate in 750 ml of THF was added to the reaction solution, and during the addition the temperature was kept below −60° C. After 4 h of stirring at −60° C., a solution of 208.6 g (0.733 mol) of 2-bromo-4-(bromomethyl)-1-chlorobenzene in 550 ml of THF was added, and once more the temperature was kept below −60° C. during the addition. The reaction mixture was slowly warmed to RT overnight, and saturated aqueous ammonium chloride solution was then added carefully. After phase separation, the aqueous phase was extracted with ethyl acetate. The combined organic phases were dried over magnesium sulphate and concentrated under reduced pressure. The crude product was purified by chromatography on silica gel (mobile phase cyclohexane/dichloromethane 4:1). This gave 95.5 g (41.4% of theory) of the title compound.

GC-MS (Method 1): $R_t$=6.54 min; m/z=288/290 (M−C$_4$H$_8$)$^+$.

LC-MS (Method 4): $R_t$=1.65 min; m/z=288/290 (M−C$_4$H$_8$)$^+$.

Example 30A tert-Butyl 1-[3-(benzylamino)-4-chlorobenzyl]cyclopropanecarboxylate

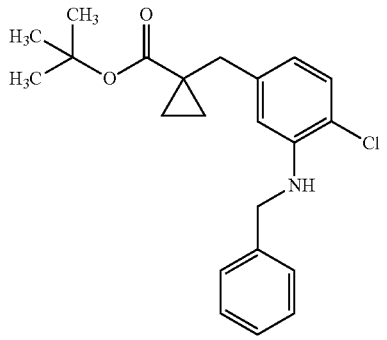 [SMILES: CC(C)(C)OC(=O)C1(Cc2ccc(Cl)c(NCc3ccccc3)c2)CC1]

Under argon, 95.0 g (274.8 mmol) of tert-butyl 1-(3-bromo-4-chlorobenzyl)cyclopropanecarboxylate, 36.0 ml (330.0 mmol) of benzylamine, 12.58 g (13.7 mmol) of tris(dibenzylideneacetone)dipalladium, 31.69 g (329.8 mmol) of sodium tert-butoxide and 6.85 g (5.29 mmol) of (+/−)-2,2'-bis(diphenylphosphino)-1,1'-binaphthyl were added in succession to 633 ml of dry toluene. The reaction mixture was stirred at 110° C. for 3.0 h and then at RT overnight. The reaction mixture was then filtered off with suction through kieselguhr, and the residue was washed thoroughly with toluene and ethyl acetate. The combined filtrates were concentrated under reduced pressure. The crude product was purified by chromatography on silica gel (mobile phase petroleum ether/ethyl acetate 10:1). This gave 50.0 g of the title compound (48.9% of theory).

LC-MS (Method 5): $R_t$=1.48 min; m/z=372 (M+H)$^+$.

Example 31A tert-Butyl 1-(3-amino-4-chlorobenzyl)cyclopropanecarboxylate

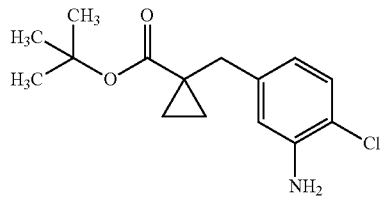 [SMILES: CC(C)(C)OC(=O)C1(Cc2ccc(Cl)c(N)c2)CC1]

50.0 g (134.4 mmol) of tert-butyl 1-[3-(benzylamino)-4-chlorobenzyl]cyclopropanecarboxylate were dissolved in 1.5 liters of ethyl acetate, and 1.43 g (1.34 mmol) of palladium (10% on carbon) were added. The reaction mixture was stirred at RT overnight under a hydrogen atmosphere at atmospheric pressure. The reaction mixture was then filtered off with suction through kieselguhr and the filtrate was concentrated. The crude product was purified by chromatography on silica gel (mobile phase petroleum ether/ethyl acetate 10:1). The product obtained was triturated using a methanol/water mixture (70:30) and the solid was isolated. This gave 24.3 g (64.1% of theory) of the target compound.

LC-MS (Method 5): $R_t$=1.22 min; m/z=282 (M+H)$^+$.

$^1$H-NMR (400 MHz, DMSO-d$_6$): δ [ppm]=0.74-0.82 (m, 2H), 1.02-1.09 (m, 2H), 1.30 (s, 9H), 2.69 (s, 2H), 5.21 (br. s, 2H), 6.42 (dd, 1H), 6.67 (d, 1H), 7.05 (d, 1H).

Example 32A 5-(4-Chloro-3-nitrobenzyl)-2,2-dimethyl-1,3-dioxane-4,6-dione

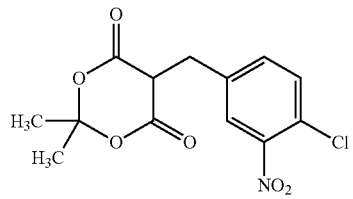 [SMILES: CC1(C)OC(=O)C(Cc2ccc(Cl)c([N+](=O)[O-])c2)C(=O)O1]

200 ml of dichloromethane, 7.87 g (54.6 mmol) of Meldrum's acid and 9.70 g (79.4 mmol) of 4N,N-dimethylaminopyridine were added to 10.0 g (49.6 mmol) of 4-chloro-3-nitrobenzoic acid. The reaction mixture was cooled to 0° C., and a solution of 8.9 ml (57.1 mmol) of N,N'-diisopropylcarbodiimide in 100 ml of dichloromethane was added dropwise. The reaction mixture was stirred at 0° C. overnight, and the precipitated solid was then filtered off through Celite. The filtrate was washed three times with saturated potassium hydrogensulphate solution and once with saturated sodium chloride solution, dried over magnesium sulphate and concentrated under reduced pressure to a volume of about 200 ml. After cooling to 0° C., first 33.5 ml of acetic acid and then, a little at a time, 4.69 g (124 mmol) of sodium borohydride were added. The reaction mixture was stirred at 0° C. overnight, and 300 ml of water were then added. After 10 min of vigorous stirring, the separated organic phase was washed with 300 ml of water and 200 ml of saturated sodium chloride solution, dried over magnesium sulphate and concentrated under reduced pressure. The residue was triturated with cyclohexane/ethyl acetate (5:1), and the precipitated solid was filtered off with suction and isolated. The mother liquor was concentrated under reduced pressure, the residue was once more triturated with cyclohexane/ethyl acetate (5:1) and the precipitated solid was isolated again. This procedure was repeated once more. All batches of solids were combined and dried under high vacuum. This gave altogether 11.15 g of the target product (about 70% of theory, still contaminated by residual 1,3-diisopropylurea).

$^1$H-NMR (400 MHz, DMSO-d$_6$): δ [ppm]=1.71 (s, 3H), 1.80 (s, 3H), 3.51 (d, 2H), 3.80 (t, 1H), 7.46 (d, 1H), 7.56 (dd, 1H), 7.90 (d, 1H).

Example 33A tert-Butyl 2-(4-chloro-3-nitrobenzyl)acrylate

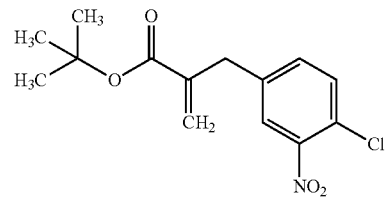 [SMILES: C=C(Cc1ccc(Cl)c([N+](=O)[O-])c1)C(=O)OC(C)(C)C]

11.1 g of 5-(4-chloro-3-nitrobenzyl)-2,2-dimethyl-1,3-dioxane-4,6-dione (contaminated by residual 1,3-diisopropylurea) were dissolved in 40 ml of THF and 40 ml (31 g) of tert-butanol, and 16.4 g (88.5 mmol) of N,N-dimethylmethyleneiminium iodide were added. The resulting suspension was stirred at 70° C. overnight and then, after cooling, added to water. The aqueous phase was extracted three times with ethyl acetate. The combined organic phases were washed with saturated sodium chloride solution, dried over magnesium sulphate and concentrated under reduced pressure. The residue was purified by chromatography on silica gel (mobile phase cyclohexane/ethyl acetate 10→50:1). This gave 8.22 g of the target product (about 78% of theory).

GC-MS (Method 1): $R_t$=6.44 min; m/z=224 (M−C$_3$H$_5$O$_2$)$^+$.

$^1$H-NMR (500 MHz, DMSO-d$_6$): δ [ppm]=1.37 (s, 9H), 3.67 (s, 2H), 5.71 (s, 1H), 6.13 (s, 1H), 7.53 (dd, 1H), 7.72 (d, 1H), 7.90 (d, 1H).

Example 34A (+/−)-tert-Butyl 1-(4-chloro-3-nitrobenzyl)-2,2-difluorocyclopropanecarboxylate

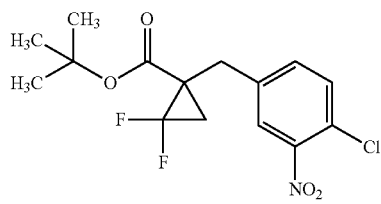

A solution of 8.22 g (27.6 mmol) of tert-butyl 2-(4-chloro-3-nitrobenzyl)acrylate in 79.5 ml of diethylene glycol dimethyl ether was heated to 140° C., and 4.2 g (27.6 mmol) of sodium chloro(difluoro)acetate were added. The reaction mixture was then heated to 160° C. and stirred at this temperature for 1 h, after which another 4.2 g of sodium chloro(difluoro)acetate were added. After a further hour at 160° C., another 4.2 g of sodium chloro(difluoro)acetate were added, and the mixture was stirred for another 2 h. After cooling to RT, the mixture was added to ice-water. The aqueous phase was extracted three times with ethyl acetate. The combined organic phases were washed with saturated sodium chloride solution, dried over magnesium sulphate and concentrated under reduced pressure. Residual diethylene glycol dimethyl ether was removed under high vacuum. From the crude product obtained, the target product was isolated by chromatography on silica gel (mobile phase cyclohexane/dichloromethane 20:1→3:1). In this manner, 1.50 g of the title compound (9.6% of theory) were obtained.

LC-MS (Method 5): $R_t$=1.27 min; m/z=365 (M+H$_2$O)$^+$.

$^1$H-NMR (400 MHz, DMSO-d$_6$): δ [ppm]=1.30 (s, 9H), 2.12-2.25 (m, 2H), 2.85 (d, 1H), 3.42 (d, 1H), 7.63 (dd, 1H), 7.77 (d, 1H), 7.98 (d, 1H).

Example 35A (+/−)-tert-Butyl 1-(3-amino-4-chlorobenzyl)-2,2-difluorocyclopropanecarboxylate

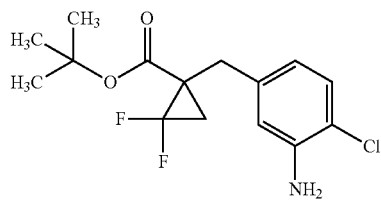 [SMILES: CC(C)(C)OC(=O)C1(Cc2ccc(Cl)c([N+](=O)[O-])c2)CC1(F)F]

1.60 g (4.60 mmol) of (+/−)-tert-butyl 1-(4-chloro-3-nitrobenzyl)-2,2-difluorocyclopropanecarboxylate were dissolved in 20 ml of dioxane, and 4.36 g (23.0 mmol) of tin(II) chloride and a few drops of 1 N hydrochloric acid were added at RT. The reaction mixture was heated at 70° C. for 1 h. After cooling to RT, 10 ml of 10% strength aqueous potassium fluoride solution were added. The mixture was extracted three times with ethyl acetate, and the combined organic phases were dried over magnesium sulphate and concentrated under reduced pressure. The residue was purified by chromatography on silica gel (mobile phase cyclohexane/ethyl acetate 50:1→10:1). This gave 1.16 g of the target product (79.3% of theory).

LC-MS (Method 4): $R_t$=1.54 min; m/z=318 (M+H)$^+$.

$^1$H-NMR (400 MHz, DMSO-d$_6$): δ [ppm]=1.32 (s, 9H), 1.79-1.98 (m, 1H), 2.01-2.22 (m, 1H), 2.53 (d, 1H, obscured), 3.19 (d, 1H), 5.19-5.34 (m, 2H), 6.19-6.43 (m, 1H), 6.66 (d, 1H), 7.09 (d, 1H).

Example 36A tert-Butyl cyclobutanecarboxylate

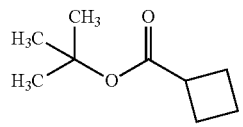

Under argon, 99 µl (0.78 mmol) of boron trifluoride/diethyl ether complex were added to 5.2 g (52.3 mmol) of cyclobutanecarboxylic acid in 100 ml of THF. A little at a time, 13.7 g (62.75 mmol) of tert-butyl 2,2,2-trichloroethaneimidoate were then added, and the mixture was subsequently stirred at room temperature overnight. 5 g of sodium bicarbonate were then added, and the reaction mixture was stirred for 15 min. After filtration, the solution was concentrated to dryness under reduced pressure. The crude product was purified by chromatography on silica gel (mobile phase cyclohexane/ethyl acetate 4:1). This gave 5.2 g (64% of theory) of the title compound as a yellow oil.

GC-MS (Method 1): $R_t$=2.08 min; m/z=101 (M−C$_4$H$_7$)$^+$.

Example 37A tert-Butyl cyclopentylacetate

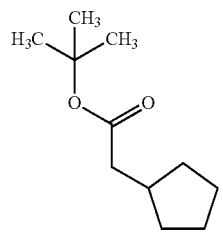

136 ml of a 1 M solution of potassium tert-butoxide in THF (136 mmol) were cooled to 0° C., and 21.0 g (143.2 mmol) of cyclopentylacetic chloride were added dropwise. After the addition had ended, the suspension was warmed to RT and stirred overnight and then added to saturated aqueous ammonium chloride solution. The mixture was extracted three times with diethyl ether. The combined organic phases were dried over magnesium sulphate and concentrated under reduced pressure. The desired product was isolated from the residue by kugelrohr distillation (1.6 mbar/160-180° C.). This gave 17.58 g of the target compound (66.6% of theory).

¹H-NMR (400 MHz, DMSO-d₆): δ [ppm]=1.02-1.20 (m, 2H), 1.39 (s, 9H), 1.42-1.63 (m, 4H), 1.66-1.81 (m, 2H), 1.98-2.14 (m, 1H), 2.15-2.23 (m, 2H).

Example 38A

Methyl 4-cyanophenylacetate

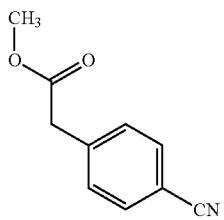

5.1 g (56.7 mmol) of copper(I) cyanide were added to a solution of 10 g (43.7 mmol) of methyl 4-bromophenylacetate in 44 ml of NMP, and, in a microwave oven, the mixture was then heated to 200° C. for 60 min. The reaction mixture was then purified by flash chromatography on silica gel (mobile phase cyclohexane/ethyl acetate 5:1). This gave 4.65 g (61% of theory) of the title compound.

GC-MS (Method 1): R$_t$=5.13 min; m/z=175 (M)⁺.

¹H-NMR (400 MHz, DMSO-d₆): δ [ppm]=3.24-3.35 (m, 3H), 3.83 (s, 2H), 7.49 (d, 2H), 7.80 (d, 2H).

Example 39A

Methyl [4-(trifluoromethyl)phenyl]acetate

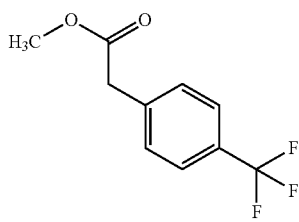

6.0 g (29.4 mmol) of [4-(trifluoromethyl)phenyl]acetic acid were dissolved in 67.1 ml of toluene and 46.2 ml of methanol, and 26.5 ml (52.9 mmol) of a 2 M solution of trimethylsilyldiazomethane in diethyl ether were added dropwise with cooling. After the addition had ended, cooling was removed and the mixture was stirred at RT for another 1 h, after which excess trimethylsilyldiazomethane was destroyed by addition of 2.0 ml of acetic acid. The reaction mixture was concentrated under reduced pressure and the crude product was purified by chromatography on silica gel (mobile phase cyclohexane/ethyl acetate 80:1). This gave 4.33 g of the target compound (67.6% of theory).

GC-MS (Method 1): R$_t$=3.23 min; m/z=218 (M)⁺.

¹H-NMR (400 MHz, DMSO-d₆): δ [ppm]=3.63 (s, 3H), 3.83 (s, 2H), 7.51 (d, 2H), 7.69 (d, 2H).

The two compounds below were obtained in an analogous manner:

Example 40A

Methyl [3-fluoro-4-(trifluoromethyl)phenyl]acetate

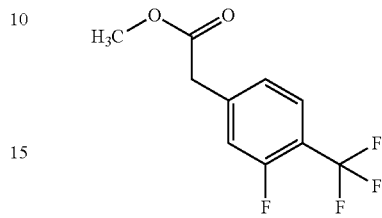

1.80 g (8.10 mmol) of [3-fluoro-4-(trifluoromethyl)phenyl]acetic acid gave 1.58 g of the target compound (82.6% of theory).

GC-MS (Method 1): R$_t$=3.31 min; m/z=236 (M)⁺.

¹H-NMR (400 MHz, DMSO-d₆): δ [ppm]=3.65 (s, 3H), 3.87 (s, 2H), 7.34 (d, 1H), 7.46 (d, 1H), 7.75 (t, 1H).

Example 41A

Methyl [4-(trifluoromethoxy)phenyl]acetate

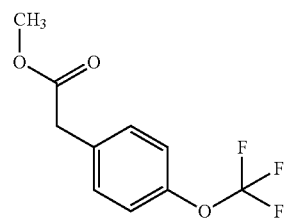 [SMILES: COC(=O)Cc1ccc(OC(F)(F)F)cc1]

1.80 g (8.18 mmol) of [4-(trifluoromethoxy)phenyl]acetic acid gave 1.09 g of the target compound (56.7% of theory).

GC-MS (Method 1): R$_t$=3.21 min; m/z=234 (M)⁺.

¹H-NMR (400 MHz, DMSO-d₆): δ [ppm]=3.62 (s, 3H), 3.75 (s, 2H), 7.26-7.35 (m, 2H), 7.35-7.46 (m, 2H).

Example 42A

1-Bromo-4-(2-bromo-1-fluoroethyl)benzene

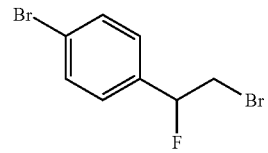 [SMILES: FC(CBr)c1ccc(Br)cc1]

5.0 g (27.31 mmol) of 4-bromostyrene were dissolved in 40 ml of dichloromethane, the mixture was cooled to 0° C. and 13.21 g (81.94 mmol) of triethylamine trihydrofluoride were added. 5.83 g (32.78 mmol) of N-bromosuccinimide were then added in three portions. The mixture was stirred at RT overnight. After dilution with dichloromethane, the reaction mixture was added to ice-water. The organic phase was washed successively with 1 N hydrochloric acid, water and saturated sodium bicarbonate solution, dried over magnesium sulphate and concentrated under reduced pressure. The residue was purified by chromatography on silica gel (mobile phase pentane). This gave 4.14 g (53.8% of theory) of the title compound.

GC-MS (Method 1): $R_t$=4.94 min; m/z=277/281/283 (M+H)$^+$ $^1$H-NMR (400 MHz, DMSO-d$_6$): δ [ppm]=3.75-4.04 (m, 2H), 5.84 (dt, 1H), 7.31-7.51 (m, 2H), 7.55-7.78 (m, 2H).

Example 43A

1-Bromo-4-(1-fluorovinyl)benzene

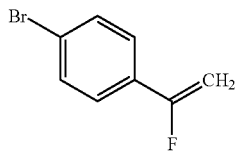

In several portions, 796 mg (7.09 mmol) of potassium tert-butoxide were added to a solution, cooled to 0° C., of 1.0 g (3.55 mmol) of 1-bromo-4-(2-bromo-1-fluoroethyl)benzene in 10 ml of pentane. The resulting suspension was stirred at 0° C. for 30 min and then at RT for 1 h. The solid was filtered off, and the filtrate was washed with saturated ammonium chloride solution, dried over magnesium sulphate and carefully concentrated under reduced pressure. This gave 0.61 g (85.6% of theory) of the title compound.

GC-MS (Method 1): $R_t$=3.14 min; m/z=200/202 (M+H)$^+$ $^1$H-NMR (400 MHz, DMSO-d$_6$): δ [ppm]=5.10 (dd, 1H), 5.47 (dd, 1H), 7.48-7.61 (m, 2H), 7.62-7.72 (m, 2H).

Example 44A tert-Butyl cyclopentyl(4-methylphenyl)acetate

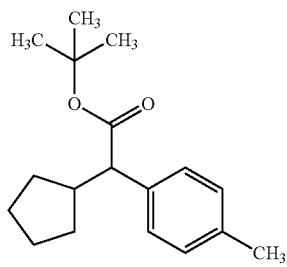 [SMILES: Cc1ccc(C(C(=O)OC(C)(C)C)C2CCCC2)cc1]

Under argon, 19.58 g (174.5 mmol) of potassium tert-butoxide were initially charged in 250 ml of DMF, the mixture was cooled to 0° C. and 30 g (145.4 mmol) of tert-butyl (4-methylphenyl)acetate, dissolved in 50 ml of DMF, were added. The mixture was then stirred at 0° C. for 30 min. 18.95 ml (174.5 mmol) of cyclopentyl bromide were then slowly added dropwise, and the mixture was stirred at 0° C. for 2 h. 200 ml of water and 200 ml of diethyl ether were then added to the reaction solution. The aqueous phase was extracted twice with diethyl ether, and the combined organic phases were dried over magnesium sulphate. After filtration, the solvent was removed under reduced pressure. This gave 36.15 g (132.7 mmol, 91% of theory) of a colourless solid.

$^1$H-NMR (400 MHz, DMSO-d$_6$, δ/ppm): 7.19 (2H, d), 7.11 (2H, d), 3.12 (1H, d), 2.45-2.29 (1H, m), 2.27 (3H, s), 1.89-1.71 (1H, m), 1.67-1.45 (3H, m), 1.44-1.15 (3H, m), 1.36 (9H, s), 1.02-0.84 (1H, m).

MS (DCI): m/z=292 (M+NH$_4$)$^+$

GC-MS (Method 1): $R_t$=5.89 min; m/z=218 (M+H–C$_4$H$_9$)$^+$.

Example 45A tert-Butyl [4-(bromomethyl)phenyl](cyclopentyl)acetate

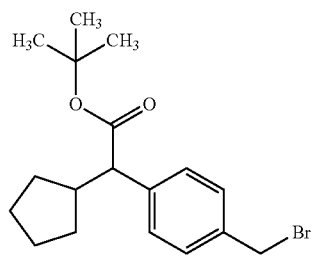 [SMILES: CC(C)(C)OC(=O)C(c1ccc(CBr)cc1)C1CCCC1]

10 g (36.44 mmol) of tert-butyl cyclopentyl(4-methylphenyl)acetate, 6.811 g (38.26 mmol) of N-bromosuccinimide and 299 mg (1.82 mmol) of 2,2'-azobis-(2-methylpropanenitrile) in 10 ml of carbon tetrachloride were stirred under reflux for two hours. After the reaction had gone to completion, the succinimide formed was filtered off and the filter residue was washed with dichloromethane. The combined filtrates were concentrated under reduced pressure. The crude product was purified chromatographically on silica gel (mobile phase cyclohexane/ethyl acetate 50:1). This gave 9.9 g (28.04 mmol, 77% of theory) of a yellowish solid.

$^1$H-NMR (400 MHz, DMSO-d$_6$, δ/ppm): 7.39 (2H, d), 7.30 (2H, d), 4.68 (2H, s), 3.21 (1H, d), 2.45-2.31 (1H, m), 1.89-1.74 (1H, m), 1.69-1.45 (3H, m), 1.44-1.16 (3H, m), 1.35 (9H, s), 1.02-0.88 (1H, m).

MS (DCI): m/z=370/372 (M+NH$_4$)$^+$.

Example 46A (+/−)-Ethyl(4-bromophenyl)(cyclopentyl)acetate

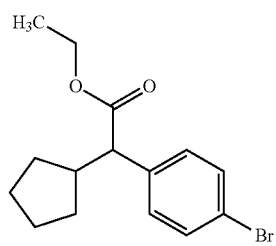 [SMILES: CCOC(=O)C(c1ccc(Br)cc1)C1CCCC1]

Under an atmosphere of argon, 5.54 g (49.4 mmol) of potassium tert-butoxide were dissolved in 100 ml of DMF, and the mixture was cooled to 0° C. 10 g (41.1 mmol) of ethyl 4-bromophenylacetate, dissolved in 20 ml of DMF, were then added. The reaction mixture was stirred at 0° C. for 30 min, and 5.29 ml (49.4 mmol) of cyclopentyl bromide were then added dropwise. The mixture was stirred at 0-5° C. for 1 h and then added to water (1 liter) and extracted with ethyl acetate.

The organic phase was washed with saturated sodium chloride solution, dried over magnesium sulphate and concentrated. This gave 12.41 g (97% of theory) of the title compound in the form of a yellowish oil.

LC-MS (Method 5): $R_t$=1.44 min; m/z=311/313 (M+H)$^+$.

$^1$H-NMR (400 MHz, DMSO-d$_6$): δ [ppm]=0.89-1.04 (m, 1H), 1.05-1.69 (m, 9H), 1.72-1.86 (m, 1H), 2.34-2.48 (m, 1H), 3.37 (d, 1H), 3.92-4.17 (m, 2H), 7.24-7.37 (m, 2H), 7.44-7.57 (m, 2H).

Example 47A (+/−)-Methyl(4-cyanophenyl)(cyclopentyl)acetate

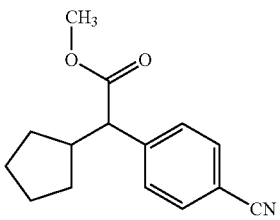 [SMILES: COC(=O)C(c1ccc(C#N)cc1)C1CCCC1]

Under an atmosphere of argon, 2.56 g (22.8 mmol) of potassium tert-butoxide were dissolved in 20 ml of DMF, the mixture was cooled to 0° C. and 2 g (11.4 mmol) of methyl 4-cyanophenylacetate were added dropwise. After the addition had ended, 1.47 ml (13.7 mmol) of cyclopentyl bromide were slowly added dropwise. The reaction mixture was stirred at 0° C. for 2 h and then at RT overnight. Water was then added, the reaction mixture was stirred for 15 min, ethyl acetate was then added and the mixture was stirred for a further 15 min. The organic phase was separated off and the aqueous phase was extracted repeatedly with ethyl acetate. The combined organic phases were dried over magnesium sulphate and concentrated. The residue was purified by flash chromatography on silica gel (mobile phase cyclohexane/ethyl acetate 5:1). This gave 1.29 g (46% of theory) of the title compound.

LC-MS (Method 5): $R_t$=1.19 min; m/z=244 (M+H)$^+$.

Example 48A (+/−)-Ethyl(4-nitrophenyl)(cyclopentyl)acetate

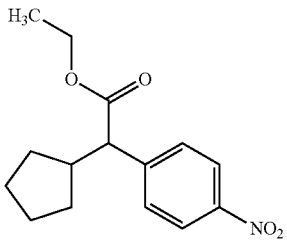 [SMILES: CCOC(=O)C(c1ccc([N+](=O)[O-])cc1)C1CCCC1]

Under argon, 644 mg (5.7 mmol) of potassium tert-butoxide were dissolved in 10 ml of DMF, and the mixture was cooled to 0° C. 1000 mg (4.8 mmol) of ethyl 4-nitrophenylacetate, dissolved in 2 ml of DMF, were then added. The reaction mixture was stirred at 0° C. for 30 min, and 855 mg (5.7 mmol) of cyclopentyl bromide were then added dropwise. The reaction mixture was subsequently heated at 70° C. for 1.5 h, then cooled, poured into water and extracted with ethyl acetate. The organic phase was dried over sodium sulphate and concentrated. The crude product obtained was purified by flash chromatography on silica gel (mobile phase isohexane/ethyl acetate 10:1). This gave 716 mg (51% of theory) of the title compound.

LC-MS (Method 5): $R_t$=1.32 min; m/z=278 (M+H)$^+$.

$^1$H-NMR (400 MHz, DMSO-d$_6$): δ [ppm]=0.91-1.05 (m, 1H), 1.14 (t, 3H), 1.19-1.70 (m, 6H), 1.74-1.89 (m, 1H), 3.62 (d, 1H), 3.96-4.18 (m, 2H), 7.65 (d, 2H), 8.20 (d, 2H).

Example 49A tert-Butyl [4-(acetoxymethyl)phenyl](cyclopentyl)acetate

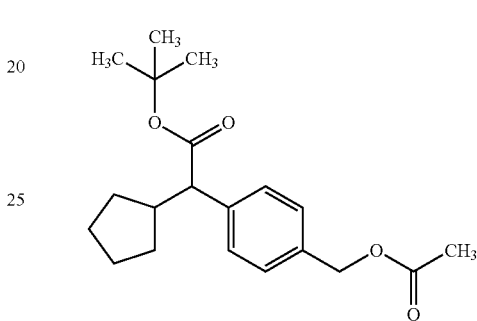

16.3 g (84.9 mmol) of caesium acetate were initially charged in 80 ml of DMF, and 20.0 g (about 75% pure, about 42.5 mmol) of tert-butyl [4-(bromomethyl)phenyl](cyclopentyl)acetate were added at RT. The mixture was stirred vigorously at 50° C. for 1.5 h and then, after cooling, added to 100 ml of ethyl acetate. The organic phase was washed successively with 80 ml of water and 80 ml of saturated sodium chloride solution, dried over magnesium sulphate and concentrated under reduced pressure. Chromatography on silica gel (mobile phase cyclohexane/ethyl acetate 40:1→10:1) gave 11.72 g of the target compound (76.4% of theory).

LC-MS (Method 5): $R_t$=1.42 min; m/z=350 (M+H$_2$O)$^+$.

$^1$H-NMR (400 MHz, DMSO-d$_6$): δ [ppm]=0.82-1.02 (m, 1H), 1.15-1.31 (m, 2H), 1.35 (s, 9H), 1.38-1.47 (m, 1H), 1.47-1.69 (m, 3H), 1.76-1.88 (m, 1H), 2.06 (s, 3H), 2.32-2.45 (m, 1H), 3.21 (d, 1H), 5.04 (s, 2H), 7.22-7.38 (m, 4H).

Example 50A

Methyl(4-chlorophenyl)(cyclopentyl)acetate

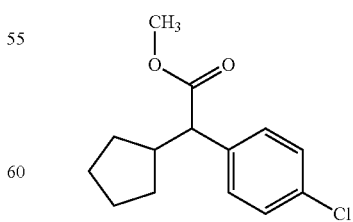

A suspension of 3.65 g (32.5 mmol) of potassium tert-butoxide in 65 ml of abs. DMF was cooled to 0° C., and a solution of 5.0 g (27.08 mmol) of methyl 4-chlorophenylacetate in about 2 ml of abs. DMF was added dropwise. The mixture was stirred at 0° C. for 30 min, and 4.84 g (32.5 mmol) of cyclopentyl bromide were then slowly added dropwise. The reaction mixture was stirred at 0° C. for 1 h and then added to water and extracted with ethyl acetate. The organic phase was dried over sodium sulphate and concentrated under reduced pressure, and the residue was dried under high vacuum. The crude product was purified by chromatography on silica gel (mobile phase cyclohexane/ethyl acetate 100:1). This gave 6.28 g of the target compound (91.8% of theory).

GC-MS (Method 1): $R_t$=6.07 min; m/z=193 $(M-C_2H_3O_2)^+$.

$^1$H-NMR (400 MHz, DMSO-$d_6$): δ [ppm]=0.96-1.04 (m, 1H), 1.08-1.37 (m, 2H), 1.37-1.48 (m, 1H), 1.49-1.70 (m, 3H), 1.79 (dtd, 1H), 2.33-2.50 (m, 1H), 3.42 (d, 1H), 3.58 (s, 3H), 7.29-7.46 (m, 4H).

The compounds below were prepared in an analogous manner:

Example 51A

Methyl cyclopentyl[4-(trifluoromethyl)phenyl]acetate

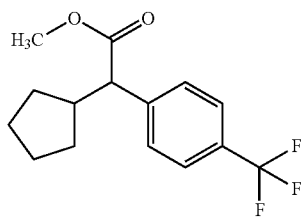 [SMILES: COC(=O)C(c1ccc(C(F)(F)F)cc1)C1CCCC1]

4.3 g (19.7 mmol) of methyl [4-(trifluoromethyl)phenyl]acetate and 3.53 g (23.7 mmol) of cyclopentyl bromide gave 4.98 g of the target compound (88.2% of theory).

LC-MS (Method 4): $R_t$=1.57 min; m/z=287 $(M+H)^+$.

$^1$H-NMR (400 MHz, DMSO-$d_6$): δ [ppm]=0.90-1.04 (m, 1H), 1.16-1.33 (m, 2H), 1.37-1.49 (m, 1H), 1.49-1.70 (m, 3H), 1.76-1.88 (m, 1H), 2.41-2.49 (m, 1H), 3.56 (d, 1H), 3.60 (s, 3H), 7.53-7.62 (m, 2H), 7.66-7.74 (m, 2H).

Example 52A

Methyl cyclopentyl(3,4-dichlorophenyl)acetate

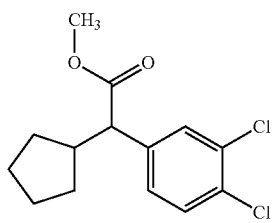 [SMILES: COC(=O)C(c1ccc(Cl)c(Cl)c1)C1CCCC1]

1.5 g (6.85 mmol) of methyl 3,4-dichlorophenylacetate and 1.22 g (8.22 mmol) of cyclopentyl bromide gave 0.70 g of the target compound (35.6% of theory).

MS (DCI): m/z=304 $(M+NH_4)^+$.

$^1$H-NMR (400 MHz, DMSO-$d_6$): δ [ppm]=0.86-1.08 (m, 1H), 1.12-1.26 (m, 1H), 1.26-1.36 (m, 1H), 1.38-1.49 (m, 1H), 1.49-1.68 (m, 3H), 1.73-1.83 (m, 1H), 2.36-2.47 (m, 1H), 3.50 (d, 1H), 3.60 (s, 3H), 7.32-7.41 (m, 1H), 7.48-7.54 (m, 1H), 7.57-7.63 (m, 1H).

Example 53A

Methyl(4-chloro-2-fluorophenyl)(cyclopentyl)acetate

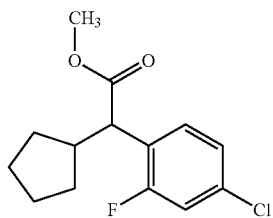 [SMILES: COC(=O)C(c1ccc(Cl)cc1F)C1CCCC1]

6.5 g (32.1 mmol) of methyl (4-chloro-2-fluorophenyl)acetate and 5.74 g (38.5 mmol) of cyclopentyl bromide gave 7.55 g of the target compound (86.9% of theory).

LC-MS (Method 5): $R_t$=1.07 min; m/z=271 $(M+H)^+$.

$^1$H-NMR (400 MHz, DMSO-$d_6$): δ [ppm]=0.88-1.01 (m, 1H), 1.20-1.30 (m, 1H), 1.34-1.64 (m, 5H), 1.79-1.91 (m, 1H), 2.41-2.48 (m, 1H), 3.60 (s, 3H), 3.69 (d, 1H), 7.30 (dd, 1H), 7.43 (dd, 1H), 7.48 (t, 1H).

Example 54A

Ethyl cyclopentyl(2,4-dichlorophenyl)acetate

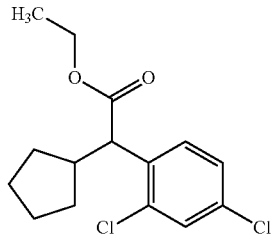 [SMILES: CCOC(=O)C(c1ccc(Cl)cc1Cl)C1CCCC1]

1.5 g (6.43 mmol) of ethyl(2,4-dichlorophenyl)acetate and 1.15 g (7.72 mmol) of cyclopentyl bromide gave 1.60 g of the target compound (82.8% of theory).

LC-MS (Method 5): $R_t$=1.52 min; m/z=191.

$^1$H-NMR (400 MHz, DMSO-$d_6$): δ [ppm]=0.86-1.01 (m, 1H), 1.13 (t, 3H), 1.25-1.40 (m, 2H), 1.40-1.49 (m, 1H), 1.49-1.70 (m, 3H), 1.79-1.91 (m, 1H), 2.45-2.53 (m, 1H), 3.87 (d, 1H), 3.99-4.13 (m, 2H), 7.45 (dd, 1H), 7.54 (d, 1H), 7.63 (d, 1H).

Example 55A

Methyl cyclopentyl[3-fluoro-4-(trifluoromethyl)phenyl]acetate

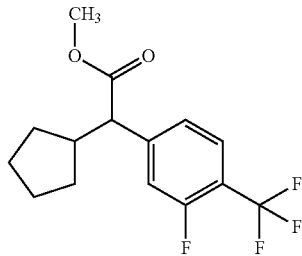 [SMILES: COC(=O)C(c1ccc(C(F)(F)F)c(F)c1)C1CCCC1]

1.50 g (6.35 mmol) of methyl [3-fluoro-4-(trifluoromethyl)phenyl]acetate and 1.14 g (7.62 mmol) of cyclopentyl bromide gave 1.78 g of the target compound (92.1% of theory).

1H-NMR (400 MHz, DMSO-d6): δ [ppm]=0.93-1.06 (m, 1H), 1.19-1.35 (m, 2H), 1.38-1.67 (m, 4H), 1.75-1.86 (m, 1H), 2.41-2.49 (m, 1H), 3.61 (s, 3H), 3.62 (d, 1H), 7.41 (d, 1H), 7.52 (d, 1H), 7.76 (t, 1H).

Example 56A

Methyl cyclopentyl[4-(trifluoromethoxy)phenyl]acetate

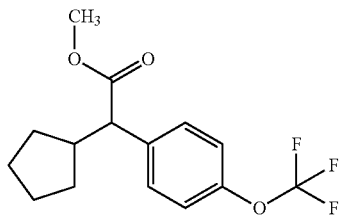 [SMILES: COC(=O)C(c1ccc(OC(F)(F)F)cc1)C1CCCC1]

1.0 g (4.27 mmol) of methyl [4-(trifluoromethoxy)phenyl]acetate and 0.76 g (5.12 mmol) of cyclopentyl bromide gave 1.09 g of the target compound (71.4% of theory).

MS (DCI): m/z=320 (M+NH$_4$)$^+$.

1H-NMR (400 MHz, DMSO-d6): δ [ppm]=0.93-1.02 (m, 1H), 1.15-1.33 (m, 2H), 1.35-1.48 (m, 1H), 1.48-1.68 (m, 3H), 1.73-1.86 (m, 1H), 2.40-2.49 (m, 1H), 3.48 (d, 1H), 3.59 (s, 3H), 7.28-7.36 (m, 2H), 7.42-7.51 (m, 2H).

Example 57A (+/−)-tert-Butyl cyclopentyl(4-fluorophenyl)acetate

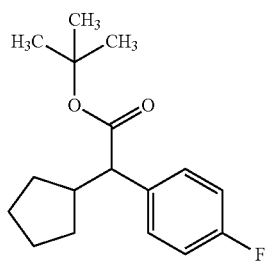 [SMILES: CC(C)(C)OC(=O)C(c1ccc(F)cc1)C1CCCC1]

Under argon, a solution of 2.0 g (10.85 mmol) of tert-butyl cyclopentylacetate in 5 ml of abs. toluene was added dropwise to 16.3 ml of a 1 M solution, cooled to −10° C., of lithium hexamethyl-disilazide in toluene (16.3 mmol). After 10 min at −10° C., the ice bath was removed and the mixture was warmed to RT. A mixture of 2.47 g (14.1 mmol) of 1-bromo-4-fluorobenzene, 73.1 mg (0.326 mmol) of palladium(II) acetate and 269 mg (0.684 mmol) of 2-dicyclohexylphosphino-2'-(N,N-dimethylamino)biphenyl in 10 ml of abs. toluene was then added to this reaction mixture. After 1 h at RT, the reaction mixture was stirred at 80° C. overnight. After cooling to RT, the precipitated salts were filtered off with suction, the residue was washed with toluene and the combined filtrates were concentrated under reduced pressure. The crude product obtained was purified chromatographically on silica gel (mobile phase first cyclohexane, then cyclohexane/ethyl acetate 50:1). This gave 2.0 g of the title compound (61.6% of theory).

1H-NMR (400 MHz, DMSO-d6): δ [ppm]=0.89-1.02 (m, 1H), 1.19-1.30 (m, 2H), 1.35 (s, 9H), 1.46-1.66 (m, 4H), 1.76-1.87 (m, 1H), 2.31-2.42 (m, 1H), 3.23 (d, 1H), 7.09-7.19 (m, 2H), 7.31-7.41 (m, 2H).

Example 58A

Ethyl 2-(4-ethylphenyl)-4,4,4-trifluoro-3-methylbutanoate (racemic diastereomer mixture)

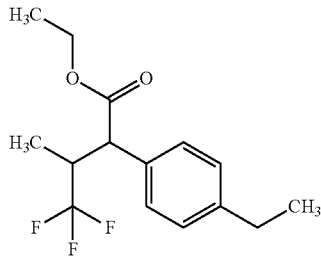 [SMILES: CCOC(=O)C(c1ccc(CC)cc1)C(C)C(F)(F)F]

Under argon, a solution of 1.29 g (7.02 mmol) of (+/−)-ethyl 4,4,4-trifluoro-3-methylbutanoate in 2 ml of abs. toluene was added dropwise to 8.1 ml of a 1 M solution, cooled to −10° C., of lithium hexamethyldisilazide in toluene (8.1 mmol). After 10 min at −10° C., a mixture of 1.0 g (5.4 mmol) of 1-bromo-4-ethylbenzene, 36.4 mg (0.16 mmol) of palladium(II) acetate and 134 mg (0.34 mmol) of 2-dicyclohexylphosphino-2'-(N,N-dimethylamino)biphenyl in 5 ml of abs. toluene was added to this reaction mixture. After the addition had ended, the mixture was warmed to RT and then stirred first at RT for 1 h and then at 80° C. for a further 3 h. After cooling to RT, the precipitated salts were filtered off with suction, the residue was washed with toluene and the combined filtrates were concentrated under reduced pressure. This gave 1.26 g of crude product (80.9% of theory) which was reacted as such.

GC-MS (Method 1): R$_t$=4.51 min and 4.53 min; in each case m/z=288 (M)$^+$ (diastereomer ratio about 1:2.3).

Example 59A (1R,2S,5R)-5-Methyl 2-(propan-2-yl)cyclohexyl-(4-methylphenyl)acetate

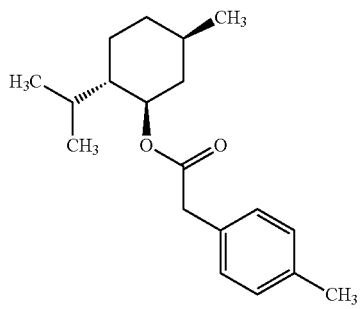 [SMILES: Cc1ccc(CC(=O)O[C@@H]2C[C@H](C)CC[C@H]2C(C)C)cc1]

303.7 g (2022.46 mmol) of (4-methylphenyl)acetic acid and 301 g (1926.2 mmol) of (1R,2S,5R)-5-methyl 2-(propan-2-yl)cyclohexanol were initially charged in 933 ml of toluene, 2.5 ml (38.5 mmol) of methanesulphonic acid were added and the mixture was stirred at reflux on a water separator overnight. The reaction solution was then allowed to cool, and a mixture of 30 ml of 45% strength aqueous sodium hydroxide solution and 400 ml of water was added. After 30 min, the phases were separated and the organic phase was dried over sodium sulphate, filtered and concentrated on a rotary evaporator. This gave 569.5 g of the target product (97% of theory).

1H-NMR (500 MHz, DMSO-d6): δ [ppm]=7.12 (s, 4H), 4.56 (td, 1H), 3.57 (s, 2H), 2.50 (br. s, 1H), 2.27 (s, 3H), 1.84

(d, 1H), 1.77-1.70 (m, 1H), 1.66-1.57 (m, 2H), 1.48-1.37 (m, 1H), 1.32 (t, 1H), 1.10-0.89 (m, 2H), 0.86 (d, 3H), 0.81 (d, 3H), 0.65 (d, 3H).

Example 60A (1R,2S,5R)-2-Isopropyl-5-methylcyclohexyl(2S)-cyclopentyl(4-methylphenyl)acetate

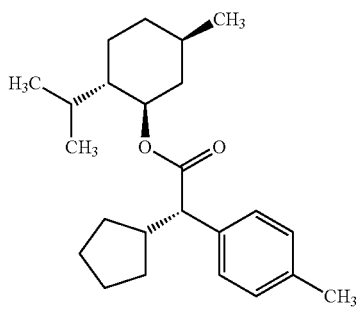 [SMILES: Cc1ccc([C@@H](C(=O)O[C@@H]2C[C@H](C)CC[C@H]2C(C)C)C2CCCC2)cc1]

Under argon, 442.73 g (3945.5 mmol) of potassium tert-butoxide were initially charged in 1230 ml of DMF at −10° C., and 569 g (1972.7 mmol) of (1R,2S,5R)-5-methyl 2-(propan-2-yl)cyclohexyl-(4-methylphenyl)acetate were added a little at a time. 352.81 g (2367.8 mmol) of cyclopentyl bromide were then added dropwise, and during the addition the temperature was kept between −5° C. and −10° C. After 90 min of stirring at −10° C., 1.6 liters of water were added and the mixture was stirred at RT for 15 min. 1.2 liters of ethyl acetate were added, the mixture was stirred for another 15 min and the phases were then separated. The organic phase was dried over sodium sulphate, filtered and concentrated on a rotary evaporator. The crude product was recrystallized in 2 liters of methanol at 50° C. This gave 423.0 g of the target product (60% of theory).

$^1$H-NMR (400 MHz, DMSO-d$_6$): δ [ppm]=7.19 (d, 2H), 7.11 (d, 2H), 4.55 (td, 1H), 3.26 (d, 1H), 2.27 (s, 3H), 1.83-1.73 (m, 2H), 1.68-1.24 (m, 11H), 1.23-1.13 (m, 1H), 1.04-0.94 (m, 2H), 0.88-0.77 (m, 8H), 0.66 (d, 3H).

Example 61A (1R,2S,5R)-2-Isopropyl-5-methylcyclohexyl(2S)-[4-(bromomethyl)phenyl](cyclopentyl)acetate

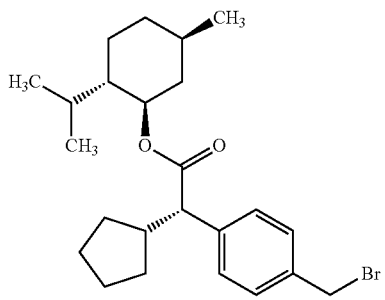 [SMILES: CC(C)[C@@H]1CC[C@@H](C)C[C@H]1OC(=O)[C@H](c1ccc(CBr)cc1)C1CCCC1]

The title compound can be prepared according to U.S. Pat. No. 5,714,494 by bromination of (1R,2S,5R)-2-isopropyl-5-methylcyclohexyl(2S)-cyclopentyl(4-methylphenyl)acetate with N-bromosuccinimide (NBS) in the presence of 2,2'-azobis-(2-methylpropanenitrile) (AIBN) in boiling carbon tetrachloride.

GC-MS (Method 1): R$_t$=9.15 min; no ionization.

LC-MS (Method 2): R$_t$=3.54 min; no ionization.

MS (DCI): m/z=452/454 (M+NH$_4$)$^+$.

Example 62A (−)-(1R,2S,5R)-2-Isopropyl-5-methylcyclohexyl (2S)-cyclopentyl(4-ethylphenyl)acetate

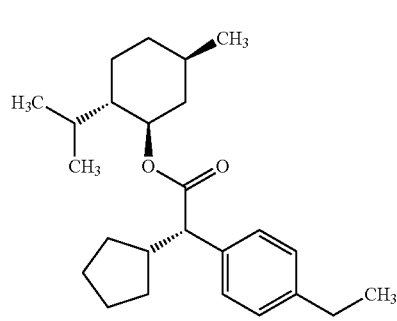 [SMILES: CCc1ccc([C@@H](C(=O)O[C@@H]2C[C@H](C)CC[C@H]2C(C)C)C2CCCC2)cc1]

14.4 ml of a 1.6 M solution of methyllithium in diethyl ether (23.0 mmol) were cooled to 0° C., and 2.30 g (12.06 mmol) of dry copper(I) iodide were added. The orange-yellow suspension was cooled to −78° C., and a solution of 5.0 g (11.48 mmol) of (1R,2S,5R)-2-isopropyl-5-methylcyclohexyl(2S)-[4-(bromomethyl)phenyl](cyclopentyl)acetate in 12.5 ml of abs. THF was added dropwise. After the addition had ended, the reaction mixture was slowly warmed to 0° C. and then stirred first at 0° C. for 3 h and then at RT for 2 h. 200 ml of 25% strength aqueous ammonia solution and 10 g of ammonium acetate were then added. The mixture was stirred vigorously for 10 min and then allowed to stand without stirring overnight. After phase separation, the aqueous phase was extracted twice with diethyl ether. The combined organic phases were washed with saturated ammonium chloride solution, dried over magnesium sulphate and concentrated under reduced pressure. The residue was purified chromatographically on silica gel (mobile phase cyclohexane/dichloromethane 10:1→5:1). This gave 3.33 g of the target compound (78.2% of theory).

MS (DCI): m/z=388 (M+NH$_4$)$^+$.

$^1$H-NMR (400 MHz, DMSO-d$_6$): δ [ppm]=0.60-0.68 (m, 3H), 0.78-0.87 (m, 8H), 0.93-1.05 (m, 2H), 1.16 (t, 3H), 1.16-1.22 (m, 1H), 1.27-1.47 (m, 4H), 1.48-1.69 (m, 6H), 1.70-1.83 (m, 2H), 2.38-2.48 (m, 1H), 2.57 (q, 2H), 3.29 (d, 1H), 4.55 (td, 1H), 7.12-7.16 (m, 2H), 7.20-7.25 (m, 2H).

[α]$_D^{20}$=−37.5°, c=0.51, chloroform.

Example 63A

1-Bromo-4-(1,1-difluoroethyl)benzene

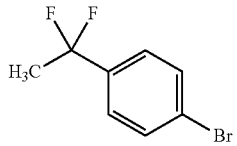

Under argon, 3.0 g (15.07 mmol) of 1-(4-bromophenyl)ethanone were initially charged in 30 ml of dichloromethane, and 15.9 ml (120.57 mmol) of [ethyl(trifluoro-$\lambda^4$-sulphanyl)amino]ethane (DAST) were added slowly. The reaction solution was then slowly warmed to 50° C. and stirred at this temperature overnight. After the reaction had ended, the reaction solution was slowly poured into ice-water. The organic phase was then separated off, and the aqueous phase was extracted three more times with dichloromethane. The combined organic phases were dried over magnesium sulphate. After filtration, the solvent was removed under reduced pressure. The crude product was purified chromatographically on silica gel (mobile phase petroleum ether/dichloromethane 4:1). This gave 2.56 g (11.58 mmol, 77% of theory) of the title compound as a yellowish liquid.

GC-MS (Method 1): $R_t$=2.84 min; m/z=220/222 (M)$^+$.

Example 64A (+)-Ethyl(3R)-4,4,4-trifluoro-3-methylbutanoate

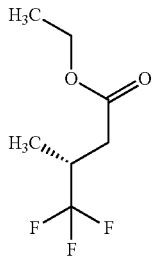

At room temperature, 133 ml (1.82 mol) of thionyl chloride were added slowly to 287 g (1.65 mol) of (3R)-4,4,4-trifluoro-3-methylbutanoic acid [A. Gerlach and U. Schulz, *Speciality Chemicals Magazine* 24 (4), 37-38 (2004); CAS Acc.-No. 142:179196] in 580 ml of ethanol. The reaction solution was then heated to 80° C. and stirred at this temperature for 2 h. The mixture was then cooled to room temperature, 250 ml of water were added slowly and the mixture was extracted three times with in each case 150 ml of tert-butyl methyl ether. The combined organic phases were dried over sodium sulphate. After filtration the solvent was removed under reduced pressure at 30° C. and a pressure of 300 mbar. The crude product was then distilled at 100 mbar and a head temperature of 65° C. This gave 225.8 g (113 mol, 74% of theory) of the title compound as a colourless liquid.

$^1$H-NMR (400 MHz, DMSO-$d_6$, δ/ppm): 4.10 (2H, q), 2.88-2.72 (1H, m), 2.66-2.57 (1H, m), 2.46-2.36 (1H, m), 1.19 (3H, t), 1.11 (3H, d).

GC-MS (Method 1): $R_t$=1.19 min; m/z=184 (M)$^+$.
$[\alpha]_D^{20}$=+16.1°, c=0.41, methanol.

Example 65A

Ethyl 4,4,4-trifluoro-3-methyl-2-(4-methylphenyl)butanoate (diastereomer mixture)

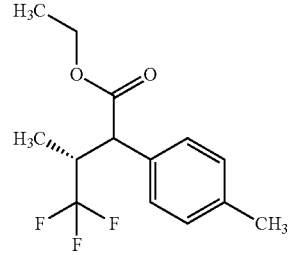 [SMILES: CCOC(=O)C(c1ccc(C)cc1)[C@@H](C)C(F)(F)F]

Under argon, 196.9 mg (0.88 mmol) of palladium(II) acetate and 724.8 mg (1.84 mmol) of 2-dicyclohexylphosphino-2'-(N,N-dimethylamino)biphenyl were initially charged in 50 ml of anhydrous toluene. 43.8 ml (43.8 mmol) of a 1 M solution of lithium hexamethyldisilazide in THF were added slowly, and the reaction solution was then stirred at RT for 10 min. The reaction solution was then cooled to −10° C., 7 g (38.0 mmol) of (+/−)-ethyl 4,4,4-trifluoro-3-methylbutanoate were added slowly and the mixture was stirred at −10° C. for 10 min. 5 g (29.2 mmol) of 4-bromotoluene, dissolved in 50 ml of toluene, were then added dropwise, and the reaction solution was warmed first to RT and then heated to 80° C. The mixture was stirred at this temperature for 2 h and then cooled to RT and stirred overnight. After the reaction had ended (monitored by TLC; mobile phase cyclohexane/dichloromethane 2:1), the reaction mixture was filtered through kiesel-guhr, the residue was washed repeatedly with ethyl acetate and dichloromethane and the combined filtrates concentrated under reduced pressure. The crude product obtained was purified chromatographically on silica gel (mobile phase petroleum ether/dichloromethane 4:1→3:1). This gave 3.91 g (14.3 mmol, 48.8% of theory) of the title compound as a colourless liquid.

$^1$H-NMR (400 MHz, DMSO-$d_6$, δ/ppm): 7.26 (2H, d), 7.20-7.12 (2H, m), 4.17-3.95 (2H, m), 3.74 (0.25H, d), 3.66 (0.75H, d), 3.35-3.07 (1H, m), 2.29 (2.25H, s), 2.28 (0.75H, s), 1.17 (0.75H, d), 1.11 (3H, t), 0.76 (2.25H, d).

GC-MS (Method 1): $R_t$=4.20 min; m/z=275 (M+H)$^+$ (diastereomer 1); $R_t$=4.23 min; m/z=275 (M+H)$^+$ (diastereomer 2).

Example 66A

Ethyl(3R)-2-(4-chlorophenyl)-4,4,4-trifluoro-3-methylbutanoate (diastereomer mixture)

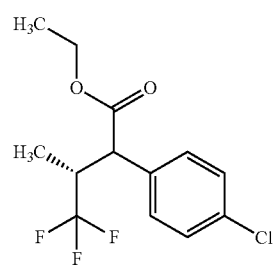 [SMILES: CCOC(=O)C(c1ccc(Cl)cc1)[C@@H](C)C(F)(F)F]

Preparation of solution A: under argon, 163.9 ml of a 1 M solution of lithium hexamethyldisilazide in toluene were cooled to −10° C. to −20° C. (cooling using acetone/dry ice), and 20 g (108.6 mmol) of (+)-ethyl(3R)-4,4,4-trifluoro-3-methylbutanoate, dissolved in 150 ml of toluene, were added slowly, and during the addition care was taken that a temperature of −10° C. was not exceeded. The solution was then stirred for another 10 min at most −10° C.

Preparation of solution B: under argon, 27.03 g (141.2 mmol) of 1-bromo-4-chlorobenzene were dissolved at RT in 100 ml of toluene, and 731 mg (3.26 mmol) of palladium(II) acetate and 2.693 g (6.84 mmol) of 2-dicyclohexylphosphino-2'-(N,N-dimethylamino)biphenyl were added. The solution was stirred at RT for 10 min.

First, the cooling bath was removed from solution A. Solution B was then slowly added dropwise to solution A, which was still cold. The combined solutions were then slowly warmed to RT and stirred at this temperature for 1 h. The reaction solution was then warmed to 80° C. (internal temperature) and stirred at this temperature for 3 h. The reaction solution was then slowly cooled to RT and stirred for another 12 h. The reaction mixture was finally filtered through kieselguhr, the residue was washed repeatedly with toluene and the combined filtrates concentrated under reduced pressure. The crude product obtained was purified chromatographically on silica gel (mobile phase cyclohexane/dichloromethane 4:1). This gave 27.4 g (92.98 mmol, 86% of theory) of the title compound as a yellow oil in a diastereomer ratio of 3:1.

GC-MS (Method 1): $R_t$=4.45 min; m/z=294 (M)$^+$ (diastereomer 1); $R_t$=4.48 min; m/z=294 (M)$^+$ (diastereomer 2).

The following compounds were obtained analogously to Synthesis Examples 65A and 66A:

| Example | Name/Structure/Starting materials | Analytical data |
|---|---|---|
| 67A | ethyl (3R)-4,4,4-trifluoro-2-(4-isopropylphenyl)-3-methylbutanoate 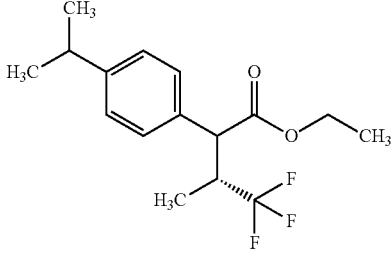 from 1-bromo-4-isopropylbenzene and ethyl (3R)-4,4,4-trifluoro-3-methylbutanoate | GC-MS (Method 1): $R_t$ = 4.61 min; m/z = 302 (M)$^+$ (diastereomer 1); $R_t$ = 4.64 min; m/z = 302 (M)$^+$ (diastereomer 2). |
| 68A | ethyl (3R)-2-(4-tert-butylphenyl)-4,4,4-trifluoro-3-methylbutanoate 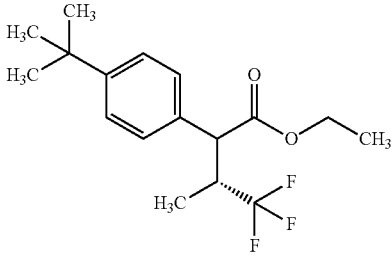 from 1-bromo-4-tert-butylbenzene and ethyl (3R)-4,4,4-trifluoro-3-methylbutanoate | GC-MS (Method 1): $R_t$ = 4.83 min; m/z = 317 (M + H)$^+$ (diastereomer 1); $R_t$ = 4.85 min; m/z = 317 (M + H)$^+$ (diastereomer 2). MS (DCI): m/z = 334 (M + NH$_4$)$^+$. |
| 69A | ethyl 4,4,4-trifluoro-3-methyl-2-[4-(trifluoromethyl)phenyl]butanoate 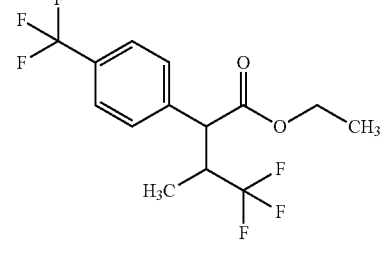 from 1-bromo-4-(trifluoromethyl)benzene and ethyl 4,4,4-trifluoro-3-methylbutanoate | GC-MS (Method 1): $R_t$ = 3.43 min; m/z = 328 (M)$^+$ (diastereomer 1); $R_t$ = 3.47 min; m/z = 328 (M)$^+$ (diastereomer 2). |

-continued

| Example | Name/Structure/Starting materials | Analytical data |
|---|---|---|
| 70A | ethyl (3R)-4,4,4-trifluoro-3-methyl-2-[4-(trifluoromethyl)phenyl]butanoate 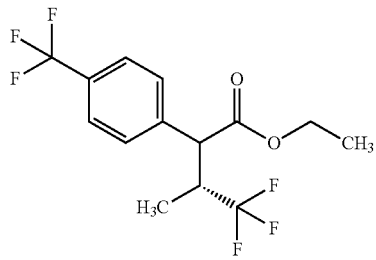 from 1-bromo-4-(trifluoromethyl)benzene and ethyl (3R)-4,4,4-trifluoro-3-methylbutanoate | GC-MS (Method 1): $R_t$ = 3.38 min; m/z = 328 (M)$^+$ (diastereomer 1); $R_t$ = 3.42 min; m/z = 328 (M)$^+$ (diastereomer 2). |
| 71A | ethyl (3R)-4,4,4-trifluoro-3-methyl-2-[4-(1,1,1-trifluoro-2-methylpropan-2-yl)phenyl]butanoate 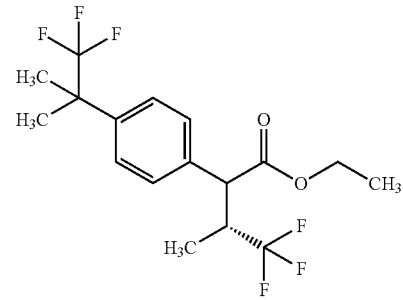 from 1-bromo-4-(1,1,1-trifluoro-2-methylpropan-2-yl)benzene and ethyl (3R)-4,4,4-trifluoro-3-methylbutanoate | GC-MS (Method 1): $R_t$ = 4.68 min; m/z = 370 (M)$^+$. |
| 72A | ethyl (3R)-2-[4-(1,1-difluoroethyl)phenyl]-4,4,4-trifluoro-3-methylbutanoate 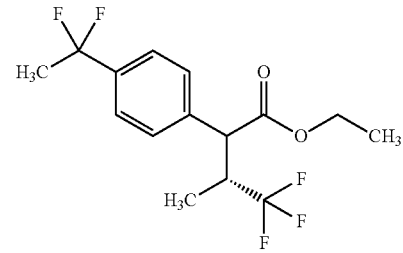 from 1-bromo-4-(1,1-difluoroethyl)benzene and ethyl (3R)-4,4,4-trifluoro-3-methylbutanoate | GC-MS (Method 1): $R_t$ = 4.31 min; m/z = 304 (M − HF)$^+$ (diastereomer 1); $R_t$ = 4.35 min; m/z = 304 (M − HF)$^+$ (diastereomer 2). MS (DCI): m/z = 342 (M + NH$_4$)$^+$. |
| 73A | ethyl (3R)-2-(4-cyclopropylphenyl)-4,4,4-trifluoro-3-methylbutanoate 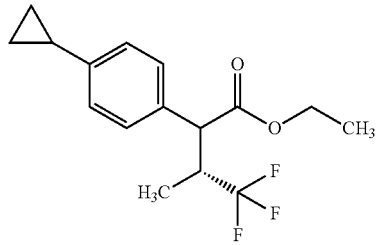 from 1-bromo-4-cyclopropylbenzene and ethyl (3R)-4,4,4-trifluoro-3-methylbutanoate | GC-MS (Method 1): $R_t$ = 5.19 min; m/z = 300 (M)$^+$ (diastereomer 1); $R_t$ = 5.21 min; m/z = 300 (M)$^+$ (diastereomer 2). |

-continued

| Example | Name/Structure/Starting materials | Analytical data |
|---------|-----------------------------------|-----------------|
| 74A | ethyl (3R)-2-(4-chloro-3-methoxyphenyl)-4,4,4-trifluoro-3-methylbutanoate<br><br>from 4-bromo-1-chloro-2-methoxybenzene and ethyl (3R)-4,4,4-trifluoro-3-methylbutanoate | GC-MS (Method 1):<br>$R_t$ = 5.34 min; m/z = 324/326 $(M)^+$. |
| 75A | ethyl 2-(4-chlorophenyl)-4,4,4-trifluoro-3-methylbutanoate<br><br>from 1-bromo-4-chlorobenzene and ethyl 4,4,4-trifluoro-3-methylbutanoate | GC-MS (Method 1):<br>$R_t$ = 4.44 min; m/z = 294/296 $(M)^+$ (diastereomer 1);<br>$R_t$ = 4.48 min; m/z = 294/296 $(M)^+$ (diastereomer 2). |
| 76A | ethyl 4,4,4-trifluoro-3-methyl-2-[4-(trifluoromethoxy)phenyl]butanoate<br><br>from 1-bromo-4-(trifluoromethoxy)benzene and ethyl 4,4,4-trifluoro-3-methylbutanoate | GC-MS (Method 1):<br>$R_t$ = 3.41 min; m/z = 344 $(M)^+$ (diastereomer 1);<br>$R_t$ = 3.44 min; m/z = 344 $(M)^+$ (diastereomer 2). |
| 77A | ethyl 2-(4-chloro-3-methylphenyl)-4,4,4-trifluoro-3-methylbutanoate<br><br>from 4-bromo-1-chloro-2-methylbenzene and ethyl 4,4,4-trifluoro-3-methylbutanoate | GC-MS (Method 1):<br>$R_t$ = 4.81 min; m/z = 308/310 $(M)^+$ (diastereomer 1);<br>$R_t$ = 4.84 min; m/z = 308/310 $(M)^+$ (diastereomer 2). |

Example 78A

Ethyl(3R)-2-(4-ethylphenyl)-4,4,4-trifluoro-3-methylbutanoate (diastereomer mixture)

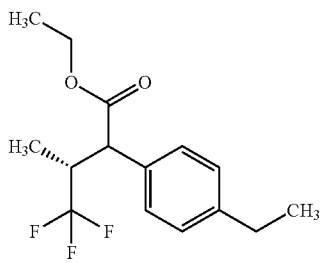 [SMILES: CCOC(=O)C(c1ccc(CC)cc1)[C@@H](C)C(F)(F)F]

24.4 ml (24.4 mmol) of a 1 M solution of lithium hexamethyldisilazide in toluene were cooled to −10° C., and a solution of 3.0 g (16.29 mmol) of (+)-ethyl(3R)-4,4,4-trifluoro-3-methylbutanoate in 15 ml of abs. toluene was added dropwise. The mixture was stirred for 10 min. At −10° C., a solution, prepared beforehand, of 3.92 g (21.18 mmol) of 1-bromo-4-ethylbenzene, 110 mg (0.49 mmol) of palladium (II)acetate and 404 mg (1.03 mmol) of 2′-dicyclohexylphosphino-2-(N,N-dimethylamino)biphenyl in 20 ml of abs. toluene was then added dropwise. The resulting reaction mixture was then stirred first at RT for 1 h and then at 80° C. for 3 h. The mixture was then concentrated under reduced pressure and the residue was taken up in ethyl acetate and added to water. The aqueous phase was re-extracted with ethyl acetate, and the combined organic phases were washed with saturated ammonium chloride solution and saturated sodium chloride solution, dried over magnesium sulphate and concentrated under reduced pressure. The residue gave, after chromatography on silica gel (mobile phase first cyclohexane, then gradient cyclohexane/ethyl acetate 200:1→50:1), 3.051 g of the title compound (64.9% of theory, diastereomer ratio about 3:1).

LC-MS (Method 4): $R_t$=1.52 min; m/z=289 (M+H)$^+$ (minor diastereomer); $R_t$=1.54 min; m/z=289 (M+H)$^+$ (major diastereomer).

$^1$H-NMR (400 MHz, DMSO-$d_6$): major diastereomer: δ [ppm]=0.76 (d, 3H), 1.13 (t, 3H), 1.17 (t, 3H), 2.55-2.63 (m, 2H), 3.21-3.31 (m, 1H), 3.67 (d, 1H), 3.95-4.16 (m, 2H), 7.15-7.23 (m, 2H), 7.25-7.31 (m, 2H).

The following compounds were prepared in a similar manner from (+)-ethyl(3R)-4,4,4-trifluoro-3-methylbutanoate and the appropriate phenyl bromides:

Example 79A

Ethyl(3R)-4,4,4-trifluoro-2-(4-fluorophenyl)-3-methylbutanoate (diastereomer mixture)

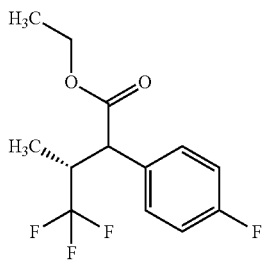 [SMILES: CCOC(=O)C(c1ccc(F)cc1)[C@@H](C)C(F)(F)F]

GC-MS (Method 1): $R_t$=3.63 min; m/z=278 (M)$^+$ (minor diastereomer); $R_t$=3.66 min; m/z=278 (M)$^+$ (major diastereomer).

$^1$H-NMR (400 MHz, DMSO-$d_6$): major diastereomer: δ [ppm]=0.77 (d, 3H), 1.12 (t, 3H), 3.23-3.30 (m, 1H), 3.79 (d, 1H), 4.01-4.14 (m, 2H), 7.19-7.24 (m, 2H), 7.43-7.47 (m, 2H).

Example 80A

Ethyl(3R)-4,4,4-trifluoro-3-methyl-2-(4-vinylphenyl)butanoate (diastereomer mixture)

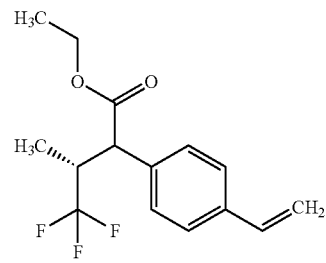 [SMILES: C=Cc1ccc(C(C(=O)OCC)[C@@H](C)C(F)(F)F)cc1]

GC-MS (Method 1): $R_t$=4.64 min and 4.66 min; in each case m/z=286 (M)$^+$.

$^1$H-NMR (400 MHz, DMSO-$d_6$): major diastereomer: δ [ppm]=0.79 (d, 3H), 1.12 (t, 3H), 3.22-3.32 (m, 1H), 3.73 (d, 1H), 3.99-4.17 (m, 2H), 5.28 (d, 1H), 5.84 (d, 1H), 6.72 (dd, 1H), 7.34-7.40 (m, 2H), 7.45-7.51 (m, 2H).

Example 81A

Ethyl(3R)-4,4,4-trifluoro-2-[4-(1-fluorovinyl)phenyl]-3-methylbutanoate (diastereomer mixture)

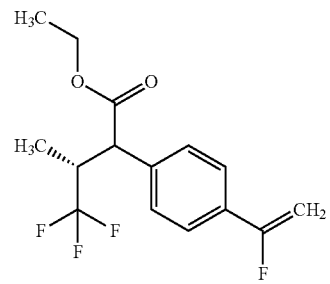 [SMILES: C=C(F)c1ccc(C(C(=O)OCC)[C@@H](C)C(F)(F)F)cc1]

GC-MS (Method 1): $R_t$=4.60 min and 4.63 min; in each case m/z=304 (M)$^+$.

LC-MS (Method 5): $R_t$=1.29 min and 1.30 min; in each case m/z=279.

$^1$H-NMR (400 MHz, DMSO-$d_6$): major diastereomer: δ [ppm]=0.79 (d, 3H), 1.12 (t, 3H), 3.34-3.38 (m, 1H), 3.81 (d, 1H), 3.99-4.17 (m, 2H), 4.97 (dd, 1H), 5.42 (dd, 1H), 7.46-7.49 (m, 2H), 7.63 (d, 2H).

Example 82A

Ethyl(3R)-2-(4-chloro-3-fluorophenyl)-4,4,4-trifluoro-3-methylbutanoate (diastereomer mixture)

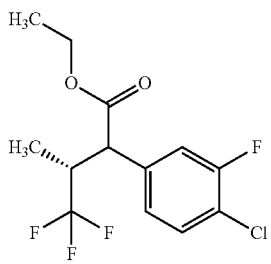 [SMILES: CCOC(=O)C(c1ccc(Cl)c(F)c1)[C@@H](C)C(F)(F)F]

GC-MS (Method 1): $R_t$=4.33 min and 4.36 min; in each case m/z=312 (M)$^+$.

$^1$H-NMR (400 MHz, DMSO-d$_6$): major diastereomer: δ [ppm]=0.80 (d, 3H), 1.08-1.19 (m, 3H), 3.34-3.41 (m, 1H), 3.88 (d, 1H), 4.01-4.18 (m, 2H), 7.28-7.34 (m, 1H), 7.51-7.64 (m, 2H).

Example 83A

Ethyl(3R)-2-(4-chloro-2-fluorophenyl)-4,4,4-trifluoro-3-methylbutanoate (diastereomer mixture)

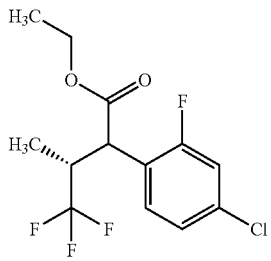

GC-MS (Method 1): $R_t$=4.21 min; m/z=312 (M)$^+$.

Example 84A

Ethyl 2-[4-(bromomethyl)phenyl]-4,4,4-trifluoro-3-methylbutanoate

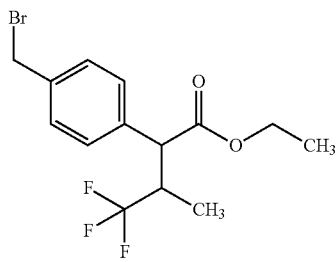 [SMILES: CCOC(=O)C(c1ccc(CBr)cc1)C(C)C(F)(F)F]

2.25 g (8.2 mmol) of ethyl 4,4,4-trifluoro-3-methyl-2-(4-methylphenyl)butanoate, 1.53 g (8.6 mmol) of N-bromosuccinimide and 67 mg (0.41 mmol) of 2,2'-azobis-(2-methylpropanenitrile) in 36 ml of trichloromethane were stirred under reflux overnight. After the reaction had gone to completion, the succinimide was filtered off, the filter residue was washed with dichloromethane and the filtrate was concentrated under reduced pressure. The crude product was purified chromatographically on silica gel (mobile phase cyclohexane/ethyl acetate 40:1). This gave 2.667 g (7.5 mmol, 92% of theory) of a yellowish oil.

GC-MS (Method 1): $R_t$=5.72 min; m/z=373 (M−Br)$^+$ (diastereomer 1); $R_t$=5.74 min; m/z=373 (M−Br)$^+$ (diastereomer 2).

Example 85A

Ethyl 4,4,4-trifluoro-3-methyl-2-[4-(2,2,2-trifluoroethyl)phenyl]butanoate

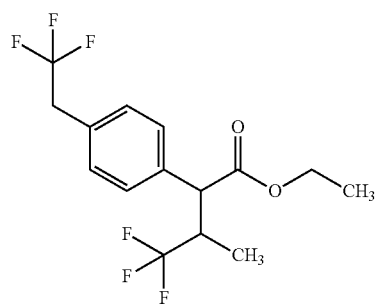 [SMILES: CCOC(=O)C(c1ccc(CC(F)(F)F)cc1)C(C)C(F)(F)F]

529 mg (2.78 mmol) of copper(I) iodide and 4 g (20.82 mmol) of methyl 2,2-difluoro-2-(fluorosulphonyl)acetate were added to 3.77 g (10.67 mmol) of ethyl 2-[4-(bromomethyl)phenyl]-4,4,4-trifluoro-3-methylbutanoate in 40 ml of 1-methylpyrrolidin-2-one, and the mixture was stirred at 80° C. overnight. After the reaction had ended, the reaction solution was slowly poured into 100 ml of ice-water. The mixture obtained was then extracted three times with diethyl ether. The combined organic phases were dried over magnesium sulphate. After filtration, the solvent was removed under reduced pressure. The crude product obtained was purified chromatographically on silica gel (mobile phase cyclohexane/dichloromethane 4:1). This gave 1.48 g (4.32 mmol, 41% of theory) of the title compound as a yellowish oil.

GC-MS (Method 1): $R_t$=4.06 min; m/z=342 (M)$^+$ (diastereomer 1); $R_t$=4.09 min; m/z=342 (M)$^+$ (diastereomer 2).

MS (DCI): m/z=360 (M+NH$_4$)$^+$.

Example 86A

Methyl(4-chlorophenyl)(3-oxocyclopentyl)acetate

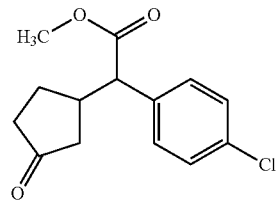 [SMILES: COC(=O)C(c1ccc(Cl)cc1)C1CCC(=O)C1]

Under argon, 14.8 ml (105.6 mmol) of diisopropylamine were initially charged in 150 ml of THF, the mixture was cooled to −30° C. and 42.3 ml (105.75 mmol) of a 2.5 M solution of n-butyllithium in hexane were added slowly. The reaction solution was then warmed to −20° C., 15 g (81.25 mmol) of methyl (4-chlorophenyl)acetate, dissolved in 90 ml of THF, were added slowly and the mixture was stirred at this temperature for 2 h. The reaction solution then cooled to −78° C., and 7.2 ml (86.1 mmol) of 2-cyclopenten-1-one, dissolved in 60 ml of THF, were added slowly. After the addition had ended, the solution was stirred at this temperature for another hour. After TLC (mobile phase cyclohexane/ethyl acetate 9:1), saturated aqueous ammonium chloride solution was added and the product was taken up in ethyl acetate. The aqueous phase was extracted twice with ethyl acetate. The combined organic phases were dried over magnesium sulphate. After filtration, the solvent was removed under reduced pressure. The crude product was purified chromatographically on silica gel (mobile phase cyclohexane/ethyl acetate 4:1). This gave 15.65 g (58.67 mmol, 72% of theory) of the title compound as a yellowish oil.

GC-MS (Method 1): $R_t$=7.02 min; m/z=266 (M)$^+$ (diastereomer 1); $R_t$=7.04 min; m/z=266 (M)$^+$ (diastereomer 2).

MS (DCI): m/z=284 (M+NH$_4$)$^+$.

Example 87A

Methyl (4-chlorophenyl)(3,3-difluorocyclopentyl)acetate

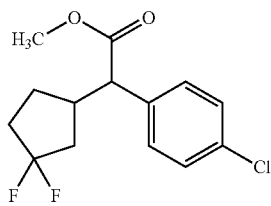 [SMILES: COC(=O)C(c1ccc(Cl)cc1)C1CCC(F)(F)C1]

Under argon, 82.5 ml (82.14 mmol) of a 50% strength solution of 1,1'-[(trifluoro-λ$^4$-sulphanyl)-imino]bis(2-methoxyethane) (Desoxofluor) in THF, diluted with 200 ml of toluene, were initially charged and cooled to 5° C., and 744 µl (5.87 mmol) of a 1 M solution of boron trifluoride/diethyl ether complex were added slowly. The mixture was stirred at 5° C. for 2 h. 15.65 g (58.67 mmol) of methyl (4-chlorophenyl)(3-oxocyclopentyl)acetate, dissolved in 200 ml of toluene, were then added slowly, and the reaction solution was subsequently warmed to 55° C. and stirred at this temperature for 60 h. The reaction mixture was then added to a mixture, cooled to 0° C., consisting of 100 ml of toluene and 100 ml of 2 M aqueous sodium hydroxide solution. The organic phase was separated off, and the aqueous phase was extracted three more times with ethyl acetate. The combined organic phases were dried over sodium sulphate. After filtration, the solvent was removed under reduced pressure. The crude product was purified chromatographically on silica gel (mobile phase cyclohexane/ethyl acetate 7:1). This gave 13.24 g (45.86 mmol, 78% of theory) of the title compound as a colourless oil.

MS (DCI): m/z=306 (M+NH$_4$)$^+$.

GC-MS (Method 1): $R_t$=5.83 min; m/z=288 (M)$^+$ (diastereomer 1); $R_t$=5.86 min; m/z=288 (M)$^+$ (diastereomer 2).

Example 88A (+/−)-Ethyl(2,2-difluorocyclopentyl)acetate

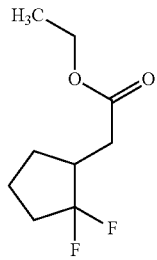

At RT, 17.0 g (99.88 mmol) of (+/−)-ethyl 2-oxocyclopentylacetate were added dropwise to a solution of 52.8 ml (399.5 mmol) of diethylaminosulphur trifluoride (DAST) in 150 ml of abs. dichloromethane. The mixture was heated at reflux overnight. After cooling, a further 13.2 ml (99.88 mmol) of diethylaminosulphur trifluoride (DAST) were added, and the mixture was stirred under reflux for another 36 h. After cooling, the mixture was diluted with dichloromethane, saturated aqueous sodium bicarbonate solution was added carefully and the mixture was then stirred vigorously. The organic phase was washed successively with saturated sodium bicarbonate solution, twice with 1 N hydrochloric acid and with saturated sodium chloride solution, dried over magnesium sulphate and concentrated under reduced pressure. From the dark-brown residue, the product was isolated by column chromatography on silica gel (mobile phase pentane/dichloro-methane 10:1→1:1). This gave 7.52 g (39% of theory) of the title compound.

GC-MS (Method 1): $R_t$=2.88 min; m/z=172.
$^1$H-NMR (400 MHz, DMSO-d$_6$): δ [ppm]=1.18 (t, 3H), 1.33-1.48 (m, 1H), 1.61-1.77 (m, 2H), 1.92-2.20 (m, 3H), 2.24-2.38 (m, 1H), 2.43-2.60 (m, 2H), 4.07 (q, 2H).

Example 89A (+/−)-Ethyl(4-chlorophenyl)(2,2-difluorocyclopentyl)acetate (diastereomer mixture)

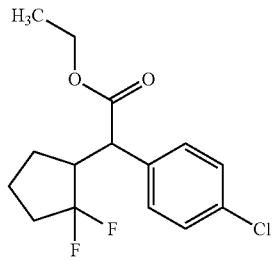 [SMILES: CCOC(=O)C(c1ccc(Cl)cc1)C1CCCC1(F)F]

22.6 ml (22.6 mmol) of a 1 M solution of lithium hexamethyldisilazide in toluene were cooled to −20° C., and a solution of 2.90 g (15.09 mmol) of (+/−)-ethyl(2,2-difluorocyclopentyl)acetate in 20 ml of abs. toluene was added dropwise. The mixture was stirred at −20° C. for 10 min. After cooling had been removed, a solution, prepared beforehand, of 3.75 g (19.61 mmol) of 4-bromochlorobenzene, 110 mg (0.49 mmol) of palladium(II) acetate and 374 mg (0.95 mmol) of 2'-dicyclohexylphosphino-2-(N,N-dimethylamino)biphenyl in 20 ml of abs. toluene was added dropwise. The resulting reaction mixture was stirred first at RT for 1 h and then at 90° C. for 2 h. After cooling, the reaction mixture was added to water. The aqueous phase was extracted three times with ethyl acetate, and the combined organic phases were dried over magnesium sulphate and concentrated under reduced pressure. The residue gave, after chromatography on silica gel (mobile phase cyclohexane/ethyl acetate 50:1), 2.70 g of the title compound (59.1% of theory, diastereomer ratio about 1:4.3).

GC-MS (Method 1): R$_t$=6.09 min and 6.20 min.

$^1$H-NMR (400 MHz, DMSO-d$_6$): δ [ppm]=1.01-1.27 (m, 3H), 1.37-1.50 (m, 1H), 1.51-1.75 (m, 3H), 1.94-2.23 (m, 3H), 2.84-3.07 (m, 1H), 3.55-3.79 (m, 1H), 3.93-4.20 (m, 2H), 7.29-7.53 (m, 4H).

Example 90A (+/−)-(4-Bromophenyl)(cyclopentyl)acetic acid

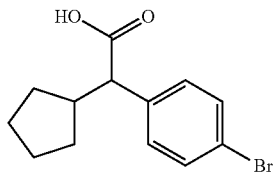 [SMILES: O=C(O)C(c1ccc(Br)cc1)C1CCCC1]

386 ml (96.4 mmol) of 10% strength aqueous sodium hydroxide solution were added to a solution of 30 g (96.4 mmol) of (+/−)-ethyl(4-bromophenyl)(cyclopentyl)acetate in 655 ml of methanol, and the mixture was heated under reflux for 3 h. After cooling, the solution was stirred into 2 liters of water, adjusted to pH 1-2 by addition of dilute hydrochloric acid and extracted with ethyl acetate. The organic phase was dried over magnesium sulphate and concentrated. This gave 27.2 g (92% of theory) of the title compound.

LC-MS (Method 2): R$_t$=2.34 min; m/z=283/285 (M+H)$^+$.

Example 91A (+/−)-(4-Cyanophenyl)(cyclopentyl)acetic acid

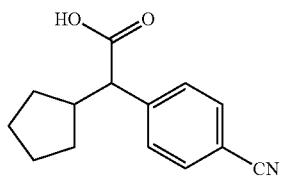 [SMILES: N#Cc1ccc(C(C(=O)O)C2CCCC2)cc1]

316.5 mg (7.9 mmol) of sodium hydroxide were added to a solution of 192.5 mg (0.79 mmol) of (+/−)-methyl(4-cyanophenyl)(cyclopentyl)acetate in 1.7 ml of THF/methanol (1:1), and the mixture was stirred at RT for 3 h. The reaction mixture was then poured into water, neutralized with 1 N hydrochloric acid and extracted with ethyl acetate. The organic phase was dried over magnesium sulphate and concentrated. This gave 125.6 mg (69% of theory) of the title compound.

LC-MS (Method 2): R$_t$=2.11 min; m/z=230 (M+H)$^+$.

Example 92A (+/−)-(4-Nitrophenyl)(cyclopentyl)acetic acid

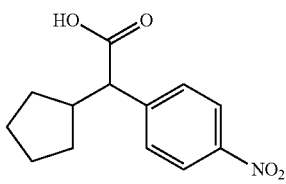 [SMILES: O=C(O)C(c1ccc([N+](=O)[O-])cc1)C1CCCC1]

1.03 g (25.8 mmol) of sodium hydroxide were added to a solution of 715 mg (2.6 mmol) of (+/−)-ethyl (4-nitrophenyl)(cyclopentyl)acetate in 6 ml of THF/methanol (1:1), and the mixture was stirred at RT overnight. The reaction mixture was then poured into water, neutralized with 1 N hydrochloric acid and extracted with ethyl acetate. The organic phase was dried over sodium sulphate and concentrated. The residue was taken up in 80 ml of diethyl ether, and 250 ml of petroleum ether were added. The precipitated solid was filtered off with suction and washed with petroleum ether. The product obtained in this manner was purified further by preparative HPLC. This gave 89.5 mg (14% of theory) of the title compound.

LC-MS (Method 2): R$_t$=2.21 min; m/z=250 (M+H)$^+$.

$^1$H-NMR (400 MHz, DMSO-d$_6$): δ [ppm]=0.86-1.07 (m, 1H), 1.20-1.74 (m, 6H), 1.81-1.96 (m, 1H), 3.49 (d, 1H), 7.63 (d, 2H), 8.20 (d, 2H), 12.58 (br. s, 1H).

Example 93A (+)-(2S)-Cyclopentyl(4-methylphenyl)acetic acid

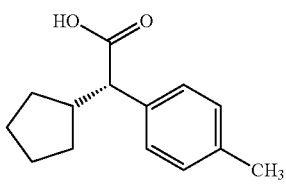 [SMILES: Cc1ccc([C@@H](C(=O)O)C2CCCC2)cc1]

A solution of 1.0 g (2.8 mmol) of (1R,2S,5R)-2-isopropyl-5-methylcyclohexyl(2S)-cyclopentyl-(4-methylphenyl)acetate in 5 ml of 1,2-dichloroethane was stirred at RT with 1.53 ml (11.2 mmol) of iodotrimethylsilane, and the mixture was stirred overnight. The reaction mixture was then diluted with 50 ml of ethyl acetate and washed with water. The organic phase was dried over magnesium sulphate and concentrated. The crude product was purified by preparative HPLC. This gave 539 mg (88% of theory) of the title compound.

LC-MS (Method 5): R$_t$=1.13 min; m/z=217 (M−H)$^−$.

[α]$_D^{20}$=+65.0°, c=0.50, chloroform.

Example 94A (+/−)[4-(Acetoxymethyl)phenyl](cyclopentyl)acetic acid

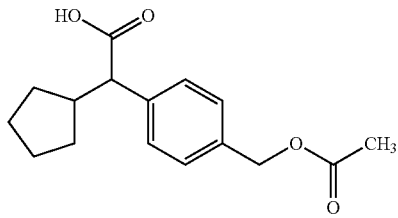 [SMILES: CC(=O)OCc1ccc(C(C(=O)O)C2CCCC2)cc1]

11.70 g (35.19 mmol) of tert-butyl [4-(acetoxymethyl)phenyl](cyclopentyl)acetate were dissolved in 108.5 ml of dichloromethane, the mixture was cooled to 0° C. and 39.2 ml of trifluoroacetic acid were added. The reaction mixture was stirred first at 0° C. for 1.5 h and then at RT for 1.5 h and then concentrated under reduced pressure. The residue was taken up in 50 ml of dichloromethane and the solution was washed four times with in each case 30 ml of water. The organic phase was dried over magnesium sulphate and concentrated under reduced pressure and the residue was dried under high vacuum. This gave 9.83 g of the target compound as a crude product (about 90% pure, yield 91% of theory).

LC-MS (Method 5): $R_t$=1.02 min; m/z=275 (M−H)⁻.

Example 95A (+/−)-(4-Chlorophenyl)(cyclopentyl)acetic acid

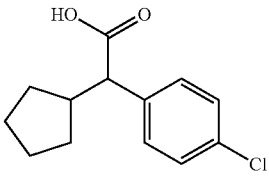 [SMILES: O=C(O)C(c1ccc(Cl)cc1)C1CCCC1]

4.63 g (18.3 mmol) of methyl (4-chlorophenyl)(cyclopentyl)acetate were dissolved in a mixture of 18.5 ml of THF and 18.5 ml of methanol, and 73.3 ml of 10% strength aqueous sodium hydroxide solution (183.2 mmol) were added at RT. The reaction mixture was stirred at RT overnight. The mixture was then acidified by addition of 1 N hydrochloric acid. The aqueous phase was repeatedly extracted with ethyl acetate, and the combined organic phases were washed with saturated sodium chloride solution, dried over sodium sulphate and concentrated under reduced pressure. This gave 4.31 g of the target compound as a crude product (yield 98.6% of theory).

LC-MS (Method 2): $R_t$=2.30 min; m/z=193 (M−CO₂H)⁺.

¹H-NMR (400 MHz, DMSO-d₆): δ [ppm]=0.87-1.03 (m, 1H), 1.17-1.33 (m, 2H), 1.35-1.47 (m, 1H), 1.47-1.69 (m, 3H), 1.77-1.90 (m, 1H), 2.33-2.47 (m, 1H), 3.27 (d, 1H), 7.30-7.42 (m, 4H), 12.36 (s, 1H).

The following carboxylic acids were prepared in an analogous manner:

| Example | Name/Structure/Starting material | Analytical data |
| --- | --- | --- |
| 96A | 2-(4-ethylphenyl)-4,4,4-trifluoro-3-methyl-butanoic acid (racemic diastereomer mixture, about 1:12)<br><br>from ethyl 2-(4-ethylphenyl)-4,4,4-trifluoro-3-methylbutanoate (racemic diastereomer mixture) | GC-MS (Method 1): $R_t$ = 4.82 min; m/z = 260 (M)⁺. ¹H-NMR (400 MHz, DMSO-d₆): major diastereomer: δ [ppm] = 0.76 (d, 3H), 1.17 (t, 3H), 2.59 (q, 2H), 3.16-3.27 (m, 1H), 3.56 (d, 1H), 7.18-7.23 (m, 2H), 7.23-7.30 (m, 2H), 12.65 (br. s, 1H). |
| 97A | (+/−)-cyclopentyl(3,4-dichlorophenyl)acetic acid<br><br>from methyl cyclopentyl(3,4-dichlorophenyl)-acetate | LC-MS (Method 5): $R_t$ = 1.22 min; m/z = 271/273 (M − H)⁻. ¹H-NMR (400 MHz, DMSO-d₆): δ [ppm] = 0.90-1.03 (m, 1H), 1.16-1.35 (m, 2H), 1.37-1.48 (m, 1H), 1.48-1.68 (m, 3H), 1.75-1.89 (m, 1H), 2.34-2.45 (m, 1H), 3.28-3.32 (m, 1H), 7.35 (dd, 1H), 7.54-7.64 (m, 2H), 12.52 (br. s, 1H). |

Example 98A (+/−)-Cyclopentyl[4-(trifluoromethyl)phenyl]acetic acid

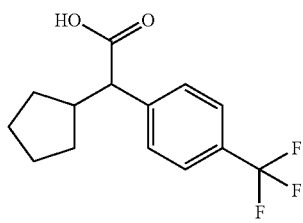 [SMILES: O=C(O)C(c1ccc(C(F)(F)F)cc1)C1CCCC1]

4.98 g (17.4 mmol) of methyl cyclopentyl[4-(trifluoromethyl)phenyl]acetate were initially charged in a mixture of in each case 24.9 ml of THF, methanol and water, and 1.04 g (43.49 mmol) of lithium hydroxide were added at 0° C. The reaction mixture was warmed to RT and stirred at this temperature for 4 h. The mixture was then diluted with water and acidified slightly with 1 N hydrochloric acid. The aqueous phase was extracted three times with ethyl acetate. The combined organic phases were dried over magnesium sulphate and concentrated under reduced pressure. This gave 4.56 g of the target compound as a crude product (yield 96.3% of theory).

LC-MS (Method 5): $R_t$=1.18 min; m/z=227 (M−CO$_2$H)$^-$.
$^1$H-NMR (400 MHz, DMSO-d$_6$): δ [ppm]=0.87-1.03 (m, 1H), 1.20-1.34 (m, 2H), 1.35-1.48 (m, 1H), 1.48-1.69 (m, 3H), 1.80-1.92 (m, 1H), 2.39-2.48 (m, 1H), 3.40 (d, 1H), 7.53-7.61 (m, 2H), 7.65-7.74 (m, 2H), 12.48 (br. s, 1H).

Example 99A (+/−)-Cyclopentyl(4-fluorophenyl)acetic acid

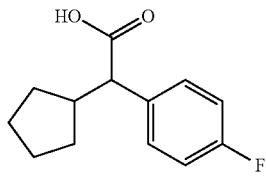 [SMILES: O=C(O)C(c1ccc(F)cc1)C1CCCC1]

2.20 g (about 88% pure, 6.96 mmol) of (+/−)-tert-butyl cyclopentyl(4-fluorophenyl)acetate were dissolved in 2.9 ml of dichloromethane, and 10.7 ml of trifluoroacetic acid were added at RT. The mixture was stirred at RT for 3 h and then concentrated under reduced pressure. The residue was dried under high vacuum overnight. The solid obtained was triturated with acetonitrile and then filtered off with suction and washed with a little acetonitrile. Drying under high vacuum gave 720 mg of a first solids batch. The filtrate obtained above was concentrated and the residue was purified by preparative RP-HPLC (mobile phase acetonitrile/water). This gave a further 529 mg of the target product (overall yield 80.8% of theory).

LC-MS (Method 5): $R_t$=1.08 min; m/z=221 (M−H)$^-$.
$^1$H-NMR (400 MHz, DMSO-d$_6$): δ [ppm]=0.85-1.03 (m, 1H), 1.16-1.33 (m, 2H), 1.35-1.47 (m, 1H), 1.48-1.69 (m, 3H), 1.75-1.90 (m, 1H), 2.35-2.47 (m, 1H), 3.26 (d, 1H), 7.09-7.19 (m, 2H), 7.31-7.41 (m, 2H), 12.30 (s, 1H).

Example 100A (+/−)-(4-Chloro-2-fluorophenyl)(cyclopentyl)acetic acid

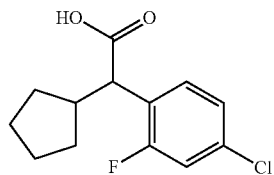 [SMILES: O=C(O)C(c1ccc(Cl)cc1F)C1CCCC1]

7.55 g (27.9 mmol) of methyl (4-chloro-2-fluorophenyl)(cyclopentyl)acetate were dissolved in 32 ml each of THF, methanol and water, and 11.15 g (287.9 mmol) of sodium hydroxide were added with ice cooling. The reaction mixture was stirred at RT overnight and then diluted with water and adjusted to pH 2 with 1 N hydrochloric acid. The aqueous phase was extracted three times with ethyl acetate. The combined organic phases were dried over sodium sulphate and concentrated under reduced pressure. The solid that remained was triturated with water, filtered off with suction and dried thoroughly under reduced pressure. This gave 6.96 g of the target compound (97.2% of theory).

LC-MS (Method 5): $R_t$=1.18 min; m/z=211 (M−CO$_2$H)$^-$.
$^1$H-NMR (400 MHz, DMSO-d$_6$): δ [ppm]=0.86-1.00 (m, 1H), 1.25-1.47 (m, 3H), 1.49-1.65 (m, 3H), 1.80-1.94 (m, 1H), 2.39-2.48 (m, 1H), 3.56 (d, 1H), 7.29 (dd, 1H), 7.41 (dd, 1H), 7.48 (t, 1H), 12.52 (br. s, 1H).

The following carboxylic acids were prepared in an analogous manner:

| Example | Name/Structure/Starting material | Analytical data |
| --- | --- | --- |
| 101A | (+/−)-cyclopentyl(2,4-dichlorophenyl)acetic acid<br><br>from ethyl cyclopentyl(2,4-dichlorophenyl)acetate | LC-MS (Method 5):<br>$R_t$ = 1.22 min; m/z = 271 (M −H)$^-$.<br>$^1$H-NMR (400 MHz, DMSO-d$_6$):<br>δ [ppm] = 0.88-0.98 (m, 1H),<br>1.27-1.36 (m, 2H), 1.39-1.47 (m, 1H), 1.48-1.69 (m, 3H), 1.83-1.93 (m, 1H), 2.42-2.48 (m, 1H), 3.78 (d, 1H), 7.42-7.46 (m, 1H), 7.52-7.56 (m, 1H), 7.60-7.64 (m, 1H), 12.59 (br. s, 1H). |

-continued

| Example | Name/Structure/Starting material | Analytical data |
|---|---|---|
| 102A | (+/-)-cyclopentyl[3-fluoro-4-(trifluoromethyl)-phenyl]acetic acid 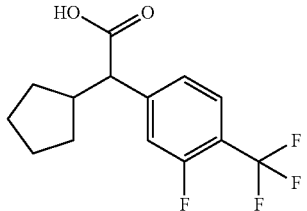 from methyl cyclopentyl[3-fluoro-4-(trifluoromethyl)phenyl]acetate | LC-MS (Method 5): $R_t$ = 1.17 min; m/z = 245 (M − CO$_2$H)$^-$. $^1$H-NMR (400 MHz, DMSO-d$_6$): δ [ppm] = 0.89-1.06 (m, 1H), 1.19-1.36 (m, 2H), 1.37-1.49 (m, 1H), 1.49-1.69 (m, 3H), 1.76-1.92 (m, 1H), 2.38-2.48 (m, 1H), 3.45 (d, 1H), 7.40 (d, 1H), 7.50 (d, 1H), 7.75 (t, 1H), 12.62 (br. s, 1H). |
| 103A | (+/-)-cyclopentyl[4-(trifluoromethoxy)phenyl]-acetic acid 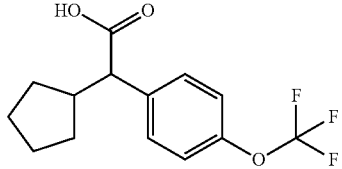 from methyl cyclopentyl[4-(trifluoromethoxy)-phenyl]acetate | LC-MS (Method 5): $R_t$ = 1.18 min; m/z = 287 (M − H)$^-$. $^1$H-NMR (400 MHz, DMSO-d$_6$): δ [ppm] = 0.88-1.02 (m, 1H), 1.20-1.33 (m, 2H), 1.37-1.48 (m, 1H), 1.48-1.69 (m, 3H), 1.78-1.90 (m, 1H), 2.35-2.47 (m, 1H), 3.32 (d, 1H), 7.27-7.35 (m, 2H), 7.42-7.50 (m, 2H), 12.40 (br. s, 1H). |

Example 104A (+)-(2S)-Cyclopentyl(4-ethylphenyl)acetic acid

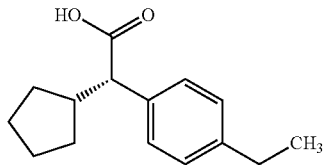 [SMILES: CCc1ccc([C@@H](C(=O)O)C2CCCC2)cc1]

515 mg (1.39 mmol) of (−)-(1R,2S,5R)-2-isopropyl-5-methylcyclohexyl (2S)-cyclopentyl(4-ethylphenyl)acetate in 17 ml trifluoroacetic acid were stirred at RT overnight. The reaction mixture was then concentrated under reduced pressure and the residue was taken up in dichloromethane. The solution was washed with water, dried over sodium sulphate and concentrated under reduced pressure. The crude product obtained was purified by chromatography on silica gel (mobile phase cyclohexane/ethyl acetate 10:1→2:1). This gave 286 mg of the target compound (88.5% of theory).

LC-MS (Method 5): $R_t$=1.17 min; m/z=231 (M−H)$^-$.

$^1$H-NMR (400 MHz, DMSO-d$_6$): δ [ppm]=0.89-1.01 (m, 1H), 1.16 (m, 3H), 1.20-1.33 (m, 2H), 1.36-1.46 (m, 1H), 1.48-1.67 (m, 3H), 1.78-1.88 (m, 1H), 2.37-2.47 (m, 1H), 2.57 (q, 2H), 3.18 (d, 1H), 7.12-7.17 (m, 2H), 7.19-7.25 (m, 2H), 12.17 (br. s, 1H).

$[α]_D^{20}$=+50.4°, c=0.455, chloroform.

Example 105A (+)-(2S,3R)-2-(4-Chlorophenyl)-4,4,4-trifluoro-3-methylbutanoic acid

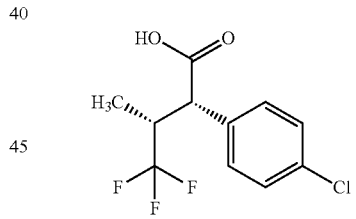

5.086 g (17.26 mmol) of ethyl(3R)-2-(4-chlorophenyl)-4,4,4-trifluoro-3-methylbutanoate were dissolved in 68 ml of dioxane, and 34 ml of 1 N aqueous sodium hydroxide solution were added.

The reaction was stirred at 50° C. for 2 h. The reaction mixture was then acidified with 1 N hydrochloric acid to pH 1 and repeatedly extracted with dichloromethane. The combined organic phases were washed with saturated sodium chloride solution, dried over sodium sulphate and concentrated under reduced pressure. This gave 3.9 g (14.63 mmol, 85% of theory, 83% de) of the target compound.

$^1$H-NMR (400 MHz, DMSO-d$_6$, δ/ppm): 12.95-12.73 (1H, br. s), 7.49-7.34 (4H, m), 3.68 (1H, d), 3.31-3.18 (1H, m), 1.20 (0.25H, d), 0.78 (2.75H, d).

GC-MS (Method 1): $R_t$=4.85 min; m/z=266 (M)$^+$.

$[α]_D^{20}$=+57.2°, c=0.41, methanol.

The compounds listed in the table below were prepared in an analogous manner:

| Example | Name/Structure/Starting material | Analytical data |
|---|---|---|
| 106A | 4,4,4-trifluoro-3-methyl-2-(4-methylphenyl)-butanoic acid<br>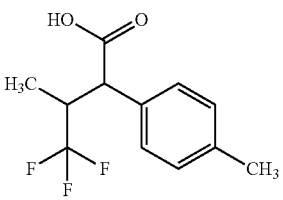<br>from ethyl 4,4,4-trifluoro-3-methyl-2-(4-methyl-phenyl)butanoate | GC-MS (Method 1):<br>$R_t$ = 4.48 min; m/z = 246 (M)$^+$. |
| 107A | (2S,3R)-4,4,4-trifluoro-3-methyl-2-[4-(trifluoromethyl)phenyl]butanoic acid<br>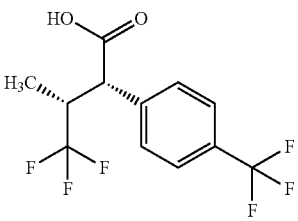<br>from ethyl (2S,3R)-4,4,4-trifluoro-3-methyl-2-[4-(trifluoromethyl)phenyl]butanoate | GC-MS (Method 1):<br>$R_t$ = 3.85 min; m/z = 300 (M)$^+$. |
| 108A | 4,4,4-trifluoro-3-methyl-2-[4-(trifluoromethyl)phenyl]butanoic acid<br>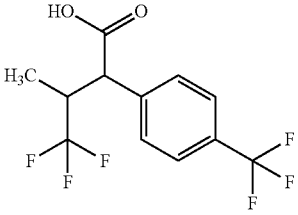<br>from ethyl 4,4,4-trifluoro-3-methyl-2-[4-(trifluoromethyl)phenyl]butanoate | GC-MS (Method 1):<br>$R_t$ = 3.85 min; m/z = 300 (M)$^+$. |
| 109A | (2S,3R)-4,4,4-trifluoro-2-(4-isopropylphenyl)-3-methylbutanoic acid<br>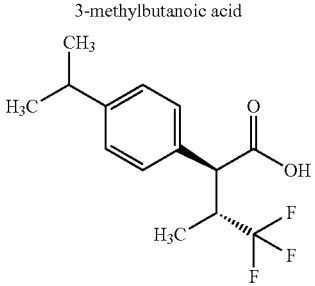<br>from ethyl (3R)-4,4,4-trifluoro-2-(4-isopropylphenyl)-3-methylbutanoate | $^1$H-NMR (400 MHz, DMSO-$d_6$, δ/ppm): 12.56 (1H, br. s), 7.25 (4H, q), 3.56 (1H, d), 3.28-3.16 (1H, m), 2.94-2.81 (1H, m), 1.19 (6H, d), 0.75 (3H, d).<br>GC-MS (Method 1):<br>$R_t$ = 4.93 min; m/z = 274 (M)$^+$. |

-continued

| Example | Name/Structure/Starting material | Analytical data |
|---|---|---|
| 110A | (2S,3R)-2-(4-tert-butylphenyl)-4,4,4-trifluoro-3-methylbutanoic acid<br>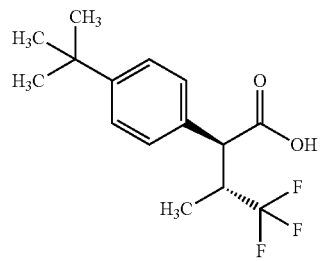<br>from ethyl (2S,3R)-2-(4-tert-butylphenyl)-4,4,4-trifluoro-3-methylbutanoate | GC-MS (Method 1):<br>$R_t$ = 5.15 min; m/z = 288 (M)$^+$. |
| 111A | (2S,3R)-4,4,4-trifluoro-3-methyl-2-[4-(1,1,1-trifluoro-2-methylpropan-2-yl)phenyl]butanoic acid<br>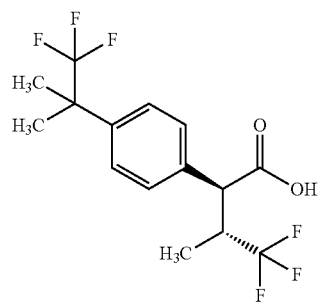<br>from ethyl (2S,3R)-4,4,4-trifluoro-3-methyl-2-[4-(1,1,1-trifluoro-2-methylpropan-2-yl)phenyl]-butanoate | $^1$H-NMR (400 MHz, DMSO-d$_6$, δ/ppm): 12.90-12.40 (1H, br. s), 7.53 (2H, d), 7.40 (2H, d), 3.69 (0.11H, d), 3.64 (0.89H, d), 3.30-3.20 (1H, m), 1.55 (6H, s), 1.21 (0.33H, d), 0.76 (2.67H, d).<br>LC-MS (Method 5):<br>$R_t$ = 1.19 min; m/z = 341 (M − H)$^-$. |
| 112A | 4,4,4-trifluoro-3-methyl-2-[4-(2,2,2-trifluoroethyl)phenyl]butanoic acid<br>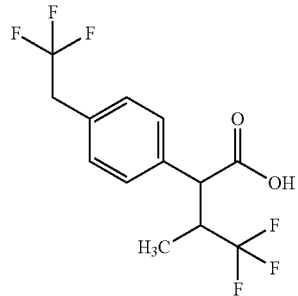<br>from ethyl 4,4,4-trifluoro-3-methyl-2-[4-(2,2,2-trifluoroethyl)phenyl]butanoate | $^1$H-NMR (400 MHz, DMSO-d$_6$, δ/ppm): 12.95-12.59 (1H, br. s), 7.37 (4H, q), 3.70-3.57 (3H, m), 3.30-3.18 (1H, m), 0.76 (3H, d).<br>GC-MS (Method 1):<br>$R_t$ = 4.45 min; m/z = 315 (M + H)$^+$. |

-continued

| Example | Name/Structure/Starting material | Analytical data |
|---|---|---|
| 113A | (4-chlorophenyl)(3,3-difluorocyclopentyl)acetic acid<br>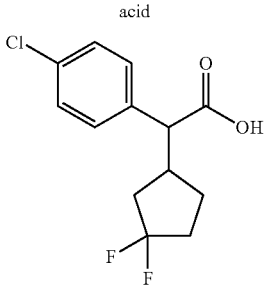<br>from methyl (4-chlorophenyl)(3,3-difluorocyclopentyl)acetate | $^1$H-NMR (400 MHz, DMSO-$d_6$, δ/ppm): 12.59 (1H, br. s), 7.38 (4H, q), 3.51 (0.5H, d), 3.48 (0.5H, d), 2.77-2.60 (1H, m), 2.42-2.27 (0.5H, m), 2.26-1.20 (5.5H, m).<br>GC-MS (Method 1):<br>$R_t$ = 6.33 min; m/z = 274 (M)$^+$ (diastereomer 1);<br>$R_t$ = 6.38 min; m/z = 274 (M)$^+$ (diastereomer 2). |
| 114A | (2S,3R)-2-[4-(1,1-difluoroethyl)phenyl]-4,4,4-trifluoro-3-methylbutanoic acid<br>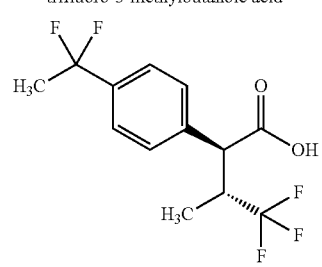<br>from ethyl (3R)-2-[4-(1,1-difluoroethyl)phenyl]-4,4,4-trifluoro-3-methylbutanoate | LC-MS (Method 2):<br>$R_t$ = 2.34 min; m/z = 295 (M − H)$^-$. |
| 115A | (2S,3R)-2-(4-cyclopropylphenyl)-4,4,4-trifluoro-3-methylbutanoic acid<br>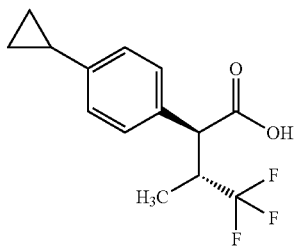<br>from ethyl (3R)-2-(4-cyclopropylphenyl)-4,4,4-trifluoro-3-methylbutanoate | $^1$H-NMR (400 MHz, DMSO-$d_6$, δ/ppm): 12.78-12.52 (1H, br. s), 7.22 (2H, d), 7.05 (2H, d), 3.54 (1H, d), 3.27-3.12 (1H, m), 1.94-1.82 (1H, m), 0.97-0.89 (2H, m), 0.75 (3H, d), 0.69-0.62 (2H, m).<br>GC-MS (Method 1):<br>$R_t$ = 5.51 min; m/z = 273 (M + H)$^+$. |
| 116A | (2S,3R)-2-(4-chloro-3-methoxyphenyl)-4,4,4-trifluoro-3-methylbutanoic acid<br>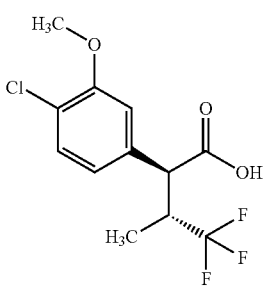<br>from ethyl (3R)-2-(4-chloro-3-methoxyphenyl)-4,4,4-trifluoro-3-methylbutanoate | $^1$H-NMR (400 MHz, DMSO-$d_6$, δ/ppm): 12.91-12.71 (1H, br. s), 7.41 (1H, d), 7.18 (1H, d), 6.98 (1H, dd), 3.86 (3H, s), 3.66 (1H, d), 3.40-3.19 (1H, m), 0.79 (3H, d).<br>LC-MS (Method 2): $R_t$ = 2.20 min; m/z = 295/297 (M − H)$^-$. |

-continued

| Example | Name/Structure/Starting material | Analytical data |
|---|---|---|
| 117A | 2-(4-chlorophenyl)-4,4,4-trifluoro-3-methyl-butanoic acid<br><br>[structure]<br><br>from ethyl 2-(4-chlorophenyl)-4,4,4-trifluoro-3-methylbutanoate | LC-MS (Method 5):<br>$R_t$ = 1.04 min; m/z = 265/267 (M – H)⁻ (diastereomer 1);<br>$R_t$ = 1.06 min; m/z = 265/267 (M – H)⁻ (diastereomer 2). |
| 118A | 4,4,4-trifluoro-3-methyl-2-[4-(trifluoromethoxy)-phenyl]butanoic acid<br><br>[structure]<br><br>from ethyl 4,4,4-trifluoro-3-methyl-2-[4-(trifluoromethoxy)phenyl]butanoate | GC-MS (Method 1):<br>$R_t$ = 3.85 min; m/z = 316 (M)⁺. |
| 119A | 2-(4-chloro-3-methylphenyl)-4,4,4-trifluoro-3-methylbutanoic acid<br><br>[structure]<br><br>from ethyl 2-(4-chloro-3-methylphenyl)-4,4,4-trifluoro-3-methylbutanoate | GC-MS (Method 1):<br>$R_t$ = 5.20 min; m/z = 280/282 (M)⁺ (diastereomer 1);<br>$R_t$ = 5.23 min; m/z = 280/282 (M)⁺ (diastereomer 2). |

Example 120A (3R)-2-(4-Ethylphenyl)-4,4,4-trifluoro-3-methylbutanoic acid (diastereomer mixture)

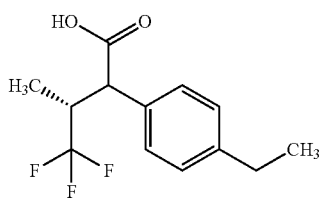 [SMILES: CCc1ccc(C(C(=O)O)[C@@H](C)C(F)(F)F)cc1]

3.0 g of (3R)-ethyl 2-(4-ethylphenyl)-4,4,4-trifluoro-3-methylbutanoate (about 88% pure, about 9.16 mmol; diastereomer mixture) were dissolved in a mixture of 12.4 ml each of methanol, THF and water, and 5.49 g (137.35 mmol) of sodium hydroxide were added a little at a time. The reaction mixture was stirred at 40° C. for 9 h. After cooling, the volatile solvents were substantially removed under reduced pressure, and the residue was diluted with water. The mixture was acidified by addition of hydrochloric acid, and the aqueous phase was extracted three times with ethyl acetate. The combined organic phases were dried over sodium sulphate and concentrated under reduced pressure, and the residue was dried under high vacuum. This gave 2.61 g of the title compound as a crude product which was not purified any further (diastereomer ratio about 9:1).

LC-MS (Method 5): $R_t$=1.08 min; m/z=259 (M–H)⁻ (minor diastereomer); $R_t$=1.11 min; m/z=259 (M–H)⁻ (major diastereomer).

¹H-NMR (400 MHz, DMSO-$d_6$): major diastereomer: δ [ppm]=0.76 (d, 3H), 1.17 (t, 3H), 2.54-2.66 (m, 4H), 3.10-3.29 (m, 1H), 3.56 (d, 1H), 7.14-7.22 (m, 2H), 7.22-7.32 (m, 2H), 12.58 (br. s, 1H).

In a similar manner (reaction temperature: RT to +40° C.; reaction time: 9-12 h), the carboxylic acids below were prepared from the corresponding esters:

Example 121A (3R)-4,4,4-Trifluoro-2-(4-fluorophenyl)-3-methylbutanoic acid (diastereomer mixture)

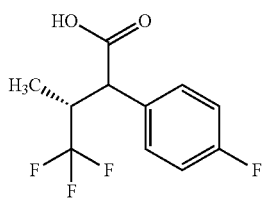 [SMILES: C[C@H](C(C(=O)O)c1ccc(F)cc1)C(F)(F)F]

diastereomer ratio about 9:1.

¹H-NMR (400 MHz, DMSO-d₆): major diastereomer: δ [ppm]=0.77 (d, 3H), 3.18-3.30 (m, 1H), 3.67 (d, 1H), 7.17-7.24 (m, 2H), 7.39-7.47 (m, 2H), 12.78 (br. s, 1H).

Example 122A (3R)-4,4,4-Trifluoro-3-methyl-2-(4-vinylphenyl) butanoic acid (diastereomer mixture)

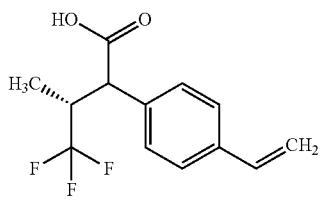 [SMILES: C=Cc1ccc(C(C(=O)O)[C@@H](C)C(F)(F)F)cc1]

diastereomer ratio about 10:1.

LC-MS (Method 5): $R_t$=1.04 min; m/z=257 (M−H)⁻ (minor diastereomer); $R_t$=1.06 min; m/z=257 (M−H)⁻ (major diastereomer).

¹H-NMR (400 MHz, DMSO-d₆): major diastereomer: δ [ppm]=0.78 (d, 3H), 3.18-3.31 (m, 1H), 3.62 (d, 1H), 5.28 (d, 1H), 5.84 (d, 1H), 6.73 (dd, 1H), 7.31-7.39 (m, 2H), 7.40-7.54 (m, 2H), 12.74 (br. s, 1H).

Example 123A (3R)-4,4,4-Trifluoro-2-[4-(1-fluorovinyl)phenyl]-3-methylbutanoic acid (diastereomer mixture)

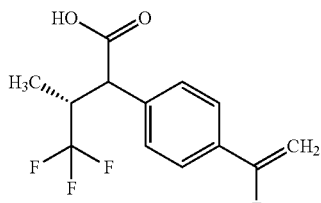

diastereomer ratio about 9:1.

GC-MS (Method 1): $R_t$=4.97 min; m/z=276 (M)⁺.

¹H-NMR (400 MHz, DMSO-d₆): major diastereomer: δ [ppm]=0.78 (d, 3H), 3.16-3.29 (m, 1H), 3.70 (d, 1H), 4.96 (dd, 1H), 5.34 (d, 1H), 5.47 (d, 1H), 7.39-7.51 (m, 2H), 7.58-7.69 (m, 2H), 12.83 (br. s, 1H).

Example 124A (4-Chlorophenyl)(2,2-difluorocyclopentyl)acetic acid (diastereomer mixture)

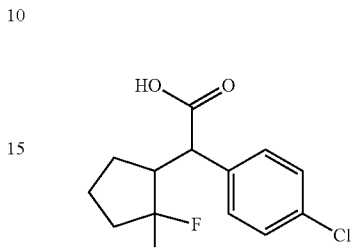

2.70 g (8.92 mmol) of ethyl (4-chlorophenyl)(2,2-difluorocyclopentyl)acetate (diastereomer mixture) were dissolved in 10 ml of methanol, 10 ml of THF and 5 ml of water, and 7.13 g (89.18 mmol) of 50% strength aqueous sodium hydroxide solution were added at RT. The reaction mixture was stirred at RT overnight. The mixture was then diluted with water and acidified with hydrochloric acid. The aqueous phase was extracted three times with ethyl acetate, the combined organic phases were dried over magnesium sulphate and concentrated under reduced pressure and the residue was dried under high vacuum. This gave 2.39 g of the target compound (97.6% of theory, diastereomer ratio about 1:1).

LC-MS (Method 5): $R_t$=1.05 min and 1.07 min; in each case m/z=273 (M−H)⁻.

In a similar manner, the carboxylic acids below were prepared from the corresponding esters:

Example 125A (3R)-2-(4-Chloro-3-fluorophenyl)-4,4,4-trifluoro-3-methylbutanoic acid (diastereomer mixture)

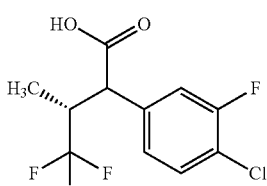

diastereomer ratio about 1:1.

GC-MS (Method 1): $R_t$=4.79 min; m/z=284 (M)⁺.

¹H-NMR (400 MHz, DMSO-d₆): both diastereomers: δ [ppm]=0.80/1.19 (in each case d, 3H), 3.18-3.29 (m, 1H), 3.74/3.77 (in each case dd, 1H), 7.28 (d, 1H), 7.43-7.65 (m, 2H), 12.91/13.24 (in each case br. s, 1H).

Example 126A (3R)-2-(4-Chloro-2-fluorophenyl)-4,4,4-trifluoro-3-methylbutanoic acid (diastereomer mixture)

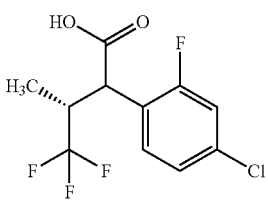 [SMILES: C[C@H](C(C(=O)O)c1ccc(Cl)cc1F)C(F)(F)F]

LC-MS (Method 4): $R_t$=1.25 min; m/z=283 (M–H)$^-$.

$^1$H-NMR (400 MHz, DMSO-$d_6$): major diastereomer: δ [ppm]=0.87 (d, 3H), 3.27-3.37 (m, 1H), 4.02 (d, 1H), 7.35 (dd, 1H), 7.45-7.52 (m, 2H), 13.02 (br. s, 1H).

Example 127A tert-Butyl 1-(3-{[(2S)-2-cyclopentyl-2-(4-methylphenyl)acetyl]amino}benzyl)cyclopropane-carboxylate

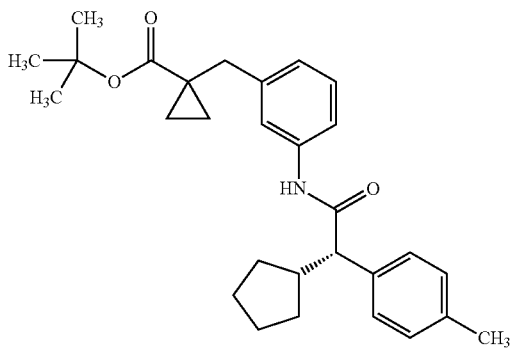 [SMILES: Cc1ccc([C@@H](C(=O)Nc2cccc(CC3(C(=O)OC(C)(C)C)CC3)c2)C2CCCC2)cc1]

At RT, 453 mg (1191 μmol) of HATU and 479 μl (2750 μmol) of N,N-diisopropylethylamine were added to a solution of 200 mg (916 μmol) of (+)-(2S)-cyclopentyl(4-methylphenyl)acetic acid in 1 ml of DMF. The mixture was stirred for 30 min. 249 mg (1008 μmol) of tert-butyl 1-(3-aminobenzyl)cyclopropanecarboxylate were then added. The reaction mixture was stirred overnight and then directly separated into its components by preparative HPLC. This gave 328 mg (80% of theory) of the title compound.

LC-MS (Method 5): $R_t$=1.49 min; m/z=448 (M+H)$^+$.

$^1$H-NMR (400 MHz, DMSO-$d_6$): δ [ppm]=0.74-0.85 (m, 2H), 0.89-1.01 (m, 1H), 1.01-1.10 (m, 2H), 1.14-1.69 (m, 15H), 1.70-1.87 (m, 1H), 2.25 (s, 3H), 2.78 (s, 2H), 6.89 (d, 1H), 7.04-7.20 (m, 3H), 7.25-7.32 (m, 2H), 7.36 (d, 1H), 7.50 (s, 1H), 9.91 (s, 1H).

Example 128A (+/−)-tert-butyl 1-[3-({[4-(acetoxymethyl)phenyl](cyclopentyl)acetyl}amino)benzyl]cyclopropane-carboxylate

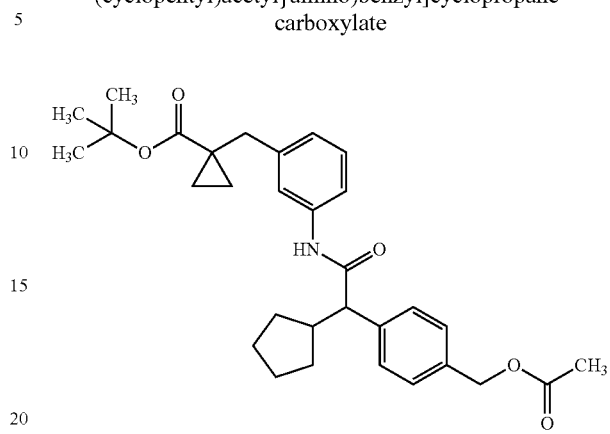

9.50 g (34.4 mmol) of (+/−)-[4-(acetoxymethyl)phenyl](cyclopentyl)acetic acid were dissolved in 67.5 ml of DMF, and 5.58 g (41.25 mmol) of 1-hydroxy-1H-benzotriazole hydrate (HOBt) were added. The mixture was cooled to 0° C., and 15.0 ml (85.95 mmol) of N,N-diisopropylethylamine and 10.63 g (42.97 mmol) of tert-butyl 1-(3-aminobenzyl)cyclopropanecarboxylate, dissolved in a little DMF, were added. 14.38 g (37.82 mmol) of HATU were then added in several portions, and the reaction mixture was slowly warmed to RT and then stirred overnight. The mixture was then added to saturated aqueous sodium carbonate solution. After phase separation, the aqueous phase was extracted repeatedly with ethyl acetate, and the combined organic phases were washed with saturated sodium chloride solution, dried over sodium sulphate and concentrated under reduced pressure. The crude product was purified by chromatography on silica gel (mobile phase dichloromethane/ethyl acetate 50:1→20:1). This gave 12.86 g of the target compound (69.4% of theory).

LC-MS (Method 5): $R_t$=1.40 min; m/z=450 (M–C$_4$H$_7$)$^+$.

$^1$H-NMR (400 MHz, DMSO-$d_6$): δ [ppm]=0.77-0.83 (m, 2H), 0.91-1.02 (m, 1H), 1.03-1.08 (m, 2H), 1.21-1.29 (m, 1H), 1.26 (s, 9H), 1.32-1.40 (m, 1H), 1.41-1.70 (m, 4H), 1.72-1.84 (m, 1H), 2.04 (s, 3H), 2.55-2.65 (m, 1H), 2.78 (s, 2H), 3.39 (d, 1H), 5.02 (s, 2H), 6.89 (d, 1H), 7.15 (t, 1H), 7.27-7.33 (m, 2H), 7.35 (d, 1H), 7.38-7.43 (m, 2H), 7.50 (s, 1H), 9.96 (s, 1H).

Example 129A (+/−)-tert-butyl 1-[3-({cyclopentyl[4-(hydroxymethyl)phenyl]acetyl}amino)benzyl]cyclopropane-carboxylate

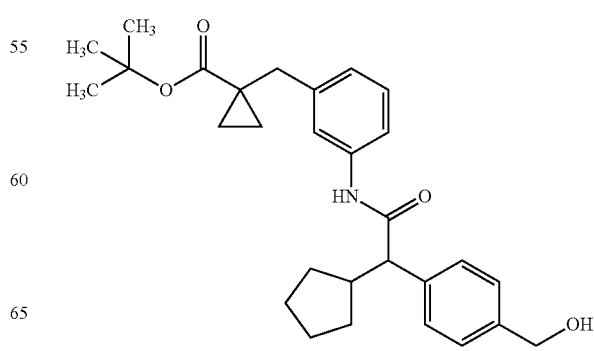

12.50 g (24.72 mmol) of (+/−)-tert-butyl 1-[3-({[4-(acetoxymethyl)phenyl](cyclopentyl)acetyl}-amino)benzyl]cyclopropanecarboxylate were dissolved in 228 ml of a 2 M solution of ammonia in methanol and stirred at 30° C. for 2 h, then at 40° C. for 2 h and finally at RT overnight. The solution was then concentrated under reduced pressure and the residue was purified by chromatography on silica gel (mobile phase cyclohexane/ethyl acetate 10:1→2:1). This gave 11.88 g (96.5% of theory) of the target compound.

LC-MS (Method 4): $R_t$=1.47 min; m/z=462 (M−H)⁻.

¹H-NMR (400 MHz, DMSO-$d_6$): δ [ppm]=0.77-0.83 (m, 2H), 0.92-1.03 (m, 1H), 1.03-1.09 (m, 2H), 1.21-1.28 (m, 1H), 1.27 (s, 9H), 1.30-1.40 (m, 1H), 1.41-1.69 (m, 4H), 1.73-1.83 (m, 1H), 2.54-2.65 (m, 1H), 2.78 (s, 2H), 3.36 (d, 1H), 4.44 (d, 2H), 5.10 (t, 1H), 6.89 (d, 1H), 7.15 (t, 1H), 7.24 (d, 2H), 7.35 (d, 3H), 7.50 (s, 1H), 9.93 (s, 1H).

Example 130A (+/−)-tert-Butyl 1-(3-{[cyclopentyl(4-formylphenyl)acetyl]amino}benzyl)cyclopropanecarboxylate

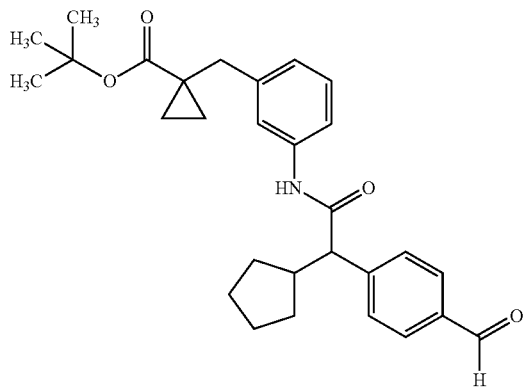 [SMILES: CC(C)(C)OC(=O)C1(Cc2cccc(NC(=O)C(c3ccc(C=O)cc3)C3CCCC3)c2)CC1]

A solution of 4.0 g (8.63 mmol) of (+/−)-tert-butyl 1-[3-({cyclopentyl[4-(hydroxymethyl)phenyl]-acetyl}amino)benzyl]cyclopropanecarboxylate in 20 ml of dichloromethane was cooled to 0° C., and 4.39 g (10.35 mmol) of Dess-Martin reagent [1,1,1-triacetoxy-1,1-dihydro-1,2-benziodoxol-3(1H)-one] were added. After the addition had ended, cooling was removed and the reaction mixture was stirred at RT for 3 h. The solution was then diluted with dichloromethane and washed successively with water, saturated sodium carbonate solution and saturated sodium chloride solution. The organic phase was dried with magnesium sulphate and concentrated under reduced pressure. The crude product was purified by chromatography on silica gel (mobile phase cyclohexane/ethyl acetate 50:1→3:1). This gave 2.27 g of the target compound (53.2% of theory).

LC-MS (Method 2): $R_t$=2.86 min; m/z=460 (M−H)⁻.

¹H-NMR (400 MHz, DMSO-$d_6$): δ [ppm]=0.78-0.84 (m, 2H), 0.92-1.02 (m, 1H), 1.03-1.08 (m, 2H), 1.26 (s, 9H), 1.27-1.39 (m, 2H), 1.42-1.51 (m, 1H), 1.51-1.70 (m, 3H), 1.76-1.86 (m, 1H), 2.58-2.68 (m, 1H), 2.78 (s, 2H), 3.53 (d, 1H), 6.91 (d, 1H), 7.16 (t, 1H), 7.36 (d, 1H), 7.51 (s, 1H), 7.60-7.68 (m, 2H), 7.82-7.90 (m, 2H), 9.97 (s, 1H), 10.06 (s, 1H).

Example 131A (+/−)-tert-Butyl 1-(3-{[cyclopentyl(4-vinylphenyl)acetyl]amino}benzyl)cyclopropanecarboxylate

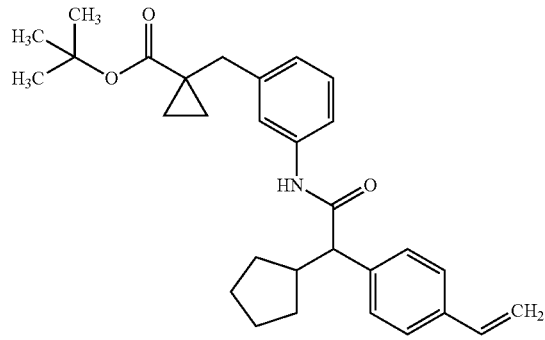 [SMILES: C=Cc1ccc(C(C(=O)Nc2cccc(CC3(C(=O)OC(C)(C)C)CC3)c2)C2CCCC2)cc1]

39.0 mg (0.98 mmol, 60% in mineral oil) of sodium hydride were suspended in 3.0 ml of abs. THF, the mixture was cooled to 0° C. and 301.8 mg (0.84 mmol) of methyltriphenylphosphonium bromide were added. The mixture was stirred at 0° C. for 30 min, and 300 mg (0.65 mmol) of (+/−)-tert-butyl 1-(3-{[cyclopentyl(4-formylphenyl)acetyl]amino}benzyl)cyclopropanecarboxylate were then added. The reaction mixture was stirred at RT overnight and then concentrated under reduced pressure. The residue was taken up in acetonitrile and filtered, and the filtrate obtained was purified by preparative RP-HPLC (mobile phase acetonitrile/water). This gave 219.3 mg (73.4% of theory) of the target compound.

LC-MS (Method 5): $R_t$=1.52 min; m/z=460 (M+H)⁺.

¹H-NMR (400 MHz, DMSO-$d_6$): δ [ppm]=0.80 (d, 2H), 0.92-1.02 (m, 1H), 1.06 (d, 2H), 1.22-1.29 (m, 1H), 1.26 (s, 9H), 1.32-1.49 (m, 2H), 1.49-1.71 (m, 3H), 1.74-1.83 (m, 1H), 2.56-2.67 (m, 1H), 2.78 (s, 2H), 3.38 (d, 1H), 5.22 (d, 1H), 5.78 (d, 1H), 6.70 (dd, 1H), 6.89 (d, 1H), 7.15 (t, 1H), 7.29-7.46 (m, 5H), 7.50 (s, 1H), 9.96 (s, 1H).

Example 132A (+/−)-tert-Butyl 1-[3-({cyclopentyl[4-(2,2-difluorovinyl)phenyl]acetyl}amino)benzyl]cyclopropanecarboxylate

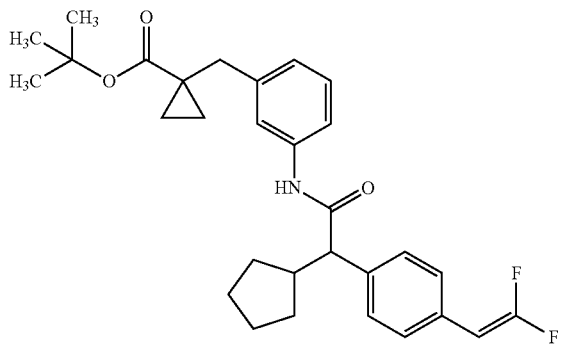 [SMILES: CC(C)(C)OC(=O)C1(Cc2cccc(NC(=O)C(c3ccc(C=C(F)F)cc3)C3CCCC3)c2)CC1]

At 60° C., 475.6 mg (3.12 mmol) of sodium chloro(difluoro)acetate were added to a mixture of 800.0 mg (1.73 mmol) of (+/−)-tert-butyl 1-(3-{[cyclopentyl(4-formylphenyl)acetyl]-amino}benzyl)cyclopropanecarboxylate and 681.9 mg (2.60 mmol) of triphenylphosphine. The mixture was heated to 110° C. and stirred at this temperature for 30 min. After cooling, the mixture was poured into water. Ethyl acetate was added, and the organic phase was separated off, washed with saturated sodium chloride solution, dried with magnesium sulphate and concentrated under reduced pressure. The crude product was purified by preparative RP-HPLC (mobile phase acetonitrile/water). This gave 319.2 mg (37.2% of theory) of the target compound.

LC-MS (Method 5): $R_t$=1.53 min; m/z=494 (M–H)⁻.

¹H-NMR (400 MHz, DMSO-$d_6$): δ [ppm]=0.76-0.85 (m, 2H), 0.92-1.03 (m, 1H), 1.03-1.09 (m, 2H), 1.19-1.26 (m, 1H), 1.26 (s, 9H), 1.32-1.41 (m, 1H), 1.41-1.69 (m, 4H), 1.74-1.84 (m, 1H), 2.57-2.64 (m, 1H), 2.78 (s, 2H), 3.38 (d, 1H), 6.90 (d, 1H), 7.15 (t, 1H), 7.28-7.33 (m, 2H), 7.36 (d, 1H), 7.38-7.45 (m, 2H), 7.50 (s, 1H), 9.97 (s, 1H).

Example 133A (+/−)-tert-Butyl 1-[3-({cyclopentyl[4-(2,2-difluoroethyl)phenyl]acetyl}amino)benzyl]cyclopropanecarboxylate

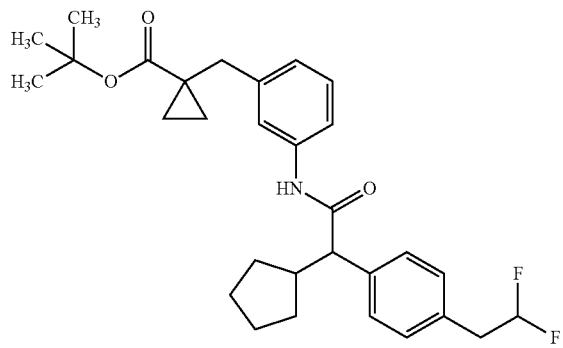 [SMILES: CC(C)(C)OC(=O)C1(Cc2cccc(NC(=O)C(c3ccc(CC(F)F)cc3)C3CCCC3)c2)CC1]

100 mg of Pd/C (10%) were added to a solution of 200.0 mg (0.404 mmol) of (+/−)-tert-butyl 1-[3-({cyclopentyl[4-(2,2-difluorovinyl)phenyl]acetyl}amino)benzyl]cyclopropanecarboxylate in 5 ml of ethanol. Under atmospheric pressure, the mixture was stirred vigorously under an atmosphere of hydrogen overnight. The reaction was then filtered off through Celite and the filtrate was concentrated under reduced pressure. The crude product was purified by preparative RP-HPLC (mobile phase acetonitrile/water). This gave 151.1 mg (75.2% of theory) of the target compound.

LC-MS (Method 5): $R_t$=1.43 min; m/z=498 (M+H)⁺.

¹H-NMR (400 MHz, DMSO-$d_6$): δ [ppm]=0.77-0.83 (m, 2H), 0.91-1.02 (m, 1H), 1.02-1.08 (m, 2H), 1.23-1.29 (m, 1H), 1.26 (s, 9H), 1.30-1.39 (m, 1H), 1.40-1.70 (m, 4H), 1.74-1.84 (m, 1H), 2.55-2.64 (m, 1H), 2.78 (s, 2H), 3.12 (td, 2H), 3.38 (d, 1H), 6.20 (dt, 1H), 6.89 (d, 1H), 7.15 (t, 1H), 7.23 (d, 2H), 7.32-7.41 (m, 3H), 7.51 (s, 1H), 9.95 (s, 1H).

Example 134A (+/−)-tert-Butyl 1-[3-({cyclopentyl[4-(trifluoromethyl)phenyl]acetyl}amino)benzyl]cyclopropanecarboxylate

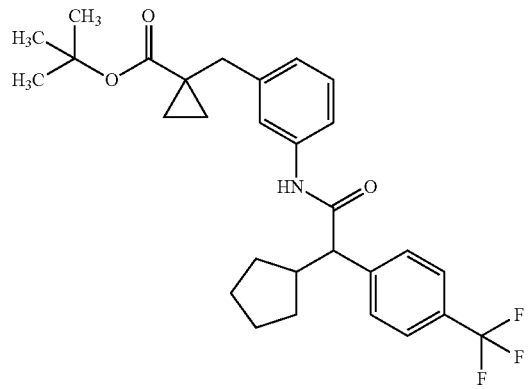 [SMILES: CC(C)(C)OC(=O)C1(Cc2cccc(NC(=O)C(c3ccc(C(F)(F)F)cc3)C3CCCC3)c2)CC1]

3.0 g (11.02 mmol) of (+/−)-cyclopentyl[4-(trifluoromethyl)phenyl]acetic acid were dissolved in 16.0 ml of DMF, and 1.79 g (13.22 mmol) of 1-hydroxy-1H-benzotriazole hydrate were added. The mixture was cooled to 0° C., and 3.8 ml (22.04 mmol) of N,N-diisopropylethylamine and 3.41 g (13.77 mmol) of tert-butyl 1-(3-aminobenzyl)cyclopropanecarboxylate, dissolved in a little DMF, were added. 5.03 g (13.22 mmol) of HATU were then added in several portions, and the reaction mixture was slowly warmed to RT and then stirred at RT for 3 h. The reaction was then added to water. After phase separation, the aqueous phase was extracted three times with ethyl acetate, and the combined organic phases were washed with saturated sodium chloride solution, dried over magnesium sulphate and concentrated under reduced pressure. The crude product was purified by chromatography on silica gel (mobile phase cyclohexane/ethyl acetate 20:1→10:1). This gave 4.89 g of the target compound (88.5% of theory).

LC-MS (Method 5): $R_t$=1.49 min; m/z=502 (M+H)⁺.

¹H-NMR (400 MHz, DMSO-$d_6$): δ [ppm]=0.77-0.83 (m, 2H), 0.92-1.00 (m, 1H), 1.03-1.08 (m, 2H), 1.25 (s, 9H), 1.26-1.40 (m, 2H), 1.43-1.50 (m, 1H), 1.50-1.72 (m, 3H), 1.75-1.86 (m, 1H), 2.56-2.72 (m, 1H), 2.78 (s, 2H), 3.52 (d, 1H), 6.91 (d, 1H), 7.17 (t, 1H), 7.33-7.39 (m, 1H), 7.50 (s, 1H), 7.61-7.66 (m, 2H), 7.66-7.73 (m, 2H), 10.06 (s, 1H).

Example 135A (+/−)-tert-Butyl 1-(3-{[(4-chlorophenyl)(cyclopentyl)acetyl]amino}benzyl)cyclopropane-carboxylate

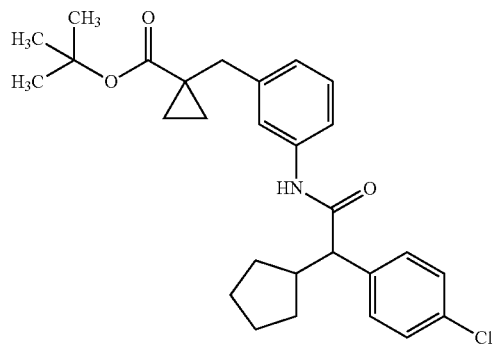 [SMILES: CC(C)(C)OC(=O)C1(Cc2cccc(NC(=O)C(c3ccc(Cl)cc3)C3CCCC3)c2)CC1]

3.50 g (14.66 mmol) of (+/−)-cyclopentyl(4-chlorophenyl)acetic acid were dissolved in 28.8 ml of DMF, and 2.38 g (17.6 mmol) of 1-hydroxy-1H-benzotriazole hydrate were added. The mixture was cooled to 0° C., and 10.2 ml (58.65 mmol) of N,N-diisopropylethylamine and 4.98 g (91% pure, 18.33 mmol) of tert-butyl 1-(3-aminobenzyl)cyclopropanecarboxylate, dissolved in a little DMF, were added. 6.13 g (16.13 mmol) of HATU were then added in several portions, and the reaction mixture was stirred at 0° C. for 30 min, then slowly warmed to RT and stirred at this temperature for another 3 h. The reaction was then added to saturated aqueous sodium carbonate solution. After phase separation, the aqueous phase was extracted repeatedly with ethyl acetate, and the combined organic phases were washed with saturated sodium chloride solution, dried over sodium sulphate and concentrated under reduced pressure. The crude product was purified by chromatography on silica gel (mobile phase dichloromethane/ethyl acetate 10:1→8:1). This gave 6.63 g of the target compound (96.6% of theory).

LC-MS (Method 4): $R_t$=1.73 min; m/z=412 (M−$C_4H_8$)$^+$.

$^1$H-NMR (400 MHz, DMSO-$d_6$): δ [ppm]=0.77-0.83 (m, 2H), 0.91-1.01 (m, 1H), 1.01-1.08 (m, 2H), 1.21-1.29 (m, 1H), 1.26 (s, 9H), 1.32-1.40 (m, 1H), 1.40-1.70 (m, 4H), 1.70-1.84 (m, 1H), 2.55-2.60 (m, 1H), 2.78 (s, 2H), 3.40 (d, 1H), 6.87-6.93 (m, 1H), 7.16 (t, 1H), 7.30-7.46 (m, 5H), 7.50 (s, 1H), 9.99 (s, 1H).

General Procedure 6: HATU-mediated Amide Coupling of Substituted Phenylacetic Acid Derivatives with Anilines At 0° C. or RT, HATU (1.0 to 2.0 eq.) was added to a solution of the phenylacetic acid derivative in question (about 0.8 to 2.0 eq., 0.15 to 1.5 mol/l) and an aniline (about 0.8 to 2.0 eq., 0.15 to 1.5 mol/l) in a mixture of DMF and pyridine (mixing ratio about 3:1 to 1.5:1). Alternatively, instead of pyridine, it is also possible to use N,N-diisopropylethylamine (2.0 to 5.0 eq.), optionally in the presence of HOBt (1.0 to 2.0 eq.). The resulting mixture was stirred at temperatures of from RT to 60° C. for 4 h to 48 h. If appropriate, a further portion of the aniline or of the phenylacetic acid together with HATU was added after 24 h. After the reaction had ended, the crude product was, after removal of the solvent under reduced pressure, purified by preparative RP-HPLC (mobile phase: acetonitrile/water gradient) or alternatively, after aqueous work-up of the reaction mixture, purified by chromatography on silica gel (mobile phase: cyclohexane/ethyl acetate or dichloromethane/methanol mixtures). It is also possible to use a combination of the two purification methods to obtain the target product in pure form.

The following compounds were prepared according to General Procedure 6:

| Example | Name/Structure/Starting materials | Analytical data |
|---|---|---|
| 136A | (+/−)-tert-butyl 1-(3-{[cyclopentyl(4-bromophenyl)acetyl]amino}-4-fluorobenzyl)cyclopropanecarboxylate | LC-MS (Method 5): $R_t$ = 1.56 min; m/z = 547/549 (M + $NH_4$)$^+$. $^1$H-NMR (400 MHz, DMSO-$d_6$): δ [ppm] = 0.80 (q, 2H), 0.89-1.00 (m, 1H), 1.01-1.06 (m, 2H), 1.22-1.72 (m, 15H), 1.72-1.88 (m, 1H), 2.77 (s, 2H), 3.60 (s, 1H), 6.90-7.03 (m, 1H), 7.11 (dd, 1H), 7.37 (d, 2H), 7.51 (d, 2H), 7.68 (dd, 1H), 9.81 (s, 1H). |
| 137A | (+/−)-tert-butyl 1-(3-{[cyclopentyl(3,4-dichlorophenyl)acetyl]amino}benzyl)cyclopropanecarboxylate<br><br>from tert-butyl 1-(3-aminobenzyl)cyclopropanecarboxylate and (+/−)-cyclopentyl(3,4-dichlorophenyl)acetic acid | LC-MS (Method 5): $R_t$ = 1.55 min; m/z = 446 (M − $C_4H_8$)$^+$. $^1$H-NMR (400 MHz, DMSO-$d_6$): δ [ppm] = 0.79-0.84 (m, 2H), 0.94-1.02 (m, 1H), 1.02-1.08 (m, 2H), 1.21-1.30 (m, 1H), 1.26 (s, 9H), 1.31-1.43 (m, 1H), 1.43-1.68 (m, 4H), 1.70-1.84 (m, 1H), 2.50-2.60 (m, 1H), 2.78 (s, 2H), 3.42 (d, 1H), 6.92 (d, 1H), 7.17 (t, 1H), 7.29-7.42 (m, 2H), 7.50 (s, 1H), 7.57-7.65 (m, 2H), 10.04 (s, 1H). |

-continued

| Example | Name/Structure/Starting materials | Analytical data |
|---|---|---|
| 138A | (+/-)-tert-butyl 1-(3-{[(4-chloro-2-fluorophenyl)(cyclopentyl)acetyl]amino}benzyl)-cyclopropanecarboxylate<br><br>from tert-butyl 1-(3-aminobenzyl)cyclopropanecarboxylate and (+/-)-(4-chloro-2-fluorophenyl)(cyclopentyl)acetic acid | LC-MS (Method 5): $R_t$ = 1.52 min; m/z = 486 (M + H)$^+$.<br>$^1$H-NMR (400 MHz, DMSO-$d_6$): δ [ppm] = 0.78-0.84 (m, 2H), 0.95-1.02 (m, 1H), 1.03-1.09 (m, 2H), 1.26 (s, 9H), 1.30-1.60 (m, 5H), 1.61-1.79 (m, 2H), 2.48-2.57 (m, 1H), 2.78 (s, 2H), 3.77 (d, 1H), 6.92 (d, 1H), 7.17 (t, 1H), 7.29 (dd, 1H), 7.34-7.43 (m, 2H), 7.52 (s, 1H), 7.70 (t, 1H), 10.12 (s, 1H). |
| 139A | (+/-)-tert-butyl 1-(3-{[cyclopentyl(2,4-dichlorophenyl)acetyl]amino}benzyl)-cyclopropanecarboxylate<br><br>from tert-butyl 1-(3-aminobenzyl)cyclopropanecarboxylate and (+/-)-cyclopentyl(2,4-dichlorophenyl)acetic acid | LC-MS (Method 5): $R_t$ = 1.56 min; m/z = 446 (M − $C_4H_8$)$^+$.<br>$^1$H-NMR (400 MHz, DMSO-$d_6$): δ [ppm] = 0.77-0.83 (m, 2H), 0.95-1.02 (m, 1H), 1.04-1.10 (m, 2H), 1.26 (s, 9H), 1.38-1.63 (m, 5H), 1.64-1.79 (m, 2H), 2.51-2.57 (m, 1H, obscured), 2.79 (s, 2H), 3.96 (d, 1H), 6.92 (d, 1H), 7.17 (t, 1H), 7.40 (d, 1H), 7.44 (dd, 1H), 7.51 (s, 1H), 7.58 (d, 1H), 7.78 (d, 1H), 10.09 (s, 1H). |
| 140A | (+/-)-tert-butyl 1-[3-({cyclopentyl[3-fluoro-4-(trifluoromethyl)phenyl]acetyl}amino)benzyl]-cyclopropanecarboxylate<br><br>from tert-butyl 1-(3-aminobenzyl)cyclopropanecarboxylate and (+/-)-cyclopentyl[3-fluoro-4-(trifluoromethyl)phenyl]acetic acid | LC-MS (Method 5): $R_t$ = 1.51 min; m/z = 520 (M + H)$^+$.<br>$^1$H-NMR (400 MHz, DMSO-$d_6$) : δ [ppm] = 0.78-0.84 (m, 2H), 0.94-1.02 (m, 1H), 1.02-1.08 (m, 2H), 1.25 (s, 9H), 1.26-1.34 (m, 1H), 1.34-1.43 (m, 1H), 1.44-1.70 (m, 4H), 1.75-1.83 (m, 1H), 2.55-2.65 (m, 1H), 2.78 (s, 2H), 3.54 (d, 1H), 6.92 (d, 1H), 7.17 (t, 1H), 7.35 (d, 1H), 7.43 (d, 1H), 7.48-7.56 (m, 2H), 7.75 (t, 1H), 10.10 (s, 1H). |

| Example | Name/Structure/Starting materials | Analytical data |
|---|---|---|
| 141A | (+/−)-tert-butyl 1-[3-({cyclopentyl[4-(trifluoromethoxy)phenyl]acetyl}amino)benzyl]-cyclopropanecarboxylate<br>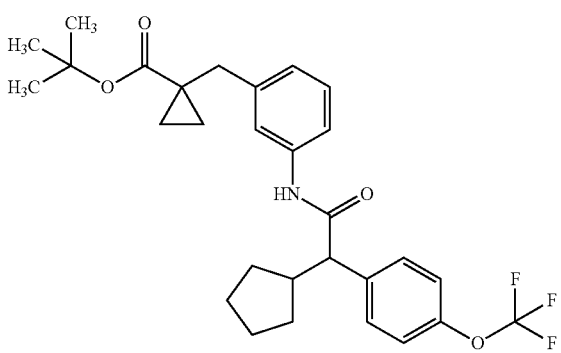<br>from tert-butyl 1-(3-aminobenzyl)-cyclopropanecarboxylate and (+/−)-cyclopentyl[4-(trifluoromethoxy)phenyl]acetic acid | LC-MS (Method 5): $R_t$ = 1.51 min; m/z = 518 (M + H)$^+$.<br>$^1$H-NMR (400 MHz, DMSO-$d_6$): δ [ppm] = 0.77-0.84 (m, 2H), 0.92-1.01 (m, 1H), 1.03-1.08 (m, 2H), 1.26 (s, 9H), 1.26-1.41 (m, 2H), 1.42-1.71 (m, 4H), 1.72-1.84 (m, 1H), 2.52-2.62 (m, 1H), 2.78 (s, 2H), 3.45 (d, 1H), 6.91 (d, 1H), 7.16 (t, 1H), 7.27-7.39 (m, 3H), 7.47-7.55 (m, 3H), 10.02 (s, 1H). |
| 142A | (+/−)-tert-butyl 1-(3-{[(4-chlorophenyl)(cyclopentyl)acetyl]amino}-2-fluorobenzyl)cyclopropanecarboxylate<br>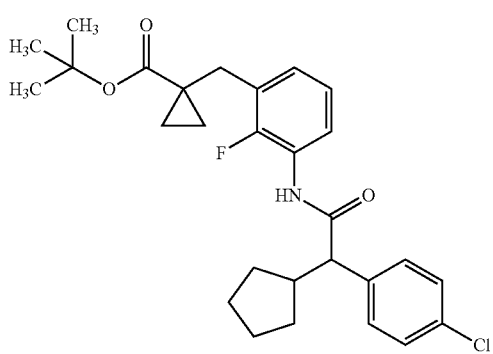<br>from tert-butyl 1-(3-amino-2-fluorobenzyl)-cyclopropanecarboxylate and (+/−)-cyclopentyl-(4-chlorophenyl)acetic acid | LC-MS (Method 4): $R_t$ = 1.77 min; m/z = 485 (M − H)$^-$.<br>$^1$H-NMR (400 MHz, DMSO-$d_6$): δ [ppm] = 0.77-0.86 (m, 2H), 0.89-1.02 (m, 1H), 1.07-1.14 (m, 2H), 1.18-1.71 (m, 15H), 1.73-1.85 (m, 1H), 2.80-2.94 (m, 2H), 3.63 (d, 1H), 7.00-7.14 (m, 2H), 7.33-7.48 (m, 4H), 7.56-7.74 (m, 1H), 9.81 (s, 1H). |
| 143A | (+/−)-tert-butyl 1-(3-{[cyclopentyl(4-cyanophenyl)acetyl]amino}-4-fluorobenzyl)-cyclopropanecarboxylate<br>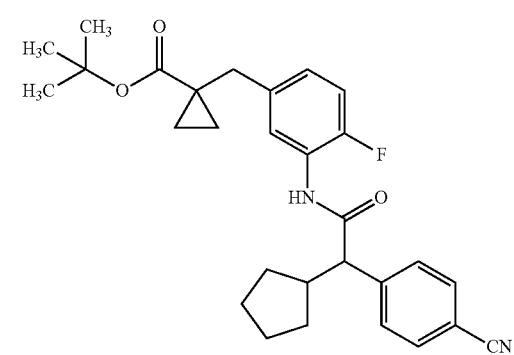<br>from tert-butyl 1-(3-amino-4-fluorobenzyl)-cyclopropanecarboxylate and (+/−)-(4-cyanophenyl)-(cyclopentyl)acetic acid | LC-MS (Method 2): $R_t$ = 2.90 min; m/z = 475 (M − H)$^-$.<br>$^1$H-NMR (400 MHz, DMSO-$d_6$): δ [ppm] = 0.76-0.84 (m, 2H), 0.88-1.00 (m, 1H), 1.03 (q, 2H), 1.19-1.73 (m, 15H), 1.75-1.86 (m, 1H), 2.76 (s, 2H), 3.72 (d, 1H), 6.94-7.04 (m, 1H), 7.12 (dd, 1H), 7.61 (d, 2H), 7.68 (dd, 1H), 7.80 (d, 2H), 9.89 (s, 1H). |

| Example | Name/Structure/Starting materials | Analytical data |
|---|---|---|
| 144A | (+/−)-tert-butyl 1-(3-{[cyclopentyl(4-nitrophenyl)acetyl]amino}-4-fluorobenzyl)-cyclopropanecarboxylate<br>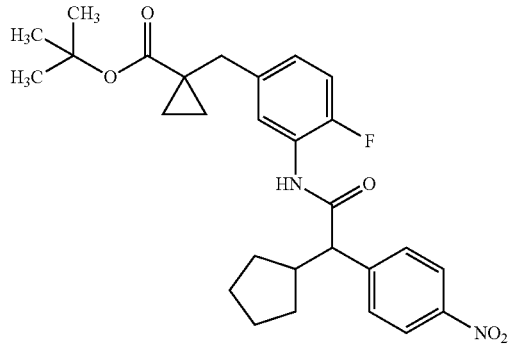<br>from tert-butyl 1-(3-amino-4-fluorobenzyl)-cyclopropanecarboxylate and (+/−)-cyclopentyl-(4-nitrophenyl)acetic acid | LC-MS (Method 5): $R_t$ = 1.47 min; m/z = 495 (M − H)⁻.<br>$^1$H-NMR (400 MHz, DMSO-$d_6$): δ [ppm] = 0.80 (q, 2H), 0.96 (dq, 1H), 1.01-1.06 (m, 2H), 1.16-1.76 (m, 15H), 1.76-1.92 (m, 1H), 2.77 (s, 2H), 3.80 (d, 1H), 6.92-7.05 (m, 1H), 7.12 (dd, 1H), 7.62-7.82 (m, 3H), 8.21 (d, 2H), 9.94 (s, 1H). |
| 145A | (+)-tert-butyl 1-(3-{[(2S)-2-cyclopentyl-2-(4-ethylphenyl)acetyl]amino}benzyl)-cyclopropanecarboxylate<br>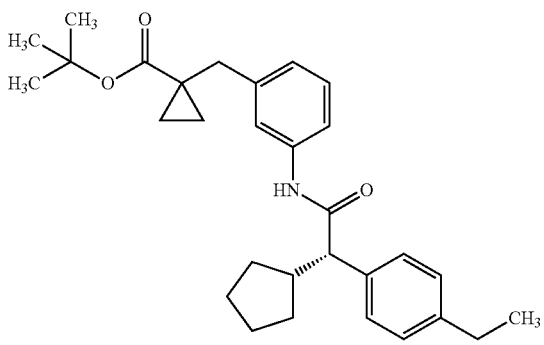<br>from tert-butyl 1-(3-aminobenzyl)-cyclopropanecarboxylate and (2S)-cyclopentyl(4-ethylphenyl)acetic acid | LC-MS (Method 5): $R_t$ = 1.54 min; m/z = 462 (M + H)⁺.<br>$^1$H-NMR (400 MHz, DMSO-$d_6$): δ [ppm] = 0.77-0.83 (m, 2H), 0.92-1.02 (m, 1H), 1.02-1.08 (m, 2H), 1.15 (t, 3H), 1.21-1.27 (m, 1H), 1.26 (s, 9H), 1.30-1.40 (m, 1H), 1.41-1.69 (m, 4H), 1.70-1.83 (m, 1H), 2.53-2.61 (m, 3H), 2.78 (s, 2H), 3.34 (d, 1H), 6.89 (d, 1H), 7.10-7.19 (m, 3H), 7.31 (d, 2H), 7.36 (d, 1H), 7.51 (s, 1H), 9.92 (s, 1H).<br>$[α]_D^{20}$ = +42.9°, c = 0.600, chloroform. |
| 146A | (+)-tert-butyl 1-(3-{[(2S)-2-cyclopentyl-2-(4-ethylphenyl)acetyl]amino}-5-fluorobenzyl)-cyclopropanecarboxylate<br>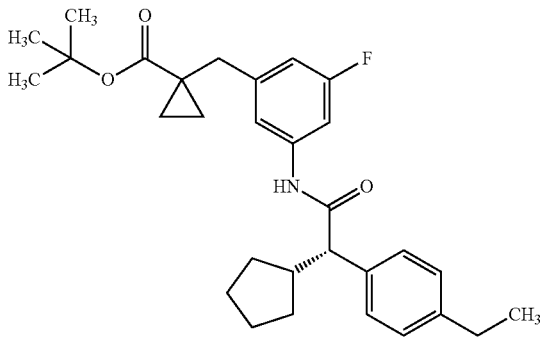<br>from tert-butyl 1-(3-amino-5-fluorobenzyl)-cyclopropanecarboxylate and (2S)-cyclopentyl-(4-ethylphenyl)acetic acid | LC-MS (Method 2): $R_t$ = 3.23 min; m/z = 478 (M − H)⁻.<br>$^1$H-NMR (400 MHz, DMSO-$d_6$): δ [ppm] = 0.81-0.89 (m, 2H), 0.91-1.03 (m, 1H), 1.09 (q, 2H), 1.15 (t, 3H), 1.18-1.23 (m, 1H), 1.25 (s, 9H), 1.30-1.40 (m, 1H), 1.41-1.68 (m, 4H), 1.70-1.84 (m, 1H), 2.51-2.62 (m, 3H), 2.78 (s, 2H), 3.32 (d, 1H), 6.71 (d, 1H), 7.09-7.18 (m, 2H), 7.23 (s, 1H), 7.26-7.33 (m, 2H), 7.39 (d, 1H), 10.14 (s, 1H).<br>$[α]_D^{20}$ = +34.1°, c = 0.500, chloroform. |

| Example | Name/Structure/Starting materials | Analytical data |
|---|---|---|
| 147A | (+)-tert-butyl 1-(3-{[(2S)-2-cyclopentyl-2-(4-ethylphenyl)acetyl]amino}-4-fluorobenzyl)-cyclopropanecarboxylate<br />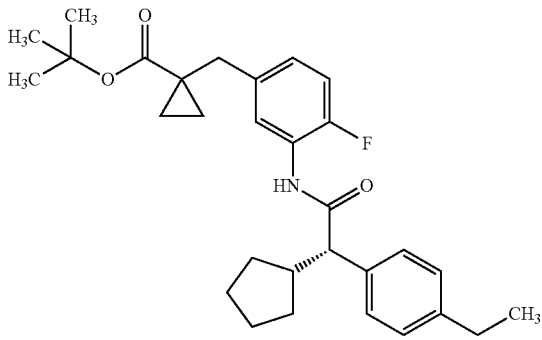<br />from tert-butyl 1-(3-amino-4-fluorobenzyl)-cyclopropanecarboxylate and (2S)-cyclopentyl(4-ethylphenyl)acetic acid | LC-MS (Method 5): $R_t$ = 1.54 min; m/z = 480 (M + H)$^+$.<br />$^1$H-NMR (400 MHz, DMSO-$d_6$): δ [ppm] = 0.80 (q, 2H), 0.91-0.99 (m, 1H), 1.00-1.05 (m, 2H), 1.16 (t, 3H), 1.26 (s, 9H), 1.26-1.40 (m, 2H), 1.40-1.48 (m, 1H), 1.48-1.71 (m, 3H), 1.71-1.84 (m, 1H), 2.55-2.62 (m, 2H), 2.76 (s, 2H), 3.55 (d, 1H), 6.91-7.03 (m, 1H), 7.04-7.11 (m, 1H), 7.14 (d, 2H), 7.32 (d, 2H), 7.70 (dd, 1H), 9.72 (s, 1H).<br />$[α]_D^{20}$ = +66.6°, c = 0.575, chloroform. |
| 148A | (+/-)-tert-butyl 1-(3-{[2-(4-ethylphenyl)-4,4,4-trifluoro-3-methylbutanoyl]amino}benzyl)-cyclopropanecarboxylate<br />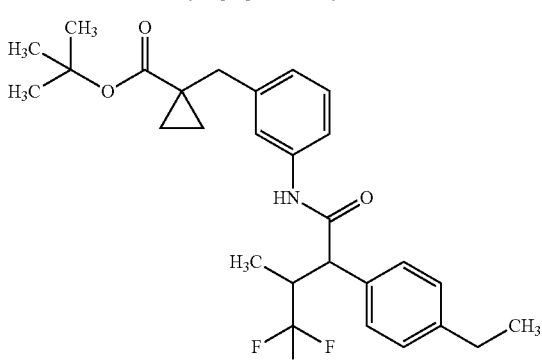<br />from tert-butyl 1-(3-aminobenzyl)-cyclopropanecarboxylate and 2-(4-ethylphenyl)-4,4,4-trifluoro-3-methylbutanoic acid | LC-MS (Method 5):<br />$R_t$ = 1.49 min; m/z = 434 (M − $C_4H_7$)$^+$.<br />$^1$H-NMR (400 MHz, DMSO-$d_6$): δ [ppm] = 0.78 (d, 3H), 0.79-0.83 (m, 2H), 1.02-1.08 (m, 2H), 1.15 (t, 3H), 1.25 (s, 9H), 2.57 (q, 2H), 2.77 (s, 2H), 3.34-3.41 (m, 1H), 3.78 (d, 1H), 6.90 (d, 1H), 7.11-7.16 (m, 1H), 7.16-7.22 (m, 2H), 7.32 (d, 3H), 7.47 (s, 1H), 10.10 (s, 1H). |
| 149A | (+/-)-tert-butyl 1-(3-{[2-(4-ethylphenyl)-4,4,4-trifluoro-3-methylbutanoyl]amino}-4-fluorobenzyl)-cyclopropanecarboxylate<br />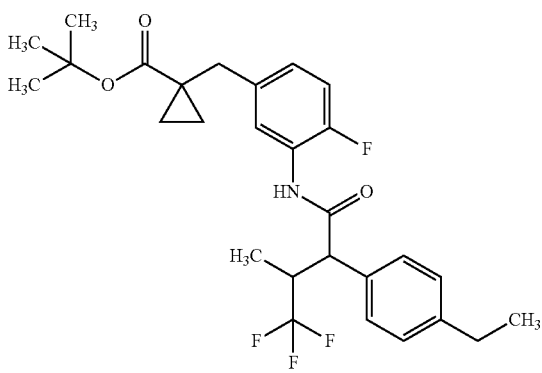<br />from tert-butyl 1-(3-amino-4-fluorobenzyl)-cyclopropanecarboxylate and 2-(4-ethylphenyl)-4,4,4-trifluoro-3-methylbutanoic acid | LC-MS (Method 5): $R_t$ = 1.50 min; m/z = 506 (M − H)$^-$.<br />$^1$H-NMR (400 MHz, DMSO-$d_6$): δ [ppm] = 0.77 (d, 3H), 0.78-0.83 (m, 2H), 0.99-1.06 (m, 2H), 1.16 (s, 3H), 1.25 (s, 9H), 2.58 (q, 2H), 2.76 (d, 2H), 3.32-3.38 (m, 1H), 4.03 (d, 1H), 6.91-7.01 (m, 1H), 7.10 (dd, 1H), 7.17-7.22 (m, 2H), 7.29-7.35 (m, 2H), 7.73 (dd, 1H), 9.93 (s, 1H). |

| Example | Name/Structure/Starting materials | Analytical data |
|---|---|---|
| 150A | (+/-)-tert-butyl 1-(3-{[(4-chlorophenyl)(cyclopentyl)acetyl]amino}-4-fluorobenzyl)cyclopropanecarboxylate<br>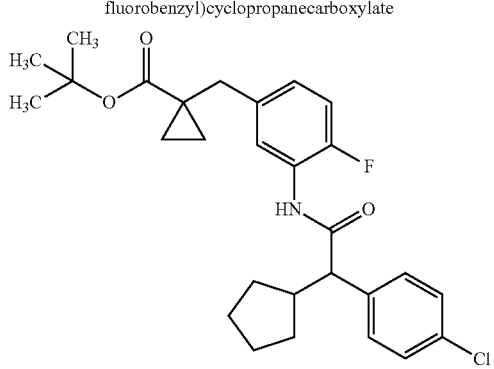<br>from tert-butyl 1-(3-amino-4-fluorobenzyl)-cyclopropanecarboxylate and (+/-)-cyclopentyl-(4-chlorophenyl)acetic acid | LC-MS (Method 5): $R_t$ = 1.51 min; m/z = 484/485 (M − H)$^-$.<br>$^1$H-NMR (400 MHz, DMSO-$d_6$): δ [ppm] = 0.80 (q, 2H), 0.91-1.00 (m, 1H), 1.03 (q, 2H), 1.26 (s, 9H), 1.27-1.40 (m, 2H), 1.40-1.70 (m, 4H), 1.72-1.85 (m, 1H), 2.53-2.59 (m, 1H), 2.77 (s, 2H), 3.61 (d, 1H), 6.93-7.03 (m, 1H), 7.11 (dd, 1H), 7.34-7.40 (m, 2H), 7.40-7.47 (m, 2H), 7.69 (dd, 1H), 9.81 (s, 1H). |
| 151A | (+/-)-tert-butyl 1-(3-{[cyclopentyl(4-fluorophenyl)acetyl]amino}-4-fluorobenzyl)-cyclopropanecarboxylate<br>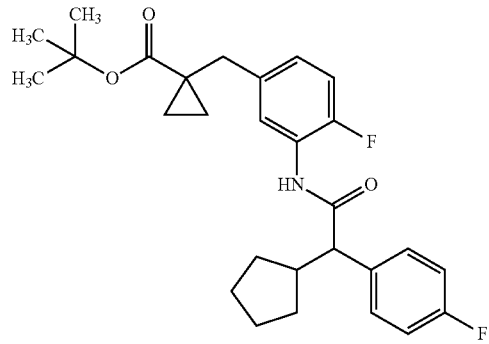<br>from tert-butyl 1-(3-amino-4-fluorobenzyl)-cyclopropanecarboxylate and (+/-)-cyclopentyl-(4-fluorophenyl)acetic acid | LC-MS (Method 5): $R_t$ = 1.49 min; m/z = 468 (M − H)$^-$.<br>$^1$H-NMR (400 MHz, DMSO-$d_6$): δ [ppm] = 0.74-0.83 (m, 2H), 0.88-1.00 (m, 1H), 1.00-1.06 (m, 2H), 1.26 (s, 9H), 1.28-1.39 (m, 2H), 1.42-1.71 (m, 4H), 1.71-1.86 (m, 1H), 2.50-2.58 (m, 1H, obscured), 2.77 (s, 2H), 3.60 (d, 1H), 6.90-7.04 (m, 1H), 7.05-7.21 (m, 3H), 7.44 (dd, 2H), 7.70 (dd, 1H), 9.78 (s, 1H). |
| 152A | (+/-)-tert-butyl 1-(3-{[(4-chloro-2-fluorophenyl)(cyclopentyl)acetyl]amino}-4-fluorobenzyl)cyclopropanecarboxylate<br>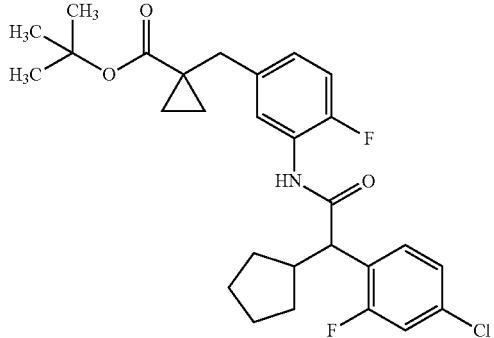<br>from tert-butyl 1-(3-amino-4-fluorobenzyl)-cyclopropanecarboxylate and (+/-)-(4-chloro-2-fluorophenyl)(cyclopentyl)acetic acid | LC-MS (Method 5): $R_t$ = 1.57 min; m/z = 502 (M − H)$^-$.<br>$^1$H-NMR (400 MHz, DMSO-$d_6$): δ [ppm] = 0.77-0.84 (m, 2H), 0.93-1.00 (m, 1H), 1.00-1.07 (m, 2H), 1.27 (s, 9H), 1.34-1.62 (m, 5H), 1.62-1.73 (m, 1H), 1.73-1.84 (m, 1H), 2.43-2.53 (m, 1H), 2.78 (s, 2H), 3.94 (d, 1H), 6.95-7.06 (m, 1H), 7.12 (dd, 1H), 7.29 (dd, 1H), 7.40 (dd, 1H), 7.59 (dd, 1H), 7.68 (t, 1H), 9.94 (s, 1H). |

| Example | Name/Structure/Starting materials | Analytical data |
| --- | --- | --- |
| 153A | (+)-tert-butyl 1-(4-fluoro-3-{[(2S,3R)-4,4,4-trifluoro-2-(4-fluorophenyl)-3-methylbutanoyl]amino}benzyl)-cyclopropanecarboxylate<br>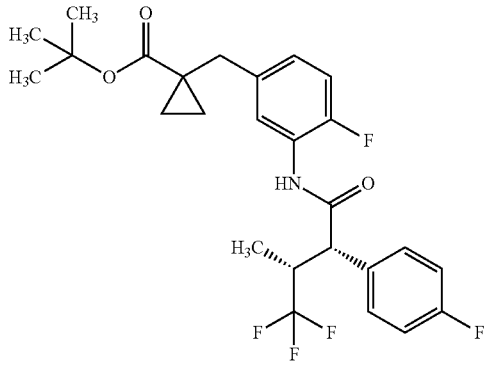<br>from tert-butyl 1-(3-amino-4-fluorobenzyl)cyclo-propanecarboxylate and (3R)-4,4,4-trifluoro-2-(4-fluorophenyl)-3-methylbutanoic acid (diastereomer mixture) | LC-MS (Method 5): $R_t$ = 1.43 min; m/z = 496 (M − H)⁻.<br>$^1$H-NMR (400 MHz, DMSO-$d_6$): δ [ppm] = 0.78 (d, 3H), 0.79-0.83 (m, 2H), 1.03 (q, 2H), 1.25 (s, 9H), 2.76 (d, 2H), 3.33-3.41 (m, 1H), 4.09 (d, 1H), 6.93-7.02 (m, 1H), 7.11 (dd, 1H), 7.20 (t, 2H), 7.47 (dd, 2H), 7.72 (dd, 1H), 9.99 (s, 1H).<br>$[α]_D^{20}$ = +109.2°, c = 0.545, chloroform. |
| 154A | (+)-tert-butyl 1-(3-{[(2S,3R)-2-(4-ethylphenyl)-4,4,4-trifluoro-3-methylbutanoyl]amino}-4-fluorobenzyl)-cyclopropanecarboxylate<br>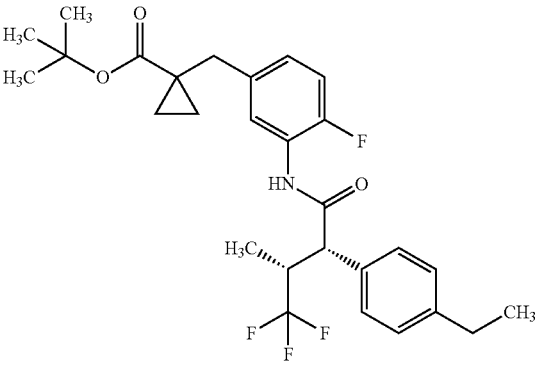<br>from tert-butyl 1-(3-amino-4-fluorobenzyl)cyclo-propanecarboxylate and (3R)-2-(4-ethylphenyl)-4,4,4-trifluoro-3-methylbutanoic acid (diastereomer mixture) | LC-MS (Method 5): $R_t$ = 1.51 min; m/z = 506 (M − H)⁻.<br>$^1$H-NMR (400 MHz, DMSO-$d_6$): δ [ppm] = 0.77 (d, 3H), 0.78-0.82 (m, 2H), 0.99-1.06 (m, 2H), 1.16 (t, 3H), 1.25 (s, 9H), 2.58 (q, 2H), 2.72-2.83 (m, 2H), 3.33-3.40 (m, 1H), 4.00-4.05 (m, 1H), 6.94-7.01 (m, 1H), 7.10 (dd, 1H), 7.16-7.23 (m, 2H), 7.31-7.36 (m, 2H), 7.73 (dd, 1H), 9.94 (s, 1H).<br>$[α]_D^{20}$ = +73.3°, c = 0.525, chloroform. |
| 155A | (+)-tert-butyl 1-(3-{[(2S,3R)-2-(4-ethylphenyl)-4,4,4-trifluoro-3-methylbutanoyl]amino}-2-fluorobenzyl)-cyclopropanecarboxylate<br>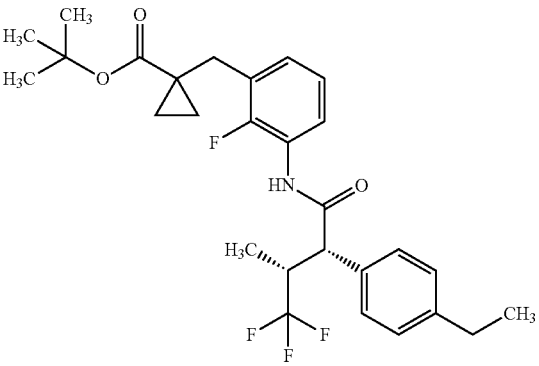<br>from tert-butyl 1-(3-amino-2-fluorobenzyl)cyclo-propanecarboxylate and (3R)-2-(4-ethylphenyl)-4,4,4-trifluoro-3-methylbutanoic acid (diastereomer mixture) | LC-MS (Method 5): $R_t$ = 1.48 min; m/z = 506 (M − H)⁻.<br>$^1$H-NMR (400 MHz, DMSO-$d_6$): δ [ppm] = 0.77 (d, 3H), 0.79-0.83 (m, 2H), 1.06-1.11 (m, 2H), 1.17 (t, 3H), 1.24 (s, 9H), 2.58 (q, 2H), 2.78-2.93 (m, 2H), 3.33-3.39 (m, 1H), 4.05 (d, 1H), 6.98-7.11 (m, 2H), 7.16-7.23 (m, 2H), 7.28-7.36 (m, 2H), 7.64 (td, 1H), 9.94 (s, 1H).<br>$[α]_D^{20}$ = +34.2°, c = 0.505, chloroform. |

| Example | Name/Structure/Starting materials | Analytical data |
|---|---|---|
| 156A | (+)-tert-butyl 1-(4-fluoro-3-{[(2S,3R)-4,4,4-trifluoro-3-methyl-2-(4-vinylphenyl)butanoyl]amino}benzyl)-cyclopropanecarboxylate<br>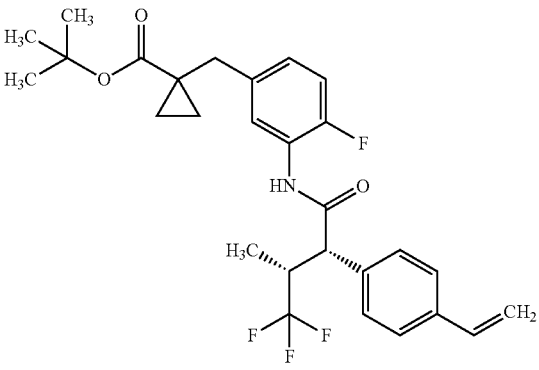<br>from tert-butyl 1-(3-amino-4-fluorobenzyl)cyclo-propanecarboxylate and (3R)-4,4,4-trifluoro-3-methyl-2-(4-vinylphenyl)butanoic acid (diastereomer mixture) | LC-MS (Method 5): $R_t$ = 1.48 min; m/z = 504 (M − H)$^-$.<br>$^1$H-NMR (400 MHz, DMSO-$d_6$): δ [ppm] = 0.75-0.82 (m, 5H), 0.99-1.06 (m, 2H), 1.25 (s, 9H), 2.76 (s, 2H), 3.34-3.46 (m, 1H), 4.04-4.11 (m, 1H), 5.26 (d, 1H), 5.83 (d, 1H), 6.72 (dd, 1H), 6.98 (td, 1H), 7.11 (dd, 1H), 7.36-7.43 (m, 2H), 7.44-7.50 (m, 2H), 7.63-7.76 (m, 1H), 9.97 (s, 1H).<br>$[α]_D^{20}$ = +103°, c = 0.260, chloroform. |
| 157A | tert-butyl 1-[4-fluoro-3-({(2S,3R)-4,4,4-trifluoro-2-[4-(1-fluoro-vinyl)phenyl]-3-methylbutanoyl}amino)benzyl]cyclopropane-carboxylate<br>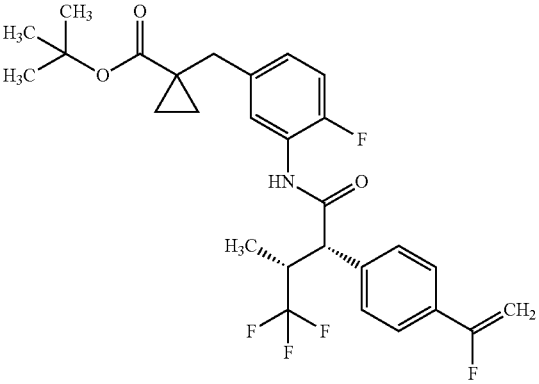<br>from tert-butyl 1-(3-amino-4-fluorobenzyl)cyclo-propanecarboxylate and (3R)-4,4,4-trifluoro-2-[4-(1-fluorovinyl)phenyl]-3-methylbutanoic acid (diastereomer mixture) | LC-MS (Method 5): $R_t$ = 1.47 min; m/z = 522 (M − H)$^-$.<br>$^1$H-NMR (400 MHz, DMSO-$d_6$): δ [ppm] = 0.76-0.83 (m, 5H), 0.99-1.05 (m, 2H), 1.24 (s, 9H), 2.76 (d, 2H), 3.40 (dd, 1H), 4.12 (d, 1H), 4.95 (dd, 1H), 5.38 (dd, 1H), 6.98-7.03 (m, 1H), 7.11 (dd, 1H), 7.44-7.53 (m, 2H), 7.60-7.66 (m, 2H), 7.70 (dd, 1H), 10.02 (s, 1H). |

-continued

| Example | Name/Structure/Starting materials | Analytical data |
| --- | --- | --- |
| 158A | tert-butyl 1-(3-{[(2S,3R)-2-(4-chlorophenyl)-4,4,4-trifluoro-3-methylbutanoyl]amino}-2-fluorobenzyl)-cyclopropanecarboxylate<br><br>from tert-butyl 1-(3-amino-2-fluorobenzyl)-cyclopropanecarboxylate and (+)-(2S,3R)-2-(4-chlorophenyl)-4,4,4-trifluoro-3-methylbutanoic acid | LC-MS (Method 5): $R_t$ = 1.46 min; m/z = 512 (M − H)$^-$.<br>$^1$H-NMR (400 MHz, DMSO-$d_6$): δ [ppm] = 0.71-0.87 (m, 5H), 1.04-1.14 (m, 2H), 1.24 (s, 9H), 2.77-2.95 (m, 2H), 4.12 (d, 1H), 6.97-7.15 (m, 2H), 7.40-7.51 (m, 4H), 7.62 (t, 1H), 10.01 (s, 1H). |
| 159A | tert-butyl 1-(2-chloro-5-{[(2S,3R)-2-(4-chlorophenyl)-4,4,4-trifluoro-3-methylbutanoyl]amino}benzyl)-cyclopropanecarboxylate<br><br>from tert-butyl 1-(5-amino-2-chlorobenzyl)cyclo-propanecarboxylate and (+)-(2S,3R)-2-(4-chlorophenyl)-4,4,4-trifluoro-3-methylbutanoic acid | LC-MS (Method 5): $R_t$ = 1.52 min; m/z = 474 (M − C$_4$H$_8$)$^+$.<br>$^1$H-NMR (400 MHz, DMSO-$d_6$): δ [ppm] = 0.79 (d, 3H), 0.81-0.85 (m, 2H), 1.15-1.18 (m, 2H), 1.20 (s, 9H), 2.90 (s, 2H), 3.34-3.44 (m, 1H), 3.83 (d, 1H), 7.30 (d, 1H), 7.38-7.46 (m, 5H), 7.63 (d, 1H), 10.31 (s, 1H). |
| 160A | (+)-tert-butyl 1-(2-chloro-3-{[(2S,3R)-2-(4-chlorophenyl)-4,4,4-trifluoro-3-methylbutanoyl]amino}benzyl)cyclopropane-carboxylate<br><br>from tert-butyl 1-(3-amino-2-chlorobenzyl)cyclo-propanecarboxylate and (+)-(2S,3R)-2-(4-chlorophenyl)-4,4,4-trifluoro-3-methylbutanoic acid | LC-MS (Method 5): $R_t$ = 1.50 min; m/z = 474 (M − C$_4$H$_8$)$^+$.<br>$^1$H-NMR (400 MHz, DMSO-$d_6$): δ [ppm] = 0.74-0.78 (m, 2H), 0.80 (d, 3H), 1.11-1.18 (m, 2H), 1.24 (s, 9H), 2.89-3.04 (m, 2H), 3.34-3.45 (m, 1H), 4.08-4.17 (m, 1H), 7.14-7.27 (m, 2H), 7.30-7.39 (m, 1H), 7.41-7.53 (m, 4H), 9.83 (s, 1H). |

| Example | Name/Structure/Starting materials | Analytical data |
|---|---|---|
| 161A | (+)-tert-butyl 1-(4-chloro-3-{[(2S,3R)-2-(4-chloro-3-fluorophenyl)-4,4,4-trifluoro-3-methylbutanoyl]amino}benzyl)cyclopropanecarboxylate<br><br>from tert-butyl 1-(3-amino-4-chlorobenzyl)-cyclopropanecarboxylate and (3R)-2-(4-chloro-3-fluorophenyl)-4,4,4-trifluoro-3-methylbutanoic acid | LC-MS (Method 4): $R_t$ = 1.72 min; m/z = 446 (M − H)⁻.<br>¹H-NMR (400 MHz, DMSO-$d_6$): δ [ppm] = 0.77-0.85 (m, 5H), 1.03 (q, 2H), 1.23 (s, 9H), 2.72-2.85 (m, 2H), 3.42 (dd, 1H), 4.12 (d, 1H), 7.05 (dd, 1H), 7.32 (dd, 1H), 7.36 (d, 1H), 7.40-7.45 (m, 1H), 7.50 (dd, 1H), 7.62 (t, 1H), 9.87 (s, 1H).<br>$[α]_D^{20}$ = +73°, c = 0.290, chloroform. |
| 162A | (+)-tert-butyl 1-(4-chloro-3-{[(2S,3R)-2-(4-chloro-2-fluorophenyl)-4,4,4-trifluoro-3-methylbutanoyl]amino}benzyl)cyclopropanecarboxylate<br><br>from tert-butyl 1-(3-amino-4-chlorobenzyl)-cyclopropanecarboxylate and (3R)-2-(4-chloro-2-fluorophenyl)-4,4,4-trifluoro-3-methylbutanoic acid | LC-MS (Method 5):<br>$R_t$ = 1.56 min; m/z = 546/548 (M − H)⁻.<br>¹H-NMR (400 MHz, DMSO-$d_6$): δ [ppm] = 0.81-0.83 (m, 2H), 0.85 (d, 3H), 1.01-1.07 (m, 2H), 1.27 (s, 9H), 2.76-2.85 (m, 2H), 3.34-3.43 (m, 1H), 4.31-4.39 (m, 1H), 7.04-7.13 (m, 1H), 7.32-7.39 (m, 3H), 7.51 (dd, 1H), 7.62 (t, 1H), 10.02 (s, 1H).<br>$[α]_D^{20}$ = +28.0°, c = 0.250, chloroform. |
| 163A | tert-butyl 1-(3-{[(2S,3R)-2-(4-chlorophenyl)-4,4,4-trifluoro-3-methylbutanoyl]amino}-4-methylbenzyl)-cyclopropanecarboxylate<br><br>from tert-butyl 1-(3-amino-4-methylbenzyl)cyclo-propanecarboxylate and (2S,3R)-2-(4-chlorophenyl)-4,4,4-trifluoro-3-methylbutanoic acid | LC-MS (Method 4):<br>$R_t$ = 1.63 min; m/z = 508/510 (M − H)⁻.<br>¹H-NMR (400 MHz, DMSO-$d_6$): δ [ppm] = 0.73-0.78 (m, 2H), 0.80 (d, 3H), 0.98-1.03 (m, 2H), 1.26 (s, 9H), 1.96 (s, 3H), 2.69-2.81 (m, 2H), 3.32-3.43 (m, 1H, partially obscured), 3.94 (d, 1H), 6.93 (dd, 1H), 7.02-7.11 (m, 2H), 7.38-7.51 (m, 4H), 9.59 (s, 1H). |

| Example | Name/Structure/Starting materials | Analytical data |
|---|---|---|
| 164A | tert-butyl 1-(3-{[(4-chlorophenyl)(3,3-difluorocyclo-pentyl)acetyl]amino}-4-fluorobenzyl)-cyclopropanecarboxylate (diastereomer mixture)<br><br>from tert-butyl 1-(3-amino-4-fluorobenzyl)cyclo-propanecarboxylate and (4-chlorophenyl)-(3,3-difluorocyclopentyl)acetic acid | LC-MS (Method 5):<br>$R_t$ = 1.44 min; m/z = 520/522 (M − H)⁻. |
| 165A | tert-butyl 1-[3-({4,4,4-trifluoro-3-methyl-2-[4-(tri-fluoromethyl)phenyl]butanoyl}amino)benzyl]-cyclopropanecarboxylate<br><br>from tert-butyl 1-(3-aminobenzyl)cyclopropane-carboxylate and 4,4,4-trifluoro-3-methyl-2-[4-(trifluoromethyl)phenyl]butanoic acid | LC-MS (Method 5): $R_t$ = 1.46 min; m/z = 528 (M − H)⁻. |
| 166A | tert-butyl 1-(4-fluoro-3-{[(2S,3R)-4,4,4-trifluoro-2-(4-isopropylphenyl)-3-methylbutanoyl]amino}-benzyl)cyclopropanecarboxylate<br><br>from tert-butyl 1-(3-amino-4-fluorobenzyl)-cyclopropanecarboxylate and (2S,3R)-4,4,4-trifluoro-2-(4-isopropylphenyl)-3-methylbutanoic acid | LC-MS (Method 5): $R_t$ = 1.55 min; m/z = 520 (M − H)⁻.<br>¹H-NMR (400 MHz, DMSO-$d_6$): δ [ppm] = 0.72-0.86 (m, 5H), 0.99-1.07 (m, 2H), 1.18 (d, 6H), 1.25 (s, 9H), 2.69-2.82 (m, 2H), 2.82-2.93 (m, 1H), 3.24-3.42 (m, 1H, partially obscured), 4.03 (d, 1H), 6.93-7.01 (m, 1H), 7.06-7.14 (m, 1H), 7.22 (d, 2H), 7.34 (d, 2H), 7.75 (dd, 1H), 9.93 (s, 1H). |

-continued

| Example | Name/Structure/Starting materials | Analytical data |
|---|---|---|
| 167A | tert-butyl 1-[3-({2S,3R)-2-[4-(1,1-difluoroethyl)-phenyl]-4,4,4-trifluoro-3-methylbutanoyl}amino)-4-fluorobenzyl]cyclopropanecarboxylate<br><br>from tert-butyl 1-(3-amino-4-fluorobenzyl)cyclopropanecarboxylate and (2S,3R)-2-[4-(1,1-difluoroethyl)phenyl]-4,4,4-trifluoro-3-methylbutanoic acid | LC-MS (Method 5): $R_t$ = 1.41 min; m/z = 542 (M − H)⁻.<br>$^1$H-NMR (400 MHz, DMSO-$d_6$): δ [ppm] = 0.74-0.84 (m, 5H), 1.00-1.05 (m, 2H), 1.24 (s, 9H), 1.95 (t, 3H), 2.70-2.82 (m, 2H), 3.34-3.48 (m, 1H), 4.15 (d, 1H), 6.95-7.02 (m, 1H), 7.07-7.15 (m, 1H), 7.52-7.60 (m, 4H), 7.71 (dd, 1H), 10.02 (s, 1H). |
| 168A | tert-butyl 1-(3-{[(2S,3R)-2-(4-tert-butylphenyl)-4,4,4-trifluoro-3-methylbutanoyl]amino}-4-fluorobenzyl)cyclopropanecarboxylate<br><br>from tert-butyl 1-(3-amino-4-fluorobenzyl)cyclopropanecarboxylate and (2S,3R)-2-(4-tert-butylphenyl)-4,4,4-trifluoro-3-methylbutanoic acid | LC-MS (Method 5): $R_t$ = 1.52 min; m/z = 534 (M − H)⁻.<br>$^1$H-NMR (400 MHz, DMSO-$d_6$): δ [ppm] = 0.73-0.83 (m, 5H), 0.99-1.07 (m, 2H), 1.24 (s, 9H), 1.26 (s, 9H), 2.70-2.83 (m, 2H), 3.27-3.42 (m, 1H, partially obscured), 4.04 (d, 1H), 6.93-7.01 (m, 1H), 7.06-7.15 (m, 1H), 7.31-7.41 (m, 4H), 7.75 (dd, 1H), 9.93 (s, 1H). |

| Example | Name/Structure/Starting materials | Analytical data |
|---|---|---|
| 169A | tert-butyl 1-(3-{[(2S,3R)-2-(4-cyclopropylphenyl)-4,4,4-trifluoro-3-methylbutanoyl]amino}-4-fluorobenzyl)cyclopropanecarboxylate<br>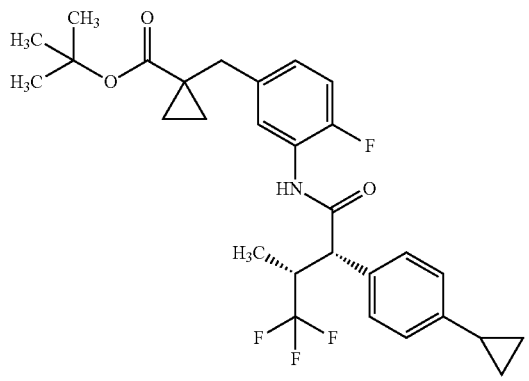<br>from tert-butyl 1-(3-amino-4-fluorobenzyl)cyclopropanecarboxylate and (2S,3R)-2-(4-cyclopropylphenyl)-4,4,4-trifluoro-3-methylbutanoic acid | LC-MS (Method 5): $R_t$ = 1.50 min; m/z = 518 (M − H)⁻.<br>$^1$H-NMR (400 MHz, DMSO-$d_6$): δ [ppm] = 0.60-0.68 (m, 2H), 0.73-0.83 (m, 5H), 0.89-0.96 (m, 2H), 0.99-1.07 (m, 2H), 1.25 (s, 9H), 1.82-1.93 (m, 1H), 2.69-2.83 (m, 2H), 3.23-3.39 (m, 1H, partially obscured), 4.01 (d, 1H), 6.92-7.00 (m, 1H), 7.01-7.14 (m, 3H), 7.29 (d, 2H), 7.71 (dd, 1H), 9.90 (s, 1H). |
| 170A | tert-butyl 1-(3-{[(2S,3R)-2-(4-chloro-3-methoxyphenyl)-4,4,4-trifluoro-3-methylbutanoyl]amino}-4-fluorobenzyl)cyclopropanecarboxylate<br>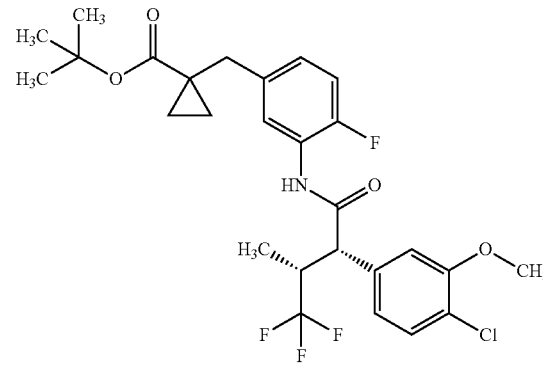<br>from tert-butyl 1-(3-amino-4-fluorobenzyl)cyclopropanecarboxylate and (2S,3R)-2-(4-chloro-3-methoxyphenyl)-4,4,4-trifluoro-3-methylbutanoic acid | LC-MS (Method 5):<br>$R_t$ = 1.44 min; m/z = 542/544 (M − H)⁻. |
| 171A | tert-butyl 1-(3-{[2-(4-chlorophenyl)-4,4,4-trifluoro-3-methylbutanoyl]amino}benzyl)cyclopropanecarboxylate<br>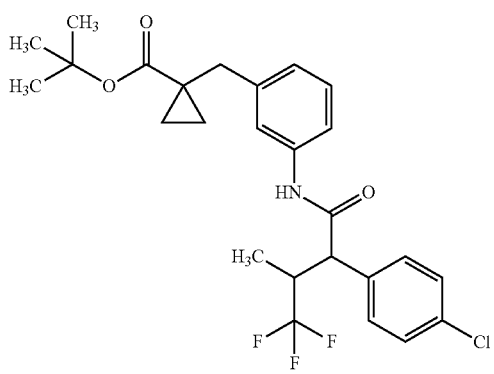<br>from tert-butyl 1-(3-aminobenzyl)cyclopropanecarboxylate and 2-(4-chlorophenyl)-4,4,4-trifluoro-3-methylbutanoic acid | LC-MS (Method 5): $R_t$ = 1.47 min; m/z = 494 (M − H)⁻. |

-continued

| Example | Name/Structure/Starting materials | Analytical data |
|---------|-----------------------------------|-----------------|
| 172A | tert-butyl 1-(3-{[4,4,4-trifluoro-3-methyl-2-(4-methyl-phenyl)butanoyl]amino}benzyl)-cyclopropanecarboxylate<br><br>from tert-butyl 1-(3-aminobenzyl)cyclopropane-carboxylate and 4,4,4-trifluoro-3-methyl-2-(4-methylphenyl)butanoic acid | LC-MS (Method 5): $R_t$ = 1.45 min; m/z = 474 (M − H)$^-$. |
| 173A | tert-butyl 1-[3-({4,4,4-trifluoro-3-methyl-2-[4-(trifluoromethoxy)phenyl]butanoyl}amino)-benzyl]cyclopropanecarboxylate<br><br>from tert-butyl 1-(3-aminobenzyl)-cyclopropanecarboxylate and 4,4,4-trifluoro-3-methyl-2-[4-(trifluoromethoxy)phenyl]butanoic acid | LC-MS (Method 5): $R_t$ = 1.48 min; m/z = 544 (M − H)$^-$. |
| 174A | tert-butyl 1-(3-{[2-(4-chloro-3-methylphenyl)-4,4,4-trifluoro-3-methylbutanoyl]amino}benzyl)cyclo-propanecarboxylate<br><br>from tert-butyl 1-(3-aminobenzyl)-cyclopropanecarboxylate and 2-(4-chloro-3-methylphenyl)-4,4,4-trifluoro-3-methylbutanoic acid | LC-MS (Method 5):<br>$R_t$ = 1.48 min; m/z = 508/510 (M − H)$^-$. |

Example 175A tert-Butyl 1-(3-{[(2S,3R)-2-(4-chlorophenyl)-4,4,4-trifluoro-3-methylbutanoyl]amino}-4-fluorobenzyl)cyclopropanecarboxylate

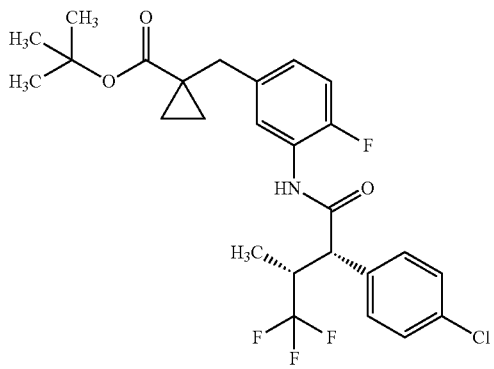 [SMILES: C[C@H]([C@H](C(=O)Nc1cc(CC2(C(=O)OC(C)(C)C)CC2)ccc1F)c1ccc(Cl)cc1)C(F)(F)F]

According to General Procedure 6, 1.2 g (4.5 mmol) of (2RS,3R)-2-(4-chlorophenyl)-4,4,4-trifluoro-3-methylbutanoic acid and 1.3 g (4.95 mmol) of tert-butyl 1-(3-amino-4-fluorobenzyl)-cyclopropanecarboxylate gave, after purification of the crude product by flash chromatography (silica gel; mobile phase cyclohexane/ethyl acetate 20:1), 1.6 g (69% of theory) of the title compound.

LC-MS (Method 5): $R_t$=1.48 min; m/z=512 (M−H)⁻.

$^1$H-NMR (400 MHz, DMSO-$d_6$): δ [ppm]=0.71-0.92 (m, 5H), 0.99-1.07 (m, 2H), 1.25 (s, 9H), 2.68-2.87 (m, 2H), 4.09 (d, 1H), 6.91-7.05 (m, 1H), 7.11 (dd, 1H), 7.35-7.54 (m, 4H), 7.70 (dd, 1H), 10.01 (s, 1H).

Example 176A tert-Butyl 1-(3-{[(4-chlorophenyl)(2,2-difluorocyclopentyl)acetyl]amino}-4-fluorobenzyl)cyclopropanecarboxylate (racemic diastereomer mixture)

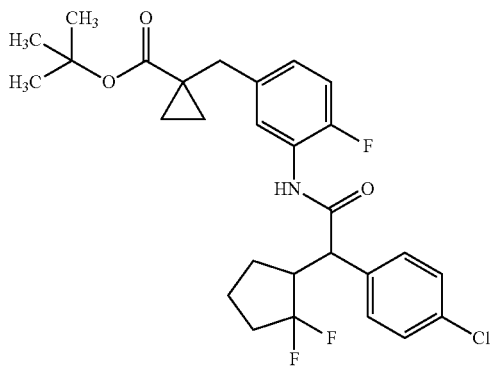 [SMILES: CC(C)(C)OC(=O)C1(Cc2ccc(F)c(NC(=O)C(c3ccc(Cl)cc3)C3CCCC3(F)F)c2)CC1]

490 mg (1.78 mmol) of (4-chlorophenyl)(2,2-difluorocyclopentyl)acetic acid (as diastereomer mixture) were added to a mixture of 4.0 ml of DMF and 1.0 ml of pyridine. At RT, 568.0 mg (2.14 mmol) of tert-butyl 1-(3-amino-4-fluorobenzyl)cyclopropanecarboxylate and 881.7 mg (2.34 mmol) of HATU were added to the resulting solution and the mixture was stirred at RT overnight. The reaction mixture was then added to saturated aqueous ammonium chloride solution and extracted three times with ethyl acetate. The combined organic phases were dried over magnesium sulphate and concentrated under reduced pressure. The crude product was purified by chromatography on silica gel (mobile phase cyclohexane/ethyl acetate 20:1). Further purification of the product obtained in this manner was carried out by preparative RP-HPLC (mobile phase acetonitrile/water). This gave 774.0 mg (83.1% of theory) of the target compound.

LC-MS (Method 5): $R_t$=1.42 min; m/z=466 (M−$C_4H_8$)⁺.

$^1$H-NMR (400 MHz, DMSO-$d_6$): both diastereomers: δ [ppm]=0.76-0.83 (m, 2H), 0.99-1.06 (m, 2H), 1.08-1.21 (m, 1H), 1.21-1.29 (m, 9H), 1.46-1.67 (m, 2H), 1.68-1.76 (m, 1H), 1.95-2.24 (m, 2H), 2.70-2.83 (m, 2H), 3.18 (m, 1H), 4.01/4.07 (d, 1H), 6.92-7.04 (m, 1H), 7.11 (ddd, 1H), 7.32-7.42 (m, 2H), 7.43-7.51 (m, 2H), 7.63-7.74 (m, 1H), 9.85 (s, 1H).

Example 177A (+/−) tert-Butyl 1-[3-(2-{[4-(2-cyanovinyl)phenyl]-2-cyclopentylacetyl}amino)-4-fluorobenzyl]-cyclopropanecarboxylate

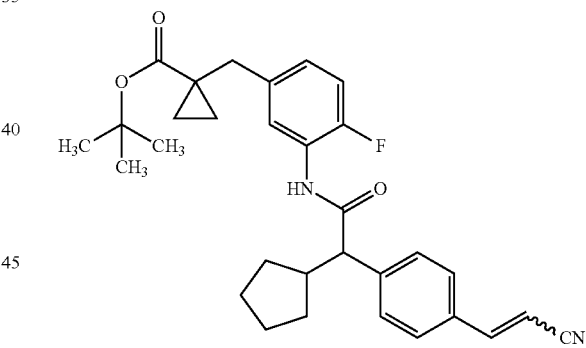

86 μl (1.3 mmol) of acrylonitrile, 8 mg (35 μmol) of palladium acetate, 32 mg (106 μmol) of tri-(o-tolyl)phosphine and 254 μl (1.8 mmol) of triethylamine were added to a solution of 627 mg (1.18 mmol) of (+/−)-tert-butyl 1-(3-{[2-(4-bromophenyl)-2-cyclopentylacetyl]amino}-4-fluorobenzyl)cyclopropanecarboxylate in 12.5 ml of DMF. In a microwave, the reaction mixture was heated at 150° C. for 1 h. The same amounts of acrylonitrile, palladium acetate, tri-(o-tolyl)phosphine and triethylamine were then added, and the mixture was once more stirred in a microwave at 150° C. for 1 h. Without further work-up, the reaction mixture was then directly separated into its components by preparative HPLC. This gave 497 mg (79% of theory) of the title compound.

LC-MS (Method 2): $R_t$=2.93 min; m/z=503 (M+H)⁺.

Example 178A tert-Butyl 1-[3-(2S)-(2-{[4-(E-2-cyanovinyl)phenyl]-2-cyclopentylacetyl}amino)-4-fluorobenzyl]cyclopropanecarboxylate

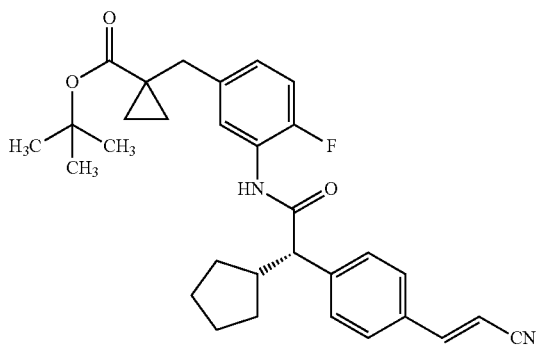 [SMILES: CC(C)(C)OC(=O)C1(Cc2ccc(F)c(NC(=O)[C@H](c3ccc(/C=C/C#N)cc3)C3CCCC3)c2)CC1]

200 mg of (+/−)-tert-butyl 1-[3-(2-{[4-(2-cyanovinyl)phenyl]-2-cyclopentylacetyl}amino)-4-fluorobenzyl]cyclopropanecarboxylate gave, by preparative HPLC on a chiral phase [column: Daicel Chiralpak AS-H, 5 μm, 250 mm×20 mm; injection volume: 0.25 ml; temperature: 38° C.; mobile phase: 80% isohexane/20% (ethanol+0.2% TFA+1% water); flow rate: 15 ml/min; detection: 220 nm], 89 mg of the pure 2S enantiomer.

$R_t$=4.64 min [column: Daicel Chiralpak AS-H, 5 μm, 250 mm×4.6 mm; mobile phase: isohexane/(isopropanol+0.2% TFA+1% water) 70:30 (v/v); flow rate: 1 ml/min; UV detection: 220 nm; temperature: 40° C.].

$^1$H-NMR (400 MHz, DMSO-$d_6$): δ [ppm]=0.76-0.86 (m, 2H), 0.90-1.00 (m, 1H), 1.00-1.07 (m, 2H), 1.21-1.72 (m, 15H), 1.71-1.88 (m, 1H), 2.76 (s, 2H), 3.59-3.69 (m, 1H), 6.44 (s, 1H), 6.92-7.05 (m, 1H), 7.11 (dd, 1H), 7.48 (d, 2H), 7.58-7.63 (m, 2H), 7.64-7.71 (m, 1H), 9.81 (s, 1H).

Example 179A (2S,3R)-2-(4-Chlorophenyl)-4,4,4-trifluoro-3-methylbutanoyl chloride

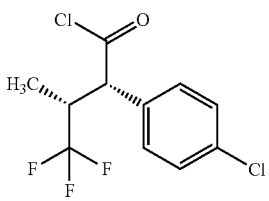

19.5 g (73.13 mmol) of (2S,3R)-2-(4-chlorophenyl)-4,4,4-trifluoro-3-methylbutanoic acid were dissolved in 860 ml of dichloromethane, and 0.5 ml of DMF was added. At −5° C. to −10° C. (ice/acetone cooling bath), 73 ml (146.26 mmol) of a 2 M solution of oxalyl chloride in dichloromethane were then slowly added dropwise, and the mixture was stirred at this temperature for 1 h. After the reaction had gone to completion, the reaction solution was concentrated under reduced pressure and the residue obtained was taken up in 200 ml of dichloromethane and then once more evaporated to dryness. This gave 20.1 g (70.5 mmol, 96% of theory) of the title compound as a colourless oil. The product obtained in this manner was used without further purification and without further spectroscopic characterization in subsequent reactions.

Example 180A (4-Chlorophenyl)(3,3-difluorocyclopentyl)acetyl chloride (diastereomer mixture)

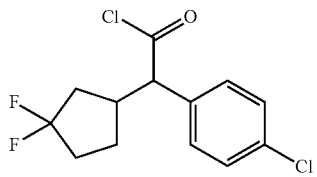 [SMILES: O=C(Cl)C(c1ccc(Cl)cc1)C1CCC(F)(F)C1]

470 mg (1.71 mmol) of (4-chlorophenyl)(3,3-difluorocyclopentyl)acetic acid were dissolved in 8 ml of dichloromethane, and a drop of DMF was added. At 0° C., 1.7 ml (3.42 mmol) of oxalyl chloride were then slowly added dropwise, and the mixture was stirred at this temperature for 1 h. After the reaction had gone to completion, the reaction solution was evaporated under reduced pressure and the residue obtained was taken up in 50 ml of dichloromethane and then once more evaporated to dryness. This gave 500 mg (99% of theory) of the title compound as a colourlees oil. The product obtained in this manner was used without further purification and without further spectroscopic characterization in subsequent reactions.

Example 181A (2S,3R)-4,4,4-Trifluoro-3-methyl-2-[4-(trifluoromethyl)phenyl]butanoyl chloride

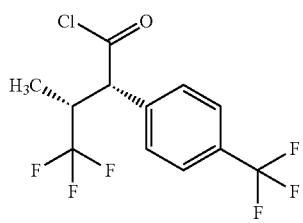 [SMILES: C[C@H]([C@H](C(=O)Cl)c1ccc(C(F)(F)F)cc1)C(F)(F)F]

The title compound was prepared in an analogous manner from (2S,3R)-4,4,4-trifluoro-3-methyl-2-[4-(trifluoromethyl)phenyl]butanoic acid.

General Procedure 7: Amide Coupling of Anilines with Acid Chlorides Generated in situ Under argon, a solution (0.1 to 1.5 mol/l) of the aniline in question (0.8 to 2.0 eq.) and N,N-diisopropylethylamine (1.0 to 3.0 eq.) in abs. THF or abs. dichloromethane was cooled to from −10° C. to 0° C., and a concentrated solution of the freshly prepared acid chloride (0.8 to 2.0 eq.) in abs. THF or abs. dichloromethane was added dropwise. After the addition had ended, the mixture was slowly warmed to RT and either worked up directly or stirred for another 2 h to 12 h at RT and then worked up. After dilution of the reaction mixture with ethyl acetate or dichloromethane, the organic phase was washed successively with 1 N hydrochloric acid and saturated sodium chloride solution, dried over magnesium sulphate or sodium sulphate and concentrated under reduced pressure. The crude product was purified by preparative RP-HPLC (mobile phase: acetonitrile/water gradient), purified by chromatography on silica gel (mobile phase: cyclohexane/ethyl acetate or dichloromethane/methanol mixtures) or purified by trituration with organic solvents such as diiso-propyl ether, for example. It is also possible to use of combination of these purification methods to isolate the target product in pure form.

The following compounds were prepared according to General Procedure 7:

| Example | Name/Structure/Starting materials | Analytical data |
|---|---|---|
| 182A | tert-butyl 1-(4,6-dichloro-3-{[(2S,3R)-2-(4-chlorophenyl)-4,4,4-trifluoro-3-methylbutanoyl]amino}-2-fluorobenzyl)-cyclopropanecarboxylate<br><br>from (2S,3R)-2-(4-chlorophenyl)-4,4,4-trifluoro-3-methylbutanoyl chloride and tert-butyl 1-(3-amino-4,6-dichloro-2-fluorobenzyl)cyclopropanecarboxylate | LC-MS (Method 5):<br>$R_t$ = 1.57 min; m/z = 580/582 $(M - H)^-$. |
| 183A | (+)-tert-butyl 1-(2-chloro-5-{[(2S,3R)-2-(4-chlorophenyl)-4,4,4-trifluoro-3-methylbutanoyl]amino}-4-fluorobenzyl)-cyclopropanecarboxylate<br><br>from (2S,3R)-2-(4-chlorophenyl)-4,4,4-trifluoro-3-methylbutanoyl chloride and tert-butyl 1-(5-amino-2-chloro-4-fluorobenzyl)cyclopropanecarboxylate | LC-MS (Method 4):<br>$R_t$ = 1.76 min; m/z = 546/548 $(M - H)^-$.<br>$^1$H-NMR (400 MHz, DMSO-$d_6$): δ [ppm] = 0.75-0.82 (m, 5H), 1.14 (q, 2H), 1.21 (s, 9H), 2.81-2.96 (m, 2H), 3.34-3.44 (m, 1H), 4.05-4.12 (m, 1H), 7.35-7.47 (m, 5H), 7.89-7.96 (m, 1H), 10.13 (s, 1H).<br>$[α]_D^{20}$ = +122.1°, c = 0.370, chloroform. |
| 184A | tert-butyl 1-(4-chloro-3-{[(4-chlorophenyl)-(3,3-difluorocyclopentyl)acetyl]amino}benzyl)-cyclopropanecarboxylate (diastereomer mixture)<br><br>from (4-chlorophenyl)(3,3-difluorocyclopentyl)acetyl chloride and tert-butyl 1-(3-amino-4-chlorobenzyl)cyclopropanecarboxylate | LC-MS (Method 4):<br>$R_t$ = 1.67 min; m/z = 536/538 $(M - H)^-$. |

| Example | Name/Structure/Starting materials | Analytical data |
| --- | --- | --- |
| 185A | tert-butyl 1-[4-chloro-3-({(2S,3R)-4,4,4-trifluoro-3-methyl-2-[4-(trifluoromethyl)phenyl]butanoyl}-amino)benzyl]cyclopropanecarboxylate<br>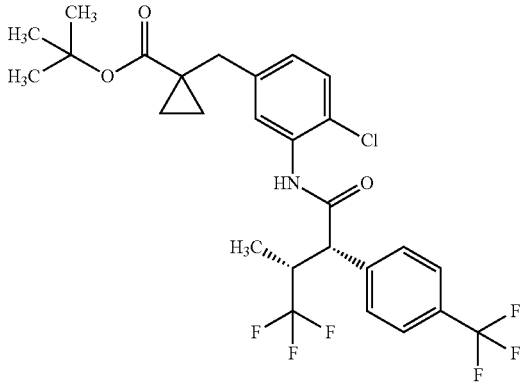 [SMILES: C[C@H]([C@H](C(=O)Nc1cc(CC2(C(=O)OC(C)(C)C)CC2)ccc1Cl)c1ccc(C(F)(F)F)cc1)C(F)(F)F]<br>from (2S,3R)-4,4,4-trifluoro-3-methyl-2-[4-(trifluoromethyl)phenyl]butanoyl chloride and tert-butyl 1-(3-amino-4-chlorobenzyl)cyclopropanecarboxylate | LC-MS (Method 4): $R_t = 1.68$ min; m/z = 562 (M − H)⁻.<br>$^1$H-NMR (400 MHz, DMSO-$d_6$): δ [ppm] = 0.76-0.84 (m, 5H), 0.99-1.07 (m, 2H), 1.22 (s, 9H), 2.70-2.85 (q, 2H), 3.36-3.52 (m, 1H), 4.22 (d, 1H), 7.05 (dd, 1H), 7.35 (d, 1H), 7.53 (d, 1H), 7.69 (d, 2H), 7.76 (d, 2H), 9.89 (s, 1H). |

Example 186A and Example 187A tert-Butyl 1-(4-chloro-3-{[(2S,3R)-2-(4-chlorophenyl)-4,4,4-trifluoro-3-methylbutanoyl]amino}-2-fluorobenzyl)cyclopropanecarboxylate and tert-butyl 1-(6-chloro-3-{[(2S,3R)-2-(4-chlorophenyl)-4,4,4-trifluoro-3-methylbutanoyl]amino}-2-fluorobenzyl)cyclopropanecarboxylate 33.0 mg of a mixture of tert-butyl 1-(3-amino-4-chloro-2-fluorobenzyl)cyclopropanecarboxylate and tert-butyl 1-(3-amino-6-chloro-2-fluorobenzyl)cyclopropanecarboxylate (Example 24A/25A, ratio about 1.5:1) were dissolved in 0.16 ml of abs. THF, the solution was cooled to −10° C. and a solution of 38 mg (0.132 mmol) of (2S,3R)-2-(4-chlorophenyl)-4,4,4-trifluoro-3-methylbutanoyl chloride in about 0.1 ml of abs. THF was added dropwise. After the addition had ended, the mixture was slowly warmed to RT, and after 2 h, water was added. The mixture was extracted three times with ethyl acetate, and the combined organic phases were washed with 1 N hydrochloric acid and saturated sodium chloride solution, dried over magnesium sulphate and concentrated under reduced pressure. The product mixture obtained was separated by preparative RP-HPLC (mobile phase acetonitrile/water). This gave 23.2 mg (38% of theory) of tert-butyl 1-(4-chloro-3-{[(2S,3R)-2-(4-chlorophenyl)-4,4,4-trifluoro-3-methylbutanoyl]amino}-2-fluorobenzyl)cyclopropanecarboxylate (Example 186A) and 18.7 mg (31% of theory) of tert-butyl 1-(6-chloro-3-{[(2S,3R)-2-(4-chlorophenyl)-4,4,4-trifluoro-3-methylbutanoyl]-amino}-2-fluorobenzyl)cyclopropanecarboxylate (Example 187A).

Example 186A tert-Butyl 1-(4-chloro-3-{[(2S,3R)-2-(4-chlorophenyl)-4,4,4-trifluoro-3-methylbutanoyl]amino}-2-fluorobenzyl)cyclopropanecarboxylate

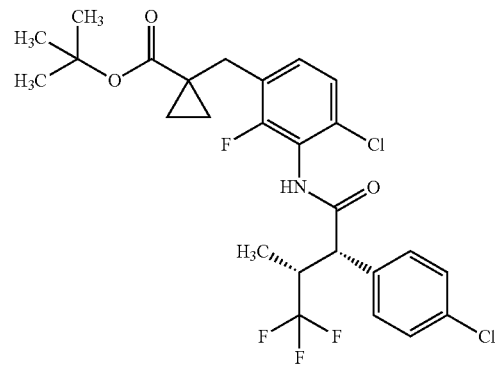 [SMILES: C[C@H]([C@H](C(=O)Nc1c(Cl)ccc(CC2(C(=O)OC(C)(C)C)CC2)c1F)c1ccc(Cl)cc1)C(F)(F)F]

LC-MS (Method 4): $R_t$=1.65 min; m/z=546/548 (M−H)⁻.

$^1$H-NMR (400 MHz, DMSO-$d_6$): δ [ppm]=0.79 (d, 5H), 1.06-1.11 (m, 2H), 1.26 (s, 9H), 2.83 (s, 2H), 3.33-3.40 (m, 1H), 3.95 (d, 1H), 7.26 (s, 2H), 7.40-7.47 (m, 4H), 10.02 (s, 1H).

Example 187A tert-Butyl 1-(6-chloro-3-{[(2S,3R)-2-(4-chlorophenyl)-4,4,4-trifluoro-3-methylbutanoyl]amino}-2-fluorobenzyl)cyclopropanecarboxylate

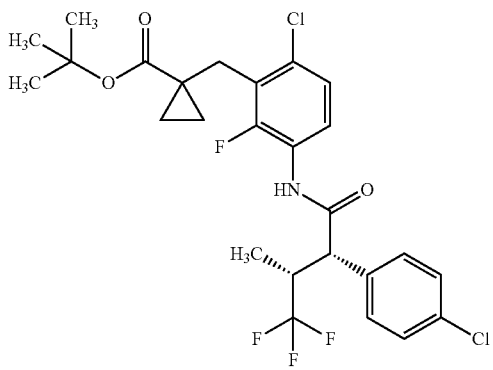 [SMILES: C[C@H]([C@H](C(=O)Nc1ccc(Cl)c(CC2(C(=O)OC(C)(C)C)CC2)c1F)c1ccc(Cl)cc1)C(F)(F)F]

LC-MS (Method 4): R$_t$=1.82 min; m/z=546/548 (M–H)⁻.
¹H-NMR (400 MHz, DMSO-d$_6$): δ [ppm]=0.45-0.53 (m, 2H), 0.78 (d, 3H), 0.97-1.06 (m, 2H), 1.32 (s, 9H), 3.16-3.24 (m, 2H), 3.34-3.44 (m, 1H), 4.11 (d, 1H), 7.24 (d, 1H), 7.45 (s, 4H), 7.70 (t, 1H), 10.17 (s, 1H).

Example 188A tert-Butyl 1-(4-chloro-3-{[(2S,3R)-2-(4-chlorophenyl)-4,4,4-trifluoro-3-methylbutanoyl]amino}-benzyl)-2,2-difluorocyclopropanecarboxylate (diastereomer mixture)

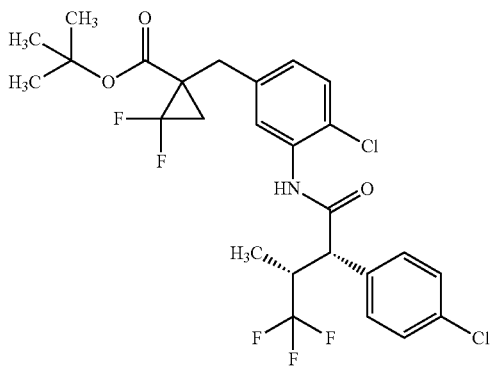 [SMILES: C[C@H]([C@H](C(=O)Nc1cc(CC2(C(=O)OC(C)(C)C)CC2(F)F)ccc1Cl)c1ccc(Cl)cc1)C(F)(F)F]

1.15 g (3.62 mmol) of (+/−)-tert-butyl 1-(3-amino-4-chlorobenzyl)-2,2-difluorocyclopropane-carboxylate were dissolved in 5 ml of DMF, and 1.49 g (5.43 mmol) of (+)-(2S,3R)-2-(4-chlorophenyl)-4,4,4-trifluoro-3-methylbutanoic acid, 2.5 ml of pyridine and 1.79 g (4.71 mmol) of HATU were added at RT. The reaction mixture was then stirred at 40° C. overnight. After cooling, the mixture was diluted with ethyl acetate and the solution was washed with 1 N hydrochloric acid and saturated sodium chloride solution, dried over magnesium sulphate and concentrated under reduced pressure. The residue was purified by chromatography on silica gel (mobile phase cyclohexane/ethyl acetate 30:1). This gave 1.82 g of the title compound (88.8% of theory).

LC-MS (Method 4): R$_t$=1.86 min; m/z=564 (M–H)⁻.
¹H-NMR (400 MHz, DMSO-d$_6$): both diastereomers: δ [ppm]=0.80 (d, 3H), 1.20/1.27 (each s, together 9H), 1.91-2.02 (m, 1H), 2.03-2.16 (m, 1H), 2.64-2.71 (m, 1H), 3.26-3.32 (m, 1H, obscured), 3.35-3.41 (m, 1H), 4.10/4.12 (each d, together 1H), 7.09 (dt, 1H), 7.34-7.52 (m, 6H), 9.84/9.86 (each d, together 1H).

Example 189A tert-Butyl 1-(4-chloro-3-{[(2S,3R)-2-(4-chlorophenyl)-4,4,4-trifluoro-3-methylbutanoyl]amino}-benzyl)cyclopropanecarboxylate

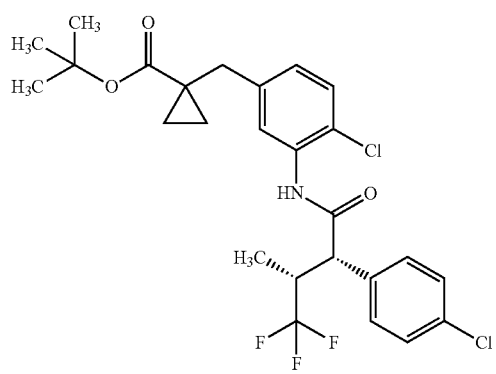 [SMILES: C[C@H]([C@H](C(=O)Nc1cc(CC2(C(=O)OC(C)(C)C)CC2)ccc1Cl)c1ccc(Cl)cc1)C(F)(F)F]

368 mg (1.38 mmol) of (2S,3R)-2-(4-chlorophenyl)-4,4,4-trifluoro-3-methylbutanoic acid were dissolved in 15 ml of dichloromethane, 246 mg (1.84 mmol) of 1-chloro-N,N,2-trimethylprop-1-en-1-amine were added and the mixture was then stirred at room temperature for 30 min. 279 µl (3.45 mmol) of pyridine and 324 mg (1.15 mmol) of tert-butyl 1-(3-amino-4-chlorobenzyl)-cyclopropanecarboxylate were then added, and the reaction mixture was stirred at room temperature for another 1 h. The reaction mixture was then concentrated under reduced pressure and the crude product obtained was purified by preparative RP-HPLC (mobile phase acetonitrile/water). This gave 540 mg of the target compound (88% of theory).

LC-MS (Method 5): R$_t$=1.52 min; m/z=528/530 (M–H)⁻.
¹H-NMR (400 MHz, DMSO-d$_6$): δ [ppm]=0.76-0.83 (m, 5H), 1.01-1.06 (m, 2H), 1.24 (s, 9H), 2.72-2.85 (m, 2H), 3.32-3.43 (m, 1H, partially obscured by H$_2$O signal), 4.10 (d, 1H), 7.05 (d, 1H), 7.35 (d, 1H), 7.41-7.50 (m, 5H), 9.83 (s, 1H).

The compounds listed in the table below were prepared in an analogous manner:

| Example | Name/Structure/Starting materials | Analytical data |
|---|---|---|
| 190A | tert-butyl 1-(4-chloro-3-{[(2S,3R)-2-(4-chloro-3-methoxyphenyl)-4,4,4-trifluoro-3-methylbutanoyl]-amino}benzyl)cyclopropanecarboxylate<br><br>from tert-butyl 1-(3-amino-4-chlorobenzyl)cyclopropanecarboxylate and (2S,3R)-2-(4-chloro-3-methoxyphenyl)-4,4,4-trifluoro-3-methylbutanoic acid | LC-MS (Method 4):<br>$R_t$ = 1.68 min; m/z = 558/560 (M − H)$^-$.<br>$^1$H-NMR (400 MHz, DMSO-$d_6$): δ [ppm] = 0.78-0.87 (m, 5H), 1.00-1.08 (m, 2H), 1.23 (s, 9H), 2.78 (q, 2H), 3.36-3.50 (m, 1H), 3.86 (s, 3H), 4.07 (d, 1H), 6.99-7.07 (m, 2H), 7.23 (d, 1H), 7.35 (d, 1H), 7.41 (d, 1H), 7.44 (d, 1H), 9.81 (s, 1H). |
| 191A | tert-butyl 1-[4-chloro-3-({(2S,3R)-4,4,4-trifluoro-3-methyl-2-[4-(1,1,1-trifluoro-2-methylpropan-2-yl)-phenyl]butanoyl}amino)benzyl]cyclopropane-carboxylate<br><br>from tert-butyl 1-(3-amino-4-chlorobenzyl)-cyclopropanecarboxylate and (2S,3R)-4,4,4-trifluoro-3-methyl-2-[4-(1,1,1-trifluoro-2-methylpropan-2-yl)-phenyl]butanoic acid | LC-MS (Method 5):<br>$R_t$ = 1.61 min; m/z = 604/606 (M − H)$^-$. |

| Example | Name/Structure/Starting materials | Analytical data |
|---|---|---|
| 192A | tert-butyl 1-[4-chloro-3-({4,4,4-trifluoro-3-methyl-2-[4-(2,2,2-trifluoroethyl)phenyl]butanoyl}amino)-benzyl]cyclopropanecarboxylate<br>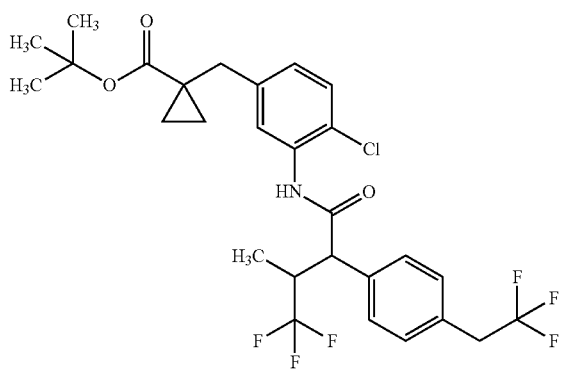 [SMILES: CC(C(C(=O)Nc1cc(CC2(C(=O)OC(C)(C)C)CC2)ccc1Cl)c1ccc(CC(F)(F)F)cc1)C(F)(F)F]<br>from tert-butyl 1-(3-amino-4-chlorobenzyl)cyclopropanecarboxylate and 4,4,4-trifluoro-3-methyl-2-[4-(2,2,2-trifluoroethyl)phenyl]butanoic acid | LC-MS (Method 5):<br>$R_t$ = 1.50 min; m/z = 576/578 $(M - H)^-$. |

Example 193A (+/−)-tert-Butyl 1-[(3-bromo-4-chlorophenyl)(hydroxy)methyl]cyclopropanecarboxylate

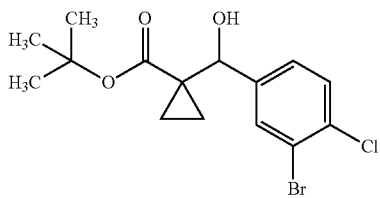 [SMILES: CC(C)(C)OC(=O)C1(C(O)c2ccc(Cl)c(Br)c2)CC1]

42.2 ml (105.5 mmol) of a 2.5 M solution of n-butyllithium in hexane were added dropwise to a solution, cooled to from −20° C. to −30° C., of 14.8 ml (105.5 mmol) of diisopropylamine in 60 ml of abs. THF. After the addition had ended, the mixture was stirred at from −20° C. to −30° C. for another 30 min. The mixture was then cooled to −78° C., and a solution of 12.0 g (84.4 mmol) of tert-butyl cyclopropanecarboxylate in 60 ml of abs. THF was added dropwise at this temperature. After 4 h at −78° C., a solution of 15.4 g (70.3 mmol) of 3-bromo-4-chlorobenzaldehyde in 60 ml of abs. THF was added. The reaction mixture was slowly warmed to RT overnight, saturated aqueous ammonium chloride solution was then added and the mixture was extracted with ethyl acetate. The organic phase was dried over magnesium sulphate and concentrated under reduced pressure. The crude product was purified by chromatography on silica gel (mobile phase cyclohexane/ethyl acetate 40:1→10:1). This gave 16.2 g of the target compound (52.5% of theory).

LC-MS (Method 4): $R_t$=1.47 min; m/z=286/288.

$^1$H-NMR (400 MHz, DMSO-$d_6$): δ [ppm]=0.84-0.99 (m, 2H), 1.02-1.17 (m, 2H), 1.24 (s, 9H), 4.88 (d, 1H), 5.55 (d, 1H), 7.39 (dd, 1H), 7.57 (d, 1H), 7.71 (d, 1H).

Example 194A (+/−)-tert-Butyl 1-[(3-bromo-4-chlorophenyl)(methoxy)methyl]cyclopropanecarboxylate

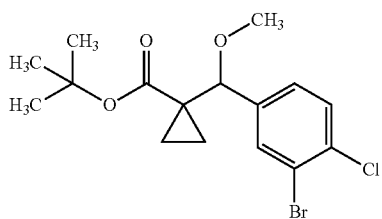 [SMILES: COC(c1ccc(Cl)c(Br)c1)C1(C(=O)OC(C)(C)C)CC1]

16.0 g (44.2 mmol) of (+/−)-tert-butyl 1-[(3-bromo-4-chlorophenyl)(hydroxy)methyl]cyclopropanecarboxylate were dissolved in 80 ml of DMF, and 4.1 ml (66.6 mmol) of methyl iodide were added at RT. The reaction mixture was cooled to +10° C., and 1.95 g (60% in mineral oil, 48.7 mmol) of sodium hydride were added in several portions. Ten minutes after the addition had ended, the mixture was warmed to RT and stirred at RT for a further 1.5 h. The reaction mixture was then added to water and extracted three times with ethyl acetate. The combined organic phases were concentrated under reduced pressure and the residue was purified by chromatography on silica gel (mobile phase cyclohexane/ethyl acetate 50:1). This gave 15.3 g of the target compound (92.2% of theory).

GC-MS (Method 1): $R_t$=6.5 min.

$^1$H-NMR (400 MHz, DMSO-$d_6$): δ [ppm]=0.76-0.82 (m, 1H), 0.89-1.08 (m, 3H), 1.30 (s, 9H), 3.16 (s, 3H), 4.69 (s, 1H), 7.36 (dd, 1H), 7.62 (d, 1H), 7.71 (d, 1H).

Example 195A (+/−)-tert-Butyl 1-{[3-(benzylamino)-4-chlorophenyl](methoxy)methyl}cyclopropanecarboxylate

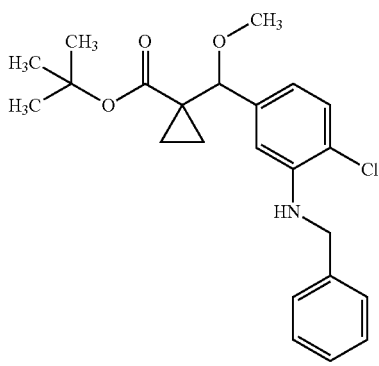 [SMILES: COC(c1ccc(Cl)c(NCc2ccccc2)c1)C1(C(=O)OC(C)(C)C)CC1]

In a dry reaction flask which had been flushed with argon, 4.60 g (47.9 mmol) of sodium tert-butoxide were suspended in 100 ml of abs. toluene, and 5.2 ml (47.9 mmol) of benzylamine, 0.99 g (1.6 mmol) of rac-2,2'-bis(diphenylphosphino)-1,1'-binaphthyl, 1.83 g (2.0 mmol) of tris(dibenzylideneacetone)dipalladium and 15.0 g (39.9 mmol) of (+/−)-tert-butyl 1-[(3-bromo-4-chlorophenyl)(methoxy)methyl]cyclopropanecarboxylate were added. The reaction mixture was heated at 110° C. for 3 h. After cooling, ethyl acetate and saturated aqueous ammonium chloride solution were added and the mixture was filtered through Celite. The organic phase was washed with saturated ammonium chloride solution and saturated sodium chloride solution, dried over magnesium sulphate and concentrated under reduced pressure. The crude product was purified by chromatography on silica gel (mobile phase cyclohexane/ethyl acetate 40:1→20:1). This gave 12.0 g of the target compound (74.8% of theory).

LC-MS (Method 5): $R_t$=1.48 min; m/z=402 (M+H)$^+$.

$^1$H-NMR (400 MHz, DMSO-d$_6$): δ [ppm]=0.22 (ddd, 1H), 0.56 (ddd, 1H), 0.68 (ddd, 1H), 0.78 (ddd, 1H), 1.30 (s, 9H), 2.98 (s, 3H), 4.40 (dd, 2H), 4.65 (s, 1H), 6.17 (t, 1H), 6.38 (d, 1H), 6.43 (dd, 1H), 7.18-7.22 (m, 2H), 7.28-7.33 (m, 4H).

Example 196A (+/−)-tert-Butyl 1-[(3-amino-4-chlorophenyl)(methoxy)methyl]cyclopropanecarboxylate

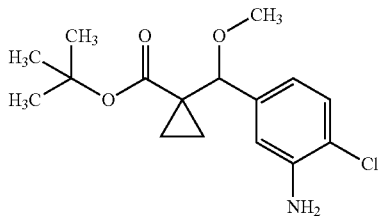 [SMILES: COC(c1ccc(Cl)c(N)c1)C1(C(=O)OC(C)(C)C)CC1]

6.20 g (15.4 mmol) of (+/−)-tert-butyl 1-{[3-(benzylamino)-4-chlorophenyl](methoxy)methyl}-cyclopropanecarboxylate were dissolved in 300 ml of ethyl acetate and inertized with argon, and 350 mg of palladium (10% on carbon) were added. At RT, the reaction mixture was stirred for a total of 24 h under an atmosphere of hydrogen at atmospheric pressure. The reaction mixture was then filtered through Celite, the residue was washed thoroughly with ethyl acetate and the combined filtrate was concentrated under reduced pressure. The crude product was purified by chromatography on silica gel (mobile phase cyclohexane/ethyl acetate 30:1→10:1). This gave 3.36 g of the target compound (69.9% of theory).

LC-MS (Method 5): $R_t$=1.22 min; m/z=312 (M+H)$^+$.

$^1$H-NMR (400 MHz, DMSO-d$_6$): δ [ppm]=0.47-0.56 (m, 1H), 0.81-0.95 (m, 3H), 1.34 (s, 9H), 3.13 (s, 3H), 4.69 (s, 1H), 5.21-5.39 (m, 2H), 6.44 (dd, 1H), 6.72 (d, 1H), 7.13 (d, 1H).

Example 197A tert-Butyl 1-[(4-chloro-3-{[(2S,3R)-2-(4-chlorophenyl)-4,4,4-trifluoro-3-methylbutanoyl]amino}-phenyl)(methoxy)methyl]cyclopropanecarboxylate (diastereomer mixture)

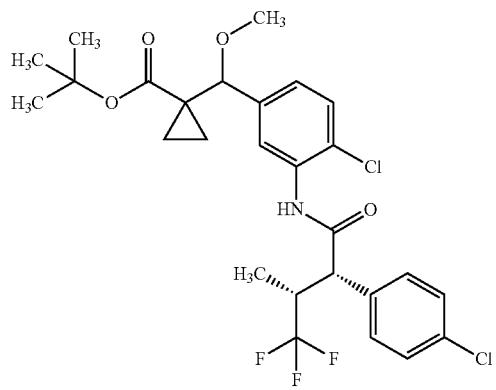 [SMILES: COC(c1ccc(Cl)c(NC(=O)[C@H](c2ccc(Cl)cc2)[C@@H](C)C(F)(F)F)c1)C1(C(=O)OC(C)(C)C)CC1]

200 mg (0.641 mmol) of (+/−)-tert-butyl 1-[(3-amino-4-chlorophenyl)(methoxy)methyl]cyclopropanecarboxylate and 188 mg (0.706 mmol) of (+)-(2S,3R)-2-(4-chlorophenyl)-4,4,4-trifluoro-3-methylbutanoic acid were dissolved in 2.3 ml of DMF and 0.7 ml of pyridine, and 293 mg (0.770 mmol) of HATU were added at RT. The reaction mixture was stirred at RT overnight. Another 0.6 eq. of (+)-(2S,3R)-2-(4-chlorophenyl)-4,4,4-trifluoro-3-methylbutanoic acid was then added, and the reaction mixture was stirred at 45° C. for 14 h. After cooling, the mixture was diluted with ethyl acetate and the solution was washed with 1 N hydrochloric acid and saturated sodium chloride solution, dried over magnesium sulphate and concentrated under reduced pressure. The residue was purified by chromatography on silica gel (mobile phase cyclohexane/ethyl acetate 30:1). This gave 168 mg of the target compound (39.9% of theory).

LC-MS (Method 5): $R_t$=1.53 min; m/z=558/560 (M−H)$^−$.

$^1$H-NMR (400 MHz, DMSO-d$_6$): both diastereomers: δ [ppm]=0.51-0.62 (m, 1H), 0.80 (d, 3H), 0.84-0.96 (m, 3H), 1.26/1.30 (each s, together 9H), 3.13 (s, 3H), 3.35-3.44 (d, 1H), 4.13/4.14 (each d, together 1H), 4.74 (s, 1H), 7.10 (dd, 1H), 7.39-7.53 (m, 6H), 9.91/9.92 (each s, together 1H).

Example 198A tert-Butyl 1-[(3-bromo-4-chlorophenyl)(hydroxy)methyl]cyclobutanecarboxylate

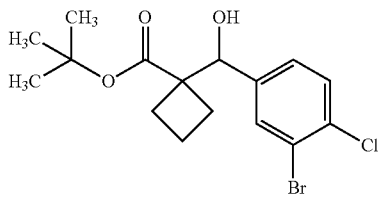 [SMILES: CC(C)(C)OC(=O)C1(C(O)c2ccc(Cl)c(Br)c2)CCC1]

21.65 ml (54.12 mmol) of a 2.5 M solution of n-butyllithium in hexane were added dropwise to a solution, cooled to from −20° C. to −30° C., of 7.6 ml (54.12 mmol) of diisopropylamine in 30 ml of abs. THF. After the addition had ended, the mixture was stirred at from −20° C. to −30° C. for another 30 min. The mixture was then cooled to −78° C., and a solution of 6.2 g (39.7 mmol) of tert-butyl cyclobutanecarboxylate in 10 ml of abs. THF was added dropwise at this temperature. After 4 h at −78° C., a solution of 7.9 g (36.1 mmol) of 3-bromo-4-chlorobenzaldehyde in 10 ml of abs. THF was then added. The reaction mixture was slowly warmed to RT overnight, saturated aqueous ammonium chloride solution was then added and the mixture was extracted with ethyl acetate. The organic phase was dried over magnesium sulphate and concentrated under reduced pressure. The crude product was purified by chromatography on silica gel (mobile phase cyclohexane/ethyl acetate 50:1→10:1). This gave 7.77 g of the target compound (56% of theory).

$^1$H-NMR (400 MHz, DMSO-$d_6$): δ [ppm]=1.33 (s, 9H), 1.55-1.77 (m, 2H), 1.98-2.11 (m, 2H), 2.21-2.35 (m, 1H), 2.35-2.47 (m, 1H), 4.70 (d, 1H), 5.89 (d, 1H), 7.31 (dd, 1H), 7.53-7.60 (m, 2H).

Example 199A tert-Butyl 1-[(3-bromo-4-chlorophenyl)(trideuteromethoxy)methyl]cyclopropanecarboxylate

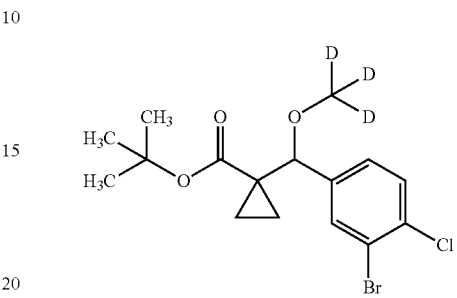

3 g (8.3 mmol) of tert-butyl 1-[(3-bromo-4-chlorophenyl)(hydroxy)methyl]cyclopropane-carboxylate were dissolved in 10 ml of DMF, and 774 µl (12.44 mmol) of trideuteromethyl iodide were added at RT. The reaction mixture was cooled to +10° C., and 398 mg (60% in mineral oil, 9.95 mmol) of sodium hydride were added in several portions. Ten minutes after the addition had ended, the mixture was warmed to RT and stirred at RT for a further 1.5 h. The reaction mixture was then added to water and extracted three times with ethyl acetate. The combined organic phases were concentrated under reduced pressure and the residue was purified by chromatography on silica gel (mobile phase cyclohexane/ethyl acetate 50:1). This gave 2.74 g of the target compound (87% of theory).

$^1$H-NMR (400 MHz, DMSO-$d_6$): δ [ppm]=0.75-0.83 (m, 1H), 0.88-1.07 (m, 3H), 1.30 (s, 9H), 4.69 (s, 1H), 7.36 (dd, 1H), 7.62 (d, 1H), 7.71 (d, 1H).

The compounds listed in the table below were prepared in an analogous manner:

| Example | Name/Structure/Starting materials | Analytical data |
|---|---|---|
| 200A | tert-butyl 1-[(3-bromo-4-chlorophenyl)-(ethoxy)methyl]cyclopropanecarboxylate<br>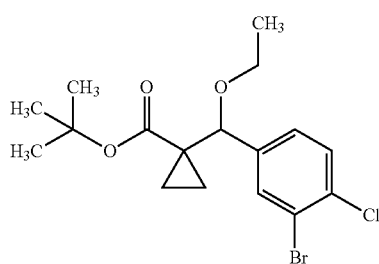 [SMILES: CCOC(c1ccc(Cl)c(Br)c1)C1(C(=O)OC(C)(C)C)CC1]<br>from tert-butyl 1-[(3-bromo-4-chlorophenyl)-(hydroxy)methyl]cyclopropanecarboxylate and iodoethane | $^1$H-NMR (400 MHz, DMSO-$d_6$): δ [ppm] = 0.71-0.79 (m, 1H), 0.89-1.04 (m, 3H), 1.07 (t, 3H), 1.31 (s, 9H), 3.25-3.43 (m, 2H, partially obscured by H$_2$O signal), 4.81 (s, 1H), 7.36 (dd, 1H), 7.61 (d, 1H), 7.70 (d, 1H). |

| Example | Name/Structure/Starting materials | Analytical data |
|---|---|---|
| 201A | tert-butyl 1-[(3-bromo-4-chlorophenyl)-(trideuteromethoxy)methyl]-cyclobutanecarboxylate<br><br>from tert-butyl 1-[(3-bromo-4-chlorophenyl)-(hydroxy)methyl]cyclobutanecarboxylate and trideuteromethyl iodide | $^1$H-NMR (400 MHz, DMSO-$d_6$): δ [ppm] = 1.34 (s, 9H), 1.47-1.59 (m, 1H), 1.62-1.75 (m, 1H), 2.05-2.15 (m, 2H), 2.20-2.35 (m, 2H), 4.35 (s, 1H), 7.32 (dd, 1H), 7.61 (d, 1H), 7.63 (d, 1H). |
| 202A | tert-butyl 1-[(3-bromo-4-chlorophenyl)-(methoxy)methyl]cyclobutanecarboxylate<br><br>from tert-butyl 1-[(3-bromo-4-chlorophenyl)-(hydroxy)methyl]cyclobutanecarboxylate and iodomethane | $^1$H-NMR (400 MHz, DMSO-$d_6$): δ [ppm] = 1.37 (s, 9H), 1.47-1.59 (m, 1H), 1.61-1.75 (m, 1H), 2.05-2.15 (m, 2H), 2.21-2.36 (m, 2H), 3.19 (s, 3H), 4.35 (s, 1H), 7.32 (dd, 1H), 7.61 (d, 1H), 7.63 (d, 1H). |
| 203A | tert-butyl 1-[(3-bromo-4-chlorophenyl)-(ethoxy)methyl]cyclobutanecarboxylate<br><br>from tert-butyl 1-[(3-bromo-4-chlorophenyl)-(hydroxy)methyl]cyclobutanecarboxylate and iodoethane | $^1$H-NMR (400 MHz, DMSO-$d_6$): δ [ppm] = 1.11 (t, 3H), 1.35 (s, 9H), 1.44-1.54 (m, 1H), 1.61-1.73 (m, 1H), 2.04-2.15 (m, 2H), 2.17-2.31 (m, 2H), 3.27-3.37 (q, 2H, obscured by H$_2$O signal), 4.47 (s, 1H), 7.34 (dd, 1H), 7.59-7.64 (m, 2H). |

The following compounds were obtained analogously to Synthesis Example 30A:

| Example | Name/Structure/Starting materials | Analytical data |
|---|---|---|
| 204A | tert-butyl 1-{[3-(benzylamino)-4-chlorophenyl]-(trideuteromethoxy)methyl}cyclopropanecarboxylate 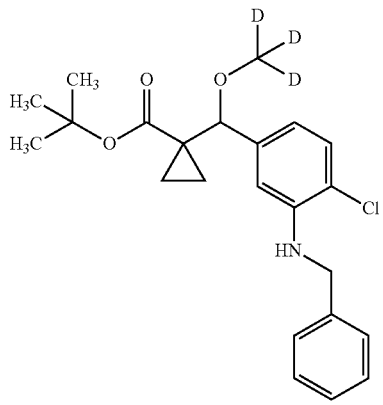 [SMILES: [2H]C([2H])([2H])OC(c1ccc(Cl)c(NCc2ccccc2)c1)C1(C(=O)OC(C)(C)C)CC1]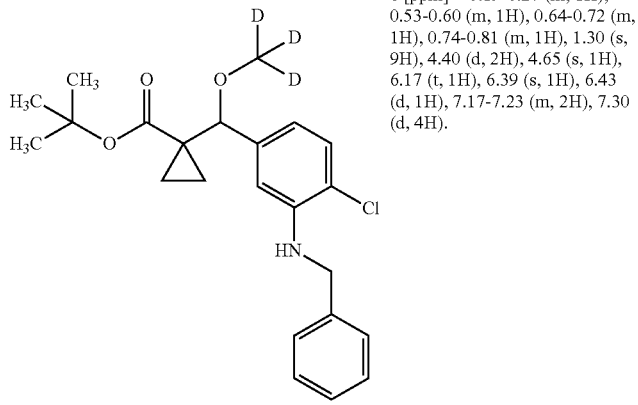 from tert-butyl 1-[(3-bromo-4-chlorophenyl)-(trideuteromethoxy)methyl]cyclopropanecarboxylate and benzylamine | LC-MS (Method 4): $R_t$ = 1.71 min; m/z = 405 (M + H)$^+$. $^1$H-NMR (400 MHz, DMSO-d$_6$): δ [ppm] = 0.19-0.27 (m, 1H), 0.53-0.60 (m, 1H), 0.64-0.72 (m, 1H), 0.74-0.81 (m, 1H), 1.30 (s, 9H), 4.40 (d, 2H), 4.65 (s, 1H), 6.17 (t, 1H), 6.39 (s, 1H), 6.43 (d, 1H), 7.17-7.23 (m, 2H), 7.30 (d, 4H). |
| 205A | tert-butyl 1-{[3-(benzylamino)-4-chlorophenyl]-(ethoxy)methyl(cyclopropanecarboxylate 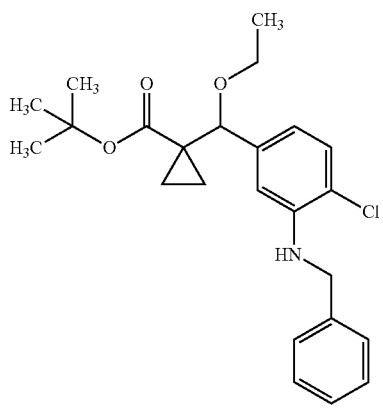 [SMILES: CCOC(c1ccc(Cl)c(NCc2ccccc2)c1)C1(C(=O)OC(C)(C)C)CC1] from tert-butyl 1-[(3-bromo-4-chlorophenyl)-(ethoxy)methyl]cyclopropanecarboxylate and benzylamine | LC-MS (Method 5): $R_t$ = 1.59 min; m/z = 416 (M + H)$^+$. $^1$H-NMR (400 MHz, DMSO-d$_6$): δ [ppm] = 0.16-0.26 (m, 1H), 0.50-0.61 (m, 1H), 0.62-0.71 (m, 1H), 0.74-0.84 (m, 1H), 0.91 (t, 3H), 1.31 (s, 9H), 3.01-3.11 (m, 1H), 3.12-3.24 (m, 1H), 4.40 (d, 2H), 4.76 (s, 1H), 6.18 (t, 1H), 6.35-6.45 (m, 2H), 7.14-7.24 (m, 2H), 7.25-7.35 (m, 4H). |

-continued

| Example | Name/Structure/Starting materials | Analytical data |
|---|---|---|
| 206A | tert-butyl 1-{[3-(benzylamino)-4-chlorophenyl]-(trideuteromethoxy)methyl}cyclobutane-carboxylate 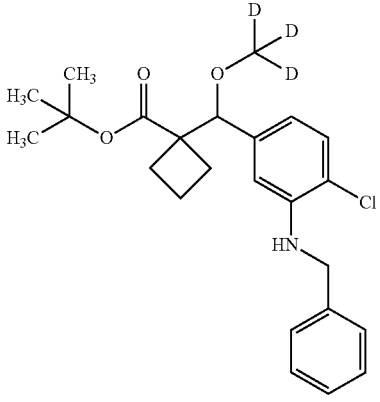 [SMILES: [2H]C([2H])([2H])OC(c1ccc(Cl)c(NCc2ccccc2)c1)C1(C(=O)OC(C)(C)C)CCC1] from tert-butyl 1-[(3-bromo-4-chlorophenyl)-(trideuteromethoxy)methyl]cyclo-butanecarboxylate and benzylamine | LC-MS (Method 5): $R_t$ = 1.59 min; m/z = 419 (M + H)$^+$. $^1$H-NMR (400 MHz, DMSO-d$_6$): δ [ppm] = 1.10-1.25 (m, 1H), 1.31 (s, 9H), 1.43-1.59 (m, 1H), 1.78-1.94 (m, 2H), 2.00 (t, 2H), 4.10 (s, 1H), 4.41 (d, 2H), 6.17 (t, 1H), 6.41-6.47 (m, 2H), 7.15-7.23 (m, 2H), 7.24-7.35 (m, 4H). |
| 207A | tert-butyl 1-{[3-(benzylamino)-4-chlorophenyl]-(methoxy)methyl}cyclobutanecarboxylate 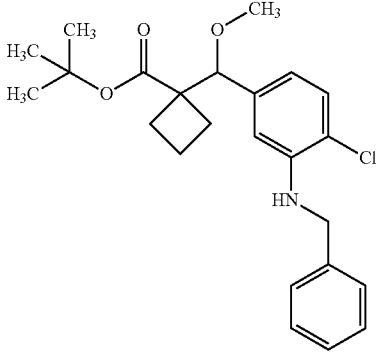 [SMILES: COC(c1ccc(Cl)c(NCc2ccccc2)c1)C1(C(=O)OC(C)(C)C)CCC1] from tert-butyl 1-[(3-bromo-4-chlorophenyl)-(methoxy)methyl]cyclobutanecarboxylate and benzylamine | LC-MS (Method 4): $R_t$ = 1.78 min; m/z = 416 (M + H)$^+$. |
| 208A | tert-butyl 1-{[3-(benzylamino)-4-chlorophenyl]-(ethoxy)methyl}cyclobutanecarboxylate 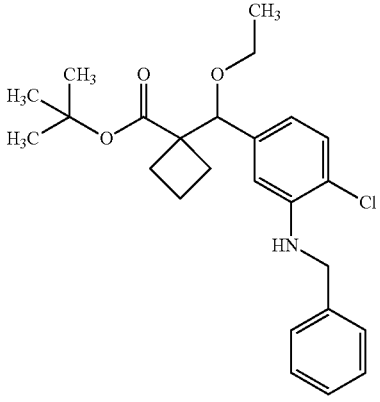 [SMILES: CCOC(c1ccc(Cl)c(NCc2ccccc2)c1)C1(C(=O)OC(C)(C)C)CCC1] from tert-butyl 1-[(3-bromo-4-chlorophenyl)-(ethoxy)methyl]cyclobutanecarboxylate and benzylamine | LC-MS (Method 5): $R_t$ = 1.67 min; m/z = 430 (M + H)$^+$. |

The following compounds were obtained analogously to Synthesis Example 196A:

| Example | Name/Structure/Starting material | Analytical data |
| --- | --- | --- |
| 209A | tert-butyl 1-[(3-amino-4-chlorophenyl)-(trideuteromethoxy)methyl]cyclopropane-carboxylate<br />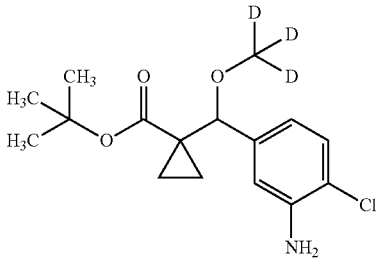 [SMILES: [2H]C([2H])([2H])OC(c1ccc(Cl)c(N)c1)C1(C(=O)OC(C)(C)C)CC1]<br />from tert-butyl 1-{[3-(benzylamino)-4-chlorophenyl](trideuteromethoxy)methyl}cyclopropanecarboxylate | LC-MS (Method 5): $R_t$ = 1.18 min; m/z = 315 (M + H)$^+$.<br />$^1$H-NMR (400 MHz, DMSO-$d_6$): δ [ppm] = 0.50-0.56 (m, 1H), 0.82-0.95 (m, 3H), 1.34 (s, 9H), 4.69 (s, 1H), 5.35 (s, 2H), 6.44 (dd, 1H), 6.72 (d, 1H), 7.13 (d, 1H). |
| 210A | tert-butyl 1-[(3-amino-4-chlorophenyl)-(ethoxy)methyl]cyclopropanecarboxylate<br />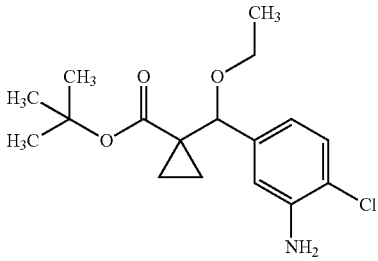 [SMILES: CCOC(c1ccc(Cl)c(N)c1)C1(C(=O)OC(C)(C)C)CC1]<br />from tert-butyl 1-{[3-(benzylamino)-4-chlorophenyl](ethoxy)methyl}cyclopropane-carboxylate | LC-MS (Method 5): $R_t$ = 1.27 min; m/z = 326 (M + H)$^+$.<br />$^1$H-NMR (400 MHz, DMSO-$d_6$): δ [ppm] = 0.46-0.54 (m, 1H), 0.79-0.95 (m, 3H), 1.07 (t, 3H), 1.35 (s, 9H), 3.25-3.38 (m, 2H, partially obscured by H$_2$O signal), 4.81 (s, 1H), 5.32 (s, 2H), 6.44 (dd, 1H), 6.72 (d, 1H), 7.12 (d, 1H). |
| 211A | tert-butyl 1-[(3-amino-4-chlorophenyl)-(trideuteromethoxy)methyl]cyclo-butanecarboxylate<br />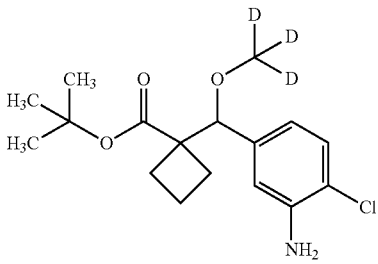 [SMILES: [2H]C([2H])([2H])OC(c1ccc(Cl)c(N)c1)C1(C(=O)OC(C)(C)C)CCC1]<br />from tert-butyl 1-{[3-(benzylamino)-4-chlorophenyl](trideuteromethoxy)methyl}cyclo-butanecarboxylate | LC-MS (Method 5): $R_t$ = 1.29 min; m/z = 329 (M + H)$^+$.<br />$^1$H-NMR (400 MHz, DMSO-$d_6$): δ [ppm] = 1.35 (s, 9H), 1.39-1.50 (m, 1H), 1.57-1.71 (m, 1H), 2.02-2.15 (m, 2H), 2.16-2.34 (m, 2H), 4.14 (s, 1H), 5.34 (s, 2H), 6.44 (dd, 1H), 6.73 (d, 1H), 7.13 (d, 1H). |

-continued

| Example | Name/Structure/Starting material | Analytical data |
| --- | --- | --- |
| 212A | tert-butyl 1-[(3-amino-4-chlorophenyl)-(methoxy)methyl]cyclobutanecarboxylate<br><br>from tert-butyl 1-{[3-(benzylamino)-4-chlorophenyl](methoxy)methyl}cyclobutane-carboxylate | LC-MS (Method 5): $R_t$ = 1.30 min; m/z = 326 (M + H)$^+$.<br>$^1$H-NMR (400 MHz, DMSO-d$_6$): δ [ppm] = 1.35 (s, 9H), 1.38-1.50 (m, 1H), 1.56-1.71 (m, 1H), 2.02-2.14 (m, 2H), 2.16-2.35 (m, 2H), 3.14 (s, 3H), 4.14 (s, 1H), 5.34 (s, 2H), 6.44 (dd, 1H), 6.73 (d, 1H), 7.13 (d, 1H). |
| 213A | tert-butyl 1-[(3-amino-4-chlorophenyl)-(ethoxy)methyl]cyclobutanecarboxylate<br><br>from tert-butyl 1-{[3-(benzylamino)-4-chlorophenyl](ethoxy)methyl}cyclobutane-carboxylate | LC-MS (Method 5): $R_t$ = 1.37 min; m/z = 340 (M + H)$^+$.<br>$^1$H-NMR (400 MHz, DMSO-d$_6$): δ [ppm] = 1.09 (t, 3H), 1.31-1.44 (m, 1H), 1.36 (s, 9H), 1.54-1.68 (m, 1H), 1.98-2.29 (m, 4H), 3.20-3.38 (m, 2H, partially obscured by H$_2$O signal), 4.27 (s, 1H), 5.33 (s, 2H), 6.46 (dd, 1H), 6.75 (d, 1H), 7.13 (d, 1H). |

The following compound was obtained analogously to Synthesis Example 29A:

| Example | Name/Structure/Starting materials | Analytical data |
| --- | --- | --- |
| 214A | tert-butyl 1-[1-(4-chlorophenyl)propyl]-cyclopropanecarboxylate<br><br>from tert-butyl cyclopropanecarboxylate and 1-(1-bromopropyl)-4-chlorobenzene [CAS Reg.-No. 2940-56-9] | GC-MS (Method 6): $R_t$ = 5.90 min; m/z = 312/314 (M + NH$_4$)$^+$.<br>GC-MS (Method 1): $R_t$ = 5.61 min; m/z = 238/240 (M − C$_4$H$_8$)$^+$. |

Example 215A

1-[1-(4-Chloro-3-nitrophenyl)propyl]cyclopropanecarboxylic acid

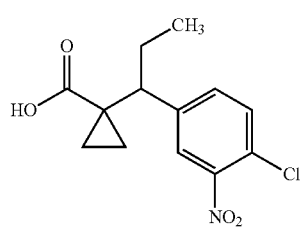 [SMILES: CCC(c1ccc(Cl)c([N+](=O)[O-])c1)C1(C(=O)O)CC1]

262 mg (0.89 mmol) of tert-butyl 1-[1-(4-chlorophenyl)propyl]cyclopropanecarboxylate were dissolved in 8 ml of dichloromethane, the mixture was cooled to 0° C. and 284 mg (2.14 mmol) of nitrosyl tetrafluoroborate were added a little at a time. The reaction solution was then stirred at a temperature between −10° C. and 0° C. for four hours. The reaction mixture was then added to water and extracted three times with dichloromethane. The combined organic phases were dried over magnesium sulphate and concentrated under reduced pressure. This gave 262 mg of the target product, which was used without further purification in the subsequent step.

LC-MS (Method 5): $R_t$=1.01 min; m/z=282/284 (M−H)⁻.

Example 216A

Methyl 1-[1-(4-chloro-3-nitrophenyl)propyl]cyclopropanecarboxylate

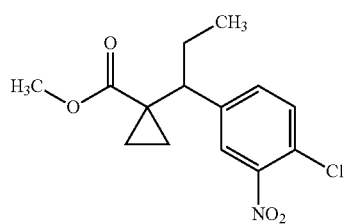

262 mg (about 0.93 mmol) of 1-[1-(4-chloro-3-nitrophenyl)propyl]cyclopropanecarboxylic acid were dissolved in 5 ml of methanol, the mixture was cooled to 0° C. and 0.14 ml (1.85 mmol) of thionyl chloride was added dropwise. The reaction solution was then slowly warmed to room temperature and stirred at this temperature overnight. The reaction mixture was then concentrated to dryness and the residue was taken up in 10 ml of dichloromethane. The solution was washed with water, dried over magnesium sulphate and concentrated under reduced pressure. This gave 224 mg of the target compound (81% of theory).

MS (DCI): m/z=315 (M+NH₄)⁺.

Example 217A

Methyl 1-[1-(3-amino-4-chlorophenyl)propyl]cyclopropanecarboxylate

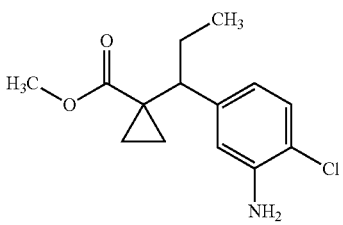 [SMILES: CCC(c1ccc(Cl)c([N+](=O)[O-])c1)C1(C(=O)OC)CC1]

224 mg (0.76 mmol) of methyl 1-[1-(4-chloro-3-nitrophenyl)propyl]cyclopropanecarboxylate were dissolved in 48 ml of ethyl acetate, the mixture was inertized with argon and 40 mg of palladium (10% on carbon) were added. At RT, the reaction mixture was stirred under an atmosphere of hydrogen at atmospheric pressure for a total of 24 h. The mixture was then filtered through Celite, the residue was washed thoroughly with ethyl acetate and the combined filtrate was concentrated under reduced pressure. This gave 195 mg of the target compound (96% of theory).

LC-MS (Method 5): $R_t$=1.15 min; m/z=268 (M+H)⁺.

¹H-NMR (400 MHz, DMSO-d₆): δ [ppm]=0.51-0.59 (m, 1H), 0.74 (t, 3H), 0.77-0.84 (m, 1H), 0.94-1.01 (m, 1H), 1.02-1.09 (m, 1H), 1.64-1.81 (m, 2H), 2.68-2.75 (m, 1H), 3.55 (s, 3H), 5.04-5.39 (m, 2H), 6.41 (dd, 1H), 6.68 (d, 1H), 7.06 (d, 1H).

Example 218A tert-Butyl 1-(3-amino-4-cyclopropylbenzyl)cyclopropanecarboxylate

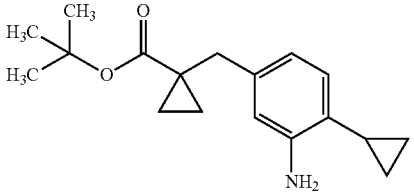

200 mg (0.71 mmol) of tert-butyl 1-(3-amino-4-chlorobenzyl)cyclopropanecarboxylate were dissolved in 6 ml of dioxane, the mixture was inertized with argon and 122 mg (1.42 mmol) of cyclopropylboronic acid, 256 mg (1.21 mmol) of potassium phosphate, 5 mg (0.02 mmol) of tricyclohexylphosphine and 6.5 mg (0.007 mmol) of tris(dibenzylideneacetone)dipalladium were added. The reaction mixture was then stirred in a microwave apparatus (Biotage) at a target temperature of 150° C. for 1 h. The reaction was checked by TLC (mobile phase cyclohexane/ethyl acetate 4:1), after which a further 10 mg of tricyclohexylphosphine and 13 mg of tris(dibenzylideneacetone)dipalladium were metered in, and the reaction mixture was stirred at 150° C. for another 2 h. The mixture was then filtered through kieselguhr, the residue was washed with dioxane and the combined filtrate was concentrated to dryness. The residue obtained was purified chromatographically on silica gel (mobile phase cyclohexane/ethyl acetate 4:1). This gave 120 mg (59% of theory) of the target compound.

LC-MS (Method 5): $R_t$=1.14 min; m/z=288 (M+H)⁺.

Example 219A tert-Butyl 1-{(4-chloro-3-{[(2S,3R)-2-(4-chlorophenyl)-4,4,4-trifluoro-3-methylbutanoyl]amino}-phenyl)(trideuteromethoxy)methyl}cyclopropanecarboxylate (diastereomer mixture)

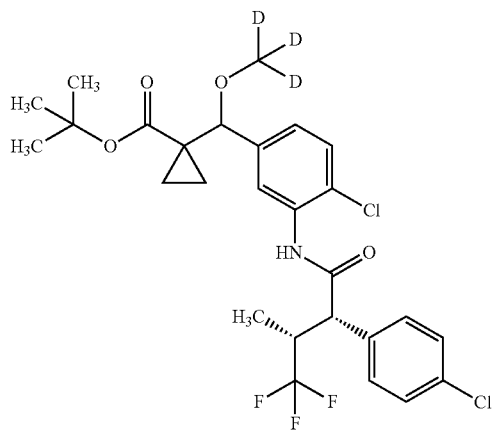 [SMILES: [2H]C([2H])([2H])OC(c1ccc(Cl)c(NC(=O)[C@H](c2ccc(Cl)cc2)[C@@H](C)C(F)(F)F)c1)C1(C(=O)OC(C)(C)C)CC1]

661 mg (2.1 mmol) of tert-butyl 1-[(3-amino-4-chlorophenyl)(trideuteromethoxy)methyl]-cyclopropanecarboxylate and 560 mg (2.1 mmol) of (2S,3R)-2-(4-chlorophenyl)-4,4,4-trifluoro-3-methylbutanoic acid were dissolved in 4 ml of DMF and 2 ml of pyridine, and 1.038 g (2.73 mmol) of HATU were added at RT. The reaction mixture was stirred at RT overnight. The mixture was then diluted with ethyl acetate, and the solution was washed with 1 N hydrochloric acid and saturated sodium chloride solution, dried over magnesium sulphate and concentrated under reduced pressure. The residue was purified by chromatography on silica gel (mobile phase cyclohexane→cyclohexane/ethyl acetate 100:1→cyclohexane/ethyl acetate 50:1). This gave 912 mg (77% of theory) of the title compound.

LC-MS (Method 5): $R_t$=1.55 min; m/z=561/563 (M−H)⁻.

$^1$H-NMR (400 MHz, DMSO-$d_6$): δ [ppm]=0.53-0.62 (m, 1H), 0.80 (d, 3H), 0.84-0.96 (m, 3H), 1.26 (s, 4.5H), 1.30 (s, 4.5H), 3.29-3.46 (m, 1H, partially obscured by H₂O signal), 4.12 (d, 0.5H), 4.15 (d, 0.5H), 4.74 (s, 1H), 7.07-7.13 (m, 1H), 7.40-7.54 (m, 6H), 9.91 (d, 1H).

The following compounds were obtained analogously to Synthesis Example 189A or 197A:

| Example | Name/Structure/Starting materials | Analytical data |
|---|---|---|
| 220A | tert-butyl 1-[(4-chloro-3-{[(2S,3R)-2-(4-chlorophenyl)-4,4,4-trifluoro-3-methylbutanoyl]-amino}phenyl)(ethoxy)methyl]cyclopropanecarboxylate (diastereomer mixture)<br><br>from tert-butyl 1-[(3-amino-4-chlorophenyl)-(ethoxy)methyl]cyclopropanecarboxylate and (2S,3R)-2-(4-chlorophenyl)-4,4,4-trifluoro-3-methylbutanoic acid | LC-MS (Method 5): $R_t$ = 1.62 min; m/z = 572/574 (M − H)⁻.<br>$^1$H-NMR (400 MHz, DMSO-$d_6$): δ [ppm] = 0.49-0.59 (m, 1H), 0.76-0.96 (m, 6H), 1.01-1.09 (m, 3H), 1.28 (s, 4.5H), 1.31 (s, 4.5H), 3.20-3.46 (m, 3H, partially obscured by H₂O signal), 4.11 (d, 0.5H), 4.14 (d, 0.5H), 4.86 (d, 1H), 7.10 (dd, 1H), 7.39-7.53 (m, 6H), 9.91 (s, 1H). |

| Example | Name/Structure/Starting materials | Analytical data |
| --- | --- | --- |
| 221A | tert-butyl 1-{(4-chloro-3-{[(2S,3R)-2-(4-chlorophenyl)-4,4,4-trifluoro-3-methylbutanoyl]-amino}phenyl)(trideuteromethoxy)methyl}-cyclobutanecarboxylate (diastereomer mixture)<br><br>from tert-butyl 1-[(3-amino-4-chlorophenyl)-(trideuteromethoxy)methyl]cyclobutanecarboxylate and (2S,3R)-2-(4-chlorophenyl)-4,4,4-trifluoro-3-methylbutanoic acid | LC-MS (Method 4): $R_t$ = 1.81 min; m/z = 575/577 (M − H)⁻. $^1$H-NMR (400 MHz, DMSO-$d_6$): δ [ppm] = 0.80 (d, 3H), 1.21 (s, 4.5H), 1.29 (s, 4.5H), 1.36-1.51 (m, 1H), 1.57-1.70 (m, 1H), 1.98-2.12 (m, 2H), 2.13-2.34 (m, 2H), 3.28-3.45 (m, 1H, partially obscured by H₂O signal), 4.15 (dd, 1H), 4.26 (d, 1H), 7.08 (dd, 1H), 7.41-7.57 (m, 6H), 9.88 (d, 1H). |
| 222A | tert-butyl 1-[(4-chloro-3-{[(2S,3R)-2-(4-chlorophenyl)-4,4,4-trifluoro-3-methylbutanoyl]amino}-phenyl)(methoxy)methyl]cyclobutanecarboxylate (diastereomer mixture)<br><br>from tert-butyl 1-[(3-amino-4-chlorophenyl)-(methoxy)methyl]cyclobutanecarboxylate and (2S,3R)-2-(4-chlorophenyl)-4,4,4-trifluoro-3-methyl-butanoic acid | LC-MS (Method 5): $R_t$ = 1.62 min; m/z = 572/574 (M − H)⁻. $^1$H-NMR (400 MHz, DMSO-$d_6$): δ [ppm] = 0.80 (d, 3H), 1.22 (s, 4.5H), 1.30 (s, 4.5H), 1.36-1.51 (m, 1H), 1.57-1.70 (m, 1H), 1.98-2.13 (m, 2H), 2.14-2.35 (m, 2H), 3.15 (d, 3H), 3.29-3.46 (m, 1H, partially obscured by H₂O signal), 4.15 (dd, 1H), 4.26 (d, 1H), 7.08 (dd, 1H), 7.41-7.57 (m, 6H), 9.88 (d, 1H). |

| Example | Name/Structure/Starting materials | Analytical data |
|---|---|---|
| 223A | tert-butyl 1-[(4-chloro-3-{[(2S,3R)-2-(4-chlorophenyl)-4,4,4-trifluoro-3-methylbutanoyl]amino}-phenyl)(ethoxy)methyl]cyclobutanecarboxylate (diastereomer mixture)<br>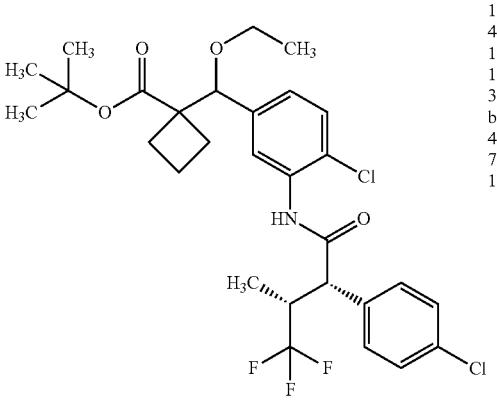<br>from tert-butyl 1-[(3-amino-4-chlorophenyl)-(ethoxy)methyl]cyclobutanecarboxylate and (2S,3R)-2-(4-chlorophenyl)-4,4,4-trifluoro-3-methylbutanoic acid | LC-MS (Method 4): $R_t$ = 1.87 min; m/z = 586/588 (M − H)$^-$.<br>$^1$H-NMR (400 MHz, DMSO-$d_6$): δ [ppm] = 0.80 (d, 3H), 1.03-1.12 (m, 3H), 1.24 (s, 4.5H), 1.32 (s, 4.5H), 1.34-1.46 (m, 1H), 1.55-1.69 (m, 1H), 1.96-2.30 (m, 4H), 3.23-3.46 (m, 3H, partially obscured by H$_2$O signal), 4.14 (dd, 1H), 4.38 (d, 1H), 7.11 (dd, 1H), 7.40-7.59 (m, 6H), 9.88 (d, 1H). |
| 224A | methyl 1-[1-(4-chloro-3-{[(2S,3R)-2-(4-chlorophenyl)-4,4,4-trifluoro-3-methylbutanoyl]amino}-phenyl)propyl]cyclopropanecarboxylate (diastereomer mixture)<br>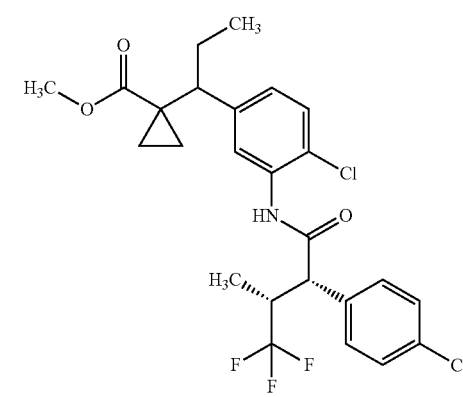<br>from methyl 1-[1-(3-amino-4-chlorophenyl)propyl]-cyclopropanecarboxylate and (2S,3R)-2-(4-chlorophenyl)-4,4,4-trifluoro-3-methylbutanoic acid | LC-MS (Method 5): $R_t$ = 1.46 min; m/z = 514/516 (M − H)$^-$. |

-continued

| Example | Name/Structure/Starting materials | Analytical data |
|---|---|---|
| 225A | tert-butyl 1-(3-{[(2S,3R)-2-(4-chlorophenyl)-4,4,4-trifluoro-3-methylbutanoyl]amino}-4-cyclopropyl-benzyl)cyclopropanecarboxylate<br>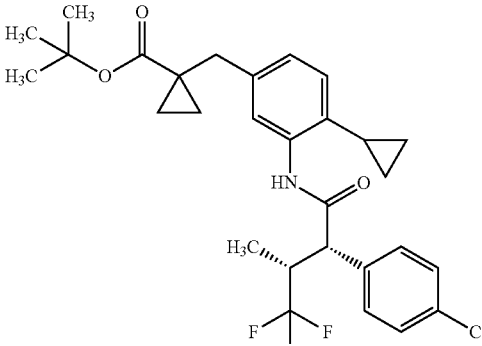<br>from tert-butyl 1-(3-amino-4-cyclopropylbenzyl)-cyclopropanecarboxylate and (2S,3R)-2-(4-chlorophenyl)-4,4,4-trifluoro-3-methylbutanoic acid | LC-MS (Method 4): $R_t$ = 1.77 min; m/z = 534/536 (M − H)⁻.<br>¹H-NMR (400 MHz, DMSO-$d_6$): δ [ppm] = 0.29-0.37 (m, 1H), 0.41-0.49 (m, 1H), 0.57-0.70 (m, 2H), 0.73-0.78 (m, 2H), 0.80 (d, 3H), 0.97-1.03 (m, 2H), 1.26 (s, 9H), 1.64-1.74 (m, 1H), 2.68-2.80 (m, 2H), 3.29-3.45 (m, 1H, partially obscured by H₂O signal), 4.01 (d, 1H), 6.80 (d, 1H), 6.93 (d, 1H), 7.14 (s, 1H), 7.42-7.50 (m, 4H), 9.68 (s, 1H). |

Example 226A tert-Butyl 1-[(4-chloro-3-nitrophenyl)(hydroxy)methyl]cyclopropanecarboxylate

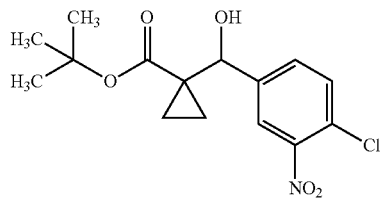 [SMILES: CC(C)(C)OC(=O)C1(C(O)c2ccc(Cl)c([N+](=O)[O-])c2)CC1]

9.7 ml (24.3 mmol) of a 2.5 M solution of n-butyllithium in hexane were added dropwise to a solution, cooled to from −20° C. to −30° C., of 3.4 ml (24.3 mmol) of diisopropylamine in 20 ml of abs. THF. After the addition had ended, the mixture was stirred at from −20° C. to −30° C. for another 30 min. The mixture was then cooled to −78° C., and a solution of 2.53 g (17.8 mmol) of tert-butyl cyclopropanecarboxylate in 15 ml of abs. THF was added dropwise at this temperature. After 4 h at −78° C., a solution of 3 g (16.2 mmol) of 4-chloro-3-nitrobenzaldehyde in 15 ml of abs. THF was then added. The reaction mixture was slowly warmed to RT overnight and then allowed to stand at RT for three days, and saturated aqueous ammonium chloride solution was then added. The mixture was extracted with ethyl acetate and the organic phase was dried over magnesium sulphate and concentrated under reduced pressure. The crude product was purified by chromatography on silica gel (mobile phase cyclohexane/ethyl acetate 50:1→20:1). This gave 3.21 g of the target compound (60.6% of theory).

LC-MS (Method 2): $R_t$=2.42 min; m/z=328 (M+H)⁺.

¹H-NMR (400 MHz, DMSO-$d_6$): δ [ppm]=0.91-1.01 (m, 2H), 1.05-1.12 (m, 1H), 1.14-1.21 (m, 1H), 1.23 (s, 9H), 4.91 (d, 1H), 5.74 (d, 1H), 7.67-7.76 (m, 2H), 8.00 (d, 1H).

The following compound was obtained analogously to Synthesis Example 226A:

| Example | Name/Structure/Starting materials | Analytical data |
|---|---|---|
| 227A | tert-butyl 1-[1-(4-chloro-3-nitrophenyl)-1-hydroxyethyl]cyclopropanecarboxylate<br>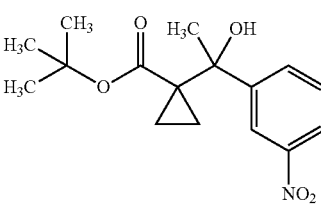<br>from 1-(4-chloro-3-nitrophenyl)ethanone and tert-butyl cyclopropanecarboxylate | LC-MS (Method 5):<br>$R_t$ = 1.21 min; m/z = 342 (M + H)⁺.<br>¹H-NMR (400 MHz, DMSO-$d_6$):<br>δ [ppm] = 0.97-1.03 (m, 1H), 1.05-1.11 (m, 1H), 1.12-1.20 (m, 1H), 1.14 (s, 9H), 1.38-1.46 (m, 1H), 1.62 (s, 3H), 5.30 (s, 1H), 7.72 (d, 1H), 7.79 (dd, 1H), 8.05 (d, 1H). |

Example 228A tert-Butyl 1-[(3-amino-4-chlorophenyl)(hydroxy)methyl]cyclopropanecarboxylate

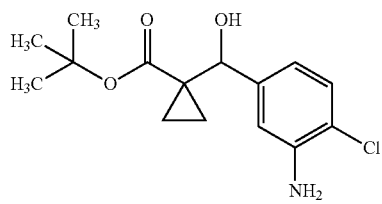 [SMILES: CC(C)(C)OC(=O)C1(C(O)c2ccc(Cl)c(N)c2)CC1]

2.72 g (8.30 mmol) of tert-butyl 1-[(4-chloro-3-nitrophenyl)(hydroxy)methyl]cyclopropane-carboxylate were dissolved in 100 ml of ethyl acetate, and 177 mg of palladium on carbon (10%) were added. For three days, the reaction mixture was stirred vigorously under a stationary atmosphere of hydrogen at atmospheric pressure. The mixture was then filtered through Celite and the filtrate obtained was evaporated to dryness. The crude product was purified by chromatography on silica gel (mobile phase cyclohexane/ethyl acetate 10:1). This gave 1.97 g of the target compound (80% of theory).

LC-MS (Method 5): $R_t$=1.02 min; m/z=298 (M+H)$^+$.

$^1$H-NMR (400 MHz, DMSO-d$_6$): δ [ppm]=0.76-0.86 (m, 2H), 0.95-1.04 (m, 2H), 1.27 (s, 9H), 4.91 (d, 1H), 5.18 (d, 1H), 5.25 (br. s, 2H), 6.51 (dd, 1H), 6.81 (d, 1H), 7.08 (d, 1H).

The following compound was obtained analogously to Synthesis Example 228A:

Example 230A tert-Butyl 1-[(4-chloro-3-{[(2S,3R)-2-(4-chlorophenyl)-4,4,4-trifluoro-3-methylbutanoyl]amino}-phenyl)(hydroxy)methyl]cyclopropanecarboxylate (diastereomer mixture)

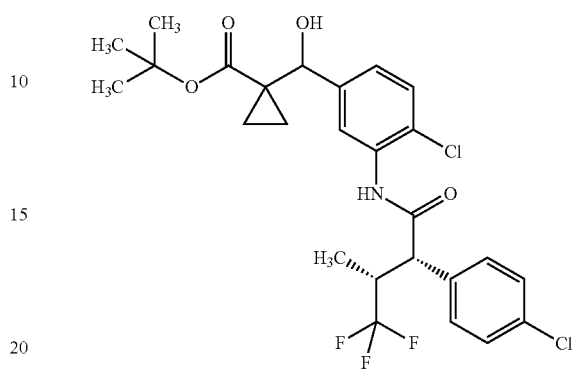

A solution of 2.65 g (9.92 mmol) of (2S,3R)-2-(4-chlorophenyl)-4,4,4-trifluoro-3-methylbutanoic acid, 1.97 g (6.62 mmol) of tert-butyl 1-[(3-amino-4-chlorophenyl)(hydroxy)methyl]cyclopropane-carboxylate and 3.27 g (8.60 mmol) of 2-(1H-7-azabenzotriazol-1-yl)-1,1,3,3-tetramethyluronium hexafluorophosphate (HATU) in 5 ml of pyridine and 10 ml of DMF was stirred at room temperature for three days. 100 ml of ethyl acetate were then added to the mixture, and the solution obtained was washed with 1 M hydrochloric acid and saturated sodium chloride solution. The solution was dried over magnesium sulphate and then filtered, and the filtrate was evaporated to dryness. The crude product was purified by chromatography on silica gel (mobile phase cyclohexane/ethyl acetate 50:1→40:1→30:1). The product obtained in this manner was taken up in 100 ml of ethyl acetate, and the solution was extracted three times with saturated sodium bicarbonate solution. The organic phase was washed once more with saturated sodium chloride solution, then dried over magnesium sulphate and finally concentrated to dryness under reduced pressure. This gave 2.75 g of the target compound (76% of theory).

LC-MS (Method 5): $R_t$=1.36 min; m/z=544/546 (M−H)$^-$.

$^1$H-NMR (400 MHz, DMSO-d$_6$): δ [ppm]=0.77-0.85 (m, 5H), 0.93-1.08 (m, 2H), 1.18 (s, 4.5H), 1.22 (s, 4.5H), 3.27-3.44 (m, 1H, partially obscured by H$_2$O signal), 4.08-4.14 (m, 1H), 4.94-4.98 (m, 1H), 5.40-5.45 (m, 1H), 7.12-7.17 (m, 1H), 7.36-7.41 (m, 1H), 7.41-7.50 (m, 4H), 7.53 (d, 0.5H), 7.55 (d, 0.5H), 9.85 (d, 1H).

| Example | Name/Structure/Starting material | Analytical data |
|---|---|---|
| 229A | tert-butyl 1-[1-(3-amino-4-chlorophenyl)-1-hydroxyethyl]cyclopropanecarboxylate<br><br>from tert-butyl 1-[1-(4-chloro-3-nitrophenyl)-1-hydroxyethyl]cyclopropanecarboxylate | LC-MS (Method 7):<br>$R_t$ = 1.13 min; m/z = 312 (M + H)$^+$.<br>$^1$H-NMR (400 MHz, DMSO-d$_6$):<br>δ [ppm] = 0.87-0.96 (m, 1H),<br>0.98-1.08 (m, 2H), 1.15 (s, 9H),<br>1.29-1.37 (m, 1H), 1.52 (s, 3H),<br>4.67 (s, 1H), 5.21 (br. s, 2H), 6.66<br>(dd, 1H), 6.98 (d, 1H), 7.07 (d, 1H). |

The following compound was obtained analogously to Synthesis Example 230A:

| Example | Name/Structure/Starting materials | Analytical data |
|---|---|---|
| 231A | tert-butyl 1-[1-(4-chloro-3-{[(2S,3R)-2-(4-chlorophenyl)-4,4,4-trifluoro-3-methylbutanoyl]amino}phenyl)-1-hydroxyethyl]cyclopropanecarboxylate (diastereomer mixture)<br>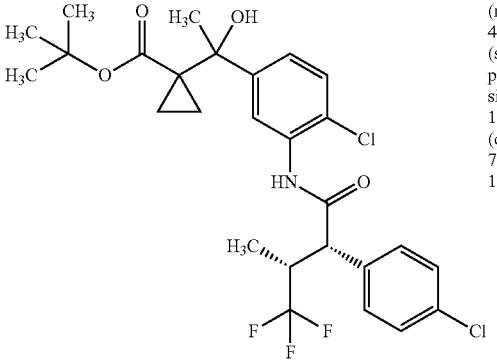<br>from tert-butyl 1-[1-(3-amino-4-chlorophenyl)-1-hydroxyethyl]cyclopropanecarboxylate and (2S,3R)-2-(4-chlorophenyl)-4,4,4-trifluoro-3-methylbutanoic acid | LC-MS (Method 5): $R_t$ = 1.42 min; m/z = 558/560 (M – H)⁻. ¹H-NMR (400 MHz, DMSO-$d_6$): δ [ppm] = 0.79 (d, 3H), 0.86-0.95 (m, 1H), 0.98-1.12 (m, 2H), 1.07 (s, 4.5H), 1.09 (s, 4.5H), 1.28-1.36 (m, 1H), 1.56 (s, 3H), 3.29-3.45 (m, 1H, partially obscured by H₂O signal), 4.12 (dd, 1H), 4.92 (d, 1H), 7.23-7.29 (m, 1H), 7.36 (d, 1H), 7.39-7.51 (m, 4H), 7.71-7.77 (m, 1H), 9.81 (s, 1H). |

Example 232A tert-Butyl 1-[(4-chloro-3-{[(2S,3R)-2-(4-chlorophenyl)-4,4,4-trifluoro-3-methylbutanoyl]amino}-phenyl)(vinyloxy)methyl]cyclopropanecarboxylate (diastereomer mixture)

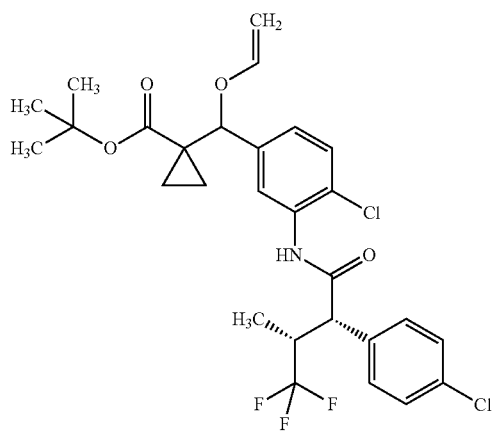 [SMILES: C=COC(c1ccc(Cl)c(NC(=O)[C@H](c2ccc(Cl)cc2)[C@@H](C)C(F)(F)F)c1)C1(C(=O)OC(C)(C)C)CC1]

Under argon, 473 mg (0.87 mmol) of tert-butyl 1-[(4-chloro-3-{[(2S,3R)-2-(4-chlorophenyl)-4,4,4-trifluoro-3-methylbutanoyl]amino}phenyl)(hydroxy)methyl]cyclopropanecarboxylate (as diastereomer mixture) were dissolved in 2.4 ml of dichloromethane, and 1.24 ml (13 mmol) of ethyl vinyl ether and 11 mg (0.03 mmol) of)bis(acetato)(1,10-phenanthrolin-$N^1$,$N^{10}$)palladium [*J. Org. Chem.* 62, 1560-1562 (1997)] were added at room temperature. The reaction solution was then heated to 50° C. and stirred at this temperature for two days. Another 1.24 ml (13 mmol) of ethyl vinyl ether and 11 mg (0.03 mmol) of)bis(acetato)(1,10-phenanthrolin-$N^1$,$N^{10}$)palladium were then added, and stirring of the reaction mixture was continued at 50° C. overnight. This procedure was repeated two more times. The reaction solution was then cooled to room temperature and concentrated to dryness under reduced pressure. The crude product was purified by chromatography on silica gel (mobile phase cyclohexane/dichloromethane 1:1). This gave 298 mg of the target compound (60% of theory).

LC-MS (Method 7): $R_t$=1.53 min; m/z=570/572 (M–H)⁻. ¹H-NMR (400 MHz, DMSO-$d_6$): δ [ppm]=0.48-0.59 (m, 1H), 0.80 (d, 3H), 0.82-0.90 (m, 1H), 0.92-0.99 (m, 1H), 1.00-1.08 (m, 1H), 1.30 (s, 4.5H), 1.32 (s, 4.5H), 3.28-3.46 (m, 1H, partially obscured by H₂O signal), 3.94 (d, 1H), 4.07-4.19 (m, 2H), 5.45 (s, 1H), 6.34-6.44 (m, 1H), 7.10 (d, 1H), 7.40-7.52 (m, 6H), 9.93 (s, 1H).

Example 233A tert-Butyl 1-[(4-chloro-3-{[(2S,3R)-2-(4-chlorophenyl)-4,4,4-trifluoro-3-methylbutanoyl]amino}-phenyl)(cyclopropyloxy)methyl]cyclopropanecarboxylate (diastereomer mixture)

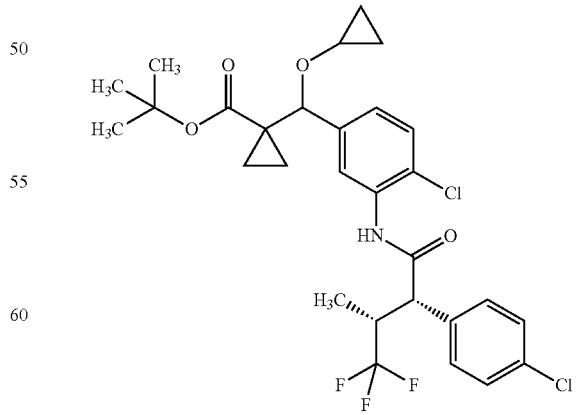

68 mg (0.52 mmol) of zinc/copper pair were taken up in 5 ml of abs. diethyl ether, and 41 μl (0.56 mmol) of chloroiodomethane were added at room temperature. A solution of 200 mg (0.35 mmol) of tert-butyl 1-[(4-chloro-3-{[(2S,3R)-2-(4-chlorophenyl)-4,4,4-trifluoro-3-methylbutanoyl]-amino}phenyl)(vinyloxy)methyl]cyclopropanecarboxylate (as diastereomer mixture) in 10 ml of abs. diethyl ether was then added dropwise to the reaction mixture. The reaction solution was then heated to reflux and stirred overnight. After cooling, the solution was filtered through kieselguhr and the kieselguhr was washed repeatedly with diethyl ether. The filtrate obtained was washed with saturated aqueous sodium bicarbonate solution and with water, dried over magnesium sulphate and concentrated to dryness under reduced pressure. The residue was purified by preparative RP-HPLC (mobile phase methanol/water 80:20, isocratic). This gave 54 mg (27% of theory) of the target compound.

LC-MS (Method 5): $R_t$=1.52 min; m/z=584/586 (M−H)$^-$.

Working Examples

General Procedure 8

Cleavage of Tert-Butyl Esters to the Corresponding Carboxylic Acids Using Trifluoroacetic Acid At 0° C. to RT, trifluoroacetic acid (TFA) was added to a solution of the tert-butyl ester in question in dichloromethane (concentration about 0.1 to 2.0 mol/l; additionally one drop of water) until a dichloromethane/TFA ratio of about 2:1 to 1:2 (v/v) had been reached. The mixture was stirred at RT for 1-24 h; if required, the mixture was warmed to up to 40° C. until complete conversion had been achieved. At RT, the reaction mixture was then concentrated under reduced pressure. The crude product was purified by chromatography on silica gel (elution with dichloromethane/ethyl acetate, cyclohexane/ethyl acetate or dichloromethane/methanol mixtures, if appropriate with addition of small amounts of acetic acid), by crystallization from diisopropyl ether, acetonitrile or acetonitrile/water mixtures, or by preparative RP-HPLC (mobile phase: acetonitrile/water gradient). It is also possible to use a combination of these purification methods to isolate the target product in pure form.

The following compounds were prepared according to General Procedure 8:

| Example | Name/Structure/Starting material | Analytical data |
|---|---|---|
| 1 | (+/−)-1-(3-{[(4-chloro-2-fluorophenyl)(cyclopentyl)acetyl]amino}benzyl)cyclopropanecarboxylic acid<br>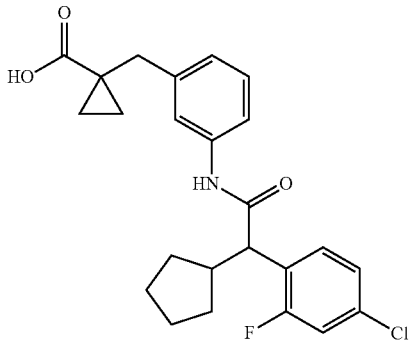<br>from (+/−)-tert-butyl 1-(3-{[(4-chloro-2-fluorophenyl)(cyclopentyl)acetyl]amino}benzyl)-cyclopropanecarboxylate | LC-MS (Method 4): $R_t$ = 1.46 min; m/z = 430 (M + H)$^+$.<br>$^1$H-NMR (400 MHz, DMSO-d$_6$): δ [ppm] = 0.76-0.84 (m, 2H), 0.99 (dd, 1H), 1.11 (q, 2H), 1.32-1.61 (m, 5H), 1.62-1.79 (m, 2H), 2.48-2.58 (m, 1H, obscured), 2.83 (s, 2H), 3.78 (d, 1H), 6.93 (d, 1H), 7.16 (t, 1H), 7.29 (dd, 1H), 7.40 (dd, 1H), 7.43-7.49 (m, 2H), 7.70 (t, 1H), 10.14 (s, 1H), 12.09 (br. s, 1H). |
| 2 | (+/−)-1-(3-{[cyclopentyl(2,4-dichlorophenyl)-acetyl]amino}benzyl)cyclopropanecarboxylic acid<br>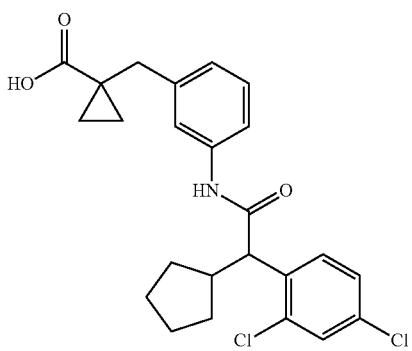 [SMILES: O=C(Nc1cccc(CC2(C(=O)O)CC2)c1)C(c1ccc(Cl)cc1F)C1CCCC1]<br>from (+/−)-tert-butyl 1-(3-{[cyclopentyl(2,4-dichlorophenyl)acetyl]amino}benzyl)cyclopropanecarboxylate | LC-MS (Method 4): $R_t$ = 1.51 min; m/z = 446/447 (M + H)$^+$.<br>$^1$H-NMR (400 MHz, DMSO-d$_6$): δ [ppm] = 0.75-0.84 (m, 2H), 0.94-1.04 (m, 1H), 1.08-1.15 (m, 2H), 1.36-1.62 (m, 5H), 1.64-1.79 (m, 2H), 2.50-2.58 (m, 1H, obscured), 2.83 (s, 2H), 3.97 (d, 1H), 6.94 (d, 1H), 7.16 (t, 1H), 7.38-7.49 (m, 3H), 7.59 (d, 1H), 7.79 (d, 1H), 10.11 (s, 1H), 12.09 (s, 1H). |

| Example | Name/Structure/Starting material | Analytical data |
| --- | --- | --- |
| 3 | (+/−)-1-[3-({cyclopentyl[3-fluoro-4-(trifluoromethyl)-phenyl]acetyl}amino)benzyl]cyclopropanecarboxylic acid<br>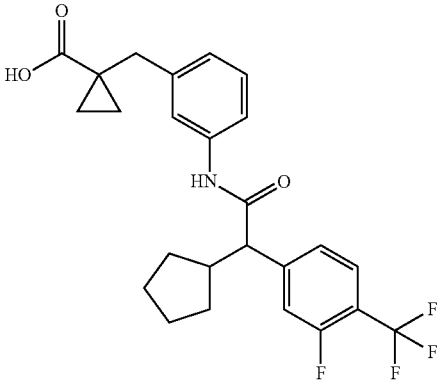 [SMILES: O=C(Nc1cccc(CC2(C(=O)O)CC2)c1)C(c1ccc(C(F)(F)F)c(F)c1)C1CCCC1]<br>from (+/−)-tert-butyl 1-[3-({cyclopentyl[3-fluoro-4-(trifluoromethyl)phenyl]acetyl}amino)-benzyl]cyclopropanecarboxylate | LC-MS (Method 4): $R_t$ = 1.48 min; m/z = 464 (M + H)$^+$.<br>$^1$H-NMR (400 MHz, DMSO-d$_6$): δ [ppm] = 0.75-0.85 (m, 2H), 0.93-1.03 (m, 1H), 1.08-1.15 (m, 2H), 1.20-1.43 (m, 2H), 1.43-1.71 (m, 4H), 1.76-1.84 (m, 1H), 2.55-2.66 (m, 1H), 2.83 (s, 2H), 3.55 (d, 1H), 6.93 (d, 1H), 7.17 (t, 1H), 7.30-7.48 (m, 3H), 7.51 (d, 1H), 7.76 (t, 1H), 10.12 (s, 1H), 12.09 (s, 1H). |
| 4 | (+/−)-1-[3-({cyclopentyl[4-(trifluoromethoxy)-phenyl]acetyl}amino)benzyl]cyclopropane-carboxylic acid<br>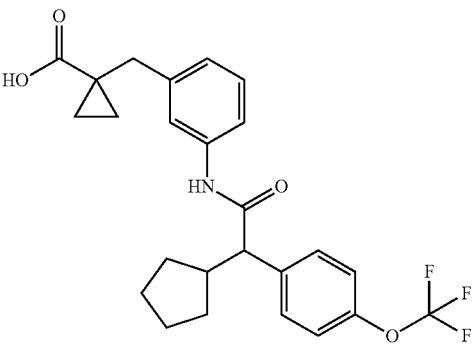 [SMILES: O=C(Nc1cccc(CC2(C(=O)O)CC2)c1)C(c1ccc(OC(F)(F)F)cc1)C1CCCC1]<br>from (+/−)-tert-butyl 1-[3-({cyclopentyl[4-(trifluoromethoxy)phenyl]acetyl}-amino)benzyl]cyclopropanecarboxylate | LC-MS (Method 4): $R_t$ = 1.47 min; m/z = 462 (M + H)$^+$.<br>$^1$H-NMR (400 MHz, DMSO-d$_6$): δ [ppm] = 0.74-0.84 (m, 2H), 0.89-1.02 (m, 1H), 1.06-1.14 (m, 2H), 1.21-1.40 (m, 2H), 1.41-1.70 (m, 4H), 1.73-1.84 (m, 1H), 2.55-2.63 (m, 1H), 2.82 (s, 2H), 3.46 (d, 1H), 6.91 (d, 1H), 7.16 (t, 1H), 7.24-7.36 (m, 2H), 7.40-7.49 (m, 2H), 7.50-7.60 (m, 2H), 10.05 (s, 1H), 12.09 (s, 1H). |
| 5 | (+/−)-1-(3-{[cyclopentyl(3,4-dichlorophenyl)-acetyl]amino}benzyl)cyclopropanecarboxylic acid<br>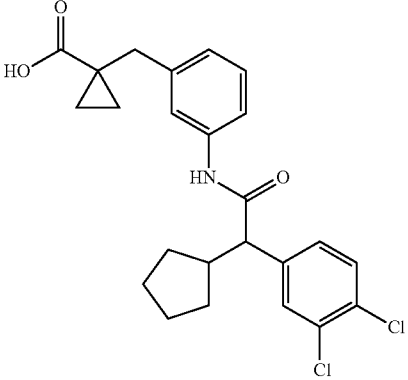 [SMILES: O=C(Nc1cccc(CC2(C(=O)O)CC2)c1)C(c1ccc(Cl)c(Cl)c1)C1CCCC1]<br>from (+/−)-tert-butyl 1-(3-{[cyclopentyl(3,4-dichlorophenyl)acetyl]amino}benzyl)-cyclopropanecarboxylate | LC-MS (Method 4): $R_t$ = 1.50 min; m/z = 446/447 (M + H)$^+$.<br>$^1$H-NMR (400 MHz, DMSO-d$_6$): δ [ppm] = 0.75-0.84 (m, 2H), 0.97 (dq, 1H), 1.07-1.15 (m, 2H), 1.19-1.31 (m, 1H), 1.31-1.42 (m, 1H), 1.42-1.70 (m, 4H), 1.71-1.85 (m, 1H), 2.54-2.62 (m, 1H), 2.83 (s, 2H), 3.42 (d, 1H), 6.93 (d, 1H), 7.16 (t, 1H), 7.32-7.49 (m, 3H), 7.54-7.67 (m, 2H), 10.06 (s, 1H), 12.09 (br. s, 1H). |

-continued

| Example | Name/Structure/Starting material | Analytical data |
|---|---|---|
| 6 | (+/−)-1-(3-{[(4-chlorophenyl)(cyclopentyl)acetyl]-amino}-2-fluorobenzyl)cyclopropanecarboxylic acid<br>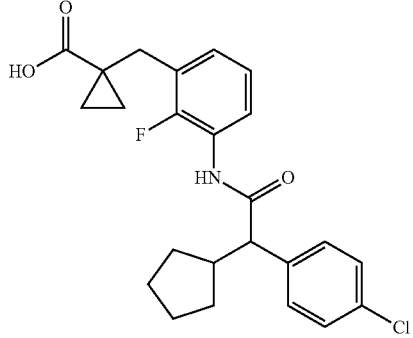 [SMILES: O=C(Nc1cccc(CC2(C(=O)O)CC2)c1F)C(c1ccc(Cl)cc1)C1CCCC1]<br>from (+/−)-tert-butyl 1-(3-{[(4-chlorophenyl)(cyclopentyl)acetyl]amino}-2-fluorobenzyl)cyclopropanecarboxylate | LC-MS (Method 5): $R_t$ = 1.25 min; m/z = 430 (M + H)$^+$.<br>$^1$H-NMR (400 MHz, DMSO-$d_6$): δ [ppm] = 0.72-0.82 (m, 2H), 0.90-1.03 (m, 1H), 1.11-1.18 (m, 2H), 1.21-1.71 (m, 7H), 1.72-1.92 (m, 1H), 2.92 (s, 2H), 6.93-7.06 (m, 1H), 7.08-7.15 (m, 1H), 7.33-7.49 (m, 4H), 7.61 (t, 1H), 9.82 (s, 1H), 12.19 (br. s, 1H). |
| 7 | (+/−)-1-(3-{[{4-[(E)-2-cyanovinyl]phenyl}-(cyclopentyl)acetyl]amino}-4-fluorobenzyl)-cyclopropanecarboxylic acid<br>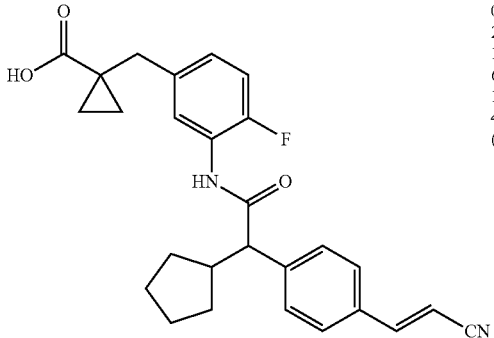<br>from (+/−)-tert-butyl 1-(3-{[{4-[(E)-2-cyanovinyl]phenyl}(cyclopentyl)acetyl]amino}-4-fluorobenzyl)cyclopropanecarboxylate | LC-MS (Method 5): $R_t$ = 1.15 min; m/z = 447 (M + H)$^+$.<br>$^1$H-NMR (400 MHz, DMSO-$d_6$): δ [ppm] = 0.73-0.84 (m, 2H), 0.90-1.03 (m, 1H), 1.04-1.14 (m, 2H), 1.23-1.71 (m, 7H), 1.80 (dd, 1H), 2.80 (s, 2H), 6.42 (d, 1H), 6.97-7.05 (m, 1H), 7.06-7.16 (m, 1H), 7.48 (d, 2H), 7.58-7.70 (m, 4H), 9.76-9.88 (m, 1H), 12.12 (br. s, 1H). |
| 8 | (+/−)-1-(3-{[(4-chlorophenyl)(cyclopentyl)acetyl]-amino}-4-fluorobenzyl)cyclopropanecarboxylic acid<br>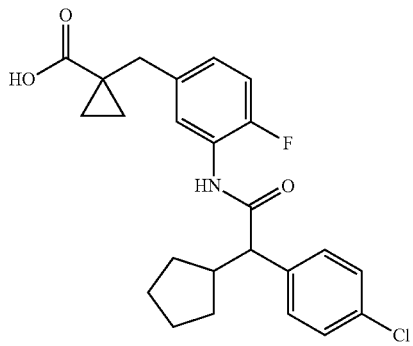 [SMILES: O=C(Nc1cc(CC2(C(=O)O)CC2)ccc1F)C(c1ccc(Cl)cc1)C1CCCC1]<br>from (+/−)-tert-butyl 1-(3-{[(4-chlorophenyl)(cyclopentyl)acetyl]amino}-4-fluorobenzyl)cyclopropanecarboxylate | LC-MS (Method 5): $R_t$ = 1.24 min; m/z = 430 (M + H)$^+$.<br>$^1$H-NMR (400 MHz, DMSO-$d_6$): δ [ppm] = 0.73-0.83 (m, 2H), 0.88-1.02 (m, 1H), 1.06-1.12 (m, 2H), 1.22-1.39 (m, 2H), 1.41-1.70 (m, 4H), 1.72-1.85 (m, 1H), 2.50-2.58 (m, 1H), 2.81 (s, 2H), 3.61 (d, 1H), 6.95-7.05 (m, 1H), 7.10 (dd, 1H), 7.33-7.41 (m, 2H), 7.41-7.46 (m, 2H), 7.66 (dd, 1H), 9.81 (s, 1H), 12.12 (s, 1H). |

-continued

| Example | Name/Structure/Starting material | Analytical data |
|---|---|---|
| 9 | (+/−)-1-(3-{[2-(4-ethylphenyl)-4,4,4-trifluoro-3-methylbutanoyl]amino}-4-fluorobenzyl)-cyclopropanecarboxylic acid<br>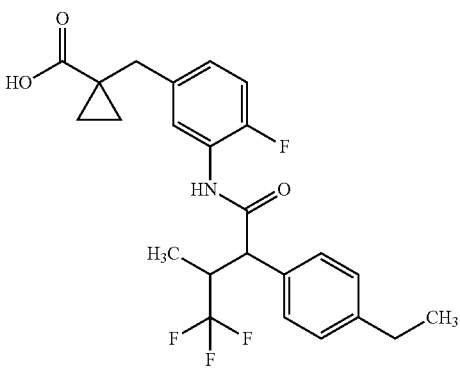<br>from (+/−)-tert-butyl 1-(3-{[2-(4-ethylphenyl)-4,4,4-trifluoro-3-methylbutanoyl]amino}-4-fluorobenzyl)cyclopropanecarboxylate | LC-MS (Method 5): $R_t$ = 1.23 min; m/z = 452 (M + H)$^+$.<br>$^1$H-NMR (400 MHz, DMSO-d$_6$):<br>δ [ppm] = 0.77 (d, 3H), 0.77-0.83 (m, 2H), 1.05-1.12 (m, 2H), 1.17 (t, 3H), 2.58 (q, 2H), 2.80 (s, 2H), 3.28-3.38 (m, 1H, obscured), 4.03 (d, 1H), 6.95-7.03 (m, 1H), 7.09 (dd, 1H), 7.17-7.23 (m, 2H), 7.31-7.35 (m, 2H), 7.69 (dd, 1H), 9.94 (s, 1H), 12.12 (br. s, 1H). |
| 10 | (+/−)-1-(3-{[cyclopentyl(4-fluorophenyl)acetyl]-amino}-4-fluorobenzyl)cyclopropanecarboxylic acid<br>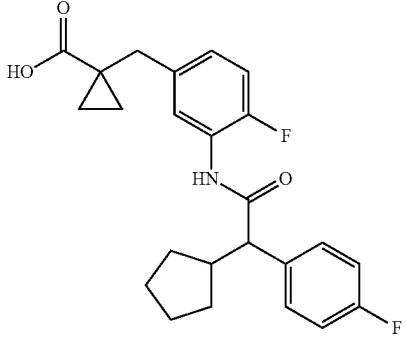 [SMILES: O=C(Nc1cc(CC2(C(=O)O)CC2)ccc1F)C(c1ccc(F)cc1)C1CCCC1]<br>from (+/−)-tert-butyl 1-(3-{[cyclopentyl(4-fluorophenyl)acetyl]amino}-4-fluorobenzyl)cyclopropanecarboxylate | LC-MS (Method 5): $R_t$ = 1.20 min; m/z = 414 (M + H)$^+$.<br>$^1$H-NMR (400 MHz, DMSO-d$_6$):<br>δ [ppm] = 0.72-0.83 (m, 2H), 0.91-1.00 (m, 1H), 1.08-1.10 (m, 2H), 1.23-1.38 (m, 2H), 1.41-1.70 (m, 4H), 1.72-1.87 (m, 1H), 2.52-2.57 (m, 1H), 2.81 (s, 2H), 3.60 (d, 1H), 6.94-7.05 (m, 1H), 7.05-7.21 (m, 3H), 7.44 (dd, 2H), 7.67 (dd, 1H), 9.79 (s, 1H), 12.12 (s, 1H). |
| 11 | (+/−)-1-(3-{[(4-chloro-2-fluorophenyl)(cyclo-pentyl)acetyl]amino}-4-fluorobenzyl)-cyclopropanecarboxylic acid<br>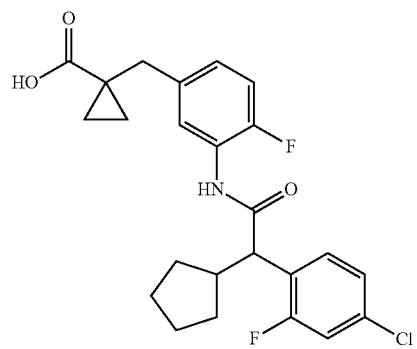 [SMILES: O=C(Nc1cc(CC2(C(=O)O)CC2)ccc1F)C(c1ccc(Cl)cc1F)C1CCCC1]<br>from (+/−)-tert-butyl 1-(3-{[(4-chloro-2-fluorophenyl)(cyclopentyl)acetyl]amino}-4-fluorobenzyl)cyclopropanecarboxylate | LC-MS (Method 5): $R_t$ = 1.27 min; m/z = 448 (M + H)$^+$.<br>$^1$H-NMR (400 MHz, DMSO-d$_6$):<br>δ [ppm] = 0.73-0.87 (m, 2H), 0.95-1.04 (m, 1H), 1.08-1.10 (m, 2H), 1.37-1.62 (m, 5H), 1.63-1.73 (m, 1H), 1.73-1.85 (m, 1H), 2.45-2.53 (m, 1H), 2.82 (s, 2H), 3.93 (d, 1H), 6.96-7.17 (m, 2H), 7.29 (dd, 1H), 7.40 (dd, 1H), 7.56 (dd, 1H), 7.68 (t, 1H), 9.94 (s, 1H), 12.13 (br. s, 1H). |

| Example | Name/Structure/Starting material | Analytical data |
|---|---|---|
| 12 | (+/−)-1-[3-({cyclopentyl[4-(2,2-difluorovinyl)-phenyl]acetyl}amino)benzyl]cyclopropane-carboxylic acid<br>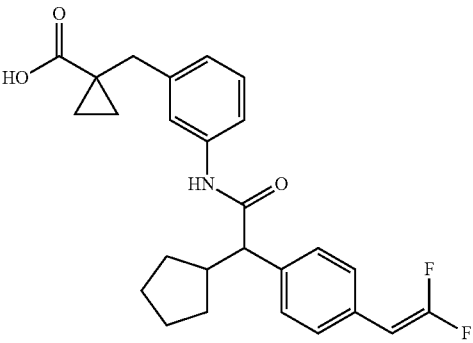 [SMILES: O=C(Nc1cccc(CC2(C(=O)O)CC2)c1)C(c1ccc(C=C(F)F)cc1)C1CCCC1]<br>from (+/−)-tert-butyl 1-[3-({cyclopentyl[4-(2,2-difluorovinyl)phenyl]acetyl}amino)benzyl]cyclo-propanecarboxylate | LC-MS (Method 5): $R_t$ = 1.27 min; m/z = 440 (M + H)$^+$.<br>$^1$H-NMR (400 MHz, DMSO-d$_6$): δ [ppm] = 0.78-0.80 (m, 2H), 0.92-1.01 (m, 1H), 1.10-1.12 (m, 2H), 1.21-1.39 (m, 2H), 1.43-1.68 (m, 4H), 1.75-1.82 (m, 1H), 2.56-2.63 (m, 1H), 2.82 (s, 2H), 3.38 (d, 1H), 5.74 (dd, 1H), 6.90 (d, 1H), 7.15 (t, 1H), 7.30-7.34 (m, 2H), 7.40-7.47 (m, 4H), 9.99 (s, 1H), 12.09 (br. s, 1H). |
| 13 | (+/−)-1-(3-{[cyclopentyl(4-vinylphenyl)acetyl]-amino}benzyl)cyclopropanecarboxylic acid<br>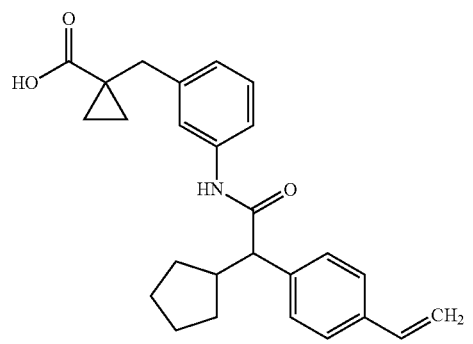 [SMILES: C=Cc1ccc(C(C(=O)Nc2cccc(CC3(C(=O)O)CC3)c2)C2CCCC2)cc1]<br>from (+/−)-tert-butyl 1-(3-{[cyclopentyl(4-vinylphenyl)acetyl]amino}benzyl)cyclopropane-carboxylate | LC-MS (Method 5): $R_t$ = 1.24 min; m/z = 404 (M + H)$^+$.<br>$^1$H-NMR (400 MHz, DMSO-d$_6$): δ [ppm] = 0.76-0.83 (m, 2H), 0.93-1.02 (m, 1H), 1.08-1.14 (m, 2H), 1.21-1.41 (m, 2H), 1.41-1.69 (m, 4H), 1.75-1.83 (m, 1H), 2.55-2.64 (m, 1H), 2.82 (s, 2H), 3.38 (d, 1H), 5.22 (d, 1H), 5.78 (d, 1H), 6.70 (dd, 1H), 6.90 (d, 1H), 7.15 (t, 1H), 7.34-7.51 (m, 6H), 9.98 (s, 1H), 12.08 (s, 1H). |
| 14 | (+/−)-1-[3-({cyclopentyl[4-(2,2-difluoroethyl)-phenyl]acetyl}amino)benzyl]cyclopropane-carboxylic acid<br>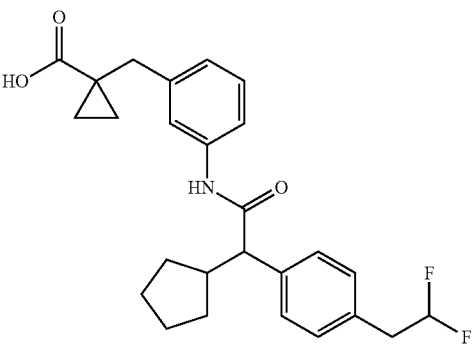<br>from (+/−)-tert-butyl 1-[3-({cyclopentyl[4-(2,2-difluoroethyl)phenyl]acetyl}amino)benzyl]-cyclopropanecarboxylate | LC-MS (Method 4): $R_t$ = 1.36 min; m/z = 442 (M + H)$^+$.<br>$^1$H-NMR (400 MHz, DMSO-d$_6$): δ [ppm] = 0.73-0.83 (m, 2H), 0.90-1.02 (m, 1H), 1.08-1.14 (m, 2H), 1.19-1.29 (m, 1H), 1.29-1.39 (m, 1H), 1.40-1.69 (m, 4H), 1.73-1.84 (m, 1H), 2.55-2.63 (m, 1H), 2.82 (s, 2H), 3.13 (td, 2H), 3.37 (d, 1H), 6.21 (dt, 1H), 6.90 (d, 1H), 7.14 (t, 1H), 7.21-7.27 (m, 2H), 7.32-7.40 (m, 2H), 7.40-7.49 (m, 2H), 9.98 (s, 1H), 12.08 (br. s, 1H). |

| Example | Name/Structure/Starting material | Analytical data |
|---|---|---|
| 15 | (+/−)-1-(3-{[(4-cyanophenyl)(cyclopentyl)acetyl]-amino}-4-fluorobenzyl)cyclopropanecarboxylic acid<br>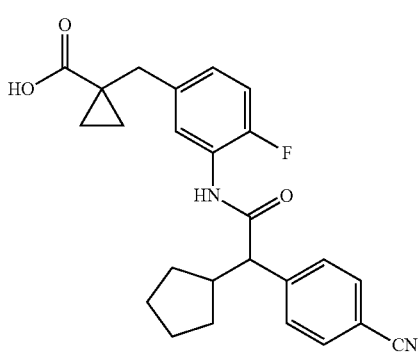 [SMILES: N#Cc1ccc(C(C(=O)Nc2cc(CC3(C(=O)O)CC3)ccc2F)C2CCCC2)cc1]<br>from (+/−)-tert-butyl 1-(3-{[(4-cyanophenyl)(cyclopentyl)acetyl]amino}-4-fluorobenzyl)cyclopropanecarboxylate | LC-MS (Method 2): $R_t$ = 2.37 min; m/z = 421 (M + H)⁺.<br>¹H-NMR (400 MHz, DMSO-d₆): δ [ppm] = 0.79 (q, 2H), 0.94 (dq, 1H), 1.05-1.14 (m, 2H), 1.23-1.74 (m, 7H), 1.74-1.89 (m, 1H), 2.80 (s, 2H), 3.72 (d, 1H), 6.98-7.05 (m, 1H), 7.06-7.16 (m, 1H), 7.57-7.69 (m, 3H), 7.76-7.85 (m, 2H), 9.89 (s, 1H), 12.12 (s, 1H). |
| 16 | (+/−)-1-(3-{[(4-nitrophenyl)(cyclopentyl)acetyl]-amino}-4-fluorobenzyl)cyclopropanecarboxylic acid<br>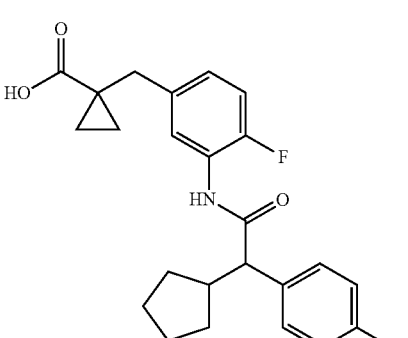<br>from (+/−)-tert-butyl 1-(3-{[(4-nitrophenyl)(cyclopentyl)acetyl]amino}-4-fluorobenzyl)cyclopropanecarboxylate | LC-MS (Method 4): $R_t$ = 1.33 min; m/z = 441 (M + H)⁺.<br>¹H-NMR (400 MHz, DMSO-d₆): δ [ppm] = 0.75-0.82 (m, 2H), 0.90-1.02 (m, 1H), 1.06-1.12 (m, 2H), 1.26-1.75 (m, 7H), 1.77-1.89 (m, 1H), 2.80 (s, 2H), 3.80 (d, 1H), 6.98-7.06 (m, 1H), 7.08-7.17 (m, 1H), 7.56-7.78 (m, 3H), 8.10-8.33 (m, 2H), 9.94 (s, 1H), 12.09 (br. s, 1H). |
| 17 | 1-(3-{[(2S)-2-cyclopentyl-2-(4-methylphenyl)-acetyl]amino}benzyl)cyclopropanecarboxylic acid<br>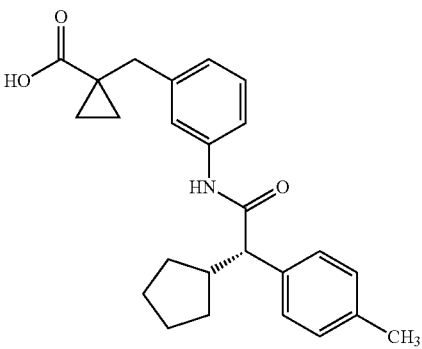 [SMILES: Cc1ccc([C@@H](C(=O)Nc2cccc(CC3(C(=O)O)CC3)c2)C2CCCC2)cc1]<br>from tert-butyl 1-(3-{[(2S)-2-cyclopentyl-2-(4-methylphenyl)acetyl]amino}benzyl)-cyclopropanecarboxylate | LC-MS (Method 5): $R_t$ = 1.22 min; m/z = 392 (M + H)⁺.<br>¹H-NMR (400 MHz, DMSO-d₆): δ [ppm] = 0.75-0.82 (m, 2H), 0.91-1.03 (m, 1H), 1.11 (q, 2H), 1.17-1.71 (m, 7H), 1.72-1.85 (m, 1H), 2.25 (s, 3H), 2.82 (s, 2H), 6.89 (d, 1H), 7.05-7.20 (m, 3H), 7.24-7.34 (m, 2H), 7.38-7.49 (m, 2H), 9.94 (s, 1H), 12.09 (br. s, 1H). |

| Example | Name/Structure/Starting material | Analytical data |
|---|---|---|
| 18 | (+)-1-(3-{[(2S)-2-{4-[(E)-2-cyanovinyl]phenyl}-2-cyclopentylacetyl]amino}-4-fluorobenzyl)-cyclopropanecarboxylic acid<br>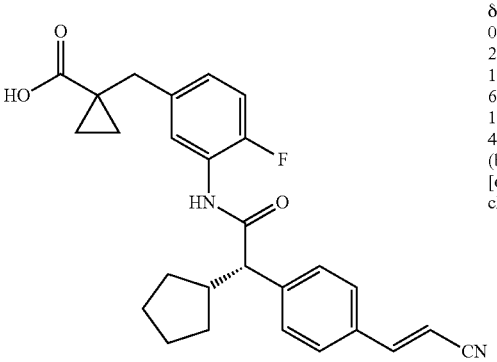<br>from (+)-tert-butyl 1-(3-{[(2S)-2-{4-[(E)-2-cyanovinyl]phenyl}-2-cyclopentylacetyl]amino}-4-fluorobenzyl)cyclopropanecarboxylate | LC-MS (Method 5): $R_t$ = 1.15 min; m/z = 447 (M + H)⁺.<br>¹H-NMR (400 MHz, DMSO-$d_6$): δ [ppm] = 0.73-0.84 (m, 2H), 0.90-1.03 (m, 1H), 1.04-1.14 (m, 2H), 1.23-1.71 (m, 7H), 1.80 (dd, 1H), 2.80 (s, 2H), 6.42 (d, 1H), 6.97-7.05 (m, 1H), 7.06-7.16 (m, 1H), 7.48 (d, 2H), 7.58-7.70 (m, 4H), 9.76-9.88 (m, 1H), 12.12 (br. s, 1H).<br>$[\alpha]_D^{20}$ = +94.1°, c = 0.505, chloroform. |
| 19 | (+)-1-(3-{[(2S)-2-cyclopentyl-2-(4-ethylphenyl)-acetyl]amino}benzyl)cyclopropanecarboxylic acid<br>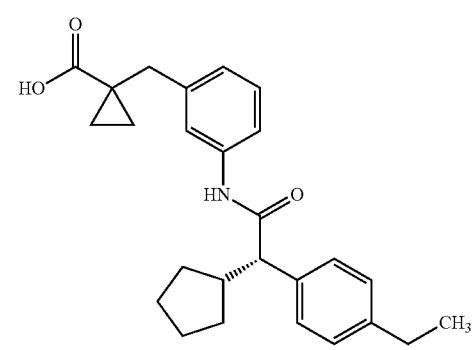 [SMILES: CCc1ccc([C@@H](C(=O)Nc2cccc(CC3(C(=O)O)CC3)c2)C2CCCC2)cc1]<br>from (+)-tert-butyl 1-(3-{[(2S)-2-cyclopentyl-2-(4-ethylphenyl)acetyl]amino}benzyl)cyclopropane-carboxylate | LC-MS (Method 5): $R_t$ = 1.28 min; m/z = 406 (M + H)⁺.<br>¹H-NMR (400 MHz, DMSO-$d_6$): δ [ppm] = 0.75-0.82 (m, 2H), 0.90-1.03 (m, 1H), 1.08-1.13 (m, 2H), 1.15 (t, 3H), 1.19-1.30 (m, 1H), 1.30-1.40 (m, 1H), 1.40-1.69 (m, 4H), 1.71-1.83 (m, 1H), 2.51-2.61 (m, 3H), 2.82 (s, 2H), 3.35 (d, 1H, obscured), 6.89 (d, 1H), 7.09-7.20 (m, 3H), 7.31 (d, 2H), 7.39-7.48 (m, 2H), 9.94 (s, 1H), 12.08 (br. s, 1H).<br>$[\alpha]_D^{20}$ = +44.9°, c = 0.340, chloroform. |
| 20 | (+)-1-(3-{[(2S)-2-cyclopentyl-2-(4-ethylphenyl)-acetyl]amino}-4-fluorobenzyl)-cyclopropanecarboxylic acid<br>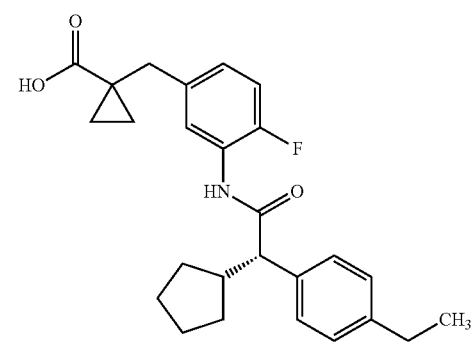 [SMILES: CCc1ccc([C@@H](C(=O)Nc2cc(CC3(C(=O)O)CC3)ccc2F)C2CCCC2)cc1]<br>from (+)-tert-butyl 1-(3-{[(2S)-2-cyclopentyl-2-(4-ethylphenyl)acetyl]amino}-4-fluorobenzyl)cyclopropanecarboxylate | LC-MS (Method 4): $R_t$ = 1.47 min; m/z = 424 (M + H)⁺.<br>¹H-NMR (400 MHz, DMSO-$d_6$): δ [ppm] = 0.74-0.83 (m, 2H), 0.89-1.03 (m, 1H), 1.07-1.10 (m, 2H), 1.16 (t, 3H), 1.22-1.40 (m, 2H), 1.40-1.69 (m, 4H), 1.72-1.85 (m, 1H), 2.53-2.63 (m, 3H), 2.80 (s, 2H), 3.54 (d, 1H), 6.95-7.04 (m, 1H), 7.05-7.11 (m, 1H), 7.11-7.18 (m, 2H), 7.28-7.35 (m, 2H), 7.67 (dd, 1H), 9.73 (s, 1H), 12.12 (s, 1H).<br>$[\alpha]_D^{20}$ = +80.9°, c = 0.505, chloroform. |

| Example | Name/Structure/Starting material | Analytical data |
|---|---|---|
| 21 | (+)-1-(3-{[(2S)-2-cyclopentyl-2-(4-ethylphenyl)-acetyl]amino}-5-fluorobenzyl)-cyclopropanecarboxylic acid<br>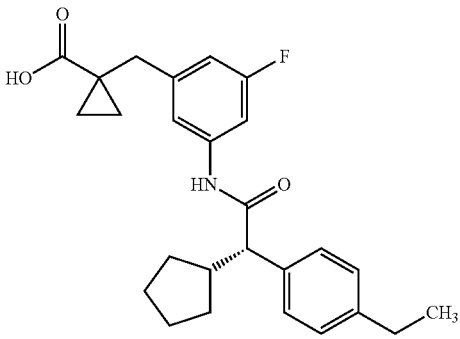 [SMILES: CCc1ccc([C@@H](C(=O)Nc2cc(F)cc(CC3(C(=O)O)CC3)c2)C2CCCC2)cc1]<br>from (+)-tert-butyl 1-(3-{[(2S)-2-cyclopentyl-2-(4-ethylphenyl)acetyl]amino}-5-fluorobenzyl)cyclopropanecarboxylate | LC-MS (Method 3): $R_t$ = 2.86 min; m/z = 424 (M + H)$^+$.<br>$^1$H-NMR (400 MHz, DMSO-d$_6$): δ [ppm] = 0.79-0.87 (m, 2H), 0.90-1.04 (m, 1H), 1.10- 1.16 (m, 2H), 1.15 (t, 3H), 1.19-1.29 (m, 1H), 1.31-1.39 (m, 1H), 1.40-1.69 (m, 4H), 1.71-1.85 (m, 1H), 2.52-2.62 (m, 3H), 2.81 (s, 2H), 3.34 (d, 1H, obscured), 6.72 (d, 1H), 7.05-7.17 (m, 3H), 7.30 (d, 2H), 7.47 (d, 1H), 10.17 (s, 1H), 12.15 (br. s, 1H).<br>$[\alpha]_D^{20}$ = +42.5°, c = 0.305, chloroform. |
| 22 | (+)-1-(4-fluoro-3-{[(2S,3R)-4,4,4-trifluoro-2-(4-fluorophenyl)-3-methylbutanoyl]amino}-benzyl)cyclopropanecarboxylic acid<br>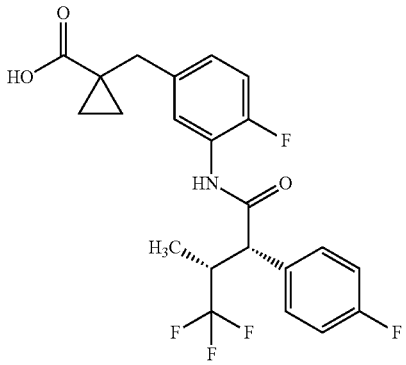 [SMILES: C[C@H]([C@H](C(=O)Nc1cc(CC2(C(=O)O)CC2)ccc1F)c1ccc(F)cc1)C(F)(F)F]<br>from (+)-tert-butyl 1-(4-fluoro-3-{[(2S,3R)-4,4,4-trifluoro-2-(4-fluorophenyl)-3-methyl-butanoyl]amino}benzyl)cyclopropanecarboxylate | LC-MS (Method 5): $R_t$ = 1.12 min; m/z = 442 (M + H)$^+$.<br>$^1$H-NMR (400 MHz, DMSO-d$_6$): δ [ppm] = 0.76-0.82 (m, 5H), 1.09 (br. s, 2H), 2.80 (s, 2H), 3.33-3.41 (m, 1H), 4.10 (d, 1H), 7.01 (br. s, 1H), 7.06-7.14 (m, 1H), 7.21 (t, 2H), 7.47 (t, 2H), 7.68 (d, 1H), 9.99 (s, 1H), 12.12 (br. s, 1H).<br>$[\alpha]_D^{20}$ = +113.3°, c = 0.53, chloroform. |
| 23 | (+)-1-(3-{[(2S,3R)-2-(4-chlorophenyl)-4,4,4-trifluoro-3-methylbutanoyl]amino}-2-fluorobenzyl)-cyclopropanecarboxylic acid<br>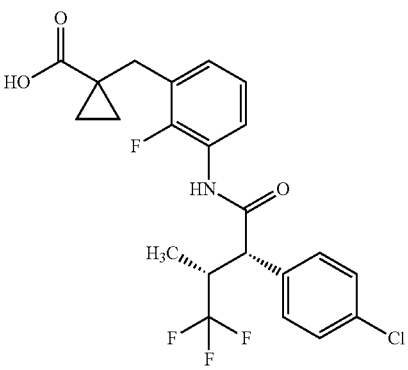 [SMILES: C[C@H]([C@H](C(=O)Nc1cccc(CC2(C(=O)O)CC2)c1F)c1ccc(Cl)cc1)C(F)(F)F]<br>from (+)-tert-butyl 1-(3-{[(2S,3R)-2-(4-chlorophenyl)-4,4,4-trifluoro-3-methylbutanoyl]amino}-2-fluorobenzyl)cyclopropanecarboxylate | LC-MS (Method 5): $R_t$ = 1.19 min; m/z = 458 (M + H)$^+$.<br>$^1$H-NMR (400 MHz, DMSO-d$_6$): δ [ppm] = 0.71-0.88 (m, 5H), 1.08-1.21 (m, 2H), 2.85-2.99 (m, 2H), 4.12 (d, 1H), 6.95-7.05 (m, 1H), 7.07-7.16 (m, 1H), 7.37-7.51 (m, 4H), 7.62 (td, 1H ), 10.03 (s, 1H), 12.19 (s, 1H).<br>$[\alpha]_D^{20}$ = +32.1°, c = 0.50, chloroform. |

| Example | Name/Structure/Starting material | Analytical data |
|---|---|---|
| 24 | (+)-1-(3-{[(2S,3R)-2-(4-ethylphenyl)-4,4,4-tri-fluoro-3-methylbutanoyl]amino}-2-fluorobenzyl)-cyclopropanecarboxylic acid<br>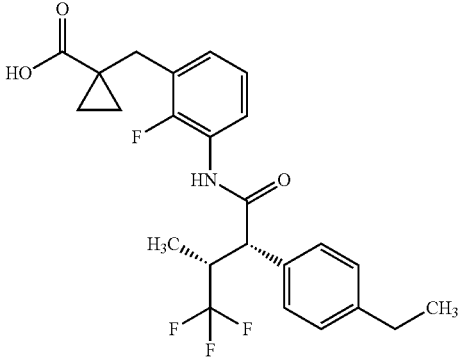 [SMILES: CCc1ccc([C@@H](C(=O)Nc2cccc(CC3(C(=O)O)CC3)c2F)[C@@H](C)C(F)(F)F)cc1]<br>from (+)-tert-butyl 1-(3-{[(2S,3R)-2-(4-ethyl-phenyl)-4,4,4-trifluoro-3-methylbutanoyl]amino}-2-fluorobenzyl)cyclopropanecarboxylate | LC-MS (Method 5): $R_t$ = 1.23 min; m/z = 452 (M + H)$^+$.<br>$^1$H-NMR (400 MHz, DMSO-d$_6$): δ [ppm] = 0.75-0.79 (m, 5H), 1.06-1.14 (m, 2H), 1.17 (t, 3H), 2.58 (q, 2H), 2.90 (s, 2H), 3.32-3.39 (m, 1H, obscured), 4.05 (d, 1H), 6.96-7.06 (m, 1H), 7.06-7.12 (m, 1H), 7.16-7.23 (m, 2H), 7.31-7.37 (m, 2H), 7.64 (t, 1H), 9.96 (s, 1H), 12.19 (br. s, 1H).<br>$[α]_D^{20}$ = +40.4°, c = 0.375, chloroform. |
| 25 | (+)-1-(3-{[(2S,3R)-2-(4-ethylphenyl)-4,4,4-tri-fluoro-3-methylbutanoyl]amino}-4-fluorobenzyl)-cyclopropanecarboxylic acid<br>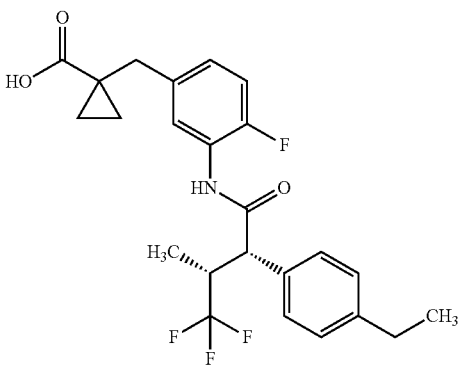 [SMILES: CCc1ccc([C@@H](C(=O)Nc2cc(CC3(C(=O)O)CC3)ccc2F)[C@@H](C)C(F)(F)F)cc1]<br>from (+)-tert-butyl 1-(3-{[(2S,3R)-2-(4-ethyl-phenyl)-4,4,4-trifluoro-3-methylbutanoyl]amino}-4-fluorobenzyl)cyclopropanecarboxylate | LC-MS (Method 5): $R_t$ = 1.23 min; m/z = 452 (M + H)$^+$.<br>$^1$H-NMR (400 MHz, DMSO-d$_6$): δ [ppm] = 0.71-0.82 (m, 5H), 1.04-1.11 (m, 2H), 1.17 (t, 3H), 2.58 (q, 2H), 2.80 (s, 2H), 3.33-3.39 (m, 1H), 4.03 (d, 1H), 6.94-7.03 (m, 1H), 7.10 (dd, 1H), 7.17-7.24 (m, 2H), 7.29-7.38 (m, 2H), 7.69 (dd, 1H), 9.94 (s, 1H), 12.12 (s, 1H).<br>$[α]_D^{20}$ = +129.3°, c = 0.475, chloroform. |
| 26 | (+)-1-(2-chloro-5-{[(2S,3R)-2-(4-chlorophenyl)-4,4,4-trifluoro-3-methylbutanoyl]amino}benzyl)-cyclopropanecarboxylic acid<br>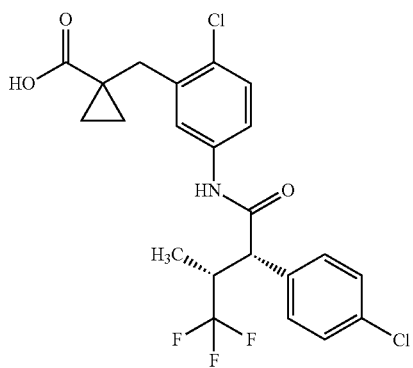 [SMILES: C[C@H]([C@H](C(=O)Nc1ccc(Cl)c(CC2(C(=O)O)CC2)c1)c1ccc(Cl)cc1)C(F)(F)F]<br>from tert-butyl 1-(2-chloro-5-{[(2S,3R)-2-(4-chlorophenyl)-4,4,4-trifluoro-3-methyl-butanoyl]amino}benzyl)cyclopropanecarboxylate | LC-MS (Method 4): $R_t$ = 1.45 min; m/z = 474/475 (M + H)$^+$.<br>$^1$H-NMR (400 MHz, DMSO-d$_6$): δ [ppm] = 0.67-0.85 (m, 5H), 1.20-1.22 (m, 2H), 2.84-3.04 (m, 2H), 3.35-3.50 (m, 1H), 3.84 (d, 1H), 7.31 (d, 1H), 7.41-7.48 (m, 4H), 7.50 (d, 1H), 7.57 (dd, 1H), 10.37 (s, 1H), 12.22 (br. s, 1H).<br>$[α]_D^{20}$ = +72.7°, c = 0.510, chloroform. |

-continued

| Example | Name/Structure/Starting material | Analytical data |
|---|---|---|
| 27 | (+)-1-(2-chloro-3-{[(2S,3R)-2-(4-chlorophenyl)-4,4,4-trifluoro-3-methylbutanoyl]amino}benzyl)-cyclopropanecarboxylic acid<br>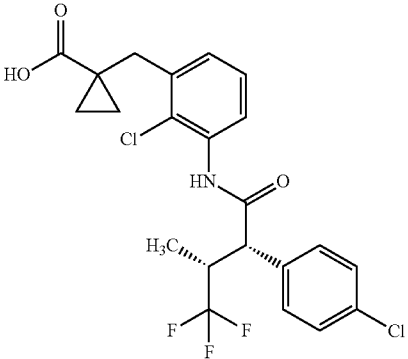 [SMILES: C[C@H]([C@H](C(=O)Nc1cccc(CC2(C(=O)O)CC2)c1Cl)c1ccc(Cl)cc1)C(F)(F)F]<br>from (+)-tert-butyl 1-(2-chloro-3-{[(2S,3R)-2-(4-chlorophenyl)-4,4,4-trifluoro-3-methyl-butanoyl]amino}benzyl)cyclopropanecarboxylate | LC-MS (Method 5): $R_t$ = 1.20 min; m/z = 472 (M − H)$^-$.<br>$^1$H-NMR (400 MHz, DMSO-$d_6$): δ [ppm] = 0.73 (br. s, 2H), 0.80 (d, 3H), 1.18 (br. s, 2H), 2.99 (br. s, 2H), 3.35-3.45 (m, 1H, obscured), 4.12 (d, 1H), 7.10-7.27 (m, 2H), 7.34 (d, 1H), 7.39-7.53 (m, 4H), 9.83 (s, 1H).<br>$[α]_D^{20}$ = +1.5°, c = 0.415, chloroform. |
| 28 | 1-(6-chloro-3-{[(2S,3R)-2-(4-chlorophenyl)-4,4,4-trifluoro-3-methylbutanoyl]amino}-2-fluorobenzyl)cyclopropanecarboxylic acid<br>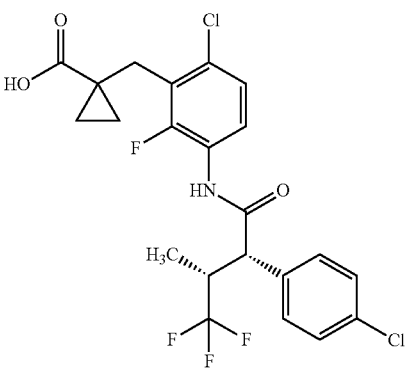 [SMILES: C[C@H]([C@H](C(=O)Nc1ccc(Cl)c(CC2(C(=O)O)CC2)c1F)c1ccc(Cl)cc1)C(F)(F)F]<br>from tert-butyl 1-(6-chloro-3-{[(2S,3R)-2-(4-chlorophenyl)-4,4,4-trifluoro-3-methylbutanoyl]-amino}-2-fluorobenzyl)cyclopropanecarboxylate | LC-MS (Method 5): $R_t$ = 1.24 min; m/z = 492/494 (M + H)$^+$.<br>$^1$H-NMR (400 MHz, DMSO-$d_6$): δ [ppm] = 0.40 (br. s, 2H), 0.78 (d, 3H), 0.98-1.09 (m, 2H), 3.28 (s, 2H), 4.11 (d, 1H), 7.24 (d, 1H), 7.45 (s, 4H), 7.58-7.76 (m, 1H), 10.19 (s, 1H), 12.38 (br. s, 1H).<br>$[α]_D^{20}$ = +31.0°, c = 0.285, chloroform. |
| 29 | (+)-1-(4,6-dichloro-3-{[(2S,3R)-2-(4-chlorophenyl)-4,4,4-trifluoro-3-methylbutanoyl]amino}-2-fluorobenzyl)cyclopropanecarboxylic acid<br>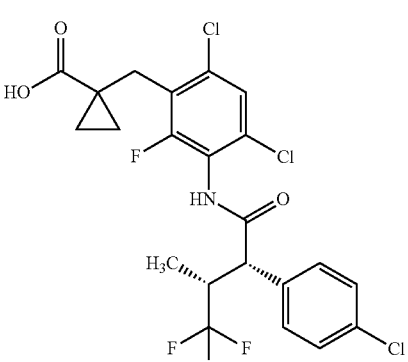<br>from tert-butyl 1-(4,6-dichloro-3-{[(2S,3R)-2-(4-chlorophenyl)-4,4,4-trifluoro-3-methylbutanoyl]-amino}-2-fluorobenzyl)cyclopropanecarboxylate | LC-MS (Method 5): $R_t$ = 1.22 min; m/z = 526/528 (M + H)$^+$.<br>$^1$H-NMR (400 MHz, DMSO-$d_6$): δ [ppm] = 0.37 (br. s, 2H), 0.79 (d, 3H), 0.95-1.04 (m, 2H), 3.25 (s, 2H), 3.96 (d, 1H), 7.42-7.45 (m, 4H), 7.57 (d, 1H), 10.16 (s, 1H), 12.42 (br. s, 1H).<br>$[α]_D^{20}$ = +27.0°, c = 0.210, chloroform. |

| Example | Name/Structure/Starting material | Analytical data |
|---|---|---|
| 30 | (+)-1-(4-chloro-3-{[(2S,3R)-2-(4-chloro-3-fluorophenyl)-4,4,4-trifluoro-3-methylbutanoyl]amino}-benzyl)cyclopropanecarboxylic acid<br>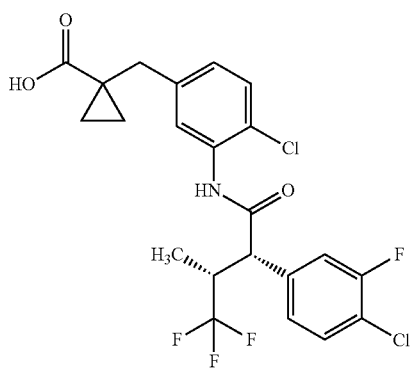 [SMILES: C[C@H]([C@H](C(=O)Nc1cc(CC2(C(=O)O)CC2)ccc1Cl)c1ccc(Cl)c(F)c1)C(F)(F)F]<br>from (+)-tert-butyl 1-(4-chloro-3-{[(2S,3R)-2-(4-chloro-3-fluorophenyl)-4,4,4-trifluoro-3-methyl-butanoyl]amino}benzyl)cyclopropanecarboxylate | LC-MS (Method 5): $R_t$ = 1.19 min; m/z = 492/494 (M + H)$^+$.<br>$^1$H-NMR (400 MHz, DMSO-d$_6$): δ [ppm] = 0.69-0.87 (m, 5H), 1.05-1.14 (m, 2H), 2.82 (s, 2H), 3.36-3.45 (m, 1H), 4.04-4.19 (m, 1H), 7.09 (dd, 1H), 7.27-7.37 (m, 2H), 7.40-7.45 (m, 1H), 7.49 (dd, 1H), 7.62 (t, 1H), 9.87 (s, 1H), 12.15 (br. s, 1H).<br>$[α]_D^{20}$ = +73°, c = 0.300, chloroform. |
| 31 | (+)-1-(2-chloro-5-{[(2S,3R)-2-(4-chlorophenyl)-4,4,4-trifluoro-3-methylbutanoyl]amino}-4-fluorobenzyl)cyclopropanecarboxylic acid<br>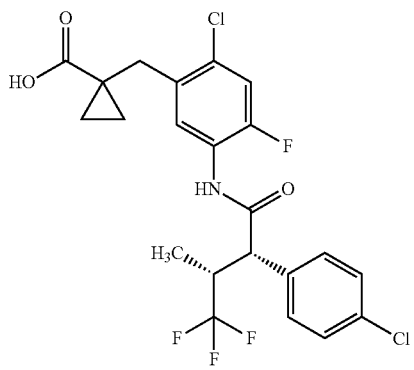 [SMILES: C[C@H]([C@H](C(=O)Nc1cc(CC2(C(=O)O)CC2)c(Cl)cc1F)c1ccc(Cl)cc1)C(F)(F)F]<br>from (+)-tert-butyl 1-(2-chloro-5-{[(2S,3R)-2-(4-chlorophenyl)-4,4,4-trifluoro-3-methylbutanoyl]-amino}-4-fluorobenzyl)cyclopropanecarboxylate | LC-MS (Method 4): $R_t$ = 1.44 min; m/z = 491/493 (M + H)$^+$.<br>$^1$H-NMR (400 MHz, DMSO-d$_6$): δ [ppm] = 0.73 (q, 2H), 0.78 (d, 3H), 1.15 (q, 2H), 2.87-3.03 (m, 2H), 3.35-3.44 (m, 1H), 4.06-4.12 (m, 1H), 7.36-7.48 (m, 5H), 7.90 (d, 1H), 10.15 (s, 1H), 12.26 (br. s, 1H).<br>$[α]_D^{20}$ = +131.1°, c = 0.500, chloroform. |
| 32 | (+)-1-(4-chloro-3-{[(2S,3R)-2-(4-chloro-2-fluorophenyl)-4,4,4-trifluoro-3-methylbutanoyl]-amino}benzyl)cyclopropanecarboxylic acid<br>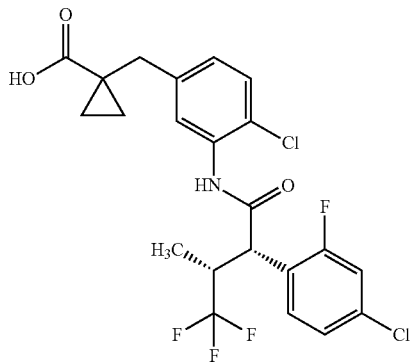 [SMILES: C[C@H]([C@H](C(=O)Nc1cc(CC2(C(=O)O)CC2)ccc1Cl)c1ccc(Cl)cc1F)C(F)(F)F]<br>from (+)-tert-butyl 1-(4-chloro-3-{[(2S,3R)-2-(4-chloro-2-fluorophenyl)-4,4,4-trifluoro-3-methyl-butanoyl]amino}benzyl)cyclopropanecarboxylate | LC-MS (Method 5): $R_t$ = 1.23 min; m/z = 490 (M − H)$^-$.<br>$^1$H-NMR (400 MHz, DMSO-d$_6$): δ [ppm] = 0.78-0.80 (m, 2H), 0.86 (d, 3H), 1.03-1.15 (m, 2H), 2.83 (s, 2H), 3.36-3.45 (m, 1H), 4.35 (d, 1H), 7.11 (dd, 1H), 7.30-7.38 (m, 3H), 7.52 (dd, 1H), 7.61 (t, 1H), 10.01 (s, 1H), 12.20 (br. s, 1H).<br>$[α]_D^{20}$ = +24.1°, c = 0.310, chloroform. |

| Example | Name/Structure/Starting material | Analytical data |
|---|---|---|
| 33 | 1-(3-{[(2S,3R)-2-(4-chlorophenyl)-4,4,4-trifluoro-3-methylbutanoyl]amino}-4-methylbenzyl)-cyclopropanecarboxylic acid<br>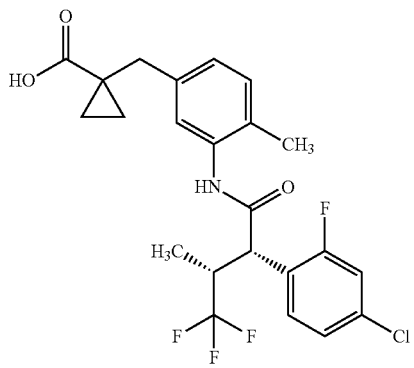 [SMILES: Cc1ccc(CC2(C(=O)O)CC2)cc1NC(=O)[C@H](c1ccc(Cl)cc1F)[C@@H](C)C(F)(F)F]<br>from tert-butyl 1-(3-{[(2S,3R)-2-(4-chlorophenyl)-4,4,4-trifluoro-3-methylbutanoyl]amino}-4-methylbenzyl)cyclopropanecarboxylate | LC-MS (Method 4): $R_t$ = 1.34 min; m/z = 452/454 (M − H)⁻.<br>¹H-NMR (400 MHz, DMSO-$d_6$): δ [ppm] = 0.70-0.77 (m, 2H), 0.80 (d, 3H), 1.02-1.10 (m, 2H), 1.94 (s, 3H), 2.80 (s, 2H), 3.31-3.44 (m, 1H, partially obscured by $H_2O$ signal), 3.95 (d, 1H), 6.93-7.00 (m, 1H), 7.01-7.08 (m, 2H), 7.38-7.52 (m, 4H), 9.59 (s, 1H), 12.06 (s, 1H). |
| 34 | 1-(3-{[(4-chlorophenyl)(3,3-difluorocyclopentyl)-acetyl]amino}-4-fluorobenzyl)cyclopropane-carboxylic acid (diastereomer mixture)<br>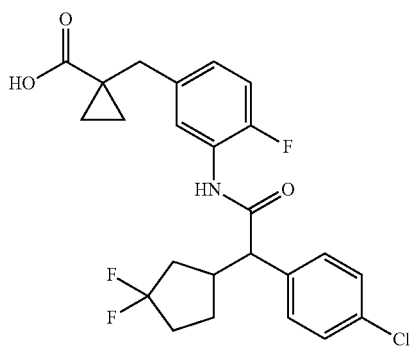 [SMILES: O=C(Nc1cc(CC2(C(=O)O)CC2)ccc1F)C(c1ccc(Cl)cc1)C1CCC(F)(F)C1]<br>from tert-butyl 1-(3-{[(4-chlorophenyl)(3,3-difluorocyclopentyl)acetyl]amino}-4-fluorobenzyl)cyclopropanecarboxylate | LC-MS (Method 4): $R_t$ = 1.37 min; m/z = 464/466 (M − H)⁻.<br>¹H-NMR (400 MHz, DMSO-$d_6$): δ [ppm] = 0.75-0.82 (m, 2H), 1.06-1.13 (m, 2H), 1.20-1.34 (m, 0.5H), 1.43-1.69 (m, 1.5H), 1.79-2.39 (m, 4H), 2.75-2.93 (m, 1H), 2.81 (s, 2H), 3.76 (t, 1H), 6.98-7.07 (m, 1H), 7.07-7.16 (m, 1H), 7.36-7.50 (m, 4H), 7.59-7.67 (m, 1H), 9.89 (s, 0.5H), 9.94 (s, 0.5H), 11.85-12.40 (br. s, 1H). |
| 35 | 1-(3-{[(4-chlorophenyl)(3,3-difluorocyclopentyl)-acetyl]amino}-4-chlorobenzyl)cyclopropane-carboxylic acid (diastereomer mixture)<br>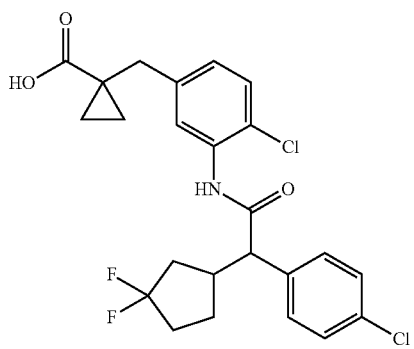 [SMILES: O=C(Nc1cc(CC2(C(=O)O)CC2)ccc1Cl)C(c1ccc(Cl)cc1)C1CCC(F)(F)C1]<br>from tert-butyl 1-(3-{[(4-chlorophenyl)(3,3-difluorocyclopentyl)acetyl]amino}-4-chlorobenzyl)cyclopropanecarboxylate | LC-MS (Method 5): $R_t$ = 1.21 min; m/z = 480/482 (M − H)⁻. |

-continued

| Example | Name/Structure/Starting material | Analytical data |
|---|---|---|
| 36 | 1-[3-({4,4,4-trifluoro-3-methyl-2-[4-(trifluoromethyl)phenyl]butanoyl}amino)benzyl]-cyclopropanecarboxylic acid<br>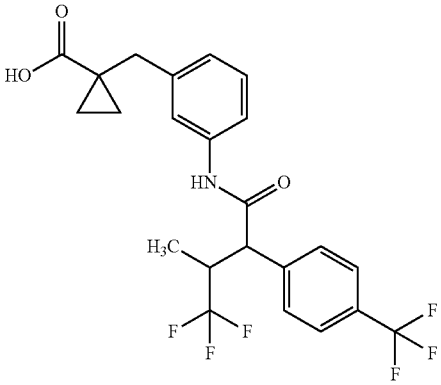 [SMILES: CC(C(C(=O)Nc1cccc(CC2(C(=O)O)CC2)c1)c1ccc(C(F)(F)F)cc1)C(F)(F)F]<br>from tert-butyl 1-[3-({4,4,4-trifluoro-3-methyl-2-[4-(trifluoromethyl)phenyl]butanoyl}amino)-benzyl}cyclopropanecarboxylate | LC-MS (Method 4): $R_t$ = 1.40 min; m/z = 472 (M − H)⁻.<br>¹H-NMR (400 MHz, DMSO-$d_6$): δ [ppm] = 0.71-0.87 (m, 4.6H), 1.07-1.15 (m, 2H), 1.23 (d, 0.4H), 2.82 (s, 2H) 3.37-3.53 (m, 0.95H), 3.63-3.77 (m, 0.05H), 3.93-4.04 (m, 1H), 6.89-6.98 (m, 1H), 7.12-7.22 (m, 1H), 7.34-7.38 (m, 1H), 7.39-7.48 (m, 1H), 7.62-7.80 (m, 4H), 10.26 (s, 0.82H), 10.35 (s, 0.18H), 12.09 (br. s, 1H). |
| 37 | 1-(4-fluoro-3-{[(2S,3R)-4,4,4-trifluoro-2-(4-isopropylphenyl)-3-methylbutanoyl]amino}-benzyl)cyclopropanecarboxylic acid<br>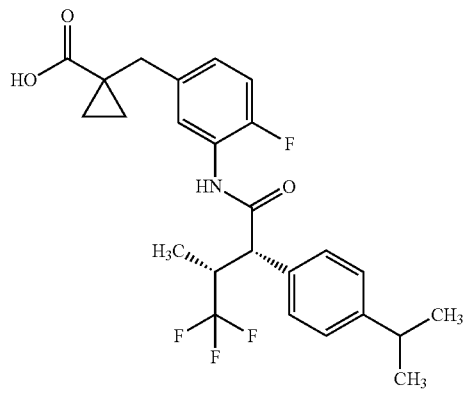 [SMILES: CC(C)c1ccc([C@@H](C(=O)Nc2cc(CC3(C(=O)O)CC3)ccc2F)[C@@H](C)C(F)(F)F)cc1]<br>from tert-butyl 1-(4-fluoro-3- {[(2S,3R)-4,4,4-trifluoro-2-(4-isopropylphenyl)-3-methyl-butanoyl]-amino}benzyl)cyclopropanecarboxylate | LC-MS (Method 2): $R_t$ = 2.70 min; m/z = 466 (M + H)⁺.<br>¹H-NMR (400 MHz, DMSO-$d_6$): δ [ppm] = 0.72-0.82 (m, 5H), 1.05-1.12 (m, 2H), 1.19 (d, 6H), 2.81 (s, 2H), 2.82-2.93 (m, 1H), 3.24-3.40 (m, 1H), 4.04 (d, 1H), 6.95-7.03 (m, 1H), 7.05-7.14 (m, 1H), 7.23 (d, 2H), 7.34 (d, 2H), 7.71 (d, 1H), 9.93 (s, 1H), 11.76-12.47 (br. s, 1H). |
| 38 | 1-[3-({(2S,3R)-2-[4-(1,1-difluoroethyl)phenyl]-4,4,4-trifluoro-3-methylbutanoyl}amino)-4-fluorobenzyl]cyclopropanecarboxylic acid<br>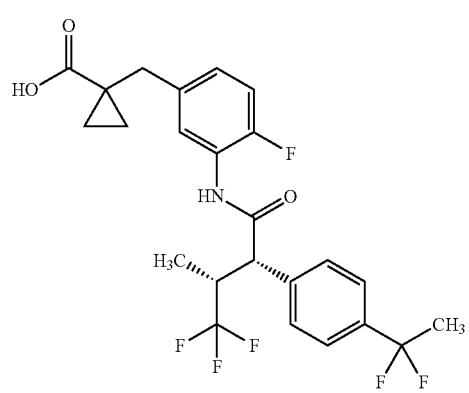 [SMILES: C[C@H]([C@H](C(=O)Nc1cc(CC2(C(=O)O)CC2)ccc1F)c1ccc(C(C)(F)F)cc1)C(F)(F)F]<br>from tert-butyl 1-[3-({(2S,3R)-2-[4-(1,1-difluoro-ethyl)phenyl]-4,4,4-trifluoro-3-methylbutanoyl}-amino)-4-fluorobenzyl]cyclopropanecarboxylate | LC-MS (Method 5): $R_t$ = 1.18 min; m/z = 488 (M + H)⁺.<br>¹H-NMR (400 MHz, DMSO-$d_6$): δ [ppm] = 0.71-0.83 (m, 5H), 1.05-1.13 (m, 2H), 1.96 (t, 3H), 2.81 (s, 2H), 3.33-3.47 (m, 1H), 4.16 (d, 1H), 6.97-7.04 (m, 1H), 7.06-7.14 (m, 1H), 7.51-7.61 (m, 4H), 7.69 (dd, 1H), 10.02 (s, 1H), 12.10 (s, 1H). |

| Example | Name/Structure/Starting material | Analytical data |
|---|---|---|
| 39 | 1-(3-{[(2S,3R)-2-(4-tert-butylphenyl)-4,4,4-trifluoro-3-methylbutanoyl]amino}-4-fluorobenzyl)cyclopropanecarboxylic acid<br>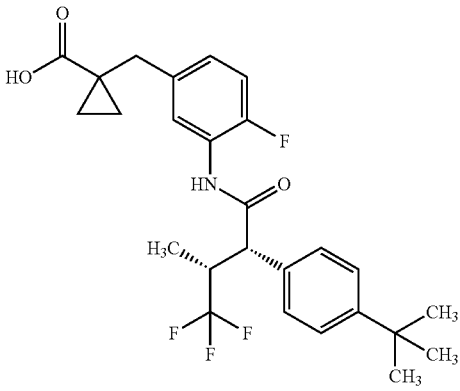 [SMILES: C[C@H]([C@H](C(=O)Nc1cc(CC2(C(=O)O)CC2)ccc1F)c1ccc(C(C)(C)C)cc1)C(F)(F)F]<br>from tert-butyl 1-(3-{[(2S,3R)-2-(4-tert-butyl-phenyl)-4,4,4-trifluoro-3-methylbutanoyl]amino}-4-fluorobenzyl)cyclopropanecarboxylate | LC-MS (Method 5): $R_t$ = 1.29 min; m/z = 480 (M + H)$^+$.<br>$^1$H-NMR (400 MHz, DMSO-d$_6$): δ [ppm] = 0.72-0.82 (m, 5H), 1.06-1.14 (m, 2H), 1.27 (s, 9H), 2.81 (s, 2H), 3.25-3.57 (m, 1H, partially obscured by H$_2$O signal), 4.05 (d, 1H), 6.96-7.03 (m, 1H), 7.06-7.13 (m, 1H), 7.37 (q, 4H), 7.72 (dd, 1H), 9.94 (s, 1H), 11.84-12.42 (br. s, 1H). |
| 40 | 1-(3-{[(2S,3R)-2-(4-cyclopropylphenyl)-4,4,4-trifluoro-3-methylbutanoyl]amino}-4-fluorobenzyl)cyclopropanecarboxylic acid<br>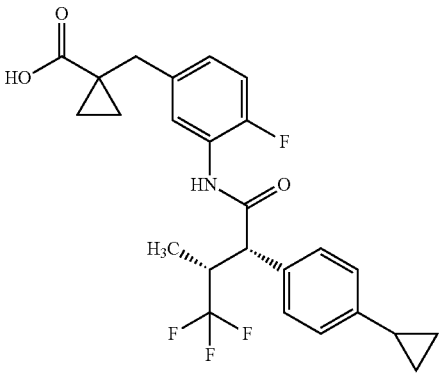 [SMILES: C[C@H]([C@H](C(=O)Nc1cc(CC2(C(=O)O)CC2)ccc1F)c1ccc(C2CC2)cc1)C(F)(F)F]<br>from tert-butyl 1-(3-{[(2S,3R)-2-(4-cyclopropyl-phenyl)-4,4,4-trifluoro-3-methylbutanoyl]amino}-4-fluorobenzyl)cyclopropanecarboxylate | LC-MS (Method 5): $R_t$ = 1.23 min; m/z = 464 (M + H)$^+$.<br>$^1$H-NMR (400 MHz, DMSO-d$_6$): δ [ppm] = 0.62-0.69 (m, 2H), 0.71-0.82 (m, 5H), 0.89-0.96 (m, 2H), 1.05-1.12 (m, 2H), 1.83-1.94 (m, 1H), 2.80 (s, 2H), 3.24-3.37 (m, 1H, partially obscured by H$_2$O signal), 4.01 (d, 1H), 6.96-7.02 (m, 1H), 7.03-7.13 (m, 3H), 7.29 (d, 2H), 7.68 (dd, 1H), 9.91 (s, 1H), 12.10 (s, 1H). |
| 41 | 1-[4-chloro-3-({(2S,3R)-4,4,4-trifluoro-3-methyl-2-[4-(trifluoromethyl)phenyl]butanoyl}amino)-benzyl]cyclopropanecarboxylic acid<br>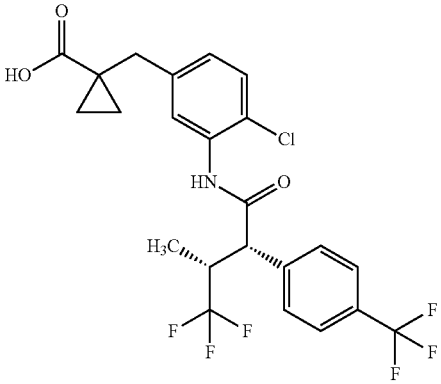 [SMILES: C[C@H]([C@H](C(=O)Nc1cc(CC2(C(=O)O)CC2)ccc1Cl)c1ccc(C(F)(F)F)cc1)C(F)(F)F]<br>from tert-butyl 1-[4-chloro-3-({(2S,3R)-4,4,4-trifluoro-3-methyl-2-[4-(trifluoromethyl)phenyl]-butanoyl}amino)benzyl]cyclopropanecarboxylate | LC-MS (Method 2): $R_t$ = 2.62 min; m/z = 506/508 (M − H)$^-$.<br>$^1$H-NMR (400 MHz, DMSO-d$_6$): δ [ppm] = 0.74-0.84 (m, 5H), 1.05-1.13 (m, 2H), 2.82 (s, 2H), 3.25-3.53 (m, 1H, partially obscured by H$_2$O signal), 4.23 (d, 1H), 7.08 (dd, 1H), 7.34 (d, 1H), 7.43 (d, 1H), 7.68 (d, 2H), 7.77 (d, 2H), 9.88 (s, 1H), 11.95-12.34 (br. s, 1H). |

| Example | Name/Structure/Starting material | Analytical data |
| --- | --- | --- |
| 42 | 1-(3-{[(2S,3R)-2-(4-chloro-3-methoxyphenyl)-4,4,4-trifluoro-3-methylbutanoyl]amino}-4-fluorobenzyl)cyclopropanecarboxylic acid<br><br>from tert-butyl 1-(3-{[(2S,3R)-2-(4-chloro-3-methoxyphenyl)-4,4,4-trifluoro-3-methyl-butanoyl]amino}-4-fluorobenzyl)cyclopropane-carboxylate | LC-MS (Method 5): $R_t$ = 1.12 min; m/z = 486/488 (M − H)$^-$.<br>$^1$H-NMR (400 MHz, DMSO-$d_6$): δ [ppm] = 0.74-0.85 (m, 5H), 1.05-1.12 (m, 2H), 2.81 (s, 2H), 3.31 -3.53 (m, 1H, obscured by H$_2$O signal), 3.87 (s, 3H), 4.06 (d, 1H), 6.97-7.05 (m, 2H), 7.07-7.14 (m, 1H), 7.21 (d, 1H), 7.42 (d, 1H), 7.66 (dd, 1H), 9.99 (s, 1H), 11.91-12.37 (br. s, 1H). |
| 43 | 1-(4-chloro-3-{[(2S,3R)-2-(4-chloro-3-methoxyphenyl)-4,4,4-trifluoro-3-methylbutanoyl]amino}-benzyl)cyclopropanecarboxylic acid<br><br>from tert-butyl 1-(4-chloro-3-{[(2S,3R)-2-(4-chloro-3-methoxyphenyl)-4,4,4-trifluoro-3-methyl-butanoyl]amino}benzyl)cyclopropanecarboxylate | LC-MS (Method 4): $R_t$ = 1.39 min; m/z = 502/504 (M − H)$^-$.<br>$^1$H-NMR (400 MHz, DMSO-$d_6$): δ [ppm] = 0.75-0.88 (m, 5H), 1.05-1.14 (m, 2H), 2.82 (s, 2H), 3.34-3.49 (m, 1H), 3.87 (s, 3H), 4.08 (d, 1H), 7.02 (dd, 1H), 7.07 (dd, 1H), 7.23 (d, 1H), 7.34 (d, 1H), 7.40-7.46 (m, 2H), 9.81 (s, 1H), 11.61-12.62 (br. s, 1H). |

-continued

| Example | Name/Structure/Starting material | Analytical data |
| --- | --- | --- |
| 44 | 1-[4-chloro-3-({(2S,3R)-4,4,4-trifluoro-3-methyl-2-[4-(1,1,1-trifluoro-2-methylpropan-2-yl)phenyl]-butanoyl}amino)benzyl]cyclopropanecarboxylic acid<br><br>from tert-butyl 1-[4-chloro-3-({(2S,3R)-4,4,4-trifluoro-3-methyl-2-[4-(1,1,1-trifluoro-2-methyl-propan-2-yl)phenyl]butanoyl}amino)benzyl]-cyclopropanecarboxylate | LC-MS (Method 5): $R_t$ = 1.29 min; m/z = 548/550 (M − H)⁻. |
| 45 | 1-(3-{[2-(4-chlorophenyl)-4,4,4-trifluoro-3-methyl-butanoyl]amino}benzyl)-cyclopropanecarboxylic acid<br><br>from tert-butyl 1-(3-{[2-(4-chlorophenyl)-4,4,4-trifluoro-3-methylbutanoyl]amino}benzyl)-cyclopropanecarboxylate | LC-MS (Method 4): $R_t$ = 1.37 min; m/z = 438/440 (M − H)⁻.<br>¹H-NMR (400 MHz, DMSO-d₆): δ [ppm] = 0.75-0.83 (m, 5H), 1.08-1.15 (m, 2H), 2.82 (s, 2H), 3.28-3.46 (m, 1H, obscured by H₂O signal), 3.85 (d, 1H), 6.93 (d, 1H), 7.16 (t, 1H), 7.34-7.51 (m, 6H), 10.20 (s, 1H), 11.60-12.40 (br. s, 1H). |
| 46 | 1-[4-chloro-3-({4,4,4-trifluoro-3-methyl-2-[4-(2,2,2-trifluoroethyl)phenyl]butanoyl}amino)-benzyl]cyclopropanecarboxylic acid<br><br>from tert-butyl 1-[4-chloro-3-({4,4,4-trifluoro-3-methyl-2-[4-(2,2,2-trifluoroethyl)phenyl]-butanoyl}amino)benzyl]cyclopropanecarboxylate | LC-MS (Method 5): $R_t$ = 1.20 min; m/z = 520/522 (M − H)⁻.<br>¹H-NMR (400 MHz, DMSO-d₆): δ [ppm] = 0.74-0.83 (m, 5H), 1.04-1.14 (m, 2H), 2.82 (s, 2H), 3.27-3.43 (m, 1H), 3.43-3.76 (q, 2H, partially obscured by H₂O signal), 4.10 (d, 1H), 7.07 (dd, 1H), 7.30-7.39 (m, 3H), 7.41-7.48 (m, 3H), 9.79 (s, 1H), 11.60-12.60 (br. s, 1H). |

| Example | Name/Structure/Starting material | Analytical data |
| --- | --- | --- |
| 47 | 1-(3-{[4,4,4-trifluoro-3-methyl-2-(4-methylphenyl)butanoyl]amino}benzyl)cyclopropanecarboxylic acid<br><br>from tert-butyl 1-(3-{[4,4,4-trifluoro-3-methyl-2-(4-methylphenyl)butanoyl]amino}benzyl)-cyclopropanecarboxylate | LC-MS (Method 4): $R_t$ = 1.35 min; m/z = 418 (M − H)⁻. |
| 48 | 1-[3-({4,4,4-trifluoro-3-methyl-2-[4-(trifluoromethoxy)phenyl]butanoyl}amino)benzyl]-cyclopropanecarboxylic acid<br><br>from tert-butyl 1-[3-({4,4,4-trifluoro-3-methyl-2-[4-(trifluoromethoxy)phenyl]butanoyl}amino)-benzyl]cyclopropanecarboxylate | LC-MS (Method 5): $R_t$ = 1.23 min; m/z = 488 (M − H)⁻.<br>¹H-NMR (400 MHz, DMSO-$d_6$): δ [ppm] = 0.72-0.86 (m, 5H), 1.07-1.16 (m, 2H), 2.82 (s, 2H), 3.27-3.48 (m, 1H, partially obscured by H₂O signal), 3.90 (d, 1H), 6.88-6.98 (m, 1H), 7.11-7.21 (m, 1H), 7.30-7.49 (m, 4H), 7.51-7.64 (m, 2H), 10.22 (s, 1H), 12.08 (s, 1H). |
| 49 | 1-(3-{[2-(4-chloro-3-methylphenyl)-4,4,4-trifluoro-3-methylbutanoyl]amino}benzyl)-cyclopropanecarboxylic acid<br><br>from tert-butyl 1-(3-{[2-(4-chloro-3-methylphenyl)-4,4,4-trifluoro-3-methylbutanoyl]amino}-benzyl)cyclopropanecarboxylate | LC-MS (Method 5): $R_t$ = 1.22 min; m/z = 452 (M − H)⁻.<br>¹H-NMR (400 MHz, DMSO-$d_6$): δ [ppm] = 0.76-0.84 (m, 5H), 1.08-1.15 (m, 2H), 2.27-2.35 (m, 3H), 2.82 (s, 2H), 3.29-3.44 (m, 1H, partially obscured by H₂O signal), 3.80 (d, 1H), 6.89-6.96 (m, 1H), 7.16 (t, 1H), 7.23-7.32 (m, 1H), 7.33-7.47 (m, 4H), 10.18 (s, 1H), 12.00-12.20 (br. s, 1H). |

Example 50

(+)-1-(4-Chloro-3-{[(2S,3R)-2-(4-chlorophenyl)-4,4,4-trifluoro-3-methylbutanoyl]amino}benzyl)-cyclopropanecarboxylic acid

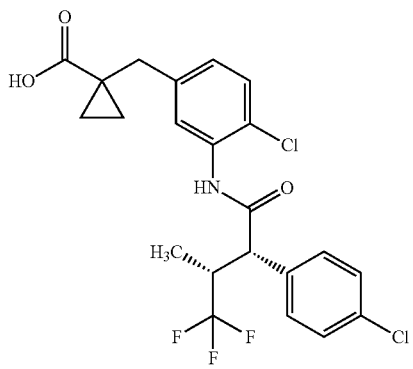 [SMILES: C[C@H]([C@H](C(=O)Nc1cc(CC2(C(=O)O)CC2)ccc1Cl)c1ccc(Cl)cc1)C(F)(F)F]

573 mg (1.08 mmol) of tert-butyl 1-(4-chloro-3-{[(2S,3R)-2-(4-chlorophenyl)-4,4,4-trifluoro-3-methylbutanoyl]amino}benzyl)cyclopropanecarboxylate were dissolved in 5 ml of dichloromethane, and 2.5 ml of TFA were added at RT. The reaction mixture was stirred at RT for 3 h and then concentrated under reduced pressure. Water was added to the crude product obtained in this manner, and the mixture was stirred at RT for 15 min. The crystals obtained were then filtered off with suction through a nutsche filter and dried under high vacuum. This gave 445 mg (86% of theory) of the title compound.

LC-MS (Method 5): $R_t$=1.23 min; m/z=472/474 (M−H)⁻.
$^1$H-NMR (400 MHz, DMSO-d$_6$): δ [ppm]=0.75-0.88 (m, 5H), 1.06-1.14 (m, 2H), 2.82 (s, 2H), 3.29-3.45 (m, 1H, partially obscured by H$_2$O signal), 4.11 (d, 1H), 7.08 (dd, 1H), 7.34 (d, 1H), 7.40-7.50 (m, 5H), 9.83 (s, 1H), 12.16 (br. s, 1H).
$[α]_D^{20}$=+95.4°, c=0.40, methanol.

Example 51

(+)-1-(3-{[(2S,3R)-2-(4-Chlorophenyl)-4,4,4-trifluoro-3-methylbutanoyl]amino}-4-fluorobenzyl)-cyclopropanecarboxylic acid

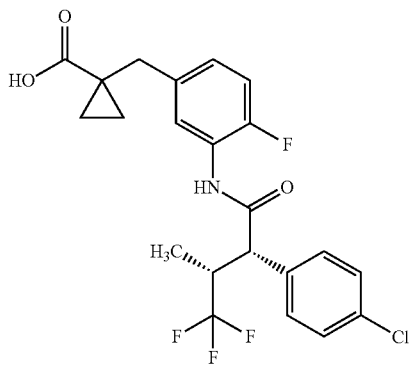 [SMILES: C[C@H]([C@H](C(=O)Nc1cc(CC2(C(=O)O)CC2)ccc1F)c1ccc(Cl)cc1)C(F)(F)F]

According to General Procedure 8, 1.59 g (3.1 mmol) of (+)-tert-butyl 1-(3-{[(2S,3R)-2-(4-chlorophenyl)-4,4,4-trifluoro-3-methylbutanoyl]amino}-4-fluorobenzyl)cyclopropanecarboxylate gave 1.36 g (96% of theory) of the title compound.

LC-MS (Method 5): $R_t$=1.20 min; m/z=458 (M+H)⁺.
$^1$H-NMR (400 MHz, DMSO-d$_6$): δ [ppm]=0.73-0.84 (m, 5H), 1.05-1.12 (m, 2H), 2.81 (s, 2H), 4.06-4.14 (m, 1H), 6.95-7.04 (m, 1H), 7.11 (dd, 1H), 7.41-7.50 (m, 4H), 7.67 (dd, 1H), 10.01 (s, 1H), 12.12 (s, 1H).
$[α]_D^{20}$=+125.6°, c=0.545, chloroform.

Example 52

1-(4-Chloro-3-{[(2S,3R)-2-(4-chlorophenyl)-4,4,4-trifluoro-3-methylbutanoyl]amino}-2-fluorobenzyl)cyclopropanecarboxylic acid

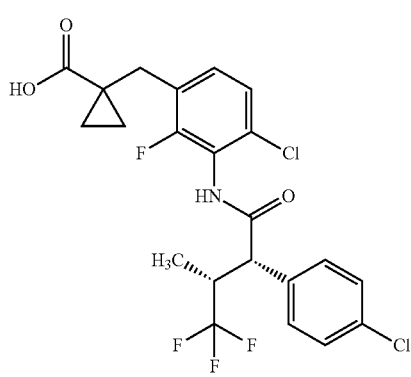 [SMILES: C[C@H]([C@H](C(=O)Nc1c(Cl)ccc(CC2(C(=O)O)CC2)c1F)c1ccc(Cl)cc1)C(F)(F)F]

22.0 mg (0.040 mmol) of tert-butyl 1-(4-chloro-3-{[(2S,3R)-2-(4-chlorophenyl)-4,4,4-trifluoro-3-methylbutanoyl]amino}-2-fluorobenzyl)cyclopropanecarboxylate were dissolved in 0.19 ml of dichloromethane, and 0.5 ml of TFA was added at RT. After 1 h at RT, the reaction mixture was concentrated under reduced pressure and the residue was dried under high vacuum overnight. This gave 17.8 mg (82.2% of theory) of the target compound.

LC-MS (Method 5): $R_t$=1.14 min; m/z=492 (M+H)⁺.
$^1$H-NMR (400 MHz, DMSO-d$_6$): δ [ppm]=0.74-0.84 (m, 5H), 1.06-1.18 (m, 2H), 2.86 (s, 2H), 3.19-3.43 (m, 1H), 3.95 (d, 1H), 7.23-7.33 (m, 2H), 7.38-7.50 (m, 4H), 10.02 (s, 1H).

Example 53

(+/−)-1-[3-({Cyclopentyl[4-(trifluoromethyl)phenyl]acetyl}amino)benzyl]cyclopropanecarboxylic acid

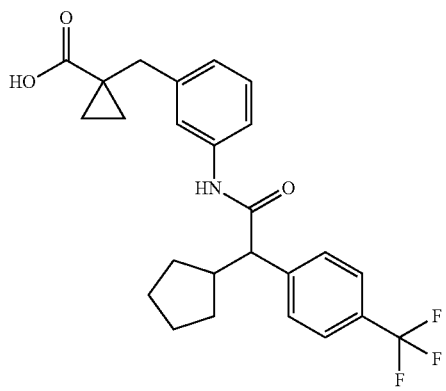 [SMILES: O=C(Nc1cccc(CC2(C(=O)O)CC2)c1)C(c1ccc(C(F)(F)F)cc1)C1CCCC1]

4.83 g (9.63 mmol) of (+/−)-tert-butyl 1-[3-({cyclopentyl[4-(trifluoromethyl)phenyl]acetyl}-amino)benzyl]cyclopropanecarboxylate were dissolved in 25 ml of dichloromethane and, after addition of a drop of water, 7.5 ml of TFA were added at RT. The reaction mixture was stirred at RT for 2 h and then concentrated under reduced pressure. The crude product was purified by chromatography on silica gel (mobile phase cyclohexane/ethyl acetate 4:1→2:1). This gave 3.89 g (90.8% of theory) of the target compound.

LC-MS (Method 4): $R_t$=1.46 min; m/z=446 (M+H)$^+$.

$^1$H-NMR (400 MHz, DMSO-d$_6$): δ [ppm]=0.74-0.83 (m, 2H), 0.96 (dq, 1H), 1.07-1.14 (m, 2H), 1.24-1.40 (m, 2H), 1.41-1.71 (m, 4H), 1.74-1.87 (m, 1H), 2.61 (dt, 1H), 2.82 (s, 2H), 3.52 (d, 1H), 6.92 (d, 1H), 7.16 (t, 1H), 7.39-7.48 (m, 2H), 7.56-7.66 (m, 2H), 7.67-7.73 (m, 2H), 10.09 (s, 1H), 12.09 (br. s, 1H).

Example 54

(+)-1-[3-({(2S)-2-Cyclopentyl-2-[4-(trifluoromethyl)phenyl]acetyl}amino)benzyl]cyclopropanecarboxylic acid

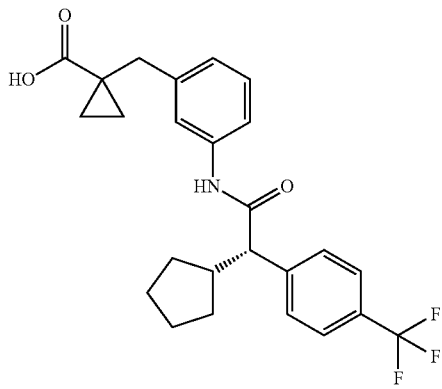 [SMILES: O=C(Nc1cccc(CC2(C(=O)O)CC2)c1)[C@H](c1ccc(C(F)(F)F)cc1)C1CCCC1]

From the racemate obtained above of 1-[3-({cyclopentyl[4-(trifluoromethyl)phenyl]acetyl}amino)-benzyl]cyclopropanecarboxylic acid (Example 53), the (+)-enantiomer was isolated by preparative HPLC on a chiral phase [column: Daicel Chiralpak AD-H, 5 μm, 250 mm×20 mm; injection volume: 0.5 ml; temperature: 30° C.; mobile phase: 70% isohexane/30% (isopropanol+0.2% TFA+1% water); flow rate: 15 ml/min; detection: 220 nm]. 3.90 g of racemate gave 1.69 g of the (+)-enantiomer.

LC-MS (Method 5): $R_t$=1.15 min; m/z=446 (M+H)$^+$.

$^1$H-NMR (400 MHz, DMSO-d$_6$): δ [ppm]=0.75-0.85 (m, 2H), 0.90-1.03 (m, 1H), 1.08-1.15 (m, 2H), 1.22-1.39 (m, 2H), 1.41-1.71 (m, 4H), 1.75-1.88 (m, 1H), 2.61 (dt, 1H), 2.83 (s, 2H), 3.53 (d, 1H), 6.92 (d, 1H), 7.16 (t, 1H), 7.38-7.49 (m, 2H), 7.57-7.66 (m, 2H), 7.67-7.76 (m, 2H), 10.09 (s, 1H), 12.09 (br. s, 1H).

$[α]_D^{20}$=+37.3°, c=0.700, chloroform.

Example 55

(+/−)-1-(3-{[(4-Chlorophenyl)(cyclopentyl)acetyl]amino}benzyl)cyclopropanecarboxylic acid

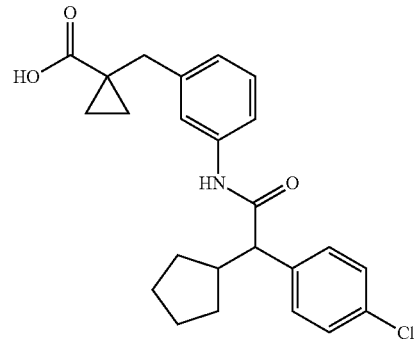 [SMILES: O=C(Nc1cccc(CC2(C(=O)O)CC2)c1)C(c1ccc(Cl)cc1)C1CCCC1]

6.60 g (14.1 mmol) of (+/−)-tert-butyl 1-(3-{[(4-chlorophenyl)(cyclopentyl)acetyl]amino}-benzyl)cyclopropanecarboxylate were dissolved in 41.8 ml of dichloromethane and, after addition of a drop of water, 10.9 ml of TFA were added at RT. The reaction mixture was stirred at RT for 1 h and then concentrated under reduced pressure. The residue was initially dried under high vacuum and then triturated with diisopropyl ether. The resulting solid was filtered off with suction and dried under high vacuum. This gave 4.52 g (77.8% of theory) of the target compound.

LC-MS (Method 4): $R_t$=1.43 min; m/z=412 (M+H)$^+$.

$^1$H-NMR (400 MHz, DMSO-d$_6$): δ [ppm]=0.73-0.82 (m, 2H), 0.90-1.01 (m, 1H), 1.08-1.17 (m, 2H), 1.21-1.39 (m, 2H), 1.41-1.70 (m, 4H), 1.71-1.85 (m, 1H), 2.56-2.63 (m, 1H), 2.82 (s, 2H), 3.40 (d, 1H), 6.91 (d, 1H), 7.15 (t, 1H), 7.32-7.50 (m, 6H), 10.02 (s, 1H), 12.10 (br. s, 1H).

Example 56

(+)-1-(3-{[(2S)-2-(4-Chlorophenyl)-2-cyclopentylacetyl]amino}benzyl)cyclopropanecarboxylic acid

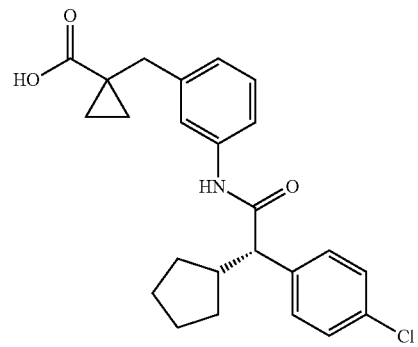 [SMILES: O=C(Nc1cccc(CC2(C(=O)O)CC2)c1)[C@H](c1ccc(Cl)cc1)C1CCCC1]

From the racemate obtained above of 1-(3-{[(4-chlorophenyl)(cyclopentyl)acetyl]amino}benzyl)-cyclopropanecarboxylic acid (Example 55), the (+)-enantiomer was isolated by preparative HPLC on a chiral phase [column: Daicel Chiralpak AD-H, 5 μm, 250 mm×20 mm; injection volume: 0.16 ml; temperature: 28° C.; mobile phase: 75% isohexane/25% (isopropanol+0.2% TFA+1% water); flow rate: 15 ml/min; detection: 220 nm]. 4.52 g of racemate gave 1.90 g of the (+)-enantiomer.

LC-MS (Method 5): $R_t$=1.23 min; m/z=412 (M+H)$^+$.

$^1$H-NMR (400 MHz, DMSO-d$_6$): δ [ppm]=0.76-0.82 (m, 2H), 0.89-1.01 (m, 1H), 1.08-1.15 (m, 2H), 1.19-1.39 (m, 2H), 1.40-1.70 (m, 4H), 1.72-1.84 (m, 1H), 2.54-2.62 (m, 1H), 2.82 (s, 2H), 3.40 (d, 1H), 6.91 (d, 1H), 7.15 (t, 1H), 7.32-7.47 (m, 6H), 10.02 (s, 1H), 12.09 (br. s, 1H).

$[α]_D^{20}$=+31.4°, c=0.560, chloroform.

Example 57 and Example 58

The racemate obtained above of 1-(3-{[(4-chloro-2-fluorophenyl)(cyclopentyl)acetyl]amino}-benzyl)cyclopropanecarboxylic acid (Example 1) was separated into the enantiomers by preparative HPLC on a chiral phase [column: Daicel Chiralpak AD-H, 5 μm, 250 mm×20 mm; injection volume: 0.35 ml; temperature: 30° C.; mobile phase: 80% isohexane/20% (ethanol+0.2% TFA+1% water); flow rate: 15 ml/min; detection: 220 nm]. 150 mg of racemate gave 67 mg of enantiomer 1 (Example 57) and 72 mg of enantiomer 2 (Example 58).

Example 57

Enantiomer 1

(+)-1-(3-{[(2S)-2-(4-Chloro-2-fluorophenyl)-2-cyclopentylacetyl]amino}benzyl)cyclopropanecarboxylic acid

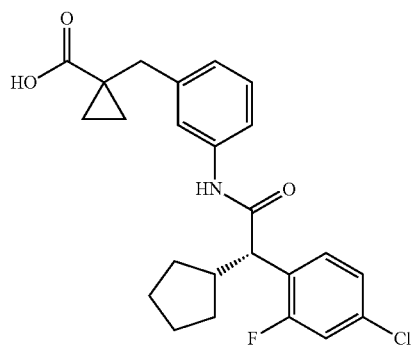

LC-MS (Method 5): $R_t$=1.28 min; m/z=430 (M+H)$^+$.

$^1$H-NMR (400 MHz, DMSO-d$_6$): δ [ppm]=0.76-0.83 (m, 2H), 0.94-1.04 (m, 1H), 0.94-1.12 (m, 2H), 1.32-1.61 (m, 5H), 1.62-1.79 (m, 2H), 2.50-2.55 (m, 1H, obscured), 2.83 (s, 2H), 3.78 (d, 1H), 6.93 (d, 1H), 7.16 (t, 1H), 7.29 (dd, 1H), 7.40 (dd, 1H), 7.43-7.49 (m, 2H), 7.70 (t, 1H), 10.13 (s, 1H), 12.10 (br. s, 1H).

$[α]_D^{20}$=+43.6°, c=0.520, chloroform.

Example 58

Enantiomer 2

(−)-1-(3-{[(2R)-2-(4-Chloro-2-fluorophenyl)-2-cyclopentylacetyl]amino}benzyl)cyclopropanecarboxylic acid

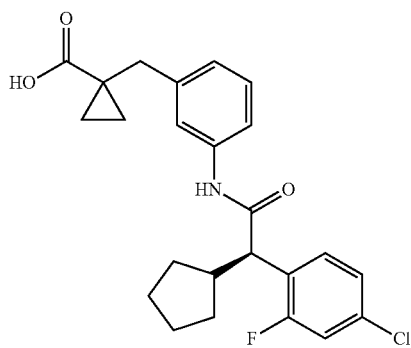 [SMILES: O=C(Nc1cccc(CC2(C(=O)O)CC2)c1)[C@@H](c1ccc(Cl)cc1F)C1CCCC1]

LC-MS (Method 5): $R_t$=1.28 min; m/z=430 (M+H)$^+$.

$^1$H-NMR (400 MHz, DMSO-d$_6$): δ [ppm]=0.76-0.84 (m, 2H), 0.94-1.03 (m, 1H), 1.07-1.15 (m, 2H), 1.33-1.61 (m, 5H), 1.63-1.79 (m, 2H), 2.52-2.57 (m, 1H, obscured), 2.83 (s, 2H), 3.78 (d, 1H), 6.93 (d, 1H), 7.16 (t, 1H), 7.29 (dd, 1H), 7.40 (dd, 1H), 7.43-7.52 (m, 2H), 7.70 (t, 1H), 10.13 (s, 1H), 12.10 (br. s, 1H).

$[α]_D^{20}$=−39.7°, c=0.540, chloroform.

Example 59

(+/−)-1-(3-{[2-(4-Ethylphenyl)-4,4,4-trifluoro-3-methylbutanoyl]amino}benzyl)cyclopropanecarboxylic acid

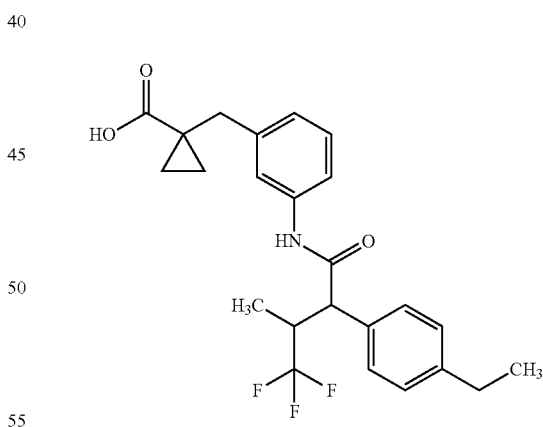

1.52 g (3.11 mmol) of (+/−)-tert-butyl 1-(3-{[2-(4-ethylphenyl)-4,4,4-trifluoro-3-methylbutanoyl]-amino}benzyl)cyclopropanecarboxylate were dissolved in 3 ml of dichloromethane, and 12 ml of TFA were added at RT. The reaction mixture was stirred at RT for 2 h and then concentrated under reduced pressure, and the residue was dried under high vacuum overnight. This residue was triturated with acetonitrile, and the resulting solid was filtered off with suction, washed with a little acetonitrile and dried under high vacuum. This gave 1.16 g (86.2% of theory) of the target compound.

LC-MS (Method 4): $R_t$=1.42 min; m/z=434 (M+H)$^+$.

$^1$H-NMR (400 MHz, DMSO-d$_6$): δ [ppm]=0.75-0.82 (m, 5H), 1.08-1.13 (m, 2H), 1.16 (t, 3H), 2.57 (q, 2H), 2.82 (s, 2H), 3.31-3.36 (m, 1H), 3.78 (d, 1H), 6.91 (d, 1H), 7.15 (t, 1H), 7.17-7.23 (m, 2H), 7.29-7.35 (m, 2H), 7.37 (s, 1H), 7.43 (d, 1H), 10.13 (s, 1H), 12.08 (br. s, 1H).

Example 60

(+)-1-(3-{[(2S,3R)-2-(4-Ethylphenyl)-4,4,4-trifluoro-3-methylbutanoyl]amino}benzyl)cyclopropanecarboxylic acid (enantiomer 1)

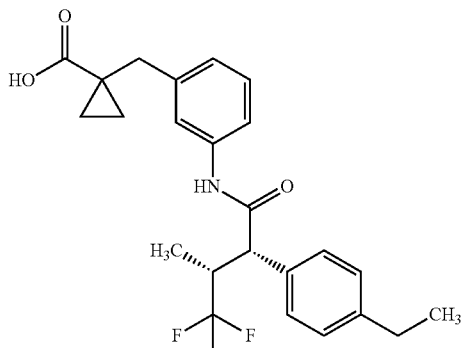

The racemate obtained above of 1-(3-{[2-(4-ethylphenyl)-4,4,4-trifluoro-3-methylbutanoyl]-amino}benzyl)cyclopropanecarboxylic acid (Example 59) was separated further by preparative HPLC on a chiral phase [column: Daicel Chiralpak AD-H, 5 μm, 250 mm×20 mm; injection volume: 0.2 ml; temperature: 28° C.; mobile phase: 75% isohexane/25% (isopropanol+0.2% TFA+1% water); flow rate: 15 ml/min; detection: 220 nm]. 1300 mg of racemate gave 641 mg of enantiomer 1.

LC-MS (Method 4): R$_t$=1.41 min; m/z=434 (M+H)$^+$.

$^1$H-NMR (400 MHz, DMSO-d$_6$): δ [ppm]=0.75-0.82 (m, 5H), 1.11 (q, 2H), 1.16 (t, 3H), 2.55-2.61 (m, 2H), 2.82 (s, 2H), 3.29-3.41 (m, 1H), 3.78 (d, 1H), 6.91 (d, 1H), 7.15 (t, 1H), 7.18-7.23 (m, 2H), 7.28-7.35 (m, 2H), 7.37 (s, 1H), 7.43 (d, 1H), 10.13 (s, 1H), 12.08 (br. s, 1H).

$[α]_D^{20}$=+73.8°, c=0.560, chloroform.

Example 61 and Example 62

The racemate obtained above of 1-(3-{[(4-chlorophenyl)(cyclopentyl)acetyl]amino}-4-fluorobenzyl)cyclopropanecarboxylic acid (Example 8) was separated into the enantiomers by preparative HPLC on a chiral phase [column: Daicel Chiralpak AD-H, 5 μm, 250 mm×20 mm; injection volume: 0.35 ml; temperature: 35° C.; mobile phase: 30% isohexane/70% isopropanol; flow rate: 15 ml/min; detection: 220 nm]. 167 mg of racemate gave 95 mg of enantiomer 1 (Example 61) and 89 mg of enantiomer 2 (Example 62) (both still comprising residual solvent).

Example 61

Enantiomer 1

(−)-1-(3-{[(2R)-2-(4-Chlorophenyl)-2-cyclopentylacetyl]amino}-4-fluorobenzyl)cyclopropanecarboxylic acid

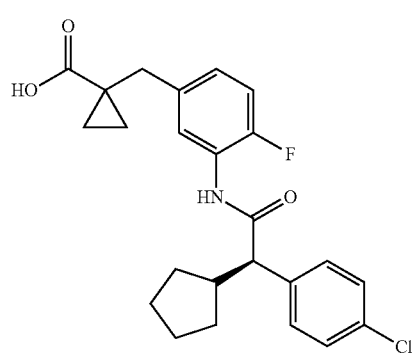 [SMILES: O=C(Nc1cc(CC2(C(=O)O)CC2)ccc1F)[C@@H](c1ccc(Cl)cc1)C1CCCC1]

LC-MS (Method 5): R$_t$=1.26 min; m/z=430 (M+H)$^+$.

$^1$H-NMR (400 MHz, DMSO-d$_6$): δ [ppm]=0.67-0.72 (m, 2H), 0.90-0.98 (m, 1H), 1.00-1.06 (m, 2H), 1.21-1.39 (m, 2H), 1.39-1.69 (m, 4H), 1.72-1.86 (m, 1H), 2.52-2.57 (m, 1H), 2.80 (s, 2H), 3.60 (d, 1H), 6.98-7.05 (m, 1H), 7.05-7.14 (m, 1H), 7.35-7.40 (m, 2H), 7.40-7.46 (m, 2H), 7.63 (dd, 1H), 9.80 (s, 1H).

$[α]_D^{20}$=−65.7°, c=0.360, chloroform.

Example 62

Enantiomer 2

(+)-1-(3-{[(2S)-2-(4-Chlorophenyl)-2-cyclopentylacetyl]amino}-4-fluorobenzyl)cyclopropanecarboxylic acid

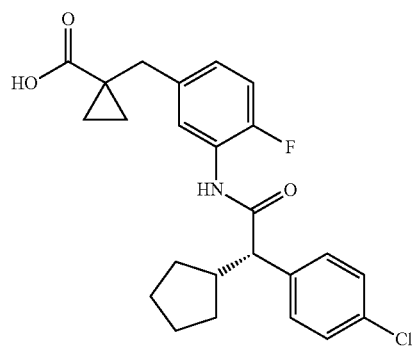

LC-MS (Method 5): R$_t$=1.26 min; m/z=430 (M+H)$^+$.

$^1$H-NMR (400 MHz, DMSO-d$_6$): δ [ppm]=0.68 (br. s, 2H), 0.90-0.99 (m, 1H), 1.01-1.04 (m, 2H), 1.26-1.39 (m, 2H), 1.40-1.70 (m, 4H), 1.74-1.85 (m, 1H), 2.52-2.57 (m, 1H), 2.80 (s, 2H), 3.60 (d, 1H), 6.98-7.04 (m, 1H), 7.05-7.12 (m, 1H), 7.34-7.40 (m, 2H), 7.41-7.46 (m, 2H), 7.63 (dd, 1H), 9.80 (s, 1H).

$[α]_D^{20}$=+63.5°, c=0.550, chloroform.

Example 63

(+)-1-(4-Fluoro-3-{[(2S,3R)-4,4,4-trifluoro-3-methyl-2-(4-vinylphenyl)butanoyl]amino}benzyl)-cyclopropanecarboxylic acid

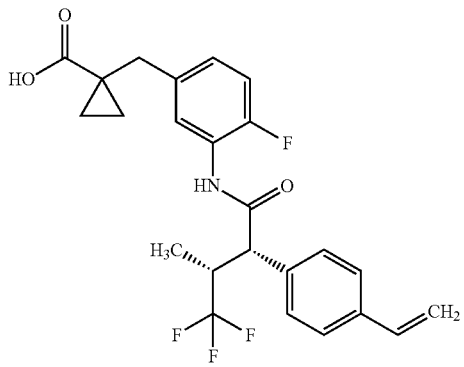 [SMILES: C=Cc1ccc([C@@H](C(=O)Nc2cc(CC3(C(=O)O)CC3)ccc2F)[C@@H](C)C(F)(F)F)cc1]

At RT, 120 mg (0.237 mmol) of (+)-tert-butyl 1-(4-fluoro-3-{[(2S,3R)-4,4,4-trifluoro-3-methyl-2-(4-vinylphenyl)butanoyl]amino}benzyl)cyclopropanecarboxylate were treated with 1.7 ml of a 4 M solution of hydrogen chloride in dioxane. The reaction mixture was stirred at RT overnight and then frozen with dry ice and subsequently lyophilized under high vacuum. The product obtained was taken up in a little dichloromethane and foamed under high vacuum. This gave 69 mg of the target compound (65% of theory).

LC-MS (Method 5): $R_t$=1.19 min; m/z=450 (M+H)$^+$.

$^1$H-NMR (400 MHz, DMSO-d$_6$): δ [ppm]=0.75-0.82 (m, 5H), 1.09 (q, 2H), 2.80 (s, 2H), 3.34-3.42 (m, 1H), 4.07 (d, 1H), 5.27 (d, 1H), 5.83 (d, 1H), 6.72 (dd, 1H), 6.95-7.03 (m, 1H), 7.10 (dd, 1H), 7.38-7.42 (m, 2H), 7.45-7.50 (m, 2H), 7.67 (dd, 1H), 9.98 (s, 1H), 12.12 (s, 1H).

$[α]_D^{20}$=+37.7°, c=0.385, chloroform.

Example 64

(+)-1-(3-{[(2S,3R)-2-(4-Acetylphenyl)-4,4,4-trifluoro-3-methylbutanoyl]amino}-4-fluorobenzyl)-cyclopropanecarboxylic acid

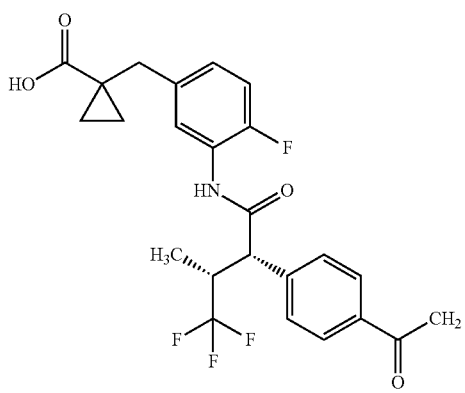 [SMILES: CC(=O)c1ccc([C@@H](C(=O)Nc2cc(CC3(C(=O)O)CC3)ccc2F)[C@@H](C)C(F)(F)F)cc1]

At RT, 90 mg (0.172 mmol) of (+)-tert-butyl 1-[4-fluoro-3-({(2S,3R)-4,4,4-trifluoro-2-[4-(1-fluorovinyl)phenyl]-3-methylbutanoyl}amino)benzyl]cyclopropanecarboxylate were stirred in 5.2 ml of a 4 M solution of hydrogen chloride in dioxane overnight. The reaction mixture was then frozen with dry ice and subsequently lyophilized under high vacuum. The resulting residue was purified by preparative RP-HPLC (mobile phase acetonitrile/water). This gave 27 mg (33.7% of theory) of the title compound.

LC-MS (Method 5): $R_t$=1.05 min; m/z=465 (M+H)$^+$.

$^1$H-NMR (400 MHz, DMSO-d$_6$): δ [ppm]=0.75-0.83 (m, 5H), 1.09 (q, 2H), 2.57 (s, 3H), 2.80 (s, 2H), 3.43 (dd, 1H), 4.19 (d, 1H), 6.96-7.04 (m, 1H), 7.10 (dd, 1H), 7.55-7.62 (m, 2H), 7.66 (dd, 1H), 7.94-8.00 (m, 2H), 10.06 (s, 1H), 12.12 (s, 1H).

$[α]_D^{20}$=+121.8°, c=0.49, chloroform.

Example 65

1-(3-{[(4-Chlorophenyl)(2,2-difluorocyclopentyl)acetyl]amino}-4-fluorobenzyl)cyclopropane-carboxylic acid (racemic diastereomer mixture)

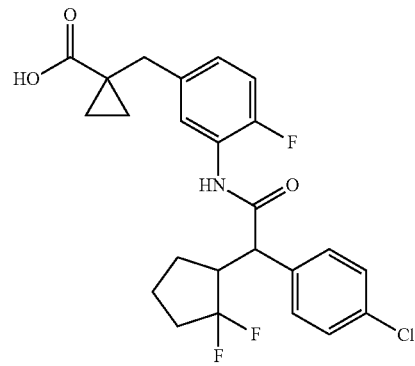 [SMILES: O=C(Nc1cc(CC2(C(=O)O)CC2)ccc1F)C(c1ccc(Cl)cc1)C1CCCC1(F)F]

750 mg (1.44 mmol) of tert-butyl 1-(3-{[(4-chlorophenyl)(2,2-difluorocyclopentyl)acetyl]amino}-4-fluorobenzyl)cyclopropanecarboxylate (as racemic diastereomer mixture) were dissolved in 1.6 ml of dichloromethane, and 5.5 ml of TFA were added at RT. The mixture was stirred at RT for 2 h and then concentrated under reduced pressure. The residue was dried under high vacuum and then triturated with acetonitrile. The precipitated solid was filtered off. The filtrate was concentrated, the residue obtained was once more triturated with acetonitrile and a further batch of solid was isolated. This procedure was repeated once more, and all solid batches were then combined. This gave a total of 553 mg (82.6% of theory) of the title compound as a mixture of four isomers.

LC-MS (Method 5): $R_t$=1.18 min; m/z=466 (M+H)$^+$.

Examples 66-68

The mixture obtained above of the racemic diastereomeric 1-(3-{[(4-chlorophenyl)(2,2-difluorocyclopentyl)acetyl]amino}-4-fluorobenzyl)cyclopropanecarboxylic acids (Example 65) was separated further by preparative HPLC on a chiral phase [column: Daicel Chiralpak AD-H, 5 µm, 250 mm×20 mm; injection volume: 10 µl; temperature: 40° C.; mobile phase: 80% isohexane/20% (isopropanol+0.2% TFA+1% water); flow rate: 15 ml/min; detection: 220 nm]. 540 mg of diastereomer mixture gave 163 mg of pure isomer 1 (Example 66). Isomer 2 and isomer 3 were initially obtained as a mixture which was separated by another preparative HPLC on the same chiral phase [injection volume: 10 µl; temperature: 40° C.; mobile phase: 85% isohexane/15% (isopropanol+0.2% TFA+1% water); flow rate: 15 ml/min; detection: 220 nm]. This gave 140 mg of pure isomer 2 (Example 67) and 107 mg of pure isomer 3 (Example 68).

Example 66

Isomer 1=Enantiomer 1 of Diastereomer 2

(−)-1-(3-{[(2R)-2-(4-Chlorophenyl)-2-(2,2-difluorocyclopentyl)acetyl]amino}-4-fluorobenzyl)-cyclopropanecarboxylic acid

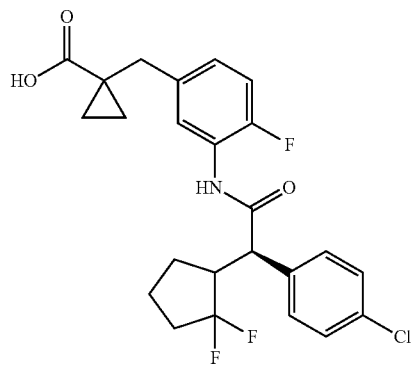 [SMILES: O=C(Nc1cc(CC2(C(=O)O)CC2)ccc1F)[C@@H](c1ccc(Cl)cc1)C1CCCC1(F)F]

LC-MS (Method 4): $R_t$=1.33 min; m/z=466 (M+H)$^+$.
$^1$H-NMR (400 MHz, DMSO-d$_6$): δ [ppm]=0.73-0.81 (m, 2H), 1.05-1.12 (m, 2H), 1.12-1.22 (m, 1H), 1.43-1.55 (m, 1H), 1.56-1.69 (m, 2H), 1.98-2.25 (m, 2H), 2.80 (s, 2H), 2.99-3.22 (m, 1H), 4.01 (d, 1H), 6.94-7.03 (m, 1H), 7.09 (dd, 1H), 7.37-7.43 (m, 2H), 7.43-7.51 (m, 2H), 7.65-7.75 (m, 1H), 9.84 (s, 1H), 12.10 (br. s, 1H).
$[α]_D^{20}$=−79.1°, c=0.525, chloroform.

Example 67

Isomer 2=Enantiomer 2 of Diastereomer 1

(+)-1-(3-{[(2S)-2-(4-Chlorophenyl)-2-(2,2-difluorocyclopentyl)acetyl]amino}-4-fluorobenzyl)-cyclopropanecarboxylic acid

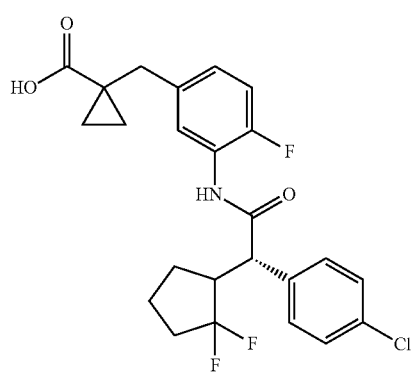 [SMILES: O=C(Nc1cc(CC2(C(=O)O)CC2)ccc1F)[C@H](c1ccc(Cl)cc1)C1CCCC1(F)F]

LC-MS (Method 4): $R_t$=1.33 min; m/z=466 (M+H)$^+$.
$^1$H-NMR (400 MHz, DMSO-d$_6$): δ [ppm]=0.73-0.81 (m, 2H), 1.05-1.11 (m, 2H), 1.11-1.22 (m, 1H), 1.45-1.53 (m, 1H), 1.56-1.69 (m, 2H), 1.97-2.24 (m, 2H), 2.81 (s, 2H), 3.01-3.20 (m, 1H), 4.01 (d, 1H), 6.93-7.02 (m, 1H), 7.09 (dd, 1H), 7.36-7.43 (m, 2H), 7.44-7.50 (m, 2H), 7.66-7.73 (m, 1H), 9.84 (s, 1H), 12.08 (br. s, 1H).
$[α]_D^{20}$=+89.6°, c=0.480, chloroform.

Example 68

Isomer 3=Enantiomer 2 of Diastereomer 2

(+)-1-(3-{[(2S)-2-(4-Chlorophenyl)-2-(2,2-difluorocyclopentyl)acetyl]amino}-4-fluorobenzyl)-cyclopropanecarboxylic acid

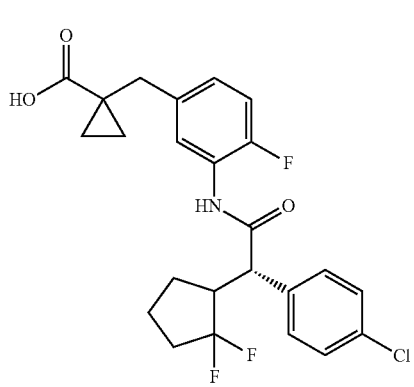 [SMILES: O=C(Nc1cc(CC2(C(=O)O)CC2)ccc1F)[C@H](c1ccc(Cl)cc1)C1CCCC1(F)F]

LC-MS (Method 4): $R_t$=1.32 min; m/z=466 (M+H)$^+$.
$^1$H-NMR (400 MHz, DMSO-d$_6$): δ [ppm]=0.75-0.82 (m, 2H), 1.05-1.12 (m, 2H), 1.50-1.64 (m, 1H), 1.67-1.79 (m, 2H), 1.94-2.22 (m, 3H), 2.80 (s, 2H), 2.85-3.02 (m, 1H), 4.07 (d, 1H), 6.96-7.05 (m, 1H), 7.07-7.15 (m, 1H), 7.34-7.40 (m, 2H), 7.43-7.51 (m, 2H), 7.63 (dd, 1H), 9.98 (s, 1H).
$[α]_D^{20}$=+96.2°, c=0.460, chloroform.

Example 69

1-(4-Chloro-3-{[(2S,3R)-2-(4-chlorophenyl)-4,4,4-trifluoro-3-methylbutanoyl]amino}benzyl)-2,2-difluorocyclopropanecarboxylic acid (diastereomer mixture)

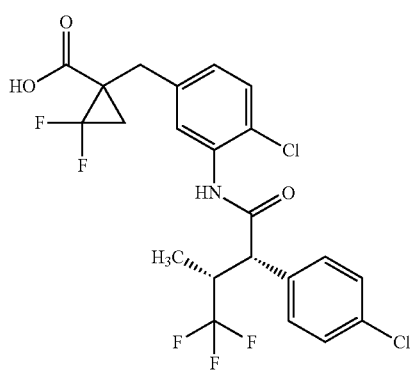 [SMILES: C[C@H]([C@H](C(=O)Nc1cc(CC2(C(=O)O)CC2(F)F)ccc1Cl)c1ccc(Cl)cc1)C(F)(F)F]

1.80 g (3.18 mmol) of tert-butyl 1-(4-chloro-3-{[(2S,3R)-2-(4-chlorophenyl)-4,4,4-trifluoro-3-methylbutanoyl]amino}benzyl)-2,2-difluorocyclopropanecarboxylate (as diastereomer mixture) were dissolved in 5 ml of dichloromethane, and 4.9 ml of TFA were added at RT. The reaction mixture was stirred at RT for 1 h and then concentrated under reduced pressure. The residue was purified by chromatography on silica gel (mobile phase first dichloromethane, then dichloromethane/ethyl acetate 10:1→5:1). This gave 1.25 g of the target compound (77.1% of theory).

LC-MS (Method 5): $R_t$=1.20 min; m/z=510 (M+H)$^+$.

$^1$H-NMR (400 MHz, DMSO-d$_6$): both diastereomers: δ [ppm]=0.80 (d, 3H), 1.81-1.94 (m, 1H), 2.10-2.20 (m, 1H), 2.65-2.75 (m, 1H), 3.36-3.41 (m, 1H), 4.11 (d, 1H), 7.07 (dd, 1H), 7.35-7.61 (m, 6H), 9.85 (s, 1H), 13.25 (br. s, 1H).

Example 70 and Example 71

The diastereomer mixture, obtained above, of 1-(4-chloro-3-{[(2S,3R)-2-(4-chlorophenyl)-4,4,4-trifluoro-3-methylbutanoyl]amino}benzyl)-2,2-difluorocyclopropanecarboxylic acid (Example 69) was separated further by preparative HPLC on a chiral phase [column: Daicel Chiralpak AD-H, 5 µm, 250 mm×20 mm; injection volume: 0.08 ml; temperature: 25° C.; mobile phase: 90% isohexane/10% ethanol; flow rate: 15 ml/min; detection: 230 nm]. 1.25 g of diastereomer mixture gave initially, in slightly contaminated form, 298 mg of diastereomer 1 and 400 mg of diastereomer 2. Further purification by preparative RP-HPLC (mobile phase methanol/water) gave 200 mg of pure diastereomer 1 (Example 70) and 202 mg of pure diastereomer 2 (Example 71).

Example 70

(+)-1-(4-Chloro-3-{[(2S,3R)-2-(4-chlorophenyl)-4,4,4-trifluoro-3-methylbutanoyl]amino}benzyl)-2,2-difluorocyclopropanecarboxylic acid (diastereomer 1)

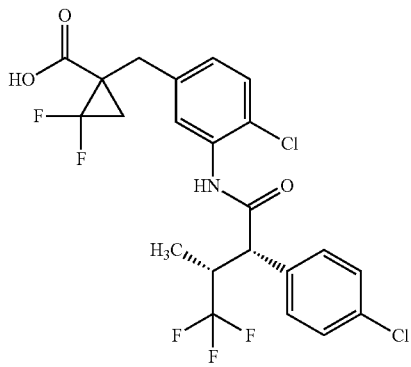 [SMILES: C[C@H]([C@H](C(=O)Nc1cc(CC2(C(=O)O)CC2(F)F)ccc1Cl)c1ccc(Cl)cc1)C(F)(F)F]

LC-MS (Method 5): $R_t$=1.20 min; m/z=510 (M+H)$^+$.

$^1$H-NMR (400 MHz, DMSO-d$_6$): δ [ppm]=0.80 (d, 3H), 1.76-1.95 (m, 1H), 1.99-2.21 (m, 1H), 2.70 (d, 1H), 3.34-3.41 (m, 1H), 4.12 (d, 1H), 7.01-7.11 (m, 1H), 7.30-7.56 (m, 6H), 9.86 (s, 1H), 13.28 (br. s, 1H).

[α]$_D^{20}$=+64.1°, c=0.48, chloroform.

Example 71

(+)-1-(4-Chloro-3-{[(2S,3R)-2-(4-chlorophenyl)-4,4,4-trifluoro-3-methylbutanoyl]amino}benzyl)-2,2-difluorocyclopropanecarboxylic acid (diastereomer 2)

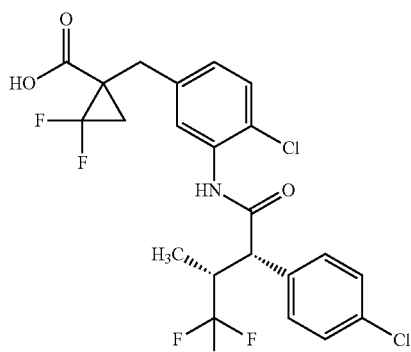

LC-MS (Method 5): $R_t$=1.20 min; m/z=510 (M+H)$^+$.

$^1$H-NMR (400 MHz, DMSO-d$_6$): δ [ppm]=0.80 (d, 3H), 1.79-1.95 (m, 1H), 2.11-2.22 (m, 1H), 2.70 (d, 1H), 3.34-3.40 (m, 1H, obscured), 4.11 (d, 1H), 7.07 (dd, 1H), 7.39 (d, 1H), 7.42-7.54 (m, 5H), 9.86 (s, 1H), 13.25 (br. s, 1H).

[α]$_D^{20}$=+32.3°, c=0.530, chloroform.

Examples 72-75

1-(4-Chloro-3-{[(4-chlorophenyl)(3,3-difluorocyclopentyl)acetyl]amino}benzyl)cyclopropane-carboxylic acid (isomers 1-4)

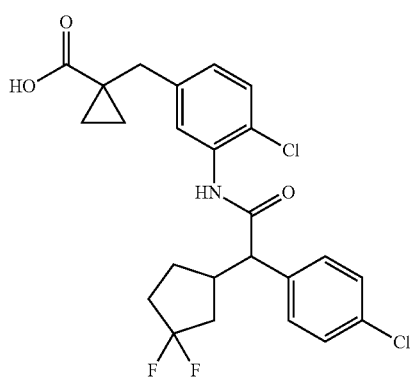 [SMILES: O=C(Nc1cc(CC2(C(=O)O)CC2)ccc1Cl)C(c1ccc(Cl)cc1)C1CCC(F)(F)C1]

340 mg (0.63 mmol) of the diastereomer mixture of 1-(4-chloro-3-{[(4-chlorophenyl)(3,3-di-fluorocyclopentyl) acetyl]amino}benzyl)cyclopropanecarboxylic acid (Example 35) were separated further by preparative HPLC on a chiral phase [column: Daicel Chiralpak AD-H, 5 µm, 250 mm×20 mm; mobile phase: isohexane/ethanol 80:20 (v/v); flow rate: 15 ml/min; UV detection: 220 nm; temperature: 35° C.]. This gave four different isomers:

Example 72

Isomer 1 yield: 56 mg $R_t$=7.31 min; chemical purity >99%; >99% ee; >99% de [column: Daicel Chiralpak AD-H, 5 µm, 250 mm×4.6 mm; mobile phase: isohexane/ethanol 80:20 (v/v); flow rate: 1 ml/min; UV detection: 220 nm; temperature: 30° C.].

LC-MS (Method 5): $R_t$=1.22 min; m/z=480/482 (M−H)⁻.
¹H-NMR (400 MHz, DMSO-$d_6$): δ [ppm]=0.75-0.83 (m, 2H), 1.06-1.13 (m, 2H), 1.52-1.71 (m, 2H), 1.79-1.96 (m, 1H), 1.97-2.31 (m, 3H), 2.76-2.93 (m, 1H), 2.82 (s, 2H), 3.77 (d, 1H), 7.09 (d, 1H), 7.36 (d, 1H), 7.38-7.49 (m, 5H), 9.77 (s, 1H), 11.95-12.30 (br. s, 1H).

Example 73

Isomer 2 yield: 48 mg
$R_t$=8.03 min; chemical purity >98.5%; >99% ee; >98% de [column: Daicel Chiralpak AD-H, 5 μm, 250 mm×4.6 mm; mobile phase: isohexane/ethanol 80:20 (v/v); flow rate: 1 ml/min; UV detection: 220 nm; temperature: 30° C.].
LC-MS (Method 5): $R_t$=1.23 min; m/z=480/482 (M−H)⁻.
¹H-NMR (400 MHz, DMSO-$d_6$): δ [ppm]=0.76-0.84 (m, 2H), 1.06-1.13 (m, 2H), 1.12-1.36 (m, 1H), 1.44-1.58 (m, 1H), 1.83-2.20 (m, 3H), 2.26-2.43 (m, 1H), 2.75-2.91 (m, 1H), 2.83 (s, 2H), 3.74 (d, 1H), 7.10 (d, 1H), 7.36 (d, 1H), 7.39-7.50 (m, 5H), 9.74 (s, 1H), 11.90-12.38 (br. s, 1H).

Example 74

Isomer 3 yield: 57 mg
$R_t$=9.94 min; chemical purity >99%; >99% ee; >99% de [column: Daicel Chiralpak AD-H, 5 μm, 250 mm×4.6 mm; mobile phase: isohexane/ethanol 80:20 (v/v); flow rate: 1 ml/min; UV detection: 220 nm; temperature: 30° C.].
LC-MS (Method 5): $R_t$=1.23 min; m/z=480/482 (M−H)⁻.
¹H-NMR: see Example 73.

Example 75

Isomer 4 yield: 68 mg
$R_t$=10.79 min; chemical purity >99%; >99% ee; >99% de [column: Daicel Chiralpak AD-H, 5 μm, 250 mm×4.6 mm; mobile phase: isohexane/ethanol 80:20 (v/v); flow rate: 1 ml/min; UV detection: 220 nm; temperature: 30° C.].
LC-MS (Method 5): $R_t$=1.22 min; m/z=480/482 (M−H)⁻.
¹H-NMR: see Example 72.

Examples 76-79

1-(3-{[(4-Chlorophenyl)(3,3-difluorocyclopentyl)acetyl]amino}-4-fluorobenzyl)cyclopropanecarboxylic acid (isomers 1-4)

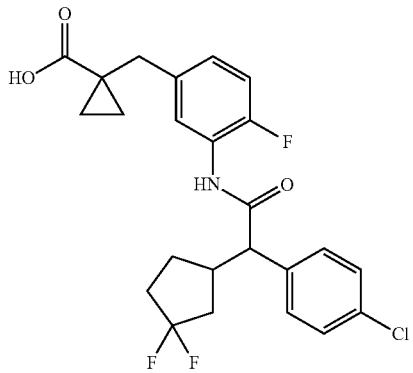 [SMILES: O=C(Nc1cc(CC2(C(=O)O)CC2)ccc1F)C(c1ccc(Cl)cc1)C1CCC(F)(F)C1]

1310 mg (2.81 mmol) of the diastereomer mixture of 1-(3-{[(4-chlorophenyl)(3,3-difluorocyclopentyl)acetyl]amino}-4-fluorobenzyl)cyclopropanecarboxylic acid (Example 34) were separated further by preparative HPLC on a chiral phase [column: Daicel Chiralpak AD-H, 5 μm, 250 mm×20 mm; mobile phase: isohexane/(isopropanol+0.2% trifluoroacetic acid+1% water) 75:25 (v/v); flow rate: 15 ml/min; UV detection: 220 nm; temperature: 30° C.]. Peak 1 and peak 2 were separated again on the same column using the mobile phase composition isohexane/(ethanol+0.2% trifluoroacetic acid+1% water) 75:25 (v/v) under otherwise identical conditions. This gave four different isomers:

Example 76

Isomer 1 yield: 245 mg
$R_t$=5.93 min; chemical purity >99%; >99% ee; >99% de [column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 40° C.].
$R_t$=6.39 min; chemical purity >99%; >99% ee; >99% de [column: Daicel Chiralpak AD-H, 5 μm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 40° C.].
LC-MS (Method 4): $R_t$=1.35 min; m/z=464/466 (M−H)⁻.
¹H-NMR (400 MHz, DMSO-$d_6$): δ [ppm]=0.75-0.83 (m, 2H), 1.05-1.13 (m, 2H), 1.50-1.68 (m, 2H), 1.79-1.94 (m, 1H), 1.95-2.04 (m, 1H), 2.06-2.30 (m, 2H), 2.76-2.92 (m, 1H), 2.81 (s, 2H), 3.77 (d, 1H), 6.99-7.06 (m, 1H), 7.07-7.16 (m, 1H), 7.38-7.47 (m, 4H), 7.61-7.67 (m, 1H), 9.94 (s, 1H), 11.70-12.50 (br. s, 1H).

Example 77

Isomer 2 yield: 210 mg
$R_t$=6.09 min; chemical purity >99%; >99% ee; >98.5% de [column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 40° C.].
$R_t$=6.93 min; chemical purity >99%; >99% ee; >98.5% de [column: Daicel Chiralpak AD-H, 5 μm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 40° C.].
LC-MS (Method 4): $R_t$=1.35 min; m/z=464/466 (M−H)⁻.
¹H-NMR (400 MHz, DMSO-$d_6$): δ [ppm]=0.75-0.83 (m, 2H), 1.05-1.13 (m, 2H), 1.20-1.35 (m, 1H), 1.43-1.56 (m, 1H), 1.79-2.20 (m, 3H), 2.23-2.39 (m, 1H), 2.75-2.89 (m, 1H), 2.81 (s, 2H), 3.74 (d, 1H), 7.00-7.06 (m, 1H), 7.07-7.15 (m, 1H), 7.38-7.48 (m, 4H), 7.59-7.66 (m, 1H), 9.89 (s, 1H), 11.44-12.68 (br. s, 1H).

Example 78 isomer 3 yield: 224 mg
$R_t$=6.65 min; chemical purity >99%; >98.7% ee; >99% de [column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 40° C.].

R$_t$=6.35 min; chemical purity >99%; >98.7% ee; >99% de [column: Daicel Chiralpak AD-H, 5 μm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 40° C.].

LC-MS (Method 4): R$_t$=1.35 min; m/z=464/466 (M−H)$^-$.
$^1$H-NMR: see Example 77.

Example 79

Isomer 4 yield: 276 mg
R$_t$=8.81 min; chemical purity >98.5%; >99% ee; >99% de [column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 40° C.].

R$_t$=7.20 min; chemical purity 99%; >98.7% ee; >99% de [column: Daicel Chiralpak AD-H, 5 μm, 250 mm×4.6 mm; mobile phase: isohexane/(ethanol+0.2% trifluoroacetic acid+1% water) 75:25 (v/v); flow rate: 1 ml/min; UV detection: 220 nm; temperature: 40° C.].

LC-MS (Method 4): R$_t$=1.35 min; m/z=464/466 (M−H)$^-$.
$^1$H-NMR: see Example 76.

Example 80 and Example 81

1-[3-({4,4,4-Trifluoro-3-methyl-2-[4-(trifluoromethyl)phenyl]butanoyl}amino)benzyl]cyclo-propanecarboxylic acid (isomers 1 and 2)

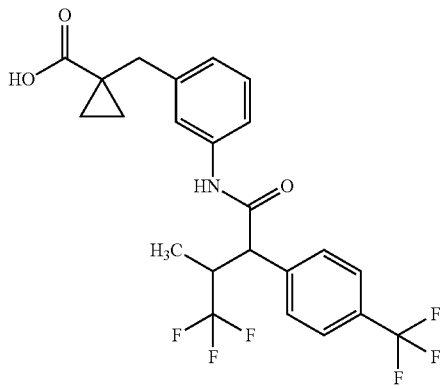

120 mg (0.25 mmol) of the diastereomer mixture of 1-[3-({4,4,4-trifluoro-3-methyl-2-[4-(trifluoromethyl)phenyl]butanoyl}amino)benzyl]cyclopropanecarboxylic acid (Example 36) were separated further by preparative HPLC on a chiral phase [column: Daicel Chiralcel OD-H, 5 μm, 250 mm×20 mm; mobile phase: isohexane/(isopropanol+0.2% trifluoroacetic acid+1% water) 88:12 (v/v); flow rate: 15 ml/min; UV detection: 220 nm; temperature: 30° C.]. This gave two different isomers:

Example 80

Isomer 1 yield: 40 mg
R$_t$=6.10 min; chemical purity >97%; >99% ee

[column: Daicel Chiralcel OD-H, 5 μm, 250 mm×4.6 mm; mobile phase: isohexane/(isopropanol+0.2% trifluoroacetic acid+1% water) 90:10 (v/v); flow rate: 1 ml/min; UV detection: 220 nm; temperature: 30° C.].

LC-MS (Method 5): R$_t$=1.21 min; m/z=474 (M+H)$^+$.

Example 81

Isomer 2 yield: 42 mg
R$_t$=6.95 min; chemical purity >99%; >98% ee [column: Daicel Chiralcel OD-H, 5 μm, 250 mm×4.6 mm; mobile phase: isohexane/(isopropanol+0.2% trifluoroacetic acid+1% water) 90:10 (v/v); flow rate: 1 ml/min; UV detection: 220 nm; temperature: 30° C.].

LC-MS (Method 5): R$_t$=1.21 min; m/z=474 (M+H)$^+$.

Example 82 and Example 83

1-[4-Chloro-3-({4,4,4-trifluoro-3-methyl-2-[4-(2,2,2-trifluoroethyl)phenyl]butanoyl}amino)-benzyl]cyclopropanecarboxylic acid (enantiomers 1 and 2)

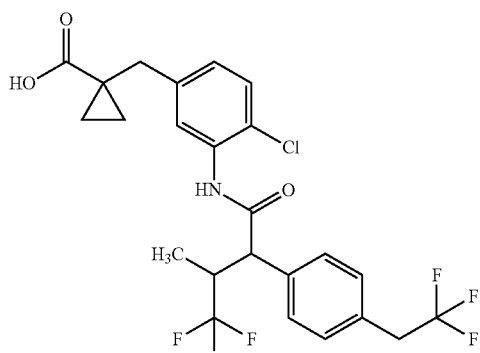

120 mg (0.23 mmol) of the racemic mixture of 1-[4-chloro-3-({4,4,4-trifluoro-3-methyl-2-[4-(2,2,2-trifluoroethyl)phenyl]butanoyl}amino)benzyl]cyclopropanecarboxylic acid (Example 46) were separated into the enantiomers by preparative HPLC on a chiral phase [column: Daicel Chiralpak AY-H, 5 μm, 250 mm×20 mm; mobile phase: isohexane/ethanol 85:15 (v/v); flow rate: 15 ml/min; UV detection: 220 nm; temperature: 45° C.]:

Example 82

Enantiomer 1 yield: 55 mg
R$_t$=4.23 min; chemical purity 97.5%; 99% ee [column: Daicel Chiralpak AY-H, 5 μm, 250 mm×4.6 mm; mobile phase: isohexane/(ethanol+0.2% trifluoroacetic acid+1% water) 85:15 (v/v); flow rate: 1 ml/min; UV detection: 220 nm; temperature: 45° C.].

LC-MS (Method 5): R$_t$=1.20 min; m/z=520/522 (M−H)$^-$.
$[\alpha]_D^{20}$=+85.3°, c=0.31, methanol.

Example 83

Enantiomer 2 yield: 56 mg
R$_t$=7.45 min; chemical purity 99%; 99% ee

Example 84 and Example 85

1-(3-{[2-(4-Chlorophenyl)-4,4,4-trifluoro-3-methylbutanoyl]amino}benzyl)cyclopropane-carboxylic acid (enantiomers 1 and 2)

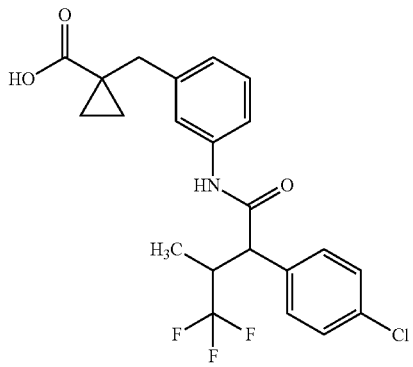 [SMILES: CC(C(C(=O)Nc1cccc(CC2(C(=O)O)CC2)c1)c1ccc(Cl)cc1)C(F)(F)F]

400 mg (0.91 mmol) of the racemic mixture of 1-(3-{[2-(4-chlorophenyl)-4,4,4-trifluoro-3-methyl-butanoyl]amino}benzyl)cyclopropanecarboxylic acid (Example 45) were separated into the enantiomers by preparative HPLC on a chiral phase [column: Daicel Chiralpak AD-H, 5 μm, 250 mm×20 mm; mobile phase: isohexane/(ethanol+0.2% trifluoroacetic acid+1% water) 90:10 (v/v); flow rate: 15 ml/min; UV detection: 220 nm; temperature: 30° C.]:

Example 84

Enantiomer 1 yield: 247 mg (still comprising residual solvent)
$R_t$=7.42 min; >99% ee
[column: Daicel Chiralpak AD-H, 5 μm, 250 mm×4.6 mm; mobile phase: isohexane/(ethanol+0.2% trifluoroacetic acid+1% water) 90:10 (v/v); flow rate: 1 ml/min; UV detection: 220 nm; temperature: 25° C.].
LC-MS (Method 5): $R_t$=1.20 min; m/z=438/440 (M–H)⁻.
$[\alpha]_D^{20}$=+60.8°, c=0.35, methanol.

Example 85

Enantiomer 2 yield: 288 mg (still comprising residual solvent)
$R_t$=9.18 min; >99% ee
[column: Daicel Chiralpak AD-H, 5 μm, 250 mm×4.6 mm; mobile phase: isohexane/(ethanol+0.2% trifluoroacetic acid+1% water) 90:10 (v/v); flow rate: 1 ml/min; UV detection: 220 nm; temperature: 25° C.].
LC-MS (Method 5): $R_t$=1.20 min; m/z=438/440 (M–H)⁻.
$[\alpha]_D^{20}$=−58.1°, c=0.37, methanol.

Example 86 and Example 87

1-(3-{[4,4,4-Trifluoro-3-methyl-2-(4-methylphenyl)butanoyl]amino}benzyl)cyclopropanecarboxylic acid (enantiomers 1 and 2)

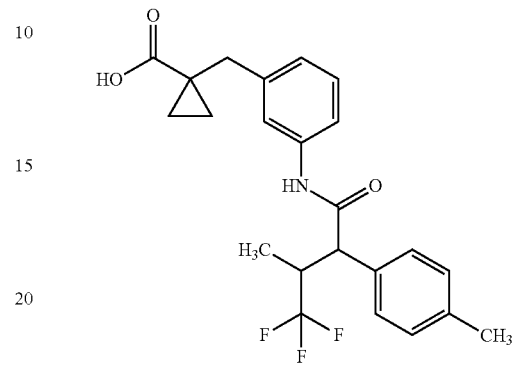

339 mg (0.81 mmol) of the racemic mixture of 1-(3-{[4,4,4-trifluoro-3-methyl-2-(4-methyl-phenyl)butanoyl]amino}benzyl)cyclopropanecarboxylic acid (Example 47) were separated into the enantiomers by preparative HPLC on a chiral phase [column: Daicel Chiralpak AD-H, 5 μm, 250 mm×20 mm; mobile phase: isohexane/(isopropanol+0.2% trifluoroacetic acid+1% water) 75:25 (v/v); flow rate: 15 ml/min; UV detection: 220 nm; temperature: 40° C.]:

Example 86

Enantiomer 1 yield: 192 mg (still comprising residual solvent)
$R_t$=4.40 min; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].
LC-MS (Method 5): $R_t$=1.16 min; m/z=418 (M–H)⁻.
¹H-NMR (400 MHz, DMSO-$d_6$): δ [ppm]=0.67-0.89 (m, 5H), 1.03-1.17 (m, 2H), 2.27 (s, 3H), 2.82 (s, 2H), 3.25-3.44 (m, 1H), 3.77 (d, 1H), 6.91 (d, 1H), 7.16 (d, 3H), 7.30 (d, 2H), 7.37 (s, 1H), 7.43 (d, 1H), 10.12 (s, 1H), 11.00-12.95 (br. s, 1H).

Example 87

Enantiomer 2 yield: 168 mg (still comprising residual solvent)
$R_t$=5.10 min; >99% ee
[column: Daicel Chiralpak AD-H, 5 μm, 250 mm×4.6 mm; mobile phase: isohexane/(isopropanol+0.2% trifluoroacetic acid+1% water) 75:25 (v/v); flow rate: 1 ml/min; UV detection: 220 nm; temperature: 25° C.].
LC-MS (Method 5): $R_t$=1.16 min; m/z=418 (M–H)⁻.
¹H-NMR: see Example 86.

---

[column: Daicel Chiralpak AY-H, 5 μm, 250 mm×4.6 mm; mobile phase: isohexane/(ethanol+0.2% trifluoroacetic acid+1% water) 85:15 (v/v); flow rate: 1 ml/min; UV detection: 220 nm; temperature: 45° C.].
LC-MS (Method 5): $R_t$=1.20 min; m/z=520/522 (M–H)⁻.
$[\alpha]_D^{20}$=−78°, c=0.255, methanol.

Example 88

1-[(4-Chloro-3-{[(2S,3R)-2-(4-chlorophenyl)-4,4,4-trifluoro-3-methylbutanoyl]amino}phenyl)-(methoxy)methyl]cyclopropanecarboxylic acid (diastereomer mixture)

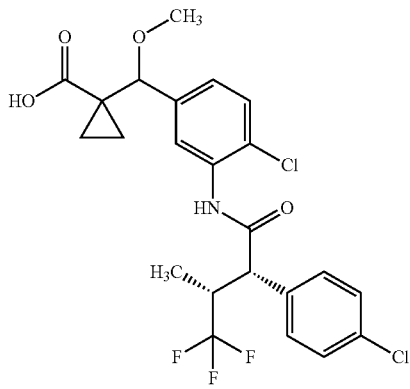 [SMILES: COC(c1ccc(Cl)c(NC(=O)[C@H](c2ccc(Cl)cc2)[C@@H](C)C(F)(F)F)c1)C1(C(=O)O)CC1]

151 mg (0.269 mmol) of tert-butyl 1-[(4-chloro-3-{[(2S, 3R)-2-(4-chlorophenyl)-4,4,4-trifluoro-3-methylbutanoyl]amino}phenyl)(methoxy)methyl]cyclopropanecarboxylate (as diastereomer mixture) were dissolved in 2.9 ml of dichloromethane, and 1.0 ml of TFA was added at RT. After 30 min at RT, the reaction mixture was concentrated under reduced pressure and the residue was concentrated under reduced pressure. The crude product obtained in this manner was purified by RP-HPLC (mobile phase acetonitrile/water). This gave 87 mg (64% of theory) of the target compound.

LC-MS (Method 4): $R_t$=1.44 min; m/z=521 (M+NH$_4$)$^+$.

$^1$H-NMR (400 MHz, DMSO-d$_6$): both diastereomers: δ [ppm]=0.37-0.45 (m, 1H), 0.80 (d, 3H), 0.82-1.05 (m, 3H), 3.13/3.14 (each s, together 3H), 4.13 (d, 1H), 4.87 (s, 1H), 6.98-7.16 (m, 1H), 7.36-7.55 (m, 6H), 9.91 (s, 1H).

Example 89 and Example 90

(+)-1-[(4-Chloro-3-{[(2S,3R)-2-(4-chlorophenyl)-4,4,4-trifluoro-3-methylbutanoyl]amino}phenyl)-(methoxy)methyl]cyclopropanecarboxylic acid (diastereomers 1 and 2)

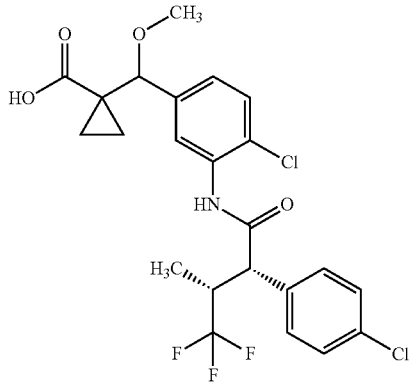 [SMILES: COC(c1ccc(Cl)c(NC(=O)[C@H](c2ccc(Cl)cc2)[C@@H](C)C(F)(F)F)c1)C1(C(=O)O)CC1]

The diastereomer mixture, obtained above, of 1-[(4-chloro-3-{[(2S,3R)-2-(4-chlorophenyl)-4,4,4-trifluoro-3-methylbutanoyl]amino}phenyl)(methoxy)methyl]cyclopropanecarboxylic acid (Example 88) was separated further by preparative HPLC on a chiral phase [column: Daicel Chiralpak AD-H, 5 μm, 250 mm×20 mm; injection volume: 0.40 ml; temperature: 25° C.; mobile phase: 90% isohexane/10% isopropanol; flow rate: 15 ml/min; detection: 220 nm]. 63 mg of diastereomer mixture gave 26 mg of diastereomer 1 (Example 89) and 34 mg of diastereomer 2 (Example 90).

Example 89

Diastereomer 1

LC-MS (Method 5): $R_t$=1.22 min; m/z=502 (M−H)$^-$.

$^1$H-NMR (400 MHz, DMSO-d$_6$): δ [ppm]=0.35-0.50 (m, 1H), 0.80 (d, 3H), 0.83-1.05 (m, 3H), 3.13 (s, 3H), 4.13 (d, 1H), 4.86 (s, 1H), 7.10 (dd, 1H), 7.38-7.54 (m, 6H), 9.91 (s, 1H), 12.33 (br. s, 1H).

$[\alpha]_D^{20}$=+28°, c=0.255, chloroform.

Example 90

Diastereomer 2

LC-MS (Method 5): $R_t$=1.22 min; m/z=502 (M−H)$^-$.

$^1$H-NMR (400 MHz, DMSO-d$_6$): δ [ppm]=0.36-0.52 (m, 1H), 0.80 (d, 3H), 0.82-1.04 (m, 3H), 3.14 (s, 3H), 4.13 (d, 1H), 4.86 (s, 1H), 7.09 (dd, 1H), 7.41 (d, 1H), 7.44-7.52 (m, 5H), 9.91 (s, 1H), 12.35 (br. s, 1H).

$[\alpha]_D^{20}$=+66°, c=0.240, chloroform.

Example 91

1-{(4-Chloro-3-{[(2S,3R)-2-(4-chlorophenyl)-4,4,4-trifluoro-3-methylbutanoyl]amino}phenyl)-(trideuteromethoxy)methyl}cyclopropanecarboxylic acid (diastereomer mixture)

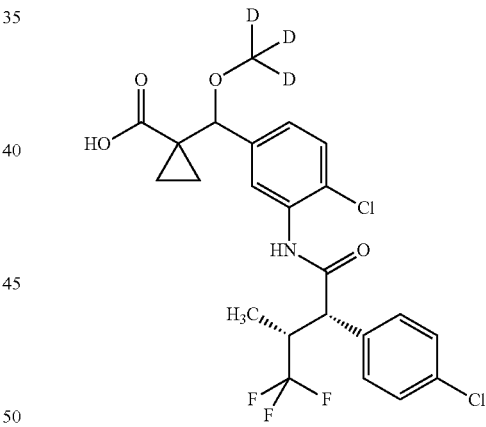

885 mg (1.57 mmol) of tert-butyl 1-{(4-chloro-3-{[(2S, 3R)-2-(4-chlorophenyl)-4,4,4-trifluoro-3-methylbutanoyl]amino}phenyl)(trideuteromethoxy)methyl}cyclopropanecarboxylate (as diastereomer mixture) were dissolved in 2 ml of dichloromethane, and 2.4 ml of TFA were added at RT. The reaction mixture was stirred at RT for 2 h and then concentrated under reduced pressure, and the residue was dried under high vacuum. The crude product obtained in this manner was purified by RP-HPLC (mobile phase methanol/water). This gave 456 mg (57% of theory) of the target compound.

LC-MS (Method 5): $R_t$=1.22 min; m/z=505/507 (M−H)$^-$.

$^1$H-NMR (400 MHz, DMSO-d$_6$): δ [ppm]=0.41-0.49 (m, 1H), 0.80 (d, 3H), 0.83-1.04 (m, 3H), 3.29-3.45 (m, 1H, partially obscured by H$_2$O signal), 4.13 (d, 1H), 4.86 (s, 1H), 7.07-7.12 (m, 1H), 7.39-7.51 (m, 6H), 9.91 (s, 1H), 12.21-12.51 (br. s, 1H).

The examples below were prepared in accordance with General Procedure 8:

| Example | Name/Structure/Starting material | Analytical data |
|---|---|---|
| 92 | 1-[(4-chloro-3-{[(2S,3R)-2-(4-chlorophenyl)-4,4,4-trifluoro-3-methylbutanoyl]amino}phenyl)-(ethoxy)methyl]cyclopropanecarboxylic acid (diastereomer mixture)<br>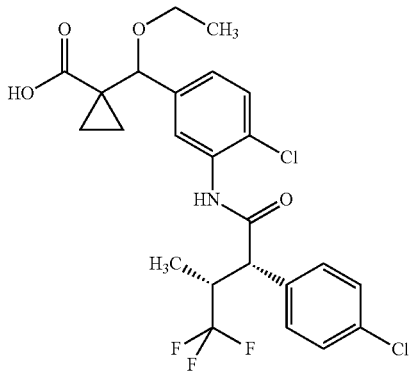 [SMILES: CCOC(c1ccc(Cl)c(NC(=O)[C@H](c2ccc(Cl)cc2)[C@@H](C)C(F)(F)F)c1)C1(C(=O)O)CC1]<br>from tert-butyl 1-[(4-chloro-3-{[(2S,3R)-2-(4-chlorophenyl)-4,4,4-trifluoro-3-methylbutanoyl]-amino}phenyl)(ethoxy)methyl]cyclopropane-carboxylate | LC-MS (Method 7): $R_t$ = 1.29 min; m/z = 516/518 (M − H)$^-$.<br>$^1$H-NMR (400 MHz, DMSO-$d_6$): δ [ppm] = 0.39-0.49 (m, 1H), 0.80 (d, 3H), 0.83-0.96 (m, 2H), 0.97-1.08 (m, 4H), 3.21-3.46 (m, 3H, partially obscured by H$_2$O signal), 4.13 (d, 1H), 4.97 (d, 1H), 7.07-7.13 (m, 1H), 7.40 (d, 1H), 7.43-7.51 (m, 5H), 9.90 (d, 1H), 12.22-12.42 (br. s, 1H). |
| 93 | 1-[(4-chloro-3-{[(2S,3R)-2-(4-chlorophenyl)-4,4,4-trifluoro-3-methylbutanoyl]amino}phenyl)-(hydroxy)methyl]cyclopropanecarboxylic acid (diastereomer mixture)<br>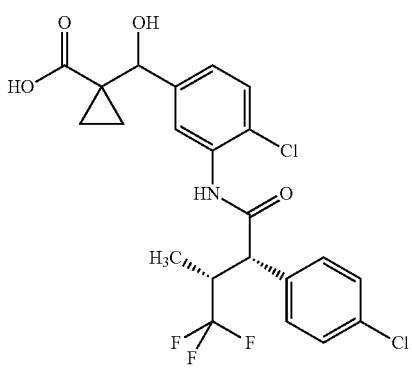 [SMILES: C[C@H]([C@H](C(=O)Nc1cc(C(O)C2(C(=O)O)CC2)ccc1Cl)c1ccc(Cl)cc1)C(F)(F)F]<br>from tert-butyl 1-[(4-chloro-3-{[(2S,3R)-2-(4-chlorophenyl)-4,4,4-trifluoro-3-methylbutanoyl]-amino}phenyl)(hydroxy)methyl]cyclopropane-carboxylate<br>or as byproduct of the ester cleavage of tert-butyl 1-[(4-chloro-3-{[(2S,3R)-2-(4-chlorophenyl)-4,4,4-trifluoro-3-methylbutanoyl]amino}phenyl)-(ethoxy)methyl]cyclopropanecarboxylate | LC-MS (Method 7): $R_t$ = 1.11 min; m/z = 488/490 (M − H)$^-$.<br>$^1$H-NMR (400 MHz, DMSO-$d_6$): δ [ppm] = 0.65-0.75 (m, 1H), 0.80 (d, 3H), 0.88-0.96 (m, 1H), 0.96-1.06 (m, 2H), 3.28-3.45 (m, 1H, partially obscured by H$_2$O signal), 4.11 (d, 1H), 5.06 (s, 1H), 5.42 (d, 1H), 7.15 (dd, 1H), 7.36 (dd, 1H), 7.43-7.50 (m, 4H), 7.53 (dd, 1H), 9.85 (s, 1H), 12.18 (s, 1H). |

| Example | Name/Structure/Starting material | Analytical data |
|---|---|---|
| 94 | 1-{(4-chloro-3-{[(2S,3R)-2-(4-chlorophenyl)-4,4,4-trifluoro-3-methylbutanoyl]amino}phenyl)-(trideuteromethoxy)methyl}cyclobutanecarboxylic acid (diastereomer mixture)<br><br>from tert-butyl 1-{(4-chloro-3-{[(2S,3R)-2-(4-chlorophenyl)-4,4,4-trifluoro-3-methylbutanoyl]-amino}phenyl)(trideuteromethoxy)methyl}-cyclobutanecarboxylate | LC-MS (Method 5): $R_t$ = 1.26 min; m/z = 519/521 (M − H)$^-$.<br>$^1$H-NMR (400 MHz, DMSO-$d_6$): δ [ppm] = 0.80 (d, 3H), 1.28-1.41 (m, 1H), 1.57-1.71 (m, 1H), 1.98-2.30 (m, 4H), 3.26-3.45 (m, 1H, partially obscured by H$_2$O signal), 4.15 (d, 1H), 4.38 (d, 1H), 7.08 (dd, 1H), 7.41-7.51 (m, 5H), 7.54 (d, 1H), 9.90 (s, 1H), 12.33 (br. s, 1H). |
| 95 | 1-[(4-chloro-3-{[(2S,3R)-2-(4-chlorophenyl)-4,4,4-trifluoro-3-methylbutanoyl]amino}phenyl)-(methoxy)methyl]cyclobutanecarboxylic acid (diastereomer mixture)<br><br>from tert-butyl 1-[(4-chloro-3-{[(2S,3R)-2-(4-chlorophenyl)-4,4,4-trifluoro-3-methylbutanoyl]-amino}phenyl)(methoxy)methyl]cyclobutane-carboxylate | LC-MS (Method 5): $R_t$ = 1.23 min; m/z = 516/518 (M − H)$^-$.<br>$^1$H-NMR (400 MHz, DMSO-$d_6$): δ [ppm] = 0.80 (d, 3H), 1.28-1.41 (m, 1H), 1.57-1.71 (m, 1H), 1.97-2.30 (m, 4H), 3.13 (s, 3H), 3.26-3.45 (m, 1H, partially obscured by H$_2$O signal), 4.15 (d, 1H), 4.38 (d, 1H), 7.08 (dd, 1H), 7.40-7.51 (m, 5H), 7.54 (d, 1H), 9.90 (s, 1H), 12.12-12.53 (br. s, 1H). |

| Example | Name/Structure/Starting material | Analytical data |
|---|---|---|
| 96 | 1-[(4-chloro-3-{[(2S,3R)-2-(4-chlorophenyl)-4,4,4-trifluoro-3-methylbutanoyl]amino}phenyl)-(ethoxy)methyl]cyclobutanecarboxylic acid (diastereomer mixture)<br>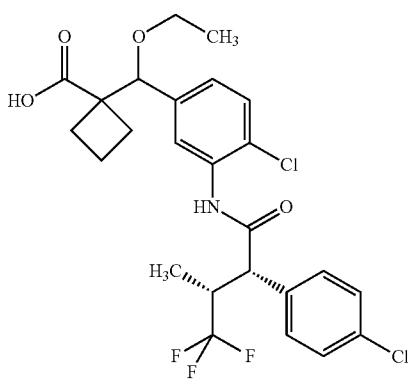 [SMILES: CCOC(c1ccc(Cl)c(NC(=O)[C@H](c2ccc(Cl)cc2)[C@@H](C)C(F)(F)F)c1)C1(C(=O)O)CCC1]<br>from tert-butyl 1-[(4-chloro-3-{[(2S,3R)-2-(4-chlorophenyl)-4,4,4-trifluoro-3-methylbutanoyl]-amino}phenyl)(ethoxy)methyl]cyclobutane-carboxylate | LC-MS (Method 5): $R_t$ = 1.32 min; m/z = 530/532 (M − H)⁻. $^1$H-NMR (400 MHz, DMSO-$d_6$): δ [ppm] = 0.80 (d, 3H), 1.03-1.10 (m, 3H), 1.27-1.41 (m, 1H), 1.56-1.70 (m, 1H), 1.97-2.29 (m, 4H), 3.23-3.46 (m, 3H, partially obscured by H₂O signal), 4.14 (d, 1H), 4.49 (d, 1H), 7.09 (dd, 1H), 7.39-7.51 (m, 5H), 7.56 (dd, 1H), 9.89 (s, 1H), 12.27-12.39 (br. s, 1H). |
| 97 | 1-(3-{[(2S,3R)-2-(4-chlorophenyl)-4,4,4-trifluoro-3-methylbutanoyl]amino}-4-cyclopropyl-benzyl)cyclopropanecarboxylic acid<br>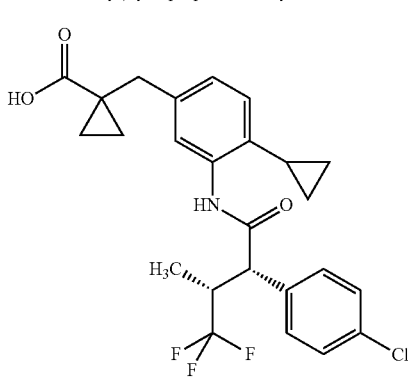<br>from tert-butyl 1-(3-{[(2S,3R)-2-(4-chlorophenyl)-4,4,4-trifluoro-3-methylbutanoyl]amino}-4-cyclopropylbenzyl)cyclopropanecarboxylate | LC-MS (Method 5): $R_t$ = 1.20 min; m/z = 478/480 (M − H)⁻. $^1$H-NMR (400 MHz, DMSO-$d_6$): δ [ppm] = 0.28-0.35 (m, 1H), 0.39-0.47 (m, 1H), 0.54-0.68 (m, 2H), 0.70-0.78 (m, 2H), 0.81 (d, 3H), 1.02-1.11 (m, 2H), 1.60-1.70 (m, 1H), 2.79 (s, 2H), 3.28-3.45 (m, 1H, partially obscured by H₂O signal), 4.01 (d, 1H), 6.80 (d, 1H), 6.96 (dd, 1H), 7.12 (d, 1H), 7.39-7.52 (m, 4H), 9.67 (s, 1H), 12.10 (br. s, 1H). |

Example 98

1-[1-(4-Chloro-3-{[(2S,3R)-2-(4-chlorophenyl)-4,4,4-trifluoro-3-methylbutanoyl]amino}phenyl)-propyl]cyclopropanecarboxylic acid (diastereomer mixture)

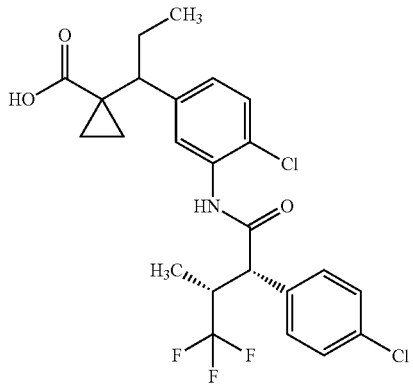 [SMILES: CCC(c1ccc(Cl)c(NC(=O)[C@H](c2ccc(Cl)cc2)[C@@H](C)C(F)(F)F)c1)C1(C(=O)O)CC1]

79 mg (0.15 mmol) of methyl 1-[1-(4-chloro-3-{[(2S,3R)-2-(4-chlorophenyl)-4,4,4-trifluoro-3-methylbutanoyl]amino}phenyl)propyl]cyclopropanecarboxylate (as diastereomer mixture) were dissolved in 3 ml of acetic acid, 1.5 ml of concentrated hydrochloric acid were added, and the mixture was heated to 100° C. and stirred at this temperature for 12 h. The reaction mixture was then cooled to room temperature, diluted with water and extracted three times with dichloromethane. The combined organic phases were dried over magnesium sulphate and concentrated under reduced pressure. The residue obtained was purified by preparative RP-HPLC (mobile phase methanol/water 7:3). This gave 36 mg of the target compound (43% of theory).

LC-MS (Method 7): $R_t$=1.33 min; m/z=500/502 (M−H)⁻.

$^1$H-NMR (400 MHz, DMSO-$d_6$): both diastereomers: δ [ppm]=0.47-0.58 (m, 1H), 0.68-0.77 (m, 4H), 0.80 (d, 3H), 0.93-1.06 (m, 2H), 1.65-1.89 (m, 2H), 2.65-2.76 (m, 1H), 3.27-3.45 (m, 1H, partially obscured by H$_2$O signal), 4.12 (d, 1H), 7.10 (d, 1H), 7.34 (d, 1H), 7.39-7.50 (m, 5H), 9.84 (s, 1H), 12.00-12.23 (br. s, 1H).

Example 99 and Example 100

(+)-1-{(4-Chloro-3-{[(2S,3R)-2-(4-chlorophenyl)-4,4,4-trifluoro-3-methylbutanoyl]amino}-phenyl)(trideuteromethoxy)methyl}cyclopropanecarboxylic acid (diastereomers 1 and 2)

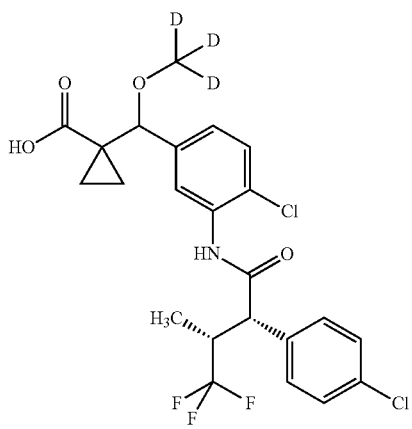 [SMILES: [2H]C([2H])([2H])OC(c1ccc(Cl)c(NC(=O)[C@H](c2ccc(Cl)cc2)[C@@H](C)C(F)(F)F)c1)C1(C(=O)O)CC1]

430 mg (0.76 mmol) of the diastereomer mixture of 1-{(4-chloro-3-{[(2S,3R)-2-(4-chlorophenyl)-4,4,4-trifluoro-3-methylbutanoyl]amino}phenyl)(trideuteromethoxy)methyl}cyclopropanecarboxylic acid (Example 91) were separated further by preparative HPLC on a chiral phase [column: Daicel Chiralpak AD-H, 5 μm, 250 mm×20 mm; mobile phase: isohexane/isopropanol 90:10 (v/v); flow rate: 20 ml/min; UV detection: 230 nm; temperature: 25° C.]:

Example 99

Diastereomer 1 yield: 180 mg $R_t$=6.51 min; chemical purity >99%; >99% de

[column: Daicel Chiralpak AD-H, 5 μm, 250 mm×4 mm; mobile phase: isohexane/(isopropanol+0.2% trifluoroacetic acid) 90:10 (v/v); flow rate: 1 ml/min; UV detection: 220 nm; temperature: 25° C.].

LC-MS (Method 5): $R_t$=1.18 min; m/z=505/507 (M−H)⁻.

$^1$H-NMR (400 MHz, DMSO-$d_6$): δ [ppm]=0.42-0.49 (m, 1H), 0.80 (d, 3H), 0.83-0.90 (m, 1H), 0.90-0.97 (m, 1H), 0.97-1.04 (m, 1H), 3.30-3.47 (m, 1H, partially obscured by H$_2$O signal), 4.13 (d, 1H), 4.85 (s, 1H), 7.10 (dd, 1H), 7.42 (d, 1H), 7.43-7.51 (m, 5H), 9.91 (s, 1H), 12.22-12.44 (br. s, 1H).

$[α]_D^{20}$=+54.0°, c=0.51, chloroform.

Example 100

Diastereomer 2 yield: 215 mg $R_t$=7.68 min; chemical purity >99%; >99% de

[column: Daicel Chiralpak AD-H, 5 μm, 250 mm×4 mm; mobile phase: isohexane/(isopropanol+0.2% trifluoroacetic acid) 90:10 (v/v); flow rate: 1 ml/min; UV detection: 220 nm; temperature: 25° C.].

LC-MS (Method 5): $R_t$=1.18 min; m/z=505/507 (M−H)⁻.

$^1$H-NMR (400 MHz, DMSO-$d_6$): δ [ppm]=0.41-0.48 (m, 1H), 0.80 (d, 3H), 0.83-0.96 (m, 1H), 0.97-1.06 (m, 1H), 3.29-3.49 (m, 1H, partially obscured by H$_2$O signal), 4.14 (d, 1H), 4.86 (s, 1H), 7.09 (dd, 1H), 7.41 (d, 1H), 7.43-7.52 (m, 5H), 9.91 (s, 1H), 12.08-12.54 (br. s, 1H).

$[α]_D^{20}$=+96.4°, c=0.47, chloroform.

Example 101 and Example 102

1-[(4-Chloro-3-{[(2S,3R)-2-(4-chlorophenyl)-4,4,4-trifluoro-3-methylbutanoyl]amino}phenyl)-(ethoxy)methyl]cyclopropanecarboxylic acid (diastereomers 1 and 2)

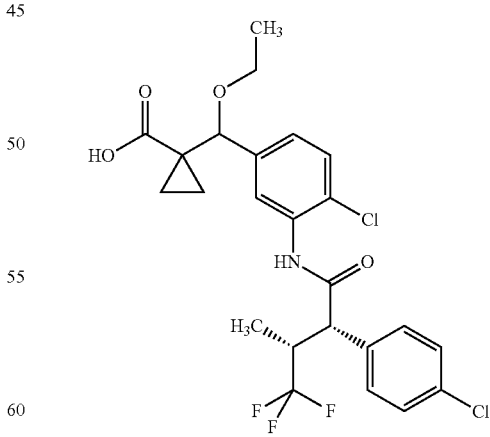

130 mg (0.25 mmol) of the diastereomer mixture of 1-[(4-chloro-3-{[(2S,3R)-2-(4-chlorophenyl)-4,4,4-trifluoro-3-methylbutanoyl]amino}phenyl)(ethoxy)methyl]cyclopropanecarboxylic acid (Example 92) were separated further by preparative HPLC on a chiral phase [column: Daicel Chiralpak AD-H, 5 μm, 250 mm×20 mm; mobile phase: isohexane/ isopropanol 93:7 (v/v); flow rate: 20 ml/min; UV detection: 230 nm; temperature: 25° C.]:

Example 101

Diastereomer 1 yield: 56 mg (still comprising residual solvent)
$R_t$=5.79 min; >99% de
[column: Daicel Chiralpak AD-H, 5 μm, 250 mm×4 mm; mobile phase: isohexane/(isopropanol+0.2% trifluoroacetic acid) 90:10 (v/v); flow rate: 1 ml/min; UV detection: 220 nm; temperature: 25° C.].
LC-MS (Method 5): $R_t$=1.27 min; m/z=516/518 (M−H)⁻.
¹H-NMR (400 MHz, DMSO-$d_6$): δ [ppm]=0.41-0.50 (m, 1H), 0.80 (d, 3H), 0.83-0.89 (m, 1H), 0.89-0.96 (m, 1H), 0.97-1.07 (m, 1H), 1.04 (t, 3H), 3.21-3.46 (m, 3H, partially obscured by $H_2O$ signal), 4.13 (d, 1H), 4.96 (s, 1H), 7.10 (dd, 1H), 7.40 (d, 1H), 7.43-7.51 (m, 5H), 9.89 (s, 1H), 12.29 (br. s, 1H).
$[α]_D^{20}$=+54.0°, c=0.42, chloroform.

Example 102

Diastereomer 2 yield: 77 mg (still comprising residual solvent)
$R_t$=6.17 min; >96% de
[column: Daicel Chiralpak AD-H, 5 μm, 250 mm×4 mm; mobile phase: isohexane/(isopropanol+0.2% trifluoroacetic acid) 90:10 (v/v); flow rate: 1 ml/min; UV detection: 220 nm; temperature: 25° C.].
LC-MS (Method 5): $R_t$=1.27 min; m/z=516/518 (M−H)⁻.
¹H-NMR (400 MHz, DMSO-$d_6$): δ [ppm]=0.40-0.47 (m, 1H), 0.80 (d, 3H), 0.83-0.95 (m, 2H), 0.97-1.10 (m, 1H), 1.05 (t, 3H), 3.21-3.46 (m, 3H, partially obscured by $H_2O$ signal), 4.13 (d, 1H), 4.97 (s, 1H), 7.09 (dd, 1H), 7.40 (d, 1H), 7.44-7.51 (m, 5H), 9.90 (s, 1H), 12.17-12.40 (br. s, 1H).
$[α]_D^{20}$=+93.6°, c=0.405, chloroform.

Example 103 and Example 104

1-[(4-Chloro-3-{[(2S,3R)-2-(4-chlorophenyl)-4,4,4-trifluoro-3-methylbutanoyl]amino}phenyl)-(hydroxy)methyl]cyclopropanecarboxylic acid (diastereomers 1 and 2)

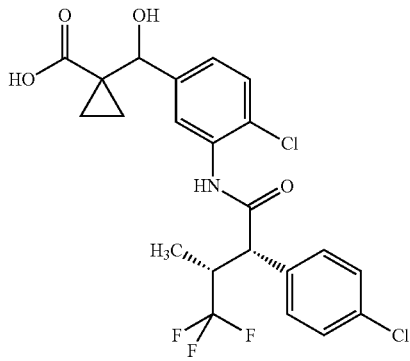 [SMILES: C[C@H]([C@H](C(=O)Nc1cc(C(O)C2(C(=O)O)CC2)ccc1Cl)c1ccc(Cl)cc1)C(F)(F)F]

850 mg (1.73 mmol) of the diastereomer mixture of 1-[(4-chloro-3-{[(2S,3R)-2-(4-chlorophenyl)-4,4,4-trifluoro-3-methylbutanoyl]amino}phenyl)(hydroxy)methyl]cyclopropanecarboxylic acid (Example 93) were separated further by supercritical fluid chromatography (SFC) on a chiral phase
[column: Daicel Chiralpak AD-H, 5 μm, 250 mm×20 mm; mobile phase: carbon monoxide/methanol 70:30 (v/v); flow rate: 100 ml/min; pressure: 120 bar; temperature: 40° C.; UV detection: 210 nm]:

Example 103

Diastereomer 1 yield: 271 mg
$R_t$=11.44 min; chemical purity >95%; >99% de
[column: Daicel Chiralpak AD-H, 5 μm, 250 mm×4.6 mm; mobile phase: isohexane/(methanol+0.2% trifluoroacetic acid) 90:10 (v/v); flow rate: 1.5 ml/min; UV detection: 210 nm; temperature: 30° C.].
LC-MS (Method 4): $R_t$=1.32 min; m/z=488/490 (M−H)⁻.
¹H-NMR (400 MHz, DMSO-$d_6$): δ [ppm]=0.65-0.74 (m, 1H), 0.80 (d, 3H), 0.87-0.94 (m, 1H), 0.96-1.05 (m, 2H), 3.27-3.45 (m, 1H, partially obscured by $H_2O$ signal), 4.11 (d, 1H), 5.06 (s, 1H), 5.76 (s, about 1H), 7.15 (dd, 1H), 7.36 (d, 1H), 7.41-7.50 (m, 4H), 7.52 (d, 1H), 9.85 (s, 1H), 11.75-12.64 (br. s, about 1H).
$[α]_D^{20}$=+96.1°, c=0.47, chloroform.

Example 104

Diastereomer 2 yield: 290 mg
$R_t$=15.24 min; chemical purity >96%; >99% de
[column: Daicel Chiralpak AD-H, 5 μm, 250 mm×4.6 mm; mobile phase: isohexane/(methanol+0.2% trifluoroacetic acid) 90:10 (v/v); flow rate: 1.5 ml/min; UV detection: 210 nm; temperature: 30° C.].
LC-MS (Method 4): $R_t$=1.32 min; m/z=488/490 (M−H)⁻.
¹H-NMR (400 MHz, DMSO-$d_6$): δ [ppm]=0.64-0.73 (m, 1H), 0.80 (d, 3H), 0.88-0.96 (m, 1H), 0.96-1.05 (m, 2H), 3.26-3.44 (m, 1H, partially obscured by $H_2O$ signal), 4.11 (d, 1H), 5.05 (s, 1H), 5.76 (s, about 1H), 7.15 (dd, 1H), 7.36 (d, 1H), 7.42-7.50 (m, 4H), 7.54 (d, 1H), 9.85 (s, 1H), 11.52-12.80 (br. s, about 1H).
$[α]_D^{20}$=+57.3°, c=0.465, chloroform.

Example 105 and Example 106

1-{(4-Chloro-3-{[(2S,3R)-2-(4-chlorophenyl)-4,4,4-trifluoro-3-methylbutanoyl]amino}phenyl)-(trideuteromethoxy)methyl}cyclobutanecarboxylic acid (diastereomers 1 and 2)

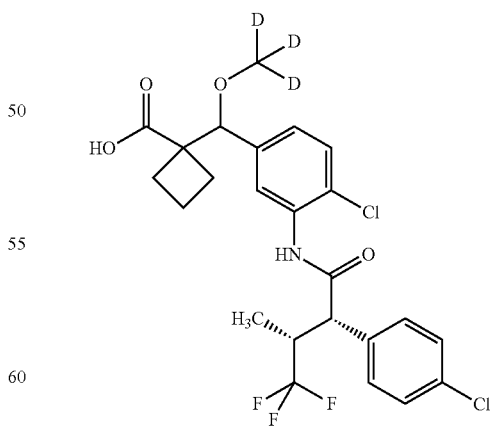

260 mg (0.50 mmol) of the diastereomer mixture of 1-{(4-chloro-3-{[(2S,3R)-2-(4-chlorophenyl)-4,4,4-trifluoro-3-methylbutanoyl]amino}phenyl)(trideuteromethoxy)methyl}cyclobutanecarboxylic acid (Example 94) were separated further by preparative HPLC on a chiral phase [column: Daicel Chiralpak AD-H, 5 μm, 250 mm×20 mm; mobile phase: isohexane/isopropanol 92:8 (v/v); flow rate: 11 ml/min; UV detection: 220 nm; temperature: 23° C.]:

Example 105

Diastereomer 1 yield: 127 mg $R_t$=8.28 min; chemical purity >99%; >99% de

[column: Daicel Chiralpak AD-H, 5 μm, 250 mm×4.6 mm; mobile phase: isohexane/(isopropanol+0.2% trifluoroacetic acid+1% water) 90:10 (v/v); flow rate: 0.8 ml/min; UV detection: 220 nm; temperature: 25° C.].

LC-MS (Method 7): $R_t$=1.29 min; m/z=519/521 (M−H)⁻.

¹H-NMR (400 MHz, DMSO-d₆): δ [ppm]=0.80 (d, 3H), 1.28-1.41 (m, 1H), 1.57-1.71 (m, 1H), 1.99-2.20 (m, 3H), 2.20-2.30 (m, 1H), 3.30-3.47 (m, 1H, partially obscured by H₂O signal), 4.15 (d, 1H), 4.38 (d, 1H), 7.08 (dd, 1H), 7.43 (d, 1H), 7.44-7.51 (m, 4H), 7.54 (d, 1H), 9.91 (s, 1H), 12.24-12.45 (br. s, 1H).

$[α]_D^{20}$=+25.4°, c=0.41, chloroform.

Example 106

Diastereomer 2 yield: 94 mg $R_t$=9.05 min; chemical purity >99%; >98% de

[column: Daicel Chiralpak AD-H, 5 μm, 250 mm×4.6 mm; mobile phase: isohexane/(isopropanol+0.2% trifluoroacetic acid+1% water) 90:10 (v/v); flow rate: 0.8 ml/min; UV detection: 220 nm; temperature: 25° C.].

LC-MS (Method 7): $R_t$=1.29 min; m/z=519/521 (M−H)⁻.

¹H-NMR (400 MHz, DMSO-d₆): δ [ppm]=0.80 (d, 3H), 1.27-1.40 (m, 1H), 1.57-1.71 (m, 1H), 1.98-2.19 (m, 3H), 2.19-2.29 (m, 1H), 3.27-3.50 (m, 1H, partially obscured by H₂O signal), 4.15 (d, 1H), 4.38 (d, 1H), 7.09 (dd, 1H), 7.41-7.51 (m, 5H), 7.54 (d, 1H), 9.90 (s, 1H), 12.21-12.47 (br. s, 1H).

$[α]_D^{20}$=+54.0°, c=0.51, chloroform.

Example 107 and Example 108

1-[(4-Chloro-3-{[(2S,3R)-2-(4-chlorophenyl)-4,4,4-trifluoro-3-methylbutanoyl]amino}phenyl)-(methoxy)methyl]cyclobutanecarboxylic acid (diastereomers 1 and 2)

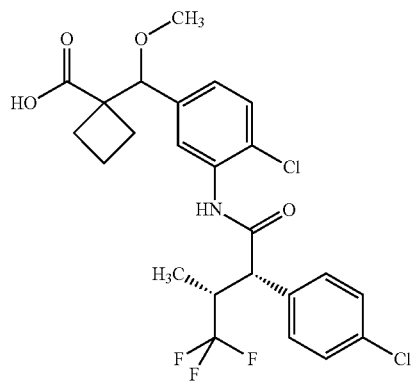 [SMILES: COC(c1ccc(Cl)c(NC(=O)[C@H](c2ccc(Cl)cc2)[C@@H](C)C(F)(F)F)c1)C1(C(=O)O)CCC1]

220 mg (0.44 mmol) of the diastereomer mixture of 1-[(4-chloro-3-{[(2S,3R)-2-(4-chlorophenyl)-4,4,4-trifluoro-3-methylbutanoyl]amino}phenyl)(methoxy)methyl]cyclobutanecarboxylic acid (Example 95) were separated further by preparative HPLC on a chiral phase [column: Daicel Chiralpak IC, 5 μm, 250 mm×20 mm; mobile phase: isohexane/isopropanol 92:8 (v/v); flow rate: 15 ml/min; UV detection: 220 nm; temperature: 30° C.]:

Example 107

Diastereomer 1 yield: 113 mg $R_t$=5.59 min; chemical purity >96.5%; >99% de

[column: Daicel Chiralpak IC, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 25° C.].

LC-MS (Method 4): $R_t$=1.49 min; m/z=516/518 (M−H)⁻.

¹H-NMR (400 MHz, DMSO-d₆): δ [ppm]=0.80 (d, 3H), 1.28-1.41 (m, 1H), 1.57-1.71 (m, 1H), 1.99-2.30 (m, 4H), 3.13 (s, 3H), 3.29-3.46 (m, 1H), 4.15 (d, 1H), 4.38 (d, 1H), 7.08 (dd, 1H), 7.41-7.51 (m, 5H), 7.54 (d, 1H), 9.90 (s, 1H), 12.03-12.68 (br. s, 1H).

$[α]_D^{20}$=+25.4°, c=0.41, chloroform.

Example 108

Diastereomer 2 yield: 98 mg $R_t$=6.27 min; chemical purity >99%; >99% de

[column: Daicel Chiralpak IC, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 25° C.].

LC-MS (Method 4): $R_t$=1.49 min; m/z=516/518 (M−H)⁻.

¹H-NMR (400 MHz, DMSO-d₆): δ [ppm]=0.80 (d, 3H), 1.27-1.41 (m, 1H), 1.57-1.71 (m, 1H), 1.98-2.29 (m, 4H), 3.13 (s, 3H), 3.27-3.45 (m, 1H, partially obscured by H₂O signal), 4.15 (d, 1H), 4.38 (d, 1H), 7.09 (dd, 1H), 7.41-7.51 (m, 5H), 7.54 (d, 1H), 9.90 (s, 1H), 12.02-12.62 (br. s, 1H).

$[α]_D^{20}$=+54.0°, c=0.51, chloroform.

Example 109 and Example 110

1-[(4-Chloro-3-{[(2S,3R)-2-(4-chlorophenyl)-4,4,4-trifluoro-3-methylbutanoyl]amino}phenyl)-(ethoxy)methyl]cyclobutanecarboxylic acid (diastereomers 1 and 2)

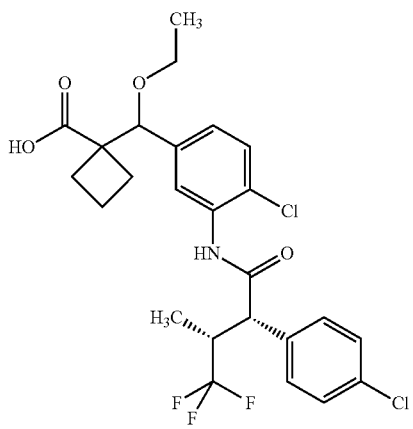 [SMILES: CCOC(c1ccc(Cl)c(NC(=O)[C@H](c2ccc(Cl)cc2)[C@@H](C)C(F)(F)F)c1)C1(C(=O)O)CCC1]

255 mg (0.48 mmol) of the diastereomer mixture of 1-[(4-chloro-3-{[(2S,3R)-2-(4-chlorophenyl)-4,4,4-trifluoro-3-methylbutanoyl]amino}phenyl)(ethoxy)methyl]cyclobutanecarboxylic acid (Example 96) were separated further by preparative HPLC on a chiral phase [column: Chiracel OZ-H, 5 μm, 250 mm×20 mm; mobile phase: isohexane/isopropanol 95:5 (v/v); flow rate: 15 ml/min; UV detection: 220 nm; temperature: 25° C.]:

Example 109

Diastereomer 1 yield: 77 mg
$R_t$=5.35 min; chemical purity >98%; >98.5% de
[column: Chiralcel OZ-H, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 25° C.].
LC-MS (Method 5): $R_t$=1.29 min; m/z=530/532 (M−H)⁻.
¹H-NMR (400 MHz, DMSO-d₆): δ [ppm]=0.80 (d, 3H), 1.06 (t, 3H), 1.28-1.41 (m, 1H), 1.56-1.70 (m, 1H), 1.97-2.29 (m, 4H), 3.28 (q, 2H, partially obscured by H₂O signal), 3.33-3.45 (m, 1H, partially obscured by H₂O signal), 4.14 (d, 1H), 4.48 (s, 1H), 7.09 (dd, 1H), 7.42 (d, 1H), 7.44-7.50 (m, 4H), 7.53-7.57 (m, 1H), 9.89 (s, 1H), 12.33 (br. s, 1H).
$[\alpha]_D^{20}$=+38.7°, c=0.51, chloroform.

Example 110

Diastereomer 2 yield: 60 mg
$R_t$=5.77 min; chemical purity >98%; >97.8% de
[column: Chiralcel OZ-H, 5 μm, 250 mm×4.6 mm; mobile phase: isohexane/(isopropanol+0.2% trifluoroacetic acid+1% water) 95:5 (v/v); flow rate: 1 ml/min; UV detection: 220 nm; temperature: 25° C.].
LC-MS (Method 5): $R_t$=1.30 min; m/z=530/532 (M−H)⁻.
¹H-NMR (400 MHz, DMSO-d₆): δ [ppm]=0.80 (d, 3H), 1.07 (t, 3H), 1.27-1.40 (m, 1H), 1.56-1.69 (m, 1H), 1.96-2.29 (m, 4H), 3.28 (q, 2H, partially obscured by H₂O signal), 3.32-3.47 (m, 1H, partially obscured by H₂O signal), 4.14 (d, 1H), 4.49 (s, 1H), 7.10 (dd, 1H), 7.42 (d, 1H), 7.44-7.50 (m, 4H), 7.57 (d, 1H), 9.89 (s, 1H), 12.33 (br. s, 1H).
$[\alpha]_D^{20}$=+109.3°, c=0.415, chloroform.

The two examples below were prepared in accordance with General Procedure 8:

| Example | Name/Structure/Starting material | Analytical data |
|---|---|---|
| 111 | 1-[1-(4-chloro-3-{[(2S,3R)-2-(4-chlorophenyl)-4,4,4-trifluoro-3-methylbutanoyl]amino}phenyl)-1-hydroxyethyl]cyclopropanecarboxylic acid (diastereomer mixture)<br><br>from tert-butyl 1-[1-(4-chloro-3-{[(2S,3R)-2-(4-chlorophenyl)-4,4,4-trifluoro-3-methylbutanoyl]-amino}phenyl)-1-hydroxyethyl]-cyclopropanecarboxylate (diastereomer mixture) | LC-MS (Method 5): $R_t$ = 1.12 min; m/z = 502/504 (M − H)⁻.<br>¹H-NMR (400 MHz, DMS0-d₆): δ [ppm] = 0.80 (d, 3H), 0.96-1.12 (m, 3H), 1.20-1.31 (m, 1H), 1.55 (s, 3H), 3.28-3.45 (m, 1H, partially obscured by H₂O signal), 4.11 (d, 1H), 4.64-5.51 (br. s, about 1H), 7.25-7.36 (m, 2H), 7.42-7.51 (m, 4H), 7.70-7.75 (m, 1H), 9.83 (s, 1H), 11.40-12.40 (br. s, about 1H). |

| Example | Name/Structure/Starting material | Analytical data |
|---|---|---|
| 112 | 1-[(4-chloro-3-{[(2S,3R)-2-(4-chlorophenyl)-4,4,4-trifluoro-3-methylbutanoyl]amino}phenyl)-(cyclopropyloxy)methyl]cyclopropanecarboxylic acid (diastereomer mixture)<br>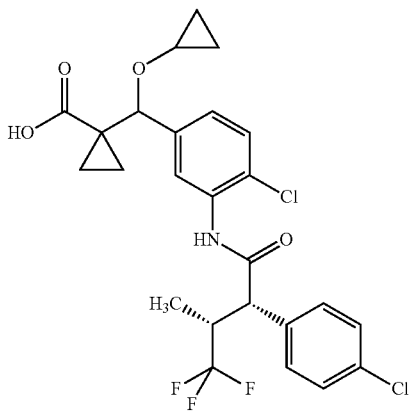 [SMILES: C[C@H]([C@H](C(=O)Nc1cc(C(OC2CC2)C2(C(=O)O)CC2)ccc1Cl)c1ccc(Cl)cc1)C(F)(F)F]<br>from tert-butyl 1-[(4-chloro-3-{[(2S,3R)-2-(4-chlorophenyl)-4,4,4-trifluoro-3-methylbutanoyl]amino}phenyl)(cyclopropyloxy)methyl]cyclopropanecarboxylate (diastereomer mixture) | LC-MS (Method 5): $R_t$ = 1.28 min; m/z 528/530 (M − H)⁻. |

Example 113 and Example 114

1-[(4-Chloro-3-{[(2S,3R)-2-(4-chlorophenyl)-4,4,4-trifluoro-3-methylbutanoyl]amino}phenyl)-(cyclopropyloxy)methyl]cyclopropanecarboxylic acid (diastereomers 1 and 2)

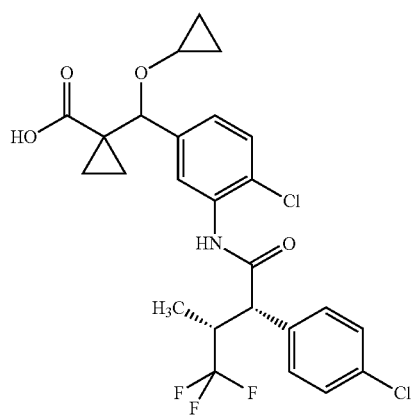 [SMILES: C[C@H]([C@H](C(=O)Nc1cc(C(OC2CC2)C2(C(=O)O)CC2)ccc1Cl)c1ccc(Cl)cc1)C(F)(F)F]

58 mg (0.11 mmol) of the diastereomer mixture of 1-[(4-chloro-3-{[(2S,3R)-2-(4-chlorophenyl)-4,4,4-trifluoro-3-methylbutanoyl]amino}phenyl)(cyclopropyloxy)methyl]cyclopropanecarboxylic acid (Example 112) were separated further by preparative HPLC on a chiral phase [column: Daicel Chiracel OD-H, 5 μm, 250 mm×20 mm; mobile phase: isohexane/(ethanol+0.2% trifluoroacetic acid+1% water) 95:5 (v/v); flow rate: 25 ml/min; UV detection: 230 nm; temperature: 25° C.]:

Example 113

Diastereomer 1 yield: 12 mg $R_t$=4.61 min; chemical purity >99%; >99% de [column: Daicel Chiralpak OD-H, 5 μm, 250 mm×4.6 mm; mobile phase: isohexane/(ethanol+0.2% trifluoroacetic acid+1% water) 90:10 (v/v); flow rate: 1 ml/min; UV detection: 220 nm; temperature: 25° C.].

LC-MS (Method 5): $R_t$=1.26 min; m/z=528/530 (M−H)⁻.

¹H-NMR (400 MHz, DMSO-$d_6$): δ [ppm]=0.27-0.42 (m, 3H), 0.43-0.50 (m, 1H), 0.55-0.63 (m, 1H), 0.76-0.83 (m, 1H), 0.80 (d, 3H), 0.88-0.95 (m, 1H), 0.96-1.04 (m, 1H), 3.08-3.15 (m, 1H), 3.31-3.45 (m, 1H, partially obscured by H₂O signal), 4.14 (d, 1H), 5.04 (s, 1H), 7.13 (dd, 1H), 7.42 (d, 1H), 7.44-7.51 (m, 5H), 9.92 (s, 1H), 12.10-12.55 (br. s, about 1H).

Example 114

Diastereomer 2 yield: 10 mg $R_t$=5.09 min; chemical purity >99%; >98.5% de [column: Daicel Chiralpak OD-H, 5 μm, 250 mm×4.6 mm; mobile phase: isohexane/(ethanol+0.2% trifluoroacetic acid+1% water) 90:10 (v/v); flow rate: 1 ml/min; UV detection: 220 nm; temperature: 25° C.].

LC-MS (Method 5): $R_t$=1.26 min; m/z=528/530 (M−H)⁻.

¹H-NMR (400 MHz, DMSO-$d_6$): δ [ppm]=0.28-0.42 (m, 3H), 0.43-0.51 (m, 1H), 0.55-0.64 (m, 1H), 0.75-0.86 (m, 1H), 0.81 (d, 3H), 0.88-0.95 (m, 1H), 0.96-1.03 (m, 1H), 3.08-3.16 (m, 1H), 3.30-3.45 (m, 1H, partially obscured by H₂O signal), 4.14 (d, 1H), 5.05 (s, 1H), 7.12 (dd, 1H), 7.42 (d, 1H), 7.44-7.53 (m, 5H), 9.92 (s, 1H), 12.32 (br. s, 1H).

B. Assessment of the Pharmacological Activity

The pharmacological effect of the compounds according to the invention can be shown in the following assays:

B-1. Stimulation of Recombinant Soluble Guanylate Cyclase (sGC) In Vitro

Investigations on the stimulation of recombinant soluble guanylate cyclase (sGC) by the compounds according to the invention with and without sodium nitroprusside, and with and without the haem-dependent sGC inhibitor 1H-1,2,4-oxadiazolo[4,3a]quinoxalin-1-one (ODQ), are carried out by the method described in detail in the following reference: M. Hoenicka, E. M. Becker, H. Apeler, T. Sirichoke, H. Schroeder, R. Gerzer and J.-P. Stasch, "Purified soluble guanylyl cyclase expressed in a baculovirus/Sf9 system: Stimulation by YC-1, nitric oxide, and carbon oxide", *J. Mol. Med.* 77 (1999), 14-23. The haem-free guanylate cyclase is obtained by adding Tween 20 to the sample buffer (0.5% in the final concentration).

The activation of sGC by a test substance is reported as x-fold stimulation of the basal activity. The result for Example 50 is shown in Table 1A and that for Example 99 is shown in Table 1B:

TABLE 1A

Stimulation (x-fold) of recombinant soluble guanylate cyclase (sGC) in vitro by Example 50

| Concentration | Haem-containing sGC | | | Haem-free sGC |
|---|---|---|---|---|
| Example 50 [μM] | Basal (n = 5) | +0.01 μM DEA/NO | +10 μM ODQ | Basal (n = 5) |
| 0 | 1.0 ± 0.0 | 6.6 ± 0.8 | 9.0 ± 1.4 | 1.0 ± 0.0 |
| 0.01 | 1.4 ± 0.1 | 7.5 ± 1.8 | 9.2 ± 1.4 | 2.6 ± 0.8 |
| 0.1 | 1.2 ± 0.1 | 7.6 ± 1.8 | 9.6 ± 1.5 | 7.1 ± 2.4 |
| 1.0 | 2.6 ± 0.4 | 9.0 ± 2.0 | 12.7 ± 1.5 | 27.2 ± 7.4 |
| 10 | 6.4 ± 0.6 | 13.3 ± 2.2 | 21.5 ± 2.2 | 41.2 ± 9.8 |
| 100 | 9.5 ± 0.9 | 14.6 ± 2.2 | 22.6 ± 2.6 | 39.0 ± 9.1 |

TABLE 1B

Stimulation (x-fold) of recombinant soluble guanylate cyclase (sGC) in vitro by Example 99

| Concentration | Haem-containing sGC | | | Haem-free sGC |
|---|---|---|---|---|
| Example 99 [μM] | Basal (n = 3) | +0.01 μM DEA/NO | +10 μM ODQ | Basal (n = 3) |
| 0 | 1.0 ± 0.0 | 4.2 ± 0.8 | 3.7 ± 0.3 | 1.0 ± 0.0 |
| 0.01 | 1.0 ± 0.0 | 4.0 ± 0.6 | 4.3 ± 0.4 | 2.0 ± 0.4 |
| 0.1 | 1.5 ± 0.2 | 4.4 ± 0.8 | 5.7 ± 0.3 | 5.2 ± 0.8 |
| 1.0 | 1.8 ± 0.3 | 5.0 ± 1.7 | 9.2 ± 0.9 | 14.9 ± 2.2 |
| 10 | 2.6 ± 0.4 | 5.3 ± 1.8 | 10.3 ± 1.3 | 19.4 ± 2.8 |

[DEA/NO = 2-(N,N-diethylamino)diazenolate 2-oxide; ODQ = 1H-1,2,4-oxadiazolo[4,3a]quinoxalin-1-one].

It is evident from Tables 1A and 1B that stimulation both of the haem-containing and of the haem-free enzyme is achieved. Furthermore, combination of Example 50 or Example 99 and 2-(N,N-diethylamino)diazenolate 2-oxide (DEA/NO), an NO donor, shows no synergistic effect, i.e. the effect of DEA/NO is not potentiated as would be expected with an sGC activator acting via a haem-dependent mechanism. In addition, the effect of the sGC activator according to the invention is not blocked by 1H-1,2,4-oxadiazolo[4,3a]quinoxalin-1-one (ODQ), a haem-dependent inhibitor of soluble guanylate cyclase ODQ, but is in fact increased. The results in Tables 1A and 1B thus confirm the mechanism of action of the compounds according to the invention as activators of soluble guanylate cyclase.

B-2. Action at a Recombinant Guanylate Cyclase Reporter Cell Line

The cellular action of the compounds according to the invention is determined at a recombinant guanylate cyclase reporter cell line, as described in F. Wunder et al., *Anal. Biochem.* 339, 104-112 (2005).

Representative results for the compounds according to the invention are listed in Table 2:

TABLE 2 sGC-activating activity in the CHO reporter cell in vitro

| Example No. | MEC [nM] |
|---|---|
| 6 | 30 |
| 8 | 3 |
| 9 | 1 |
| 11 | 1 |
| 12 | 100 |
| 13 | 30 |
| 14 | 100 |
| 15 | 30 |
| 16 | 10 |
| 22 | 10 |
| 25 | 0.3 |
| 27 | 100 |
| 28 | 3 |
| 30 | 0.3 |
| 32 | 2.3 |
| 33 | 3 |
| 34 | 10 |
| 35 | 10 |
| 37 | 0.1 |
| 38 | 0.3 |
| 39 | 0.3 |
| 40 | 0.3 |
| 41 | 1 |
| 42 | 3 |
| 43 | 3 |
| 44 | 0.3 |
| 46 | 1 |
| 49 | 30 |
| 50 | 0.4 |
| 51 | 0.3 |
| 52 | 10 |
| 53 | 10 |
| 62 | 1 |
| 63 | 0.3 |
| 64 | 200 |
| 65 | 5.3 |
| 67 | 3 |
| 68 | 1 |
| 69 | 3 |
| 71 | 3 |
| 73 | 1.7 |
| 78 | 3 |
| 80 | 3 |
| 82 | 1.7 |
| 84 | 20 |
| 89 | 3 |
| 97 | 10 |
| 98 | 0.3 |
| 99 | 1 |
| 101 | 0.3 |
| 103 | 60 |
| 104 | 20 |
| 105 | 3 |
| 107 | 3 |
| 109 | 0.3 |
| 111 | 30 |
| 113 | 0.3 |
| 114 | 3 |

(MEC = minimum effective concentration).

In comparison, in this test the two compounds 1-(3-{[(2,4-dichlorobenzoyl)amino]methyl}-4-methoxybenzyl)cyclopropanecarboxylic acid and 2-(3-{[(2-chloro-4-propoxybenzoyl)amino]-methyl}-4-ethoxybenzyl)tetrahydrofuran-2-carboxylic acid [Example 11 and Example 73, respectively, of EP 1 452 521-A1] selected from the prior art and described therein as PPAR agonists each have an MEC of >10 µM (see also results of Test B-6. below).

B-3. Stimulation of sGC Enzyme Activity

Soluble guanylate cyclase (sGC) converts on stimulation GTP into cGMP and pyrophosphate (PPi). PPi is detected with the aid of the assay described below. The signal produced in the assay increases as the reaction progresses and serves as a measure of the sGC enzyme activity under the given stimulation.

To carry out the assay, 29 µl of enzyme solution [0-10 nM soluble guanylate cyclase (prepared according to Honicka et al., *J. Mol. Med.* 77, 14-23 (1999)) in 50 mM TEA, 2 mM MgCl$_2$, 0.1% BSA (fraction V), 0.005% Brij®, pH 7.5] are initially introduced into a microplate, and 1 µl of the substance to be tested (as a serially diluted solution in DMSO) is added. The mixture is incubated at room temperature for 10 min. Then 20 µl of detection mix [1.2 nM Firefly Luciferase (*Photinus pyralis* luciferase, Promega), 29 µM dehydroluciferin (prepared according to Bitler & McElroy, *Arch. Biochem. Biophys.* 72, 358 (1957)), 122 µM luciferin (Promega), 153 µM ATP (Sigma) and 0.4 mM DTT (Sigma) in 50 mM TEA, 2 mM MgCl$_2$, 0.1% BSA (fraction V), 0.005% Brij®, pH 7.5] are added. The enzyme reaction is started by adding 20 µl of substrate solution [1.25 mM guanosine 5'-triphosphate (Sigma) in 50 mM TEA, 2 mM MgCl$_2$, 0.1% BSA (fraction V), 0.005% Brij®, pH 7.5] and measured continuously in a luminometer. The extent of the stimulation by the substance to be tested can be determined relative to the signal of the unstimulated reaction.

The activation of haem-free guanylate cyclase is examined by addition of 25 µM of 1H-1,2,4-oxadiazolo[4,3-a]quinoxalin-1-one (ODQ) to the enzyme solution and subsequent incubation for 30 minutes and compared to the stimulation of the native enzyme.

Representative results for the compounds according to the invention are listed in Table 3:

TABLE 3

Activating action at the sGC enzyme in vitro

| Example No. | MEC [nM] | EC$_{50}$ [nM] |
|---|---|---|
| 30 | 0.6 | 7.6 |
| 32 | 0.9 | 7.3 |
| 43 | 3.4 | 24 |
| 50 | 0.7 | 7.3 |
| 51 | 3.0 | 21 |
| 62 | 2.2 | 30 |
| 68 | 2.6 | 45 |
| 73 | 3.8 | 83 |
| 82 | 3.4 | 44 |
| 89 | 3.9 | 70 |
| 99 | 4.1 | 53 |
| 101 | 0.7 | 4.6 |
| 105 | 36 | 240 |
| 107 | 22 | 330 |
| 109 | 0.7 | 20 |

(MEC = minimum effective concentration; EC$_{50}$ = concentration at 50% of maximum efficacy).

In comparison, in this test the two compounds 1-(3-{[(2,4-dichlorobenzoyl)amino]methyl}-4-methoxybenzyl)cyclopropanecarboxylic acid and 2-(3-{[(2-chloro-4-propoxybenzoyl)amino]-methyl}-4-ethoxybenzyl)tetrahydrofuran-2-carboxylic acid [Example 11 and Example 73, respectively, of EP 1 452 521-A1] selected from the prior art and described therein as PPAR agonists each have an MEC of >10 µM (see also results of Test B-6. below).

B-4. Vasorelaxant Effect In Vitro

Rabbits are anaesthetized and sacrificed by intravenous injection of thiopental sodium (about 50 mg/kg) and exsanguinated. The saphenous artery is removed and divided into rings 3 mm wide. the rings are mounted singly on in each case a pair of triangular hooks open at the end and made of 0.3 mm-thick special wire (Remanium®). Each ring is placed under an initial tension in 5 ml organ baths with Krebs-Henseleit solution which is at 37° C., is gassed with carbogen and has the following composition: NaCl 119 mM; KCl 4.8 mM; CaCl$_2$×2 H$_2$O 1 mM; MgSO$_4$×7 H$_2$O 1.4 mM; KH$_2$PO$_4$ 1.2 mM; NaHCO$_3$ 25 mM; glucose 10 mM; bovine serum albumin 0.001%. The force of contraction is detected with Statham UC2 cells, amplified and digitized via A/D converters (DAS-1802 HC, Keithley Instruments, Munich) and recorded in parallel on chart recorders. Contractions are induced by addition of phenylephrine.

After several (generally 4) control cycles, the substance to be investigated is added in each further run in increasing dosage, and the level of the contraction achieved under the influence of the test substance is compared with the level of the contraction reached in the last preceding run. The concentration necessary to reduce the contraction reached in the preceding control by 50% is calculated from this (IC$_{50}$). The standard application volume is 5 µl. The proportion of DMSO in the bath solution corresponds to 0.1%.

Representative results for the compounds according to the invention are listed in Table 4:

TABLE 4

Vasorelaxant effect in vitro

| Example No. | IC$_{50}$ [nM] |
|---|---|
| 30 | 606 |
| 50 | 145 |
| 101 | 685 |
| 109 | 338 |

B-5. Radiotelemetric Measurement of Blood Pressure and Heart Rate on Conscious SH Rats A commercially available telemetry system from Data Sciences International DSI, USA, is employed for the measurements on conscious SH rats described below.

The system consists of 3 main components: (1) implantable transmitters, (2) receivers, which are linked via a multiplexer to a (3) data acquisition computer. The telemetry system makes it possible to continuously record the blood pressure and heart rate of conscious animals in their usual habitat.

The investigations are carried out on adult female spontaneously hypertensive rats (SH rats) with a body weight of >200 g. After transmitter implantation, the experimental animals are housed singly in type 3 Makrolon cages. They have free access to standard feed and water. The day/night rhythm in the experimental laboratory is changed by the room lighting at 6.00 am and at 7.00 pm.

The telemetry transmitters (TAM PA-C40, DSI) as employed are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi, 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed. An antibiotic (Tardomyocel COMP, Bayer A G, 1 ml/kg s.c.) is administered postoperatively for prophylaxis of infection.

Outline of Experiment:

The substances to be investigated are administered orally by gavage in each case to a group of animals (n=6). The test substances are dissolved in suitable solvent mixtures, or suspended in 0.5% strength Tylose, appropriate for an administration volume of 5 ml/kg of body weight. A solvent-treated group of animals is employed as control.

The telemetry measuring unit is configured for 24 animals. Each experiment is recorded under an experiment number.

Each of the instrumented rats living in the system is assigned a separate receiving antenna (1010 Receiver, DSI). The implanted transmitters can be activated externally by means of an incorporated magnetic switch and are switched to transmission in the run-up to the experiment. The emitted signals can be detected online by a data acquisition system (Dataquest™ A.R.T. for Windows, DSI) and be appropriately processed. The data are stored in each case in a file created for this purpose and bearing the experiment number.

In the standard procedure, the following are measured for 10-second periods in each case: (1) systolic blood pressure (SBP), (2) diastolic blood pressure (DBP), (3) mean arterial pressure (MAP) and (4) heart rate (HR).

The acquisition of measured values is repeated under computer control at 5-minute intervals. The source data obtained as absolute value are corrected in the diagram with the currently measured barometric pressure and stored as individual data. Further technical details are given in the documentation from the manufacturing company (DSI).

The test substances are administered at 9.00 am on the day of the experiment. Following the administration, the parameters described above are measured over 24 hours. After the end of the experiment, the acquired individual data are sorted using the analysis software (Dataquest™ A.R.T. Analysis). The void value is assumed to be the time 2 hours before administration of the substance, so that the selected data set includes the period from 7.00 am on the day of the experiment to 9.00 am on the following day.

The data are smoothed over a presettable time by determination of the average (15-minute average, 30-minute average) and transferred as a text file to a storage medium. The measured values presorted and compressed in this way are transferred into Excel templates and tabulated.

B-6. Cellular Peroxisome Proliferator-Activated Receptor (PPAR) Transactivation Assay (for Comparison)

a) Test Principle:

A cellular assay is used to test for potentially activating properties of the compounds according to the invention with respect to the three human isoforms of the peroxisome proliferator-activated receptors (PPARα, PPARγ and PPARδ).

Since mammalian cells contain different endogenous nuclear receptors which may complicate an unambiguous interpretation of the results, an established chimera system is used in which the respective ligand binding domain of the human PPAR isoforms is fused to the DNA binding domain of the yeast transcription factor GAL4. The resulting GAL4-PPARα, γ and δ chimeras are co-transfected and stably expressed in CHO cells having a reporter construct.

b) Cloning:

The GAL4-PPAR expression constructs contain the ligand binding domain of PPARα (amino acids 167-468), PPARγ (amino acids 203-506) and PPARδ (amino acids 138-442) which are PCR-amplified and cloned into the vector pcDNA3.1. The respective expression vectors already contain the GAL4 DNA binding domain (amino acids 1-147) of the vector pFC2-dbd (Stratagene). The reporter construct, which contains five copies of the GAL4 binding site upstream of a thymidine kinase promoter, expresses firefly luciferase (*Photinus pyralis*) following activation and binding of GAL4-PPARα, γ or δ.

c) Test Procedure and Evaluation:

The day before the test, CHO-K1 cells (chinese hamster ovary; ATCC CCL-61) each stably expressing one of the above-described GAL4-PPAR chimeras and the luciferase reporter gene construct are sown in medium [Optimem (GIBCO) with 2% activated carbon-purified foetal calf serum (Hyclone), 1.35 mM sodium pyruvate (GIBCO) and 0.2% sodium bicarbonate (GIBCO)] in a density of $1 \times 10^3$ cells in 96-well microtitre plates (Greiner) and kept in a cell incubator (96% atmospheric humidity, 5% v/v $CO_2$, 37° C.). On the test day, the substances to be tested are taken up in the medium mentioned above, but without addition of calf serum, and added in various concentrations to the cells. After a stimulation period of 6 h, the luciferase activity is measured using a video camera. The relative light units measured give, as a function of the substance concentration, a sigmoidal stimulation curve. The $EC_{50}$ values are calculated using the computer programme GraphPad PRISM (Version 3.02). The maximum effect of a test substance in the respective PPAR assay is determined as efficacy in percent in comparison to an appropriate reference compound whose maximum effect is defined as 100%.

The reference compound selected here was the compound 2-(3-{[(2-chloro-4-propoxybenzoyl)-amino]methyl}-4-ethoxybenzyl)tetrahydrofuran-2-carboxylic acid [Example 73 of EP 1 452 521-A1] which is described in the prior art as a potent pan-PPAR agonist. A second comparative substance, 1-(3-{[(2,4-dichlorobenzoyl)amino]methyl}-4-methoxybenzyl)cyclopropanecarboxylic acid [Example 11 of EP 1 452 521-A1], was found to be virtually ineffective in this test.

Table 5 below lists the $EC_{50}$ and efficacy values of representative exemplary compounds and the two comparative substances mentioned above:

TABLE 5

| Example No. | PPARα $EC_{50}$/ efficacy | PPARγ $EC_{50}$/ efficacy | PPARδ $EC_{50}$/ efficacy |
|---|---|---|---|
| 30 | >10 μM; 0% | 2.3 μM; 20% | >10 μM; 0% |
| 32 | >10 μM; 0% | 1.9 μM; 30% | >10 μM; 0% |
| 33 | >10 μM; 0% | 4.0 μM; 10% | >10 μM; 0% |
| 38 | >10 μM; 0% | >10 μM; 0% | >10 μM; 0% |
| 40 | >10 μM; 0% | 0.12 μM; 10% | >10 μM; 0% |
| 42 | >10 μM; 0% | 2.0 μM; 10% | >10 μM; 0% |
| 43 | >10 μM; 0% | 1.8 μM; 10% | >10 μM; 0% |
| 44 | >10 μM; 0% | >10 μM; 0% | >10 μM; 0% |
| 50 | >10 μM; 0% | 3.0 μM; 45% | >10 μM; 0% |

TABLE 5-continued

| Example No. | PPARα EC$_{50}$/ efficacy | PPARγ EC$_{50}$/ efficacy | PPARδ EC$_{50}$/ efficacy |
| --- | --- | --- | --- |
| 51 | >10 µM; 0% | 1.9 µM; 20% | >10 µM; 0% |
| 68 | >10 µM; 0% | >10 µM; 0% | >10 µM; 0% |
| 71 | >10 µM; 0% | 0.46 µM; 20% | >10 µM; 0% |
| 73 | >10 µM; 0% | >10 µM; 0% | >10 µM; 0% |
| 82 | >10 µM; 0% | 2.3 µM; 20% | >10 µM; 0% |
| 89 | >10 µM; 0% | >10 µM; 0% | >10 µM; 0% |
| 99 | >10 µM; 0% | >10 µM; 0% | >10 µM; 0% |
| 101 | >10 µM; 0% | >10 µM; 0% | >10 µM; 0% |
| 105 | >10 µM; 0% | 1.0 µM; 10% | >10 µM; 0% |
| 107 | >10 µM; 0% | 2.0 µM; 10% | >10 µM; 0% |
| Example 11 of EP 1 452 521 | >1 µM; 0% | >1 µM; 0% | >1 µM; 10% |
| Example 73 of EP 1 452 521 | 0.0053 µM; 100% | 0.0089 µM; 100% | 0.0084 µM; 100% |

Thus, according to these studies, the compounds of the present invention have no agonistic properties with respect to the human PPARα and PPARδ receptor. The activity with respect to the human PPARγ receptor, which can be observed in some cases, is to be considered as comparatively marginal, and it has to be assumed that it does not contribute to the pharmacological activity profile according to the invention of sGC activation, in particular vascular action.

C. Exemplary embodiments of pharmaceutical compositions

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
Tablet weight 212 mg, diameter 8 mm, radius of curvature 12 mm.

Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400. 20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

I.V. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of formula (I)

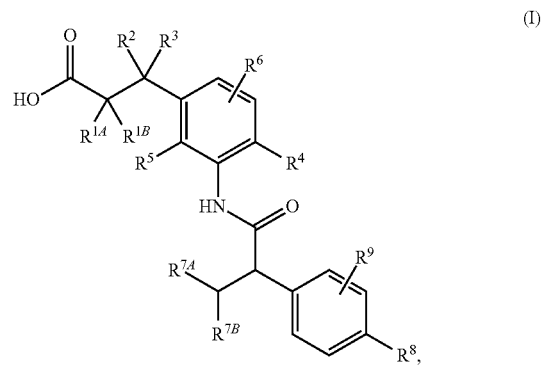

in which
$R^{1A}$ and $R^{1B}$ are attached to one another and together with the carbon atom to which they are attached form a cycloalkyl group of the formula

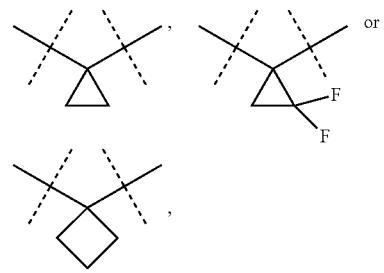

$R^2$ represents hydrogen, methyl, ethyl, vinyl, hydroxyl, methoxy, trideuteromethoxy, trifluoromethoxy, ethoxy or cyclopropyloxy,
$R^3$ represents hydrogen, methyl, ethyl, isopropyl or cyclopropyl,
$R^4$ represents hydrogen, fluorine, chlorine, bromine, cyano, methyl, trifluoromethyl, ethyl, isopropyl, cyclopropyl, cyclobutyl, methoxy or trifluoromethoxy,
$R^5$ represents hydrogen, fluorine, chlorine, methyl, trifluoromethyl or trifluoromethoxy,
$R^6$ represents hydrogen, fluorine, chlorine, methyl, trifluoromethyl or trifluoromethoxy,
$R^{7A}$ represents methyl or ethyl,
$R^{7B}$ represents trifluoromethyl,
or
$R^{7A}$ and $R^{7B}$ are attached to one another and together with the carbon atom to which they are attached form an optionally difluoro-substituted cyclopentyl ring of the formula

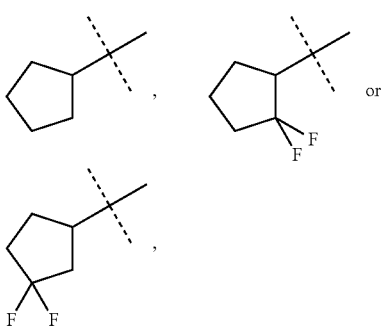

R⁸ represents fluorine, chlorine, bromine, nitro, cyano, trifluoromethoxy, acetyl, 2-cyanovinyl, $(C_1\text{-}C_4)$-alkyl, $(C_2\text{-}C_4)$-alkenyl, cyclopropyl or cyclobutyl, where $(C_1\text{-}C_4)$-alkyl and $(C_2\text{-}C_4)$-alkenyl may be substituted up to three times by fluorine and cyclopropyl and cyclobutyl may be substituted up to two times by fluorine, and R⁹ represents hydrogen, fluorine, chlorine, methyl, trifluoromethyl, ethyl, methoxy or trifluoromethoxy, and salts, solvates and solvates of the salts thereof.

2. The compound of claim 1, wherein $R^{1A}$ and $R^{1B}$ are attached to one another and together with the carbon atom to which they are attached form a cycloalkyl group of the formula

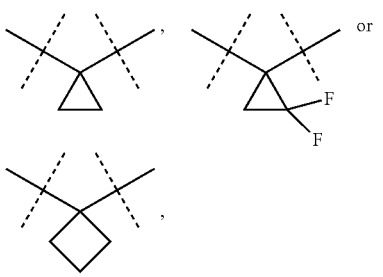

$R^2$ represents hydrogen, methyl, ethyl, hydroxyl, methoxy, trideuteromethoxy, ethoxy or cyclopropyloxy, $R^3$ represents hydrogen, methyl or ethyl, $R^4$ represents hydrogen, fluorine, chlorine, methyl or cyclopropyl, $R^5$ represents hydrogen, fluorine, chlorine or methyl, $R^6$ represents hydrogen, fluorine, chlorine or methyl, $R^{7A}$ represents methyl, $R^{7B}$ represents trifluoromethyl, or $R^{7A}$ and $R^{7B}$ are attached to one another and together with the carbon atom to which they are attached form an optionally difluoro-substituted cyclopentyl ring of the formula

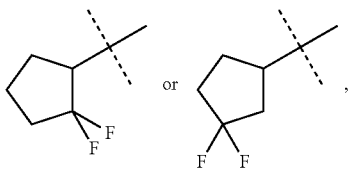

$R^8$ represents fluorine, chlorine, acetyl, 2-cyanovinyl, $(C_1\text{-}C_4)$-alkyl, $(C_2\text{-}C_3)$-alkenyl, cyclopropyl or cyclobutyl, where $(C_1\text{-}C_4)$-alkyl and $(C_2\text{-}C_3)$-alkenyl may be substituted up to three times by fluorine, and $R^9$ represents hydrogen, fluorine, chlorine, methyl, trifluoromethyl or methoxy, or a salt thereof.

3. The compound of claim 1, wherein $R^{1A}$ and $R^{1B}$ are attached to one another and together with the carbon atom to which they are attached form an optionally difluoro-substituted cyclopropyl ring of the formula

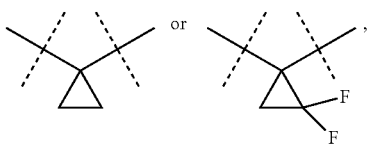

$R^2$ represents hydrogen or ethyl, $R^3$ represents hydrogen, $R^4$ represents hydrogen, fluorine or chlorine, $R^5$ represents hydrogen or fluorine, $R^6$ represents hydrogen, $R^{7A}$ represents methyl, $R^{7B}$ represents trifluoromethyl, or $R^{7A}$ and $R^{7B}$ are attached to one another and together with the carbon atom to which they are attached form a difluoro-substituted cyclopentyl ring of the formula

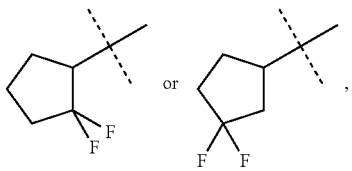

$R^8$ represents chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl, 2,2-difluorovinyl or cyclopropyl, and $R^9$ represents hydrogen, fluorine, chlorine or methoxy, or a salt thereof.

4. The compound of claim 1, wherein $R^{1A}$ and $R^{1B}$ are attached to one another and together with the carbon atom to which they are attached form a cyclopropyl or cyclobutyl ring of the formula

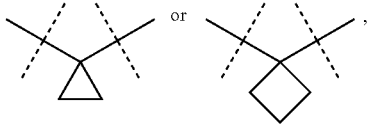

$R^2$ represents hydroxyl, methoxy, trideuteromethoxy, ethoxy or cyclopropyloxy, $R^3$ represents hydrogen, $R^4$ represents hydrogen, fluorine or chlorine, $R^5$ represents hydrogen or fluorine, $R^6$ represents hydrogen, $R^{7A}$ represents methyl, $R^{7B}$ represents trifluoromethyl, or $R^{7A}$ and $R^{7B}$ are attached to one another and together with the carbon atom to which they are attached form a difluoro-substituted cyclopentyl ring of the formula

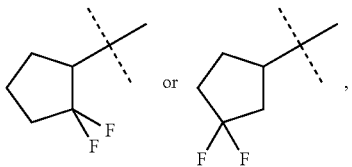

$R^8$ represents chlorine, methyl, trifluoromethyl, ethyl, 1,1-difluoroethyl, 2,2,2-trifluoroethyl, isopropyl, tert-butyl, 1,1,1-trifluoro-2-methylpropan-2-yl, vinyl, 2,2-difluorovinyl or cyclopropyl, and $R^9$ represents hydrogen, fluorine, chlorine or methoxy, or a salt thereof.

5. A method of making a compound claim 1, comprising: coupling a carboxylic acid of the formula (II)

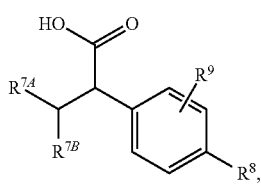

(II)

in which $R^{7A}$, $R^{7B}$, $R^8$ and $R^9$ have the meanings given in claim 1, in an inert solvent with the aid of a condensing agent or via the intermediate of the corresponding carbonyl chloride in the presence of a base with an amine of the formula (III)

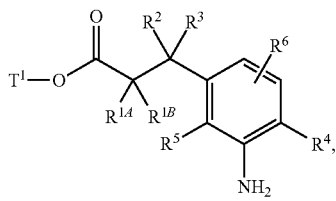

(III)

in which $R^{1A}$, $R^{1B}$, $R^2$, $R^3$, $R^4$, $R^5$ and $R^6$ have the meanings given in claim 1 and $T^1$ represents $(C_1$-$C_4)$-alkyl or benzyl, to give a carboxamide of the formula (IV)

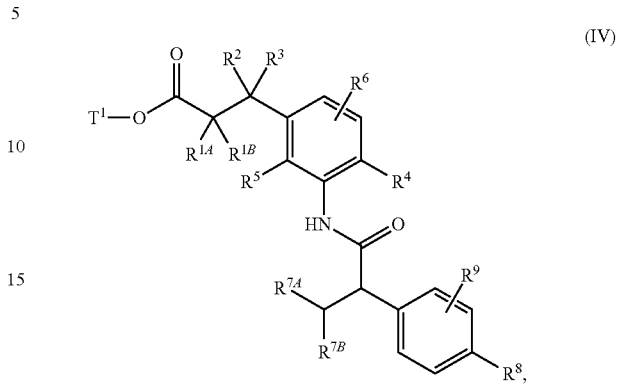

(IV)

in which $R^{1A}$, $R^{1B}$, $R^2$, $R^3$, $R^4$, $R^5$, $R^6$, $R^{7A}$, $R^{7B}$, $R^8$, $R^9$ and $T^1$ have the meanings given above, and removing the ester radical $T^1$ basic or acidic solvolysis or, in the case that $T^1$ represents benzyl, also by hydrogenolysis thereby producing a compound of claim 1.

6. The method of claim 5, further comprising producing a mixture of compounds of formula (I) and separating the compounds into their enantiomers and/or diastereomers and/or reacting the compounds with an appropriate (i) solvent and/or (ii) base to produce salts thereof.

7. A method of treatment of heart failure, angina pectoris, hypertension, pulmonary hypertension, ischaemias, microcirculation impairments, thromboembolic disorders, renal insufficiency, fibrotic disorders and arteriosclerosis comprising administering a compound of claim 1 to a human or animal in need thereof.

8. A pharmaceutical composition comprising a compound of claim 1 and an inert, non-toxic, pharmaceutically suitable excipient.

9. The pharmaceutical composition of claim 8, further comprising an additional active ingredient selected from the group consisting of an organic nitrate, an NO donor, a cGMP-PDE inhibitor, a stimulator of guanylate cyclase, an agent having antithrombotic activity, an agent for lowering blood pressure, and an agent for altering lipid metabolism.

10. A method of treatment of heart failure, angina pectoris, hypertension, pulmonary hypertension, ischaemias, microcirculation impairments, thromboembolic disorders, renal insufficiency, fibrotic disorders and arteriosclerosis comprising administering the pharmaceutical composition to claim 8 to a human or animal in need thereof.

* * * * *